(12) United States Patent
Cui et al.

(10) Patent No.: US 11,466,009 B2
(45) Date of Patent: Oct. 11, 2022

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Zhihao Cui, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 62 days.

(21) Appl. No.: 16/689,007

(22) Filed: Nov. 19, 2019

(65) Prior Publication Data

US 2020/0087311 A1    Mar. 19, 2020

Related U.S. Application Data

(63) Continuation-in-part of application No. 16/215,673, filed on Dec. 11, 2018, now Pat. No. 11,349,080.
(Continued)

(51) Int. Cl.
*H01L 51/50* (2006.01)
*C07D 487/04* (2006.01)
(Continued)

(52) U.S. Cl.
CPC ......... *C07D 487/04* (2013.01); *C07D 498/04* (2013.01); *C07D 513/04* (2013.01); *C07D 517/04* (2013.01); *H01L 51/0067* (2013.01); *H01L 51/0072* (2013.01); *H01L 51/0085* (2013.01)

(58) Field of Classification Search
None
See application file for complete search history.

(56) References Cited

U.S. PATENT DOCUMENTS

| 5,703,436 | A | 12/1997 | Forrest et al. |
| 5,707,745 | A | 1/1998 | Forrest et al. |

(Continued)

FOREIGN PATENT DOCUMENTS

| CA | 2145375 | 9/1995 |
| CN | 101222024 | 7/2008 |

(Continued)

OTHER PUBLICATIONS

Tang, et al., "Organicelectroluminescent diodes",Appl. Phys. Ltt51,913(1987).
(Continued)

*Primary Examiner* — Gregory D Clark
(74) *Attorney, Agent, or Firm* — Barnes & Thornburg LLP; Jeffrey R. Stone

(57) ABSTRACT

Organic electroluminescent materials and devices are disclosed. The organic electroluminescent materials are novel benzodithiophene or its analogous structure compounds, which can be used as charge transporting materials, hole injection materials, or the like in an electroluminescent device. These novel compounds can offer excellent performance compared with existing materials, for example, to further improve the voltage, efficiency and/or lifetime of the OLEDs.

22 Claims, 3 Drawing Sheets

Related U.S. Application Data

(60) Provisional application No. 62/597,941, filed on Dec. 13, 2017.

(51) Int. Cl.
*H01L 51/00* (2006.01)
*C07D 517/04* (2006.01)
*C07D 498/04* (2006.01)
*C07D 513/04* (2006.01)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0170491 | A1 | 9/2003 | Liao et al. |
| 2003/0230980 | A1 | 12/2003 | Forrest et al. |
| 2004/0172116 | A1 | 9/2004 | Seifert et al. |
| 2005/0121667 | A1 | 6/2005 | Kuehl et al. |
| 2007/0018569 | A1 | 1/2007 | Kawamura et al. |
| 2010/0210762 | A1 | 8/2010 | Hanaki et al. |
| 2011/0155976 | A1 | 6/2011 | Furukawa et al. |
| 2013/0175481 | A1 | 7/2013 | Blouin et al. |
| 2015/0155490 | A1 | 6/2015 | Ryu et al. |
| 2015/0349273 | A1 | 12/2015 | Hung et al. |
| 2016/0013426 | A1 | 1/2016 | Yoshioka et al. |
| 2016/0359122 | A1 | 12/2016 | Boudreault et al. |
| 2019/0081250 | A1 | 3/2019 | Yoshioka et al. |
| 2019/0181349 | A1 | 6/2019 | Xia |
| 2020/0062778 | A1 | 2/2020 | Cui et al. |

FOREIGN PATENT DOCUMENTS

| | | | |
|---|---|---|---|
| CN | 109912619 | | 6/2019 |
| CN | 112745333 | | 5/2021 |
| DE | 102020104604 | | 5/2021 |
| JP | H0680672 | | 3/1994 |
| JP | 2009067720 | | 4/2009 |
| JP | 2009242339 | * | 10/2009 ........... C07D 495/04 |
| JP | 2011154226 | | 8/2011 |
| JP | 2021070681 | | 5/2021 |
| JP | 2017518288 | | 7/2021 |
| KR | 020160067021 | A | 6/2016 |
| KR | 1020170126103 | A | 11/2017 |
| KR | 1020180090232 | A | 8/2018 |
| KR | 20180137942 | | 12/2018 |
| KR | 1020210053130 | | 5/2021 |
| WO | 2009022738 | | 2/2009 |
| WO | 2010098326 | | 9/2010 |
| WO | 2012109747 | | 8/2012 |
| WO | 2014126200 | | 8/2014 |
| WO | 2019053968 | | 3/2019 |

OTHER PUBLICATIONS

Joyama, et al., "Highly efficient organic light-emitting diodes from delayed fluorescence", Nature vol. 492, 13, 12, 2012.
Ortiz, et al., "Quinoidal Oligothiophenes: Towardsd Biradical Ground-State Species", Chemistry A European Journal, 2010, 16, 470-484.
Suzuki, et al., "New electron acceptors containing thieno [3,4-b] pyrazine units", Journal of Materials Chemistry, 1998, 8(5), 1117-1119.
Suzuki, et al., "TCNQ analogues composed of heterocyclic rings", Synthetic Metals, 102(1999), 1480-1481.
Takahashi, et al., "Extensive Quioidal Oligothiophenes with Dicyanomethylene Groups at Terminal Positions as Highly Amphoteric Redox Molecules", Journal of American Chemical Society, 2005, 127, 8928-8929.
Wang, et al., "Donor-acceptor-donor type organic semiconductor containing quioidal benzo-[1,2-b:4,5-b'] dithiophene for high performance n-channel field-effect transistors", Chemical Communication, 2014, 50, 985-987.
Yoshida, et al., "Novel Electron Acceptors Bearing a Heteroquinonoid System. 4.1 Synthesis, Properties, and Charge-Transfer Complexes of 2,7-Bis(dicyanomethylene)-2,7-dihydrobenzo[2,1-b:3,4-b']dithiophene, 2,7-Bis(dicyanomethylene)-2,7-dihydrobenzo[1,2-b:4,3b']dithiophene, and 2,6-Bis(dicyanomethylene)-2,6-dihydrobenzo[1,2-b:4,5-b']dithiophene", Journal of Organic Chemistry, 1994, 59, 3077-3081.
Kashiki, et al., "Alkylated 2,6-Bis(dicyanomethylene)-2,6-dihydrobenzo[1,2-b:4,5-b']dithiophenes: New Soluble n-Channel Organic Semiconductors for Air-stable OFETs", Chemistry Letters, 38 (2009), 6, 568-569.
Fujii, et al., "2-6-Bis(Dicyanomethylene)-2,6-Dihydrobenzo[1,2-b;4,5-b']Dithiophene as a Novel Electron Acceptor", Synthetic Metals, 55-57 (1993), 1910-1913.
Chinese first office action and its English translation relating to Application No. 201811460845.3, dated Feb. 3, 2021.
Search report and its English translation relating to Application No. 201811460453.
U.S. Non-final rejection dated Jul. 6, 2021, relating to U.S. Appl. No. 16/215,673, filed Dec. 11, 2018.
German First Office Action dated Oct. 16, 2020 for Application No. DE102020104604A1 and its English translation.
Japanese First Office Action date of drafting Jan. 7, 2021, for Japanese Patent Application No. JP2020-027305 and its English translation.
Notice of Allowance and Fee(s) Due (dated Feb. 3, 2022).
Supplementary Search Report (dated Jul. 28, 2021).
English Translation of Supplementary Search Report (machine translation).
Non-Patent Literature—Solar Photovoltaic Technologies and Applications, including English abstract.
Non-Patent Literature—Dyes and Pigments 149 (2018) 882-892.
Notification to Grant Patent Right for Invention (dated Feb. 8, 2022).
English Translation of Notification to Grant Patent Right for Invention (machine translation).
First Office Action of CN 201911046002.3 (dated Dec. 23, 2021).
English Translation of First Office Action of CN 201911046002.3 (machine translation).
Search Report of CN 201911046002.3 (issued together with the CN OA1).
English translation of Search Report of CN 201911046002.3 (machine translation).
Notice of Allowance of JP2020027305 (dated Mar. 1, 2022).
English Translation of Notice of Allowance of JP2020027305 (machine translation).
Notice of Allowance of KR20200021188 (dated Mar. 14, 2022).
English Translation of Notice of Allowance of KR20200021188 (machine translation).
Notice of Allowance issued in U.S. Appl. No. 16/668,080 and is dated May 26, 2022.

* cited by examiner

ORGANIC ELECTROLUMINESCENT MATERIALS AND DEVICES

CROSS-REFERENCE TO RELATED APPLICATIONS

This application is a continuation-in-part of U.S. application Ser. No. 16/215,673, filed Dec. 11, 2018 and entitled "ORGANIC ELECTROLUMINESCENT MATERIALS AND DEVICES," which claims priority to U.S. Provisional Application No. 62/597,941, filed Dec. 13, 2017 and entitled "ORGANIC ELECTROLUMINESCENT MATERIALS AND DEVICES," the entirety of each of which is incorporated herein by reference.

FIELD

The present invention relates to a compound for use in organic electronic devices, such as organic light-emitting devices. More particularly, it relates to a novel compound having a structure of dehydrobenzodioxazole, dehydrobenzodithiazole or dehydrobenzodiselenazole, or the like, and an organic electroluminescent device and a compound formulation comprising the compound.

BACKGROUND ART

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency, Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

In an OLED device, a hole injection layer (HIL) facilitates hole injection from the ITO anode to the organic layers. To achieve a low device driving voltage, it is important to have a minimum charge injection barrier from the anode. Various HIL materials have been developed such as triarylamine compounds having a shallow HOMO energy levels, very electron deficient heterocycles, and triarylamine compounds doped with P-type conductive dopants. To improve OLED performance such as longer device lifetime, higher efficiency and/or lower voltage, it is crucial to develop HIL, HTL materials with better performance.

The organic light emitting display device uses a hole injection layer and an electron injection layer to promote charge injection. The hole injection layer is a functional layer formed from a single material or more than one material. Methods involving a single material generally utilize materials with deep LUMO levels, while methods involving more than one material are performed by doping a hole transporting material with a P-type, deep-LUMO material. The commonality between these two methods is the use of deep-LUMO materials.

US20050121667 discloses the use of an organic mesomeric compound as organic dopant for doping an organic semiconducting matrix material for varying the electrical properties thereof. The mesomeric compound is a quinone or quinone derivative, and under same evaporation conditions, has a lower volatility than F4-TCNQ. General structures disclosed therein include

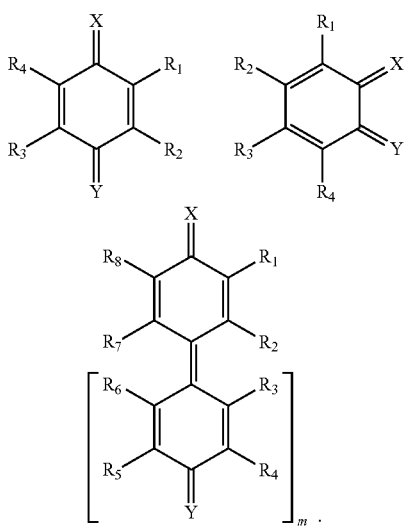

This application focuses primarily on the unique properties of a quinone or quinone derivative when used as a dopant, but it does not disclose or teach the properties and use of any compound that has a parent core structure similar to the present application.

However, materials with deep LUMO levels are not easily synthesized due to their substituents with strong electron-withdrawing ability, and it is difficult to possess both deep LUMO level, high stability, and high film-forming ability. For example, F4-TCNQ (a P-type hole injection material), although having a deep LUMO level, has an extremely low vapor deposition temperature, affecting deposition control and production performance reproducibility and device thermal stability; and, for another example, HATCN has problems in film formation in devices due to strong crystallinity, and the LUMO level thereof is not deep enough to be used as a P-type dopant. Since the hole injection layer has a great influence on the voltage, efficiency and lifetime of an OLED device, it is very important and urgent in the industry for the development of materials with a deep LUMO level, high stability and high film-forming ability.

SUMMARY

The present invention aims to solve at least part of above problems by using a charge transporting layer or a hole injection layer, which comprising a benzodithiophene or its analogous structure compound. In addition, a charge generation layer comprising a benzodithiophene or its analogous structure compound is provided, which can be used for the p type charge generation layer in tandem OLEDs structure and can provide better device performance, for example, to further improve the voltage, efficiency and/or lifetime of the OLEDs.

According to an embodiment of the present invention, a compound having Formula 1 is disclosed:

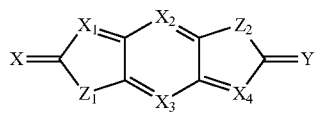

Formula 1 wherein
$X_1$, $X_2$, $X_3$, and $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, Se, S=O, and $SO_2$;

X and Y are each independently selected from the group consisting of S, Se, NR', and CR''R''';

R, R', R'', and R''' are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfonyl group, a sulfinyl group, a sulfonyl group, a phosphine group, and combinations thereof;

Any adjacent substitution can be optionally joined to form a ring or fused structure.

According to yet another embodiment, an organic light-emitting device is also disclosed, which comprises an anode, a cathode, and organic layer between the anode and the cathode, wherein the organic layer comprises a compound having Formula 1:

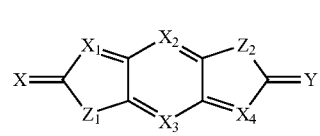

Formula 1 wherein
$X_1$ to $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, Se, S=O, and $SO_2$;

X and Y are each independently selected from the group consisting of S, Se, NR', and CR''R''';

R, R', R'', and R''' are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfonyl group, a sulfonyl group, a phosphino group, and combinations thereof;

Any adjacent substitution can be optionally joined to form a ring or fused structure.

According to yet another embodiment, an organic light-emitting device is also disclosed, which comprises a plurality of stacks between an anode and a cathode, the stacks comprise a first light-emitting layer and a second light-emitting layer, wherein the first stack comprises a first light-emitting layer, the second stack comprises a second light-emitting layer, and a charge generation layer is disposed between the first stack and the second stack, wherein the charge generation layer comprises a p type charge generation layer and an n type charge generation layer, wherein the p type charge generation layer comprises a compound having Formula 1:

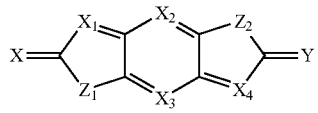

Formula 1 wherein $X_1$ to $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, Se, S═O. and $SO_2$;

X and Y are each independently selected from the group consisting of S, Se, NR', and CR"R'";

R, R', R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphine group, and combinations thereof;

Any adjacent substitution can be optionally joined to form a ring or fused structure.

The novel compounds comprising a benzodithiophene or its analogous structure disclosed in the present invention can be used as charge transporting materials, hole injection materials, or the like in an organic electroluminescent device. Compared with existing materials, these novel compounds can offer excellent device performance.

The present invention also intends to provide a series of novel compounds having a structure of dehydrobenzodioxazole, dehydrobenzodithiazole or dehydrobenzodiselenazole, or the like, to address at least some of the above problems. The compounds can be used as charge-transporting materials and charge injection materials in organic electroluminescent devices. These novel compounds greatly improve the performance such as voltage and lifetime of organic electroluminescent devices.

According to an embodiment of the present invention, a compound having Formula 1' is disclosed:

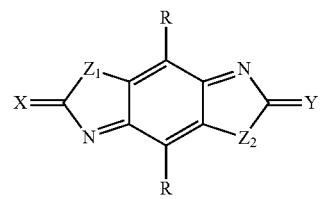

Formula 1' wherein each of X and Y is independently selected from the group consisting of CR"R'", NR', O, S and Se;

wherein each of $Z_1$ and $Z_2$ is independently selected from the group consisting of O, S and Se;

wherein each of R, R', R", R'" is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1. to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein each R may be same or different, and at least one of R, R', R" and R'" is a group having at least one electron-withdrawing group; and wherein adjacent substituents can be optionally joined to form a ring or a fused structure.

According to yet another embodiment of the present invention, an electroluminescent device is also disclosed, which comprises an anode, a cathode, and an organic layer disposed between the anode and the cathode, wherein the organic layer comprises a compound having Formula 1':

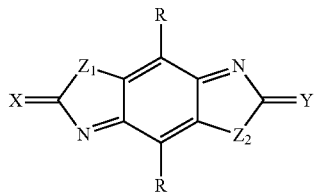

Formula 1' wherein each of X and Y is independently selected from the group consisting of CR"R'", NR', O, S and Se;
wherein each of $Z_1$ and $Z_2$ is independently selected from the group consisting of O, S and Se;
wherein each of $R_1$, R', R" and R'" is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
wherein adjacent substituents can be optionally joined to form a ring or a fused structure; and
wherein each R may be same or different, and at least one of R, R', R" and R'" is a group having at least one electron-withdrawing group.

According to another embodiment of the present invention, a compound formulation is also disclosed, which comprises the compound having the structure of Formula 1'.

The novel compounds having a structure of dehydrobenzodioxazole, dehydrobenzodithiazole or dehydrobenzodiselenazole or the like as disclosed in the present invention can be used as charge-transporting materials and charge injection materials in electroluminescent devices. Such novel compounds greatly improve the performance such as voltage and lifetime of organic electroluminescent devices.

DETAILED DESCRIPTION

Figure 1:
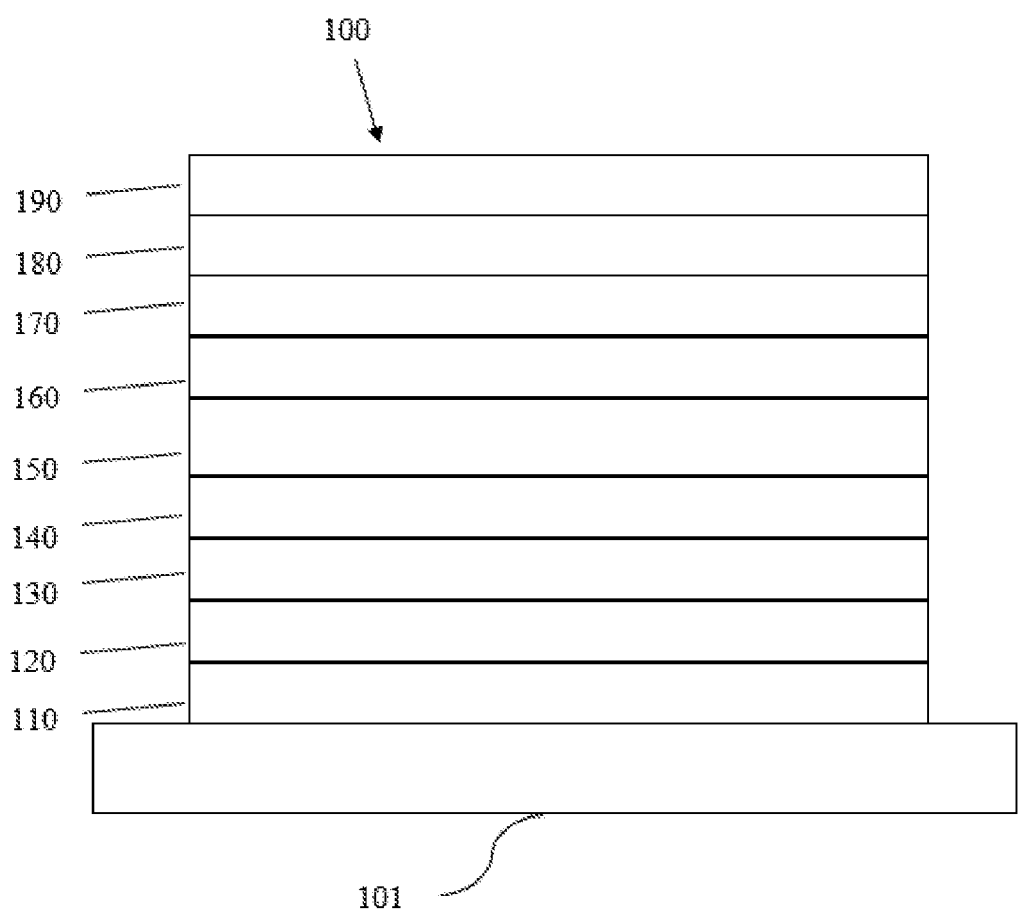
FIG. 1 schematically shows an organic light emitting device that can incorporate the compound and compound formulation disclosed herein.

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols, 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely, such as an electron blocking layer. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum. Also for example, the hole transporting layer may comprise the first hole transporting layer and the second hole transporting layer.

In one embodiment, an OLED may be described as having an "organic layer" disposed between a cathode and an anode. This organic layer may comprise a single layer or multiple layers.

Figure 2:
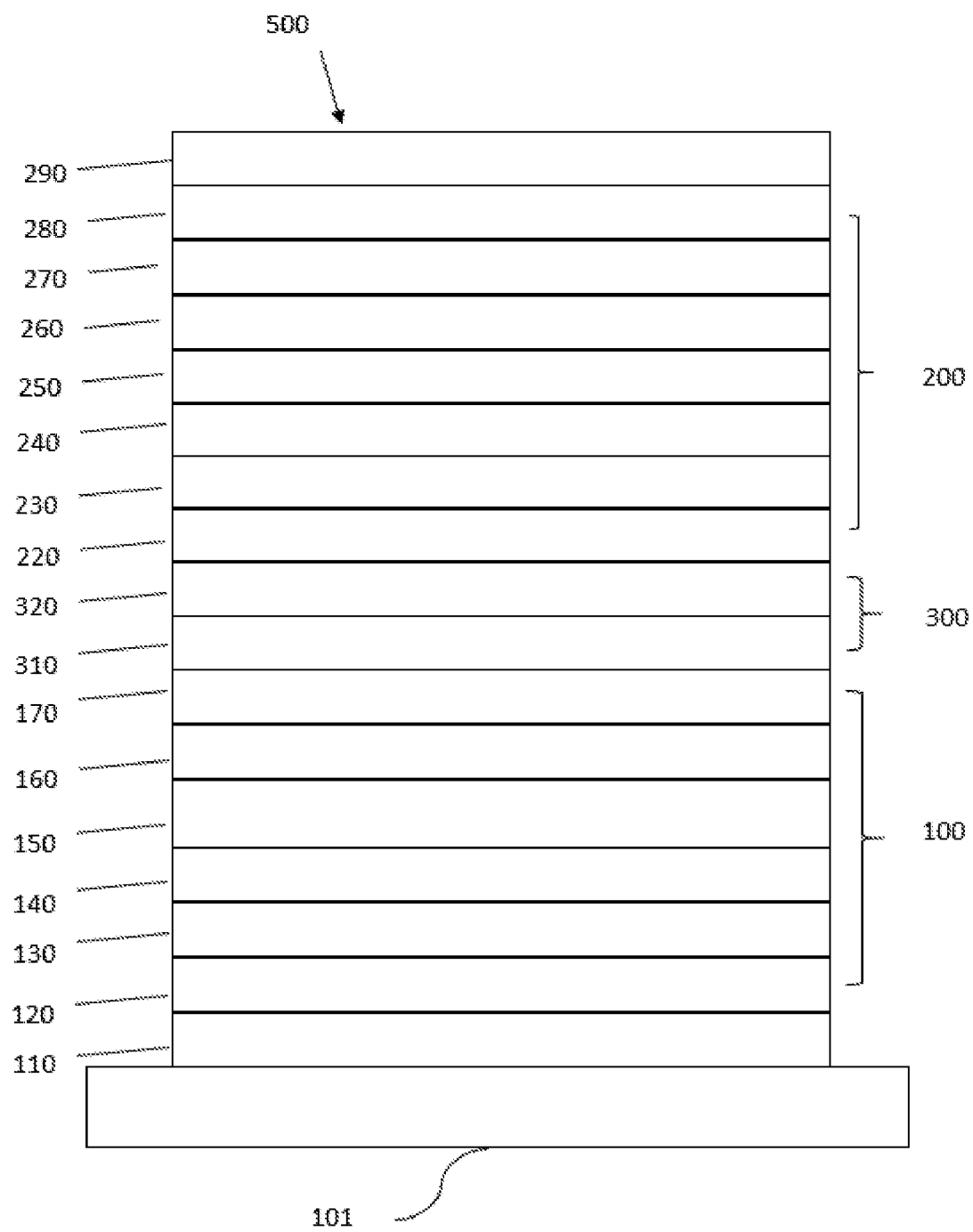
FIG. 2 schematically shows a tandem organic light emitting device that can incorporate the compound and compound formulation disclosed herein.

In one embodiment, two or more MED units may be series connection to form a tandem OLED. FIG. 2 schematically shows the tandem organic light emitting device 500 without limitation. The device 500 may include a substrate 101, an anode 110, a first unit 100, a charge generation layer 300, a second unit 200, and a cathode 290. Wherein the first unit 100 includes a hole injection layer 120, a hole transporting layer 130, an electron blocking layer 140, an emissive layer 150, a hole blocking layer 160, an electron transporting layer 170, and the second unit 200 includes a hole injection layer 220, a hole transporting layer 230, an electron blocking layer 240, an emissive layer 250, a hole blocking layer 260, an electron transporting layer 270, and an electron injection layer 280. The charge generation layers 300 include an N type charge generation layer 310 and a P type charge generation layer 320. The device 500 may be manufactured by sequentially depositing the described layers.

Figure 3:
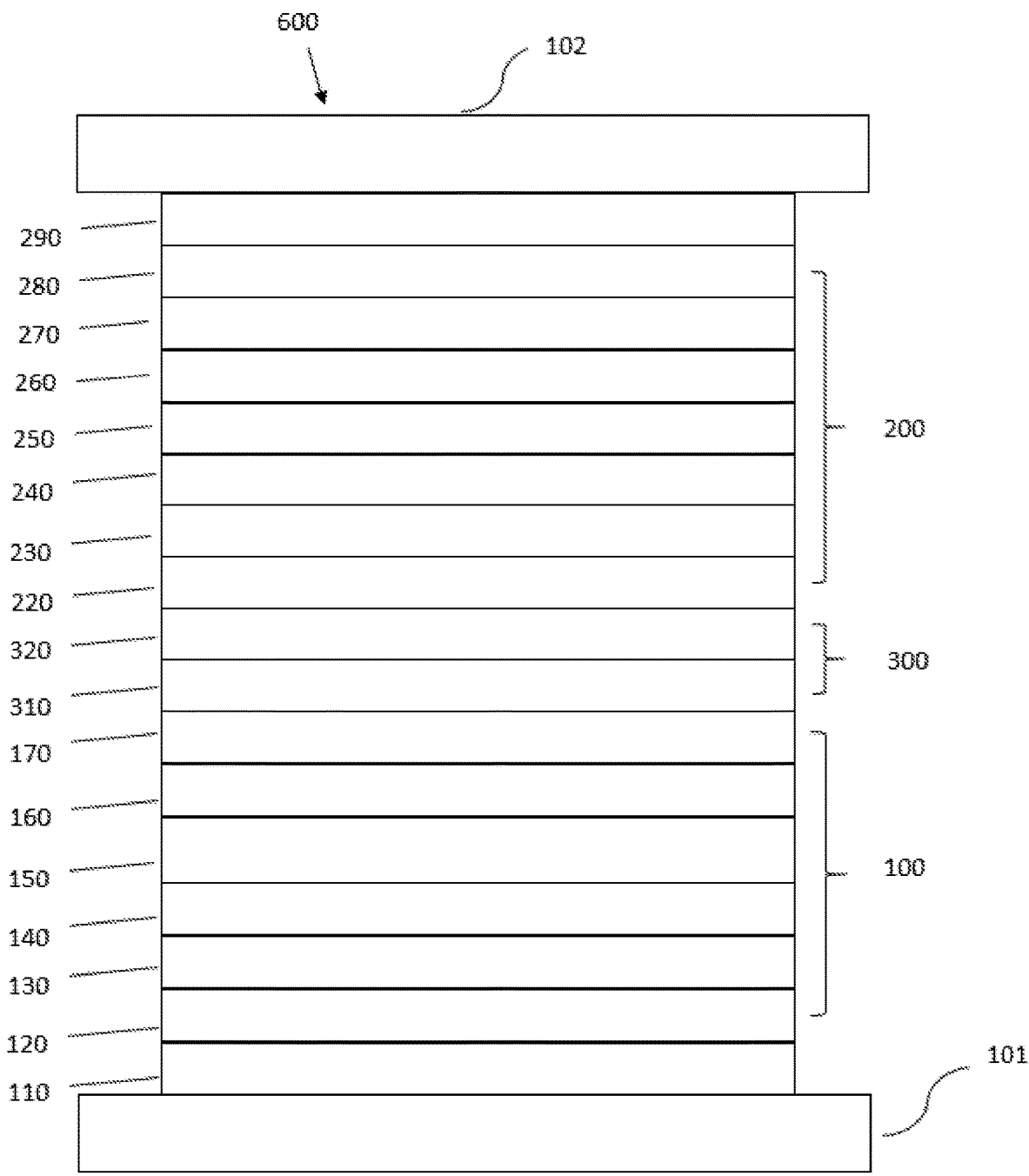
FIG. 3 schematically shows another tandem organic light emitting device that can incorporate the compound and compound formulation disclosed herein.
Figure 4:
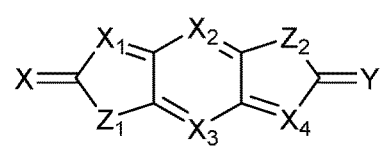
FIG. 4 shows the structural Formula 1 of compound disclosed herein.

An OLED can be encapsulated by a barrier layer. FIG. 3 schematically shows the organic light emitting device 600 without limitation. FIG. 3 differs from FIG. 2 in that the organic light emitting device include a barrier layer 102, which is above the cathode 290, to protect it from harmful species from the environment such as moisture and oxygen. Any material that can provide the barrier function can be used as the barrier layer such as glass and organic-inorganic hybrid layers. The barrier layer should be placed directly or indirectly outside of the MED device. Multilayer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or nits) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein maybe used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

it is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of terms of substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group. 3,4-xylyl group. 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha-naphthylmethyl group, 1-alpha-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo [f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions.

In the present disclosure, unless otherwise defined, when any term of the group consisting of substituted alkyl, substituted cycloalkyl, substituted heteroalkyl, substituted aralkyl, substituted alkoxy, substituted aryloxy, substituted alkenyl, substituted alkynyl, substituted aryl, substituted heteroaryl, substituted alkylsilyl, substituted arylsilyl, substituted amine, substituted acyl, substituted carbonyl, substituted carboxylic acid group, substituted ester group, substituted sulfinyl, substituted sulfonyl and substituted phosphoroso is used, it means that any group of alkyl, cycloalkyl, heteroalkyl, aralkyl, alkoxy, aryloxy, alkenyl, alkynyl, aryl, heteroaryl, alkylsilyl, arylsilyl, amine, acyl, carbonyl, carboxylic acid group, ester group, sulfinyl, sulfonyl and phosphoroso may be substituted with one or more groups selected from the group consisting of deuterium, a halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted aralkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an alkynyl group, an acyl group, a carbonyl group, a carboxylic acid group, an ester group, an ether group, a cyano group, an isocyano group, a thiol group, a sulfonyl group, a sulfinyl group and a phosphoroso group, and combinations thereof.

In the compounds mentioned in the present disclosure, adjacent substituents in the compounds cannot connect to form a ring unless otherwise explicitly defined, for example, adjacent substituents can be optionally joined to form a ring. In the compounds mentioned in the present disclosure, adjacent substituents can be optionally joined to form a ring, including both the case where adjacent substituents can be joined to form a ring, and the case where adjacent substituents are not joined to form a ring. When adjacent substituents can be optionally joined to form a ring, the ring formed may be monocyclic or polycyclic, as well as alicyclic, heteroalicyclic, aromatic or heteroarotnatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

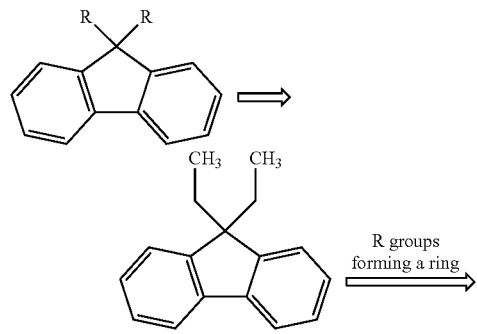

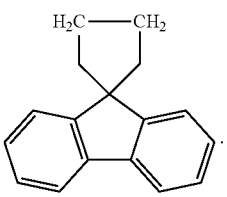

The expression that adjacent substituents can be optionally joined to form a ring is also intended to mean that two substituents bonded to carbon atoms which are directly bonded to each other are joined to each other via a chemical bond to form a ring, which can be exemplified by the following formula:

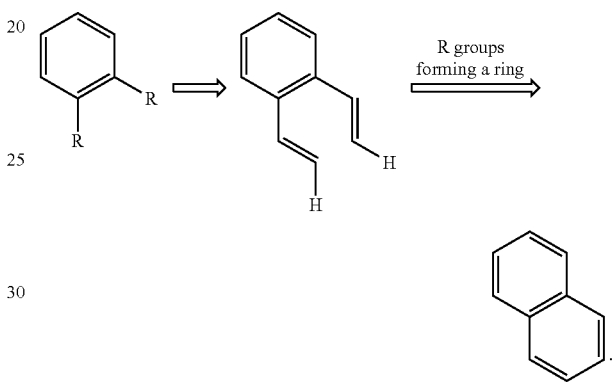

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

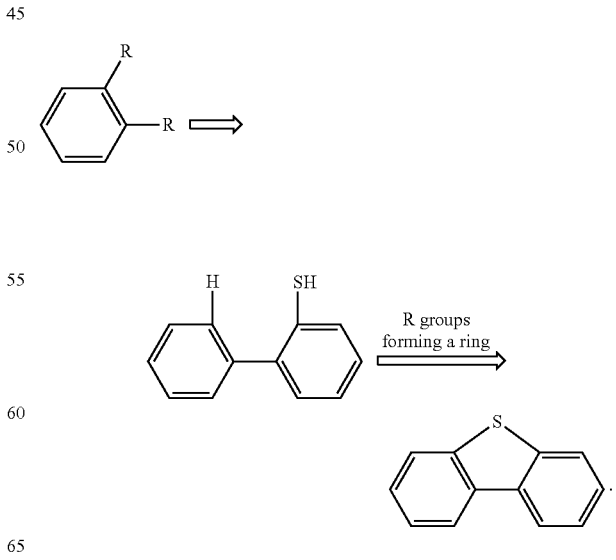

According to an embodiment of the present invention, a compound having Formula 1' is disclosed:

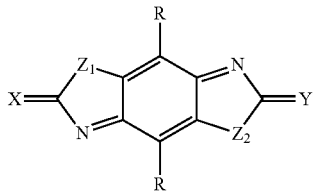

Formula 1' wherein each of X and Y is independently selected from the group consisting of CR"R'", NR' O, S and Se;
wherein each of $Z_1$ and $Z_2$ is independently selected from the group consisting of O, S and Se;
wherein each of R, R', R" and R'" is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sultinyl sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
wherein each R may be same or different, and at least one of R, R', R" and R'" is a group having at least one electron-withdrawing group; and wherein adjacent substituents can be optionally joined to form a ring or a fused structure.

According to an embodiment of the present invention, each of X and Y is independently selected from CR"R'" or NR', wherein R', R" and R'" are groups having at least one electron-withdrawing group.

According to an embodiment of the present invention, each of X and Y is independently selected from CR"R'" or NR', and R, R', R" and R'" are groups having at least one electron-withdrawing group.

According to an embodiment of the present invention, each of X and Y is independently selected from the group consisting of O, S and Se, and at least one of R groups is a group having at least one electron-withdrawing group.

According to an embodiment of the present invention, each of X and Y is independently selected from the group consisting of O, S and Se, and R groups are groups having at least one electron-withdrawing group.

According to an embodiment of the present invention, the Hammett's constant of the electron-withdrawing group is ≥0.05, preferably ≥0.3, more preferably ≥0.5.

The electron-withdrawing group of the present invention has a Hammett's substituent constant value of ≥0.05, preferably ≥0.3, more preferably ≥0.5, and thus has a strong electron-withdrawing ability, which can significantly reduce the LUMO energy level of the compound and improve charge mobility.

It should be noted that the Hammett's substituent constant value includes Hammett's substituent para-position constant and/or meta-position constant. As long as one of the para-constant and the meta-constant is equal to or greater than 0.05, the group is preferred for the present invention.

According to an embodiment of the present invention, the electron-withdrawing group is selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxy group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms, and an arylsilyl group having 6 to 20 carbon atoms, which is substituted with one or more of halogen, nitroso, nitro, acyl, carbonyl, a carboxylic acid group, an ester group, cyano, isocyano, SCN, OCN, $SF_5$, boranyl, sulfinyl, sulfonyl, phosphoroso, an aza-aromatic ring group, and combinations thereof.

According to an embodiment of the present invention, the electron-withdrawing group is selected from the group consisting of F, $CF_3$, $OCF_3$, $SF_5$, $SO_2CF_3$, cyano, isocyano, SCN, OCN, pyrimidinyl, triazinyl, and combinations thereof.

According to an embodiment of the present invention, each of X and Y is independently selected from the group consisting of:

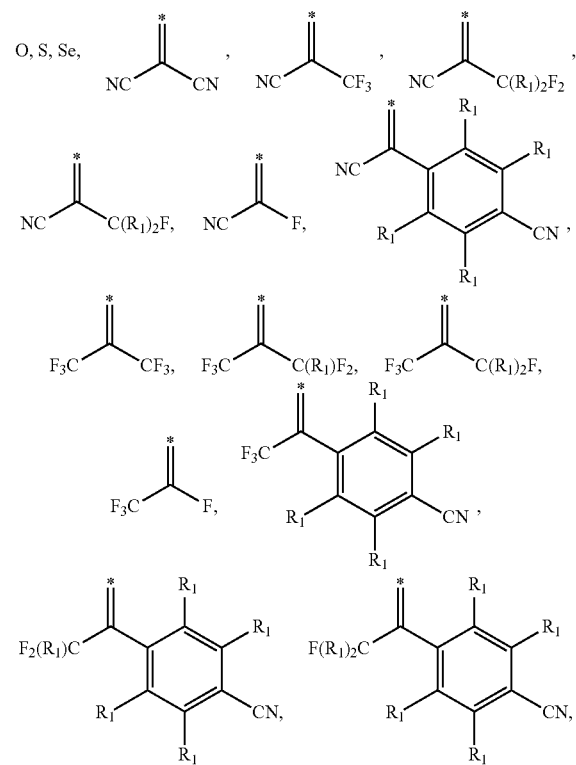

-continued

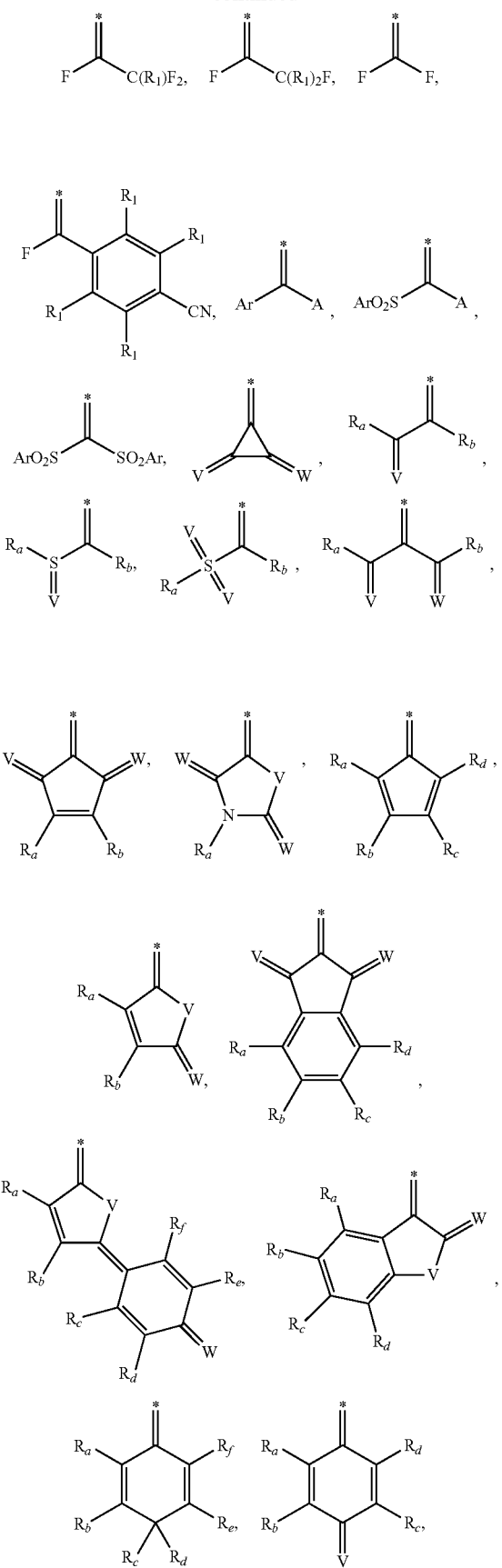

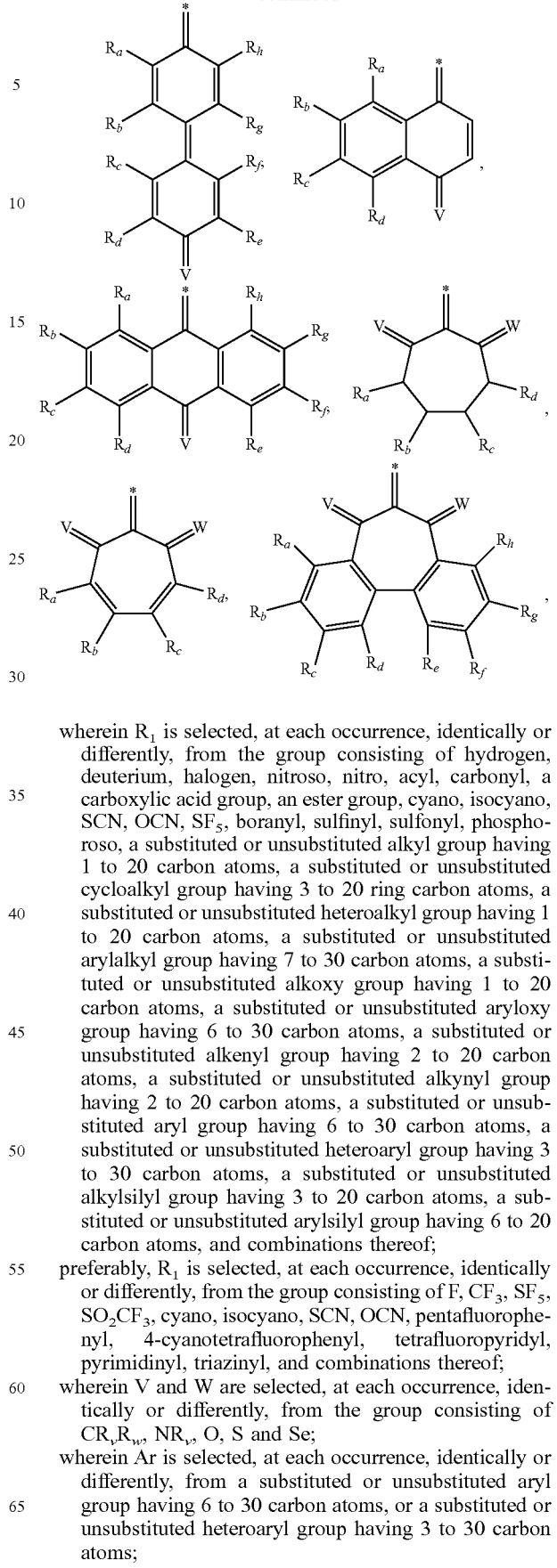

wherein $R_1$ is selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

preferably, $R_1$ is selected, at each occurrence, identically or differently, from the group consisting of F, $CF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof;

wherein V and W are selected, at each occurrence, identically or differently, from the group consisting of $CR_vR_w$, $NR_v$, O, S and Se;

wherein Ar is selected, at each occurrence, identically or differently, from a substituted or unsubstituted aryl group having 6 to 30 carbon atoms, or a substituted or unsubstituted heteroaryl group having 3 to 30 carbon atoms;

wherein A, $R_a$, $R_b$, $R_c$, $R_d$, $R_e$, $R_f$, $R_g$, $R_h$, $R_v$ and $R_w$ are selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein A is a group having at least one electron-withdrawing group, and for any one of the structures, when one or more of $R_a$, $R_b$, $R_c$, $R_d$, $R_e$, $R_f$, $R_g$, $R_h$, $R_v$ and $R_w$ is(are) present, at least one of them is a group having at least one electron-withdrawing group; preferably, the group having at least one electron-withdrawing group is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

In the present embodiment, "*" indicates the position at which the X and Y groups are attached to the dehydrobenzodioxazole ring, the dehydrobenzodithiazole ring or the dehydrobenzodiselenazole ring in Formula 1'.

According to an embodiment of the present invention, each of X and Y is independently selected from the group consisting of:

O, S, Se,

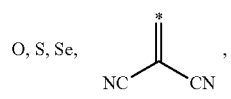

A1

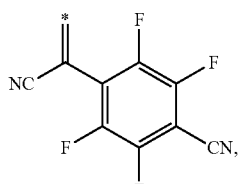

A2

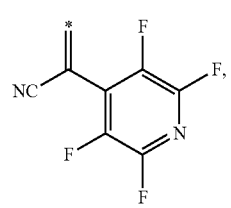

A3

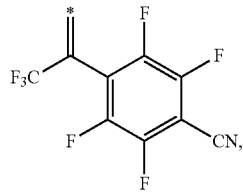

A4

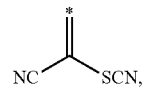

A5

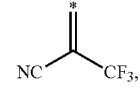

A6

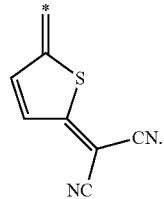

A7

In the present embodiment, "*" indicates the position at which the X and Y groups are attached to the dehydrobenzodioxazole ring, the dehydrobenzodithiazole ring or the dehydrobenzodiselenazole ring in Formula 1'.

According to an embodiment of the present invention, each of R groups is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, an unsubstituted alkyl group having 1 to 20 carbon atoms, an unsubstituted cycloalkyl group having 3 to 20 ring carbon atoms, an unsubstituted alkoxy group having 1 to 20 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms, and a heteroaryl group having 3 to 30 carbon atoms which are substituted with one or more groups selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, and combinations thereof.

According to an embodiment of the present invention, each of R groups is independently selected from the group consisting of hydrogen, deuterium, methyl, isopropyl, $NO_2$, $SO_2CH_3$, $SCF_3$, $C_2F_5$, $OC_2F_5$, $OCH_3$, p-methylphenyl, diphenylmethylsilyl, phenyl, methoxyphenyl, 2,6-diisopropylphenyl, biphenyl, polyfluorophenyl, difluoropyridyl, nitrophenyl, dimethylthiazolyl, vinyl substituted with one or more of CN and $CF_3$, ethynyl substituted with one of CN and $CF_3$, dimethylphosphoroso, diphenylphosphoroso, F, $CF_3$, $OCF_3$, $SF_5$, $SO_2CF_3$, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and CF$_3$, tetrafluoropyridyl, pyrimidinyl, triazinyl, diphenylboranyl, oxaboraanthryl, and combinations thereof.
According to an embodiment of the present invention, wherein X and Y are
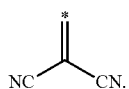
According to an embodiment of the present invention, wherein each of R groups is independently selected from the group consisting of:
B1
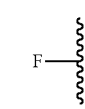
B2
B3
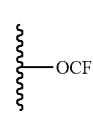
B4
B5
B6
B7
B8
B9
B10
B11
-continued
B12
B13
B14
B15
B16
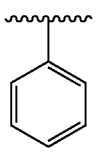
B17
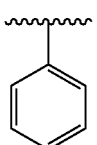
B18
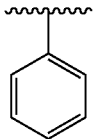
B19
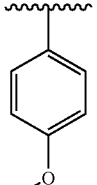
B20
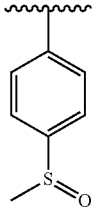

| | |
|---|---|
| 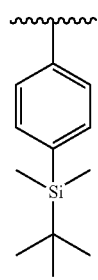 | B21 |
| 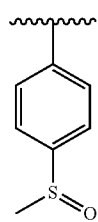 | B22 |
| 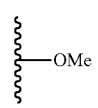 | B23 |
| 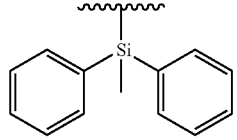 | B24 |
| 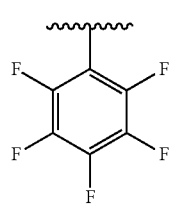 | B25 |
| 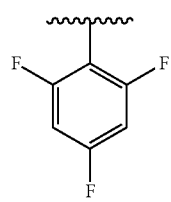 | B26 |
| 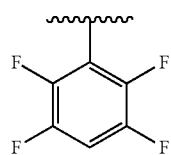 | B27 |
| 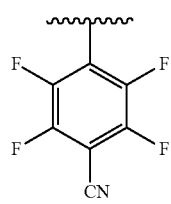 | B28 |
| 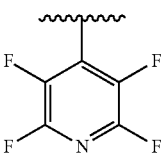 | B29 |
| 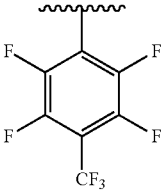 | B30 |
| 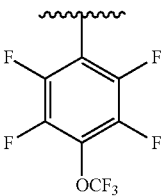 | B31 |
| 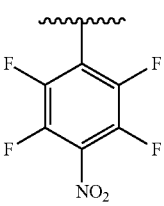 | B32 |
| 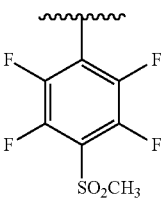 | B33 |
| 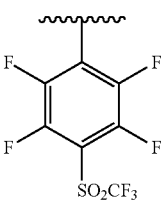 | B34 |
| 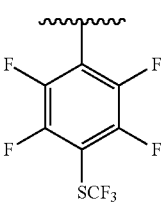 | B35 |
| 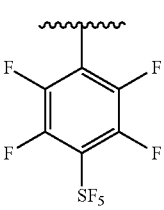 | B36 |

-continued
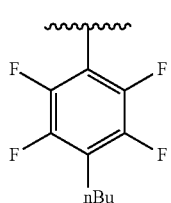 B37
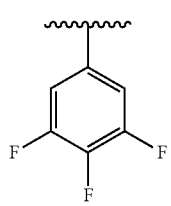 B38
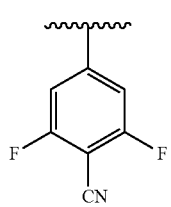 B39
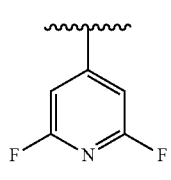 B40
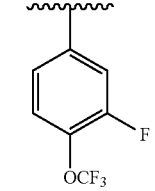 B41
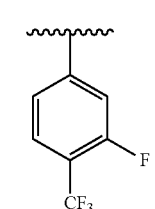 B42
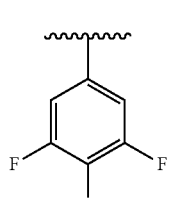 B43
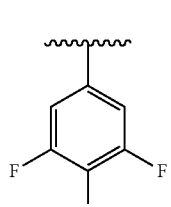 B44
-continued
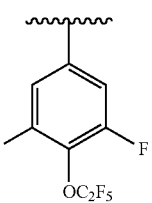 B45
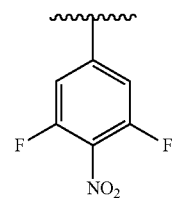 B46
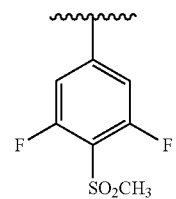 B47
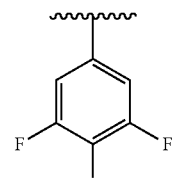 B48
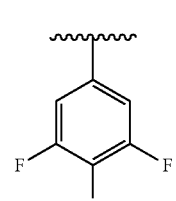 B49
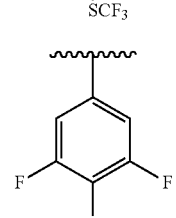 B50
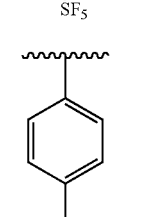 B51
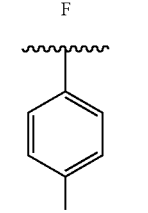 B52

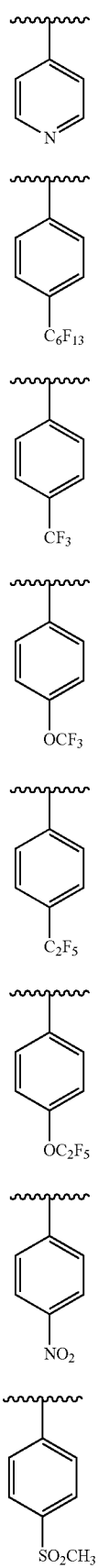
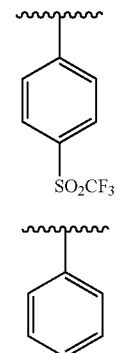
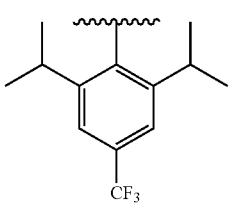
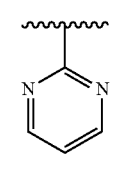
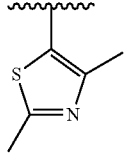
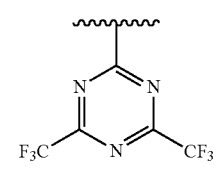
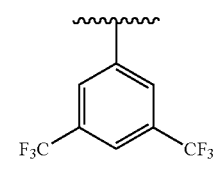
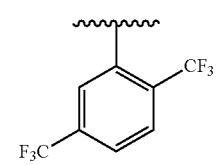

| | |
|---|---|
| 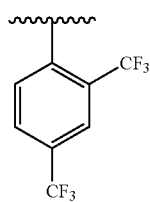 B70 | 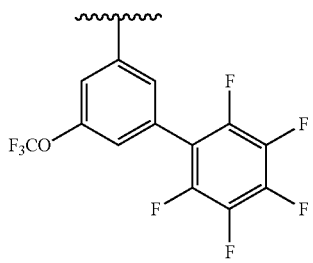 B76 |
| 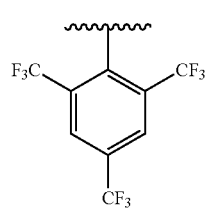 B71 | 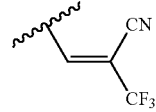 B77 |
| 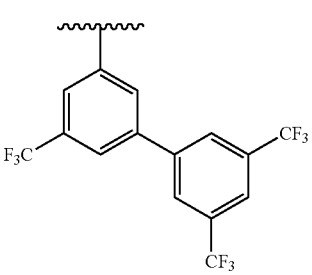 B72 | 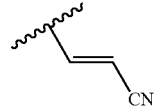 B78 |
| | 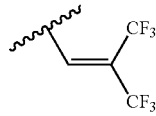 B79 |
| 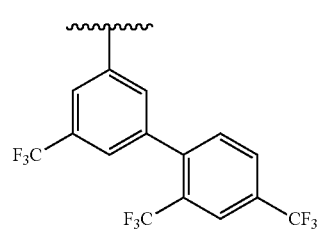 B73 | 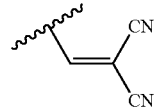 B80 |
| | 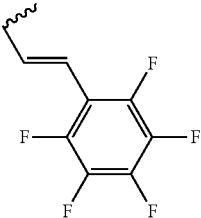 B81 |
| 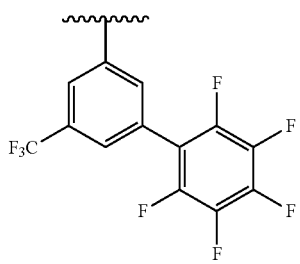 B74 | 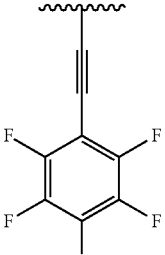 B82 |
| 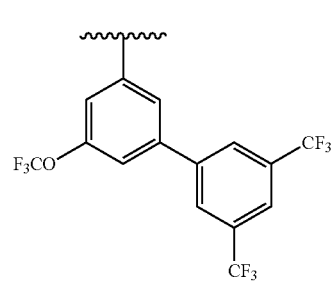 B75 | B83 |
| | 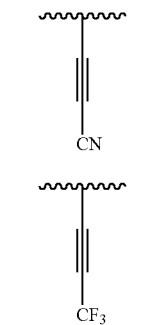 B84 |

-continued

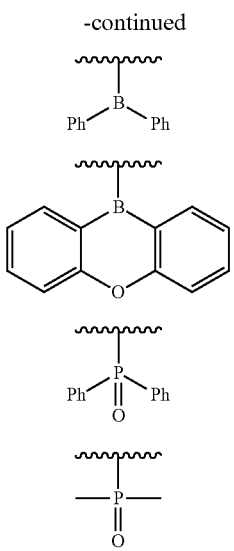

B85

B86

B87

B88

In the present embodiment, " ~~~ " indicates the position at which the R group is attached to the dehydrobenzodioxazole ring, the dehydrobenzodithiazole ring or the dehydrobenzodiselenazole ring in Formula 1'.

According to an embodiment of the present invention, the two R groups in Formula 1' are the same.

According to an embodiment of the present invention, the compound is selected from the group consisting of Compound 1 to Compound 1356. The specific structure of Compound 1 to Compound 1356 is set forth in claim 11.

According to an embodiment of the present invention, an electroluminescent device is also disclosed, which comprises:
  an anode,
  a cathode, and
  an organic layer disposed between the anode and the cathode, wherein the organic layer comprises a compound having Formula 1:

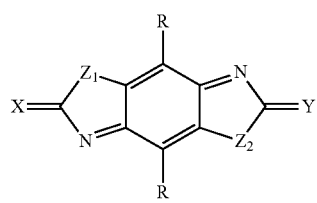

Formula 1' wherein each of X and Y is independently selected from the group consisting of CR"R''', NR', O, S and Se;
wherein each of $Z_1$ and $Z_2$ is independently selected from the group consisting of O, S and Se;
wherein each of R, R', R" and R''' is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
wherein each R may be same or different, and at least one of R, R', R" and R''' is a group having at least one electron-withdrawing group; and
wherein adjacent substituents can be optionally joined to form a ring or a fused structure.

According to an embodiment of the present invention, in the device, the organic layer is a hole injection layer, and the hole injection layer is formed from the compound alone.

According to an embodiment of the present invention, in the device, the organic layer is a hole injection layer, and the hole injection layer is formed from the compound comprising a dopant which comprises at least one hole transporting material; wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex, and wherein the molar doping ratio of the compound to the hole transporting material is from 10000:1 to 1:10000.

According to an embodiment of the present invention, in the hole injection layer, the molar doping ratio of the compound to the hole transporting material is from 10:1 to 1:100.

According to an embodiment of the present invention, the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer; wherein the organic layer comprising the compound having Formula 1' is the p-type charge generation layer; preferably, the p-type charge generation layer further comprises at least one hole transporting material and is formed by doping the compound with at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex, wherein the molar doping ratio of the compound to the hole transporting material is from 10000:1 to 1:10000.

According to an embodiment of the present invention, in the p-type charge generation layer, the molar doping ratio of the compound to the hole transporting material is from 10:1 to 1:100.

According to an embodiment of the present invention, the charge generation layer further includes a buffer layer disposed between the p-type charge generation layer and the n-type charge generation layer, wherein the buffer layer comprises the compound.

According to another embodiment of the present invention, a compound formulation is also disclosed, which comprises a compound represented by Formula 1. The specific structure of the compound is shown in any of the foregoing embodiments.

According to an embodiment of the present invention, a compound having Formula 1 is disclosed:

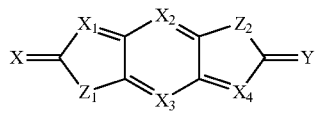

Formula 1 wherein $X_1$, $X_2$, $X_3$, and $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, Se, S=O, and $SO_2$;

X and Y are each independently selected from the group consisting of S, Se, NR', or CR"R'";

R, R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

In one embodiment of the present invention, wherein $Z_1$ and $Z_2$ are S.

In one embodiment of the present invention, wherein $X_2$ and $X_3$ are N.

In one embodiment of the present invention, wherein $X_2$ and $X_3$ are each independently selected from CR, each R may be same or different, and at least one of R comprises at least one electron withdrawing group.

In one embodiment of the present invention, wherein $X_2$ and $X_3$ are each independently selected from CR, each R may be same or different, and each R comprises at least one electron withdrawing group.

In one embodiment of the present invention, wherein R are selected from the group consisting of fluorine, chlorine, trifluoromethyl, trifluoromethoxyl, pentafluoroethyl, pentafluoroethoxyl, cyano, nitro group, methyl sulfonyl, trifluoromethyl sulfonyl, trifluoromethylthio, pentafluorosulfanyl, pyridyl, 3-fluorophenyl, 4-fluorophenyl, 3-cyanophenyl, 4-cyanophenyl, 4-trifluoromethylphenyl, 3-trifluoromethoxylphenyl, 4-trifluoromethoxylphenyl, 4-pentafluoroethylphenyl, 4-pentafluoroethoxylphenyl, 4-nitrophenyl, 4-methyl sulfonyl phenyl, 4-trifluoromethyl sulfonyl phenyl, 3-trifluoromethylsulfanylphenyl, 4-trifluoromethylsulfanylphenyl, 4-pentafluorosulfanylphenyl, pyrimidyl, 2,6-dimethyl-1,3,5-triazine, and combinations thereof.

In one embodiment of the present invention, wherein X and Y are each independently CR"R'".

In one embodiment of the present invention, wherein R', R", and R'" are each independently selected from the group consisting of trifluoromethyl, cyano, pentafluorophenyl, 4-cyano-2,3,5,6-tetrafluorophenyl, and pyridyl.

In one embodiment of the present invention, wherein the compound has the formula:

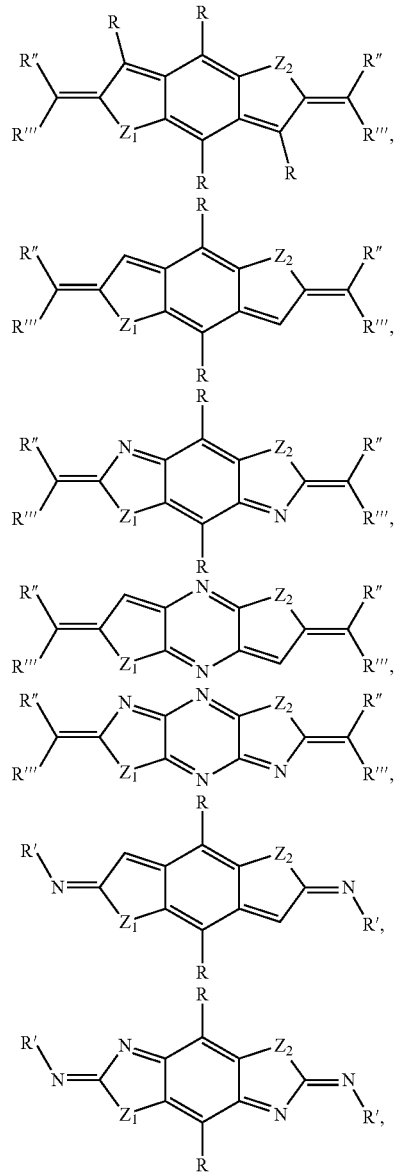

-continued

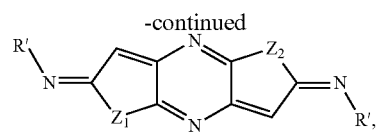

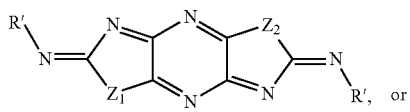

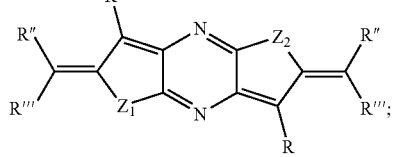

In each formula above, each R can be same or different, at least one of R in each formula comprises at least one electron withdrawing group;

$Z_1$ and $Z_2$ are each independently selected from the group consisting of O, S, Se, S=O, and $SO_2$;

R, R', R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfonyl group, a sulfonyl group, a phosphino group, and combinations thereof;

Any adjacent substitution can be optionally joined to form a ring or fused structure.

In one embodiment of the present invention, wherein the compound is selected from the group consisting of:

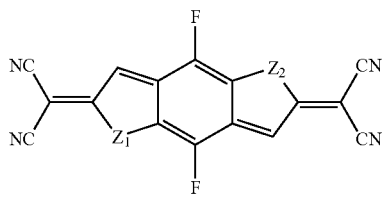

$Z_1 = Z_2 = $ O Compound O-1
$Z_1 = Z_2 = $ S Compound S-1
$Z_1 = Z_2 = $ Se Compound Se-1

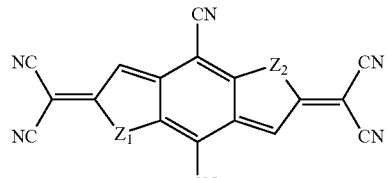

$Z_1 = Z_2 = $ O Compound O-2
$Z_1 = Z_2 = $ S Compound S-2
$Z_1 = Z_2 = $ Se Compound Se-2

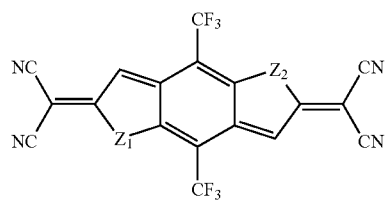

$Z_1 = Z_2 = $ O Compound O-3
$Z_1 = Z_2 = $ S Compound S-3
$Z_1 = Z_2 = $ Se Compound Se-3

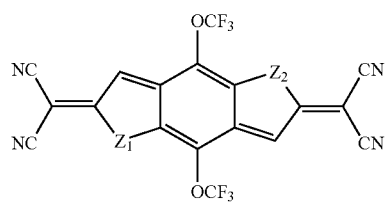

$Z_1 = Z_2 = $ O Compound O-4
$Z_1 = Z_2 = $ S Compound S-4
$Z_1 = Z_2 = $ Se Compound Se-4

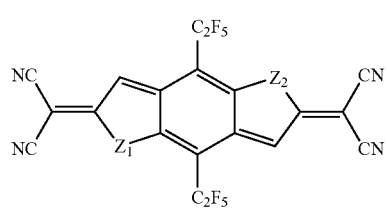

$Z_1 = Z_2 = $ O Compound O-5
$Z_1 = Z_2 = $ S Compound S-5
$Z_1 = Z_2 = $ Se Compound Se-5

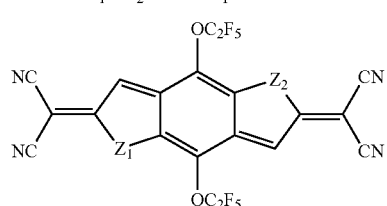

$Z_1 = Z_2 = $ O Compound O-6
$Z_1 = Z_2 = $ S Compound S-6
$Z_1 = Z_2 = $ Se Compound Se-6

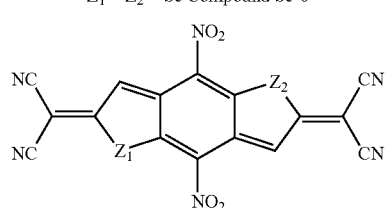

$Z_1 = Z_2 = $ O Compound O-7
$Z_1 = Z_2 = $ S Compound S-7
$Z_1 = Z_2 = $ Se Compound Se-7

-continued

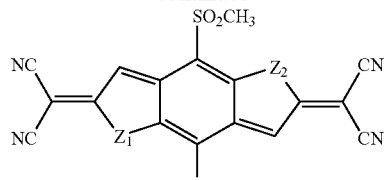

Z₁ = Z₂ = O Compound O-8
Z₁ = Z₂ = S Compound S-8
Z₁ = Z₂ = Se Compound Se-8

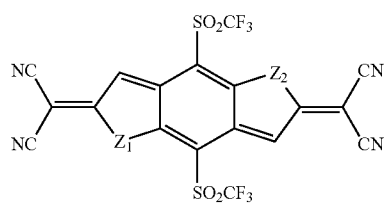

Z₁ = Z₂ = O Compound O-9
Z₁ = Z₂ = S Compound S-9
Z₁ = Z₂ = Se Compound Se-9

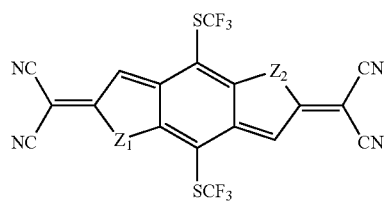

Z₁ = Z₂ = O Compound O-10
Z₁ = Z₂ = S Compound S-10
Z₁ = Z₂ = Se Compound Se-10

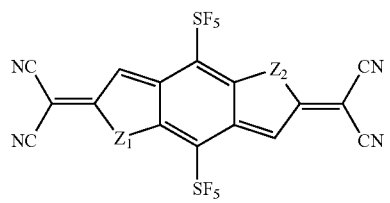

Z₁ = Z₂ = O Compound O-11
Z₁ = Z₂ = S Compound S-11
Z₁ = Z₂ = Se Compound Se-11

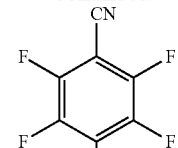

Z₁ = Z₂ = O Compound O-12
Z₁ = Z₂ = S Compound S-12
Z₁ = Z₂ = Se Compound Se-12

-continued

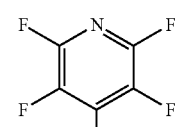

Z₁ = Z₂ = O Compound O-13
Z₁ = Z₂ = S Compound S-13
Z₁ = Z₂ = Se Compound Se-13

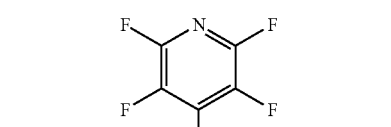

Z₁ = Z₂ = O Compound O-14
Z₁ = Z₂ = S Compound S-14
Z₁ = Z₂ = Se Compound Se-14

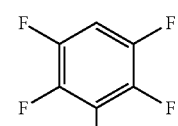

Z₁ = Z₂ = O Compound O-15
Z₁ = Z₂ = S Compound S-15
Z₁ = Z₂ = Se Compound Se-15

-continued

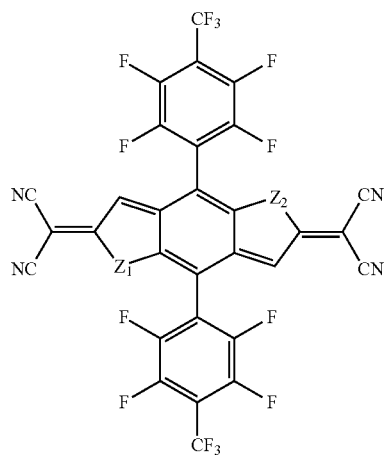

Z₁ = Z₂ = O Compound O-16
Z₁ = Z₂ = S Compound S-16
Z₁ = Z₂ = Se Compound Se-16

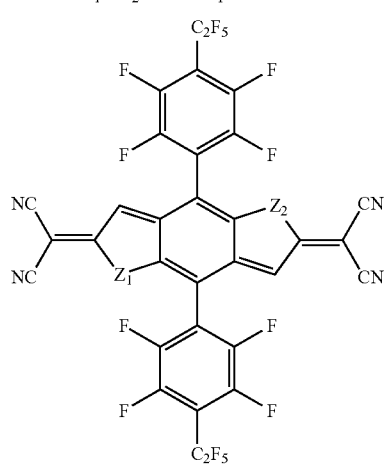

Z₁ = Z₂ = O Compound O-17
Z₁ = Z₂ = S Compound S-17
Z₁ = Z₂ = Se Compound Se-17

-continued

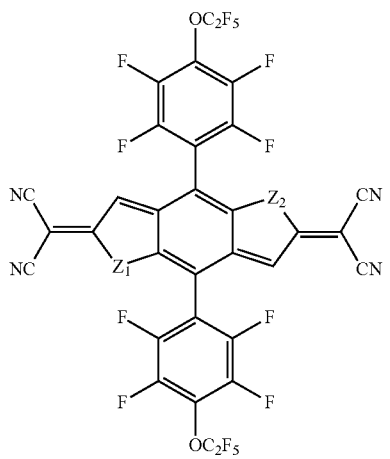

Z₁ = Z₂ = O Compound O-19
Z₁ = Z₂ = S Compound S-19
Z₁ = Z₂ = Se Compound Se-19

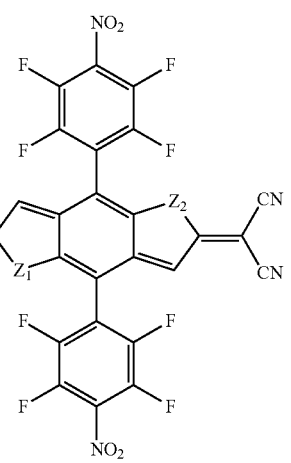

Z₁ = Z₂ = O Compound O-20
Z₁ = Z₂ = S Compound S-20
Z₁ = Z₂ = Se Compound Se-20

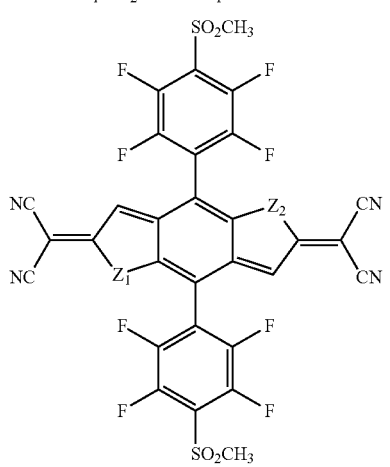

Z₁ = Z₂ = O Compound O-21
Z₁ = Z₂ = S Compound S-21
Z₁ = Z₂ = Se Compound Se-21

Z₁ = Z₂ = O Compound O-18
Z₁ = Z₂ = S Compound S-18
Z₁ = Z₂ = Se Compound Se-18

-continued

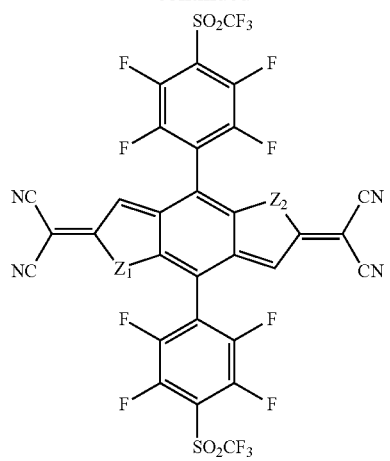

$Z_1 = Z_2 = $ O Compound O-22
$Z_1 = Z_2 = $ S Compound S-22
$Z_1 = Z_2 = $ Se Compound Se-22

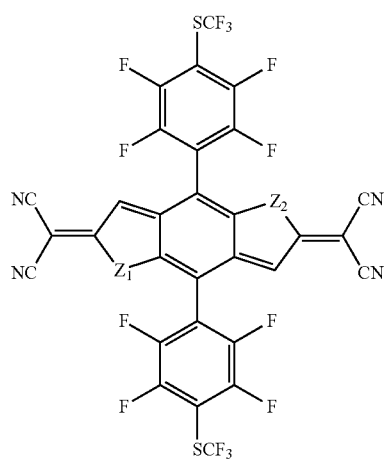

$Z_1 = Z_2 = $ O Compound O-23
$Z_1 = Z_2 = $ S Compound S-23
$Z_1 = Z_2 = $ Se Compound Se-23

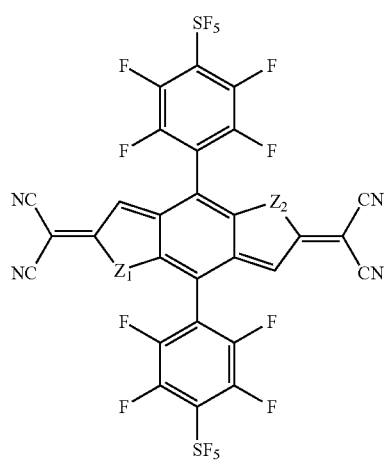

$Z_1 = Z_2 = $ O Compound O-24
$Z_1 = Z_2 = $ S Compound S-24
$Z_1 = Z_2 = $ Se Compound Se-24

-continued

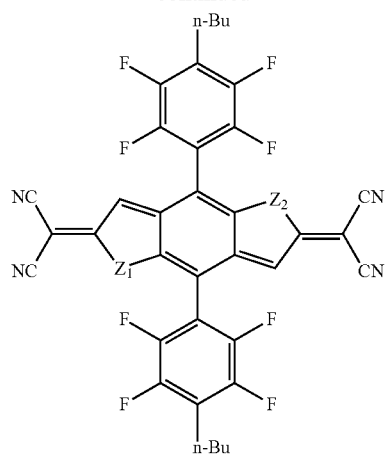

$Z_1 = Z_2 = $ O Compound O-25
$Z_1 = Z_2 = $ S Compound S-25
$Z_1 = Z_2 = $ Se Compound Se-25

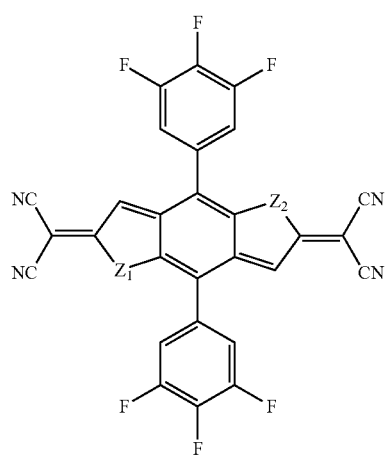

$Z_1 = Z_2 = $ O Compound O-26
$Z_1 = Z_2 = $ S Compound S-26
$Z_1 = Z_2 = $ Se Compound Se-26

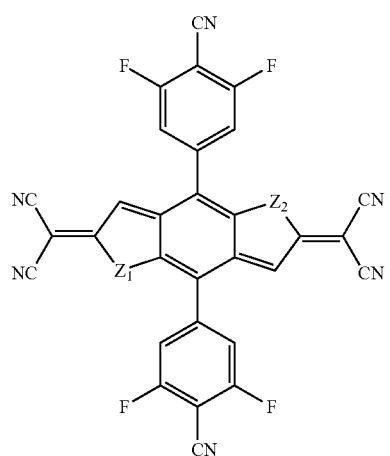

$Z_1 = Z_2 = $ O Compound O-27
$Z_1 = Z_2 = $ S Compound S-27
$Z_1 = Z_2 = $ Se Compound Se-27

-continued

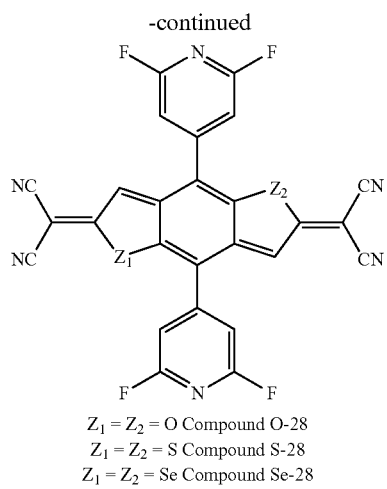

Z₁ = Z₂ = O Compound O-28
Z₁ = Z₂ = S Compound S-28
Z₁ = Z₂ = Se Compound Se-28

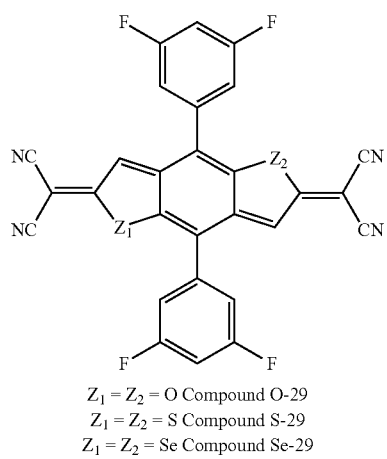

Z₁ = Z₂ = O Compound O-29
Z₁ = Z₂ = S Compound S-29
Z₁ = Z₂ = Se Compound Se-29

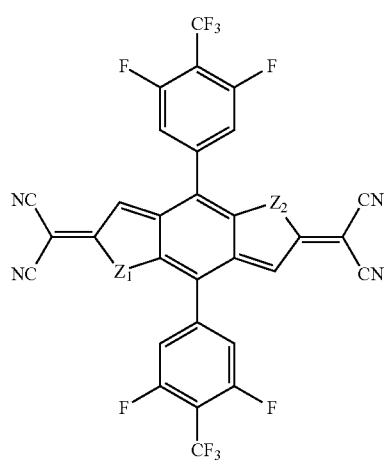

Z₁ = Z₂ = O Compound O-30
Z₁ = Z₂ = S Compound S-30
Z₁ = Z₂ = Se Compound Se-30

-continued

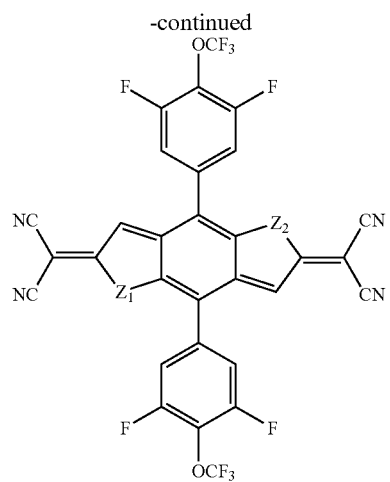

Z₁ = Z₂ = O Compound O-31
Z₁ = Z₂ = S Compound S-31
Z₁ = Z₂ = Se Compound Se-31

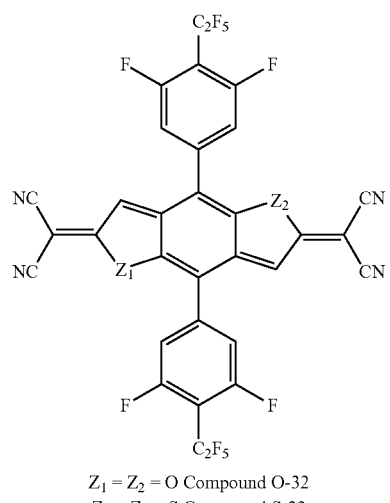

Z₁ = Z₂ = O Compound O-32
Z₁ = Z₂ = S Compound S-32
Z₁ = Z₂ = Se Compound Se-32

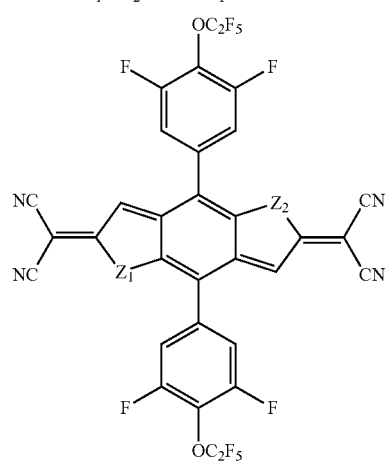

Z₁ = Z₂ = O Compound O-33
Z₁ = Z₂ = S Compound S-33
Z₁ = Z₂ = Se Compound Se-33

-continued

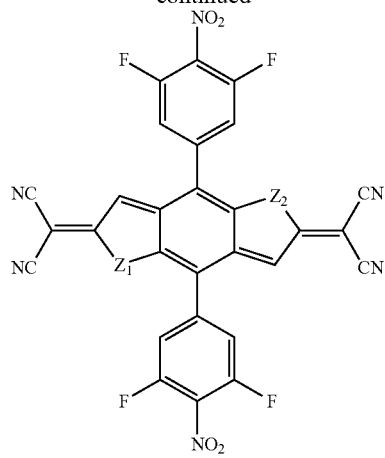

Z₁ = Z₂ = O Compound O-34
Z₁ = Z₂ = S Compound S-34
Z₁ = Z₂ = Se Compound Se-34

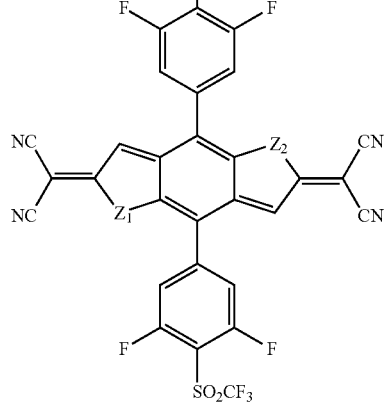

Z₁ = Z₂ = O Compound O-35
Z₁ = Z₂ = S Compound S-35
Z₁ = Z₂ = Se Compound Se-35

Z₁ = Z₂ = O Compound O-36
Z₁ = Z₂ = S Compound S-36
Z₁ = Z₂ = Se Compound Se-36

-continued

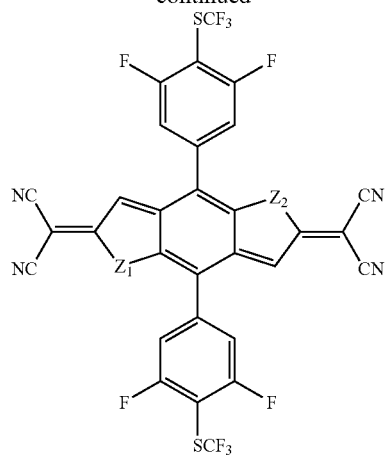

Z₁ = Z₂ = O Compound O-37
Z₁ = Z₂ = S Compound S-37
Z₁ = Z₂ = Se Compound Se-37

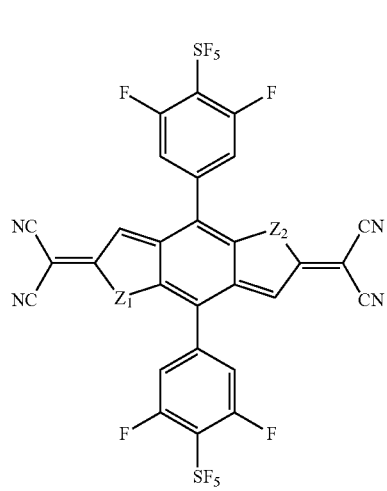

Z₁ = Z₂ = O Compound O-38
Z₁ = Z₂ = S Compound S-38
Z₁ = Z₂ = Se Compound Se-38

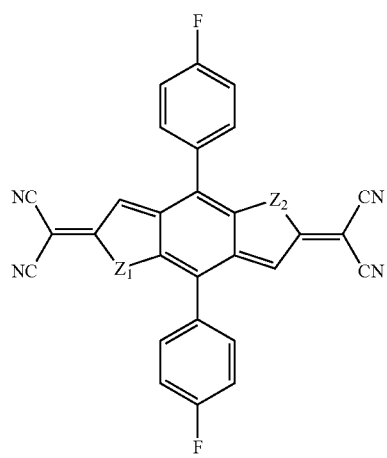

Z₁ = Z₂ = O Compound O-39
Z₁ = Z₂ = S Compound S-39
Z₁ = Z₂ = Se Compound Se-39

-continued

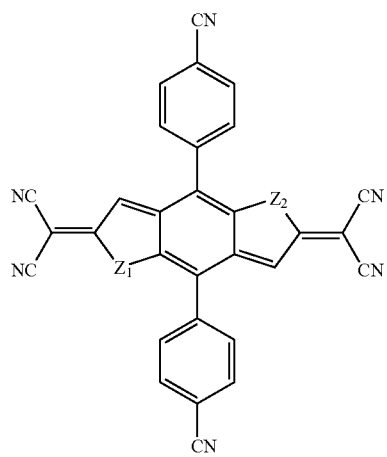

Z₁ = Z₂ = O Compound O-40
Z₁ = Z₂ = S Compound S-40
Z₁ = Z₂ = Se Compound Se-40

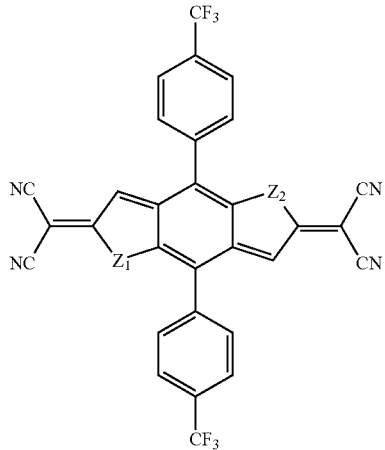

Z₁ = Z₂ = O Compound O-43
Z₁ = Z₂ = S Compound S-43
Z₁ = Z₂ = Se Compound Se-43

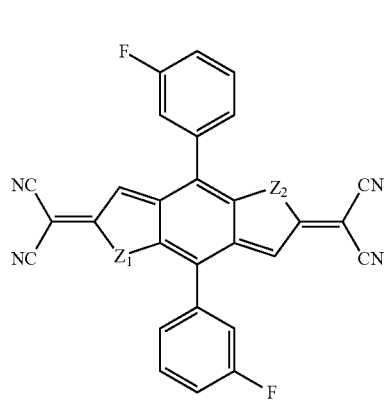

Z₁ = Z₂ = O Compound O-41
Z₁ = Z₂ = S Compound S-41
Z₁ = Z₂ = Se Compound Se-41

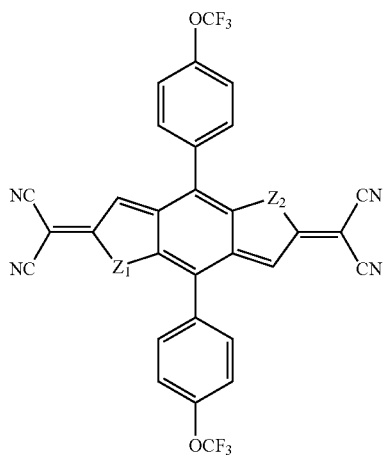

Z₁ = Z₂ = O Compound O-44
Z₁ = Z₂ = S Compound S-44
Z₁ = Z₂ = Se Compound Se-44

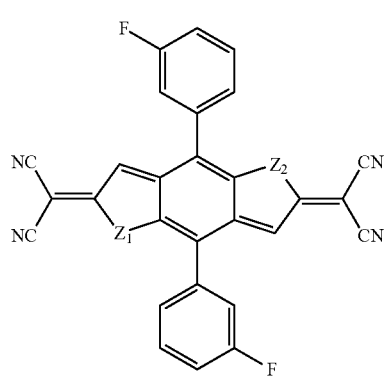

Z₁ = Z₂ = O Compound O-42
Z₁ = Z₂ = S Compound S-42
Z₁ = Z₂ = Se Compound Se-42

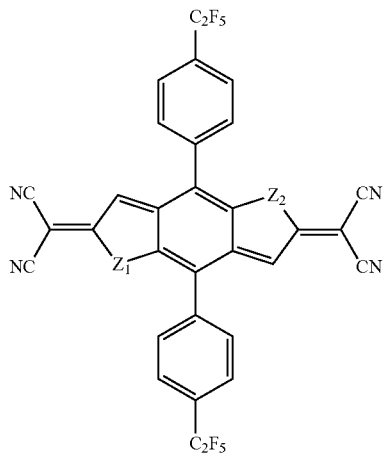

Z₁ = Z₂ = O Compound O-45
Z₁ = Z₂ = S Compound S-45
Z₁ = Z₂ = Se Compound Se-45

-continued

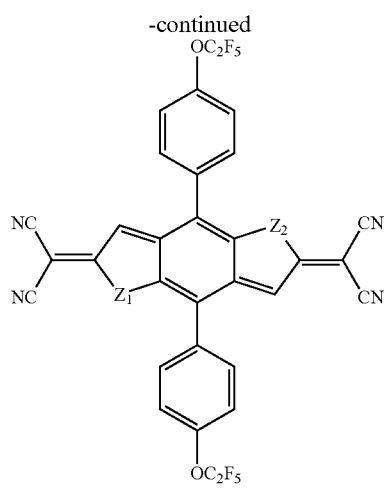

Z₁ = Z₂ = O Compound O-46
Z₁ = Z₂ = S Compound S-46
Z₁ = Z₂ = Se Compound Se-46

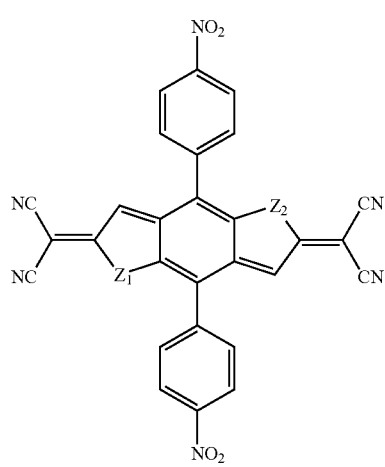

Z₁ = Z₂ = O Compound O-47
Z₁ = Z₂ = S Compound S-47
Z₁ = Z₂ = Se Compound Se-47

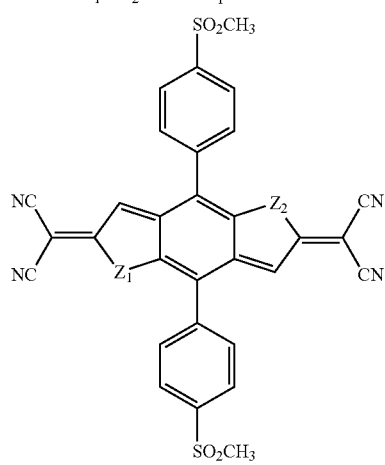

Z₁ = Z₂ = O Compound O-48
Z₁ = Z₂ = S Compound S-48
Z₁ = Z₂ = Se Compound Se-48

-continued

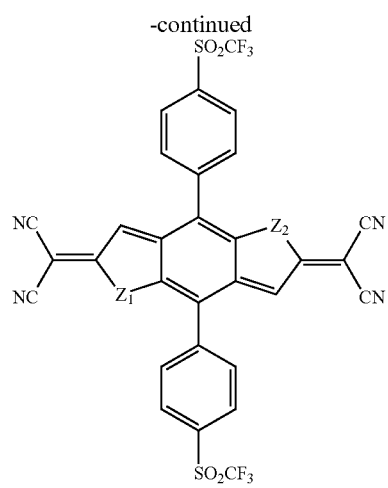

Z₁ = Z₂ = O Compound O-49
Z₁ = Z₂ = S Compound S-49
Z₁ = Z₂ = Se Compound Se-49

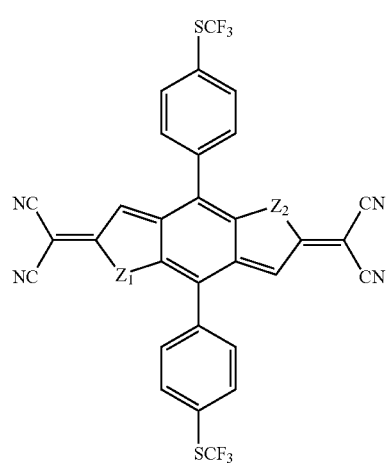

Z₁ = Z₂ = O Compound O-50
Z₁ = Z₂ = S Compound S-50
Z₁ = Z₂ = Se Compound Se-50

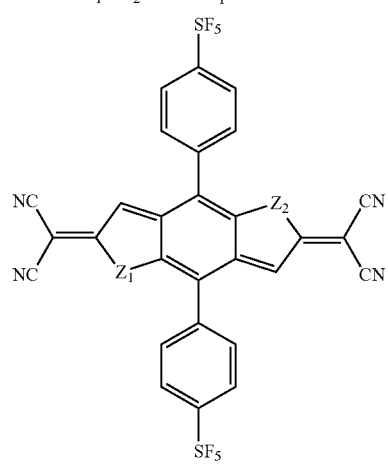

Z₁ = Z₂ = O Compound O-51
Z₁ = Z₂ = S Compound S-51
Z₁ = Z₂ = Se Compound Se-51

-continued

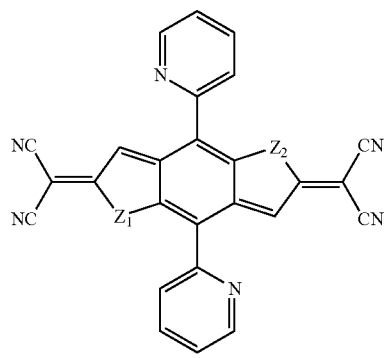

Z₁ = Z₂ = O Compound O-52
Z₁ = Z₂ = S Compound S-52
Z₁ = Z₂ = Se Compound Se-52

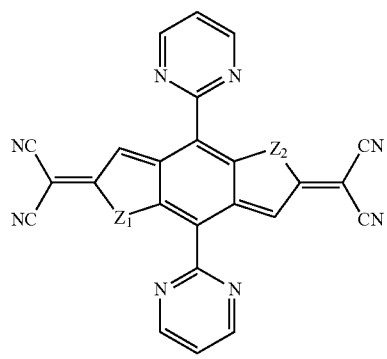

Z₁ = Z₂ = O Compound O-53
Z₁ = Z₂ = S Compound S-53
Z₁ = Z₂ = Se Compound Se-53

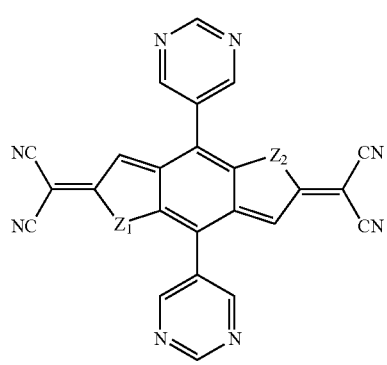

Z₁ = Z₂ = O Compound O-54
Z₁ = Z₂ = S Compound S-54
Z₁ = Z₂ = Se Compound Se-54

-continued

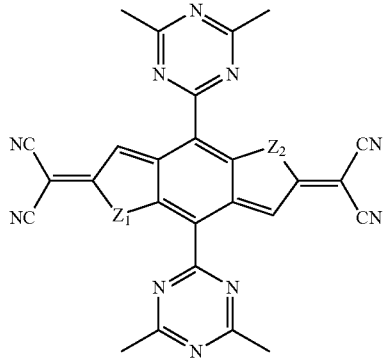

Z₁ = Z₂ = O Compound O-55
Z₁ = Z₂ = S Compound S-55
Z₁ = Z₂ = Se Compound Se-55

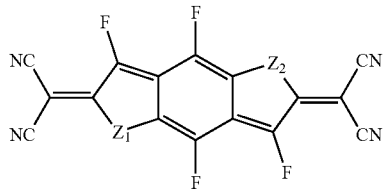

Z₁ = Z₂ = O Compound O-56
Z₁ = Z₂ = S Compound S-56
Z₁ = Z₂ = Se Compound Se-56

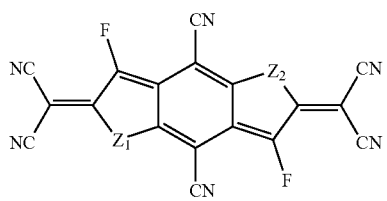

Z₁ = Z₂ = O Compound O-57
Z₁ = Z₂ = S Compound S-57
Z₁ = Z₂ = Se Compound Se-57

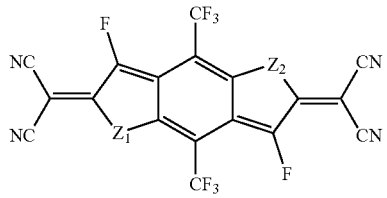

Z₁ = Z₂ = O Compound O-58
Z₁ = Z₂ = S Compound S-58
Z₁ = Z₂ = Se Compound Se-58

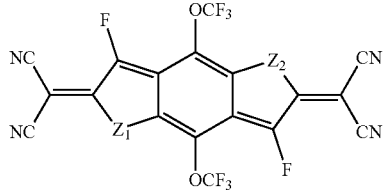

Z₁ = Z₂ = O Compound O-59
Z₁ = Z₂ = S Compound S-59
Z₁ = Z₂ = Se Compound Se-59

53
-continued


$Z_1 = Z_2 = O$ Compound O-60
$Z_1 = Z_2 = S$ Compound S-60
$Z_1 = Z_2 = Se$ Compound Se-60

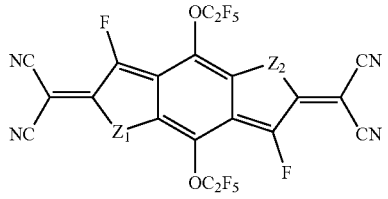

$Z_1 = Z_2 = O$ Compound O-61
$Z_1 = Z_2 = S$ Compound S-61
$Z_1 = Z_2 = Se$ Compound Se-61

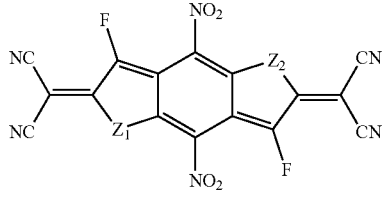

$Z_1 = Z_2 = O$ Compound O-62
$Z_1 = Z_2 = S$ Compound S-62
$Z_1 = Z_2 = Se$ Compound Se-62

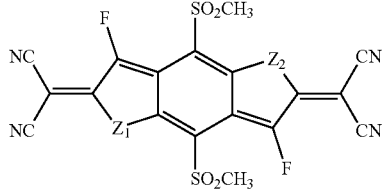

$Z_1 = Z_2 = O$ Compound O-63
$Z_1 = Z_2 = S$ Compound S-63
$Z_1 = Z_2 = Se$ Compound Se-63

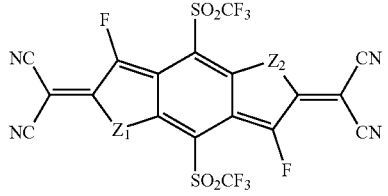

$Z_1 = Z_2 = O$ Compound O-64
$Z_1 = Z_2 = S$ Compound S-64
$Z_1 = Z_2 = Se$ Compound Se-64

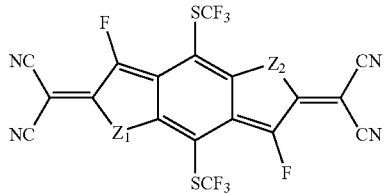

$Z_1 = Z_2 = O$ Compound O-65
$Z_1 = Z_2 = S$ Compound S-65
$Z_1 = Z_2 = Se$ Compound Se-65

54
-continued

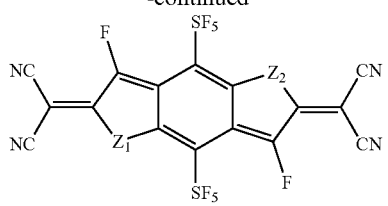

$Z_1 = Z_2 = O$ Compound O-66
$Z_1 = Z_2 = S$ Compound S-66
$Z_1 = Z_2 = Se$ Compound Se-66

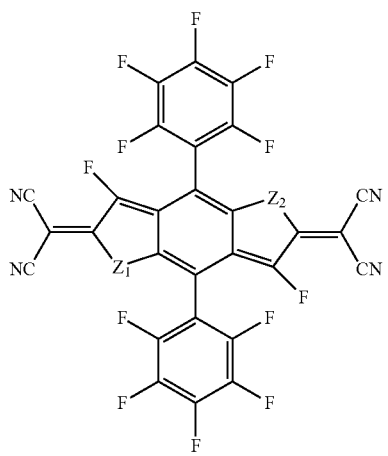

$Z_1 = Z_2 = O$ Compound O-67
$Z_1 = Z_2 = S$ Compound S-67
$Z_1 = Z_2 = Se$ Compound Se-67

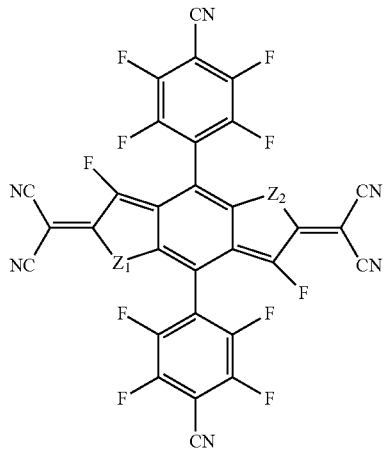

$Z_1 = Z_2 = O$ Compound O-68
$Z_1 = Z_2 = S$ Compound S-68
$Z_1 = Z_2 = Se$ Compound Se-68

-continued

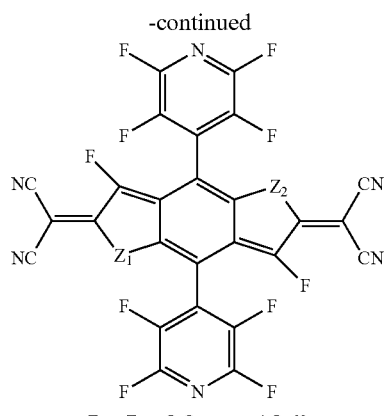

$Z_1 = Z_2 = O$ Compound O-69
$Z_1 = Z_2 = S$ Compound S-69
$Z_1 = Z_2 = Se$ Compound Se-69

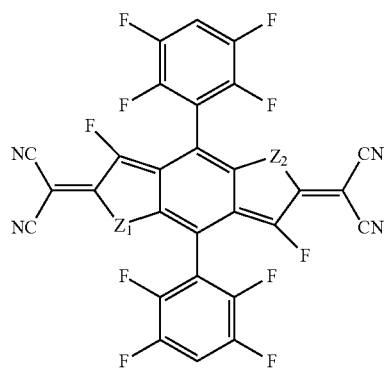

$Z_1 = Z_2 = O$ Compound O-70
$Z_1 = Z_2 = S$ Compound S-70
$Z_1 = Z_2 = Se$ Compound Se-70

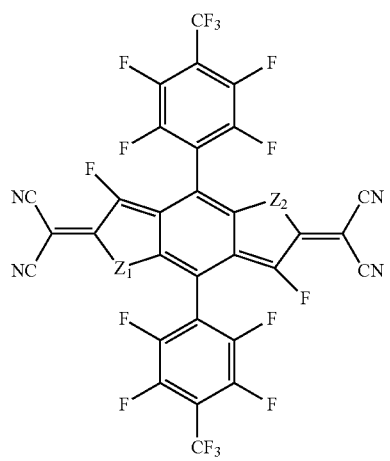

$Z_1 = Z_2 = O$ Compound O-71
$Z_1 = Z_2 = S$ Compound S-71
$Z_1 = Z_2 = Se$ Compound Se-71

-continued

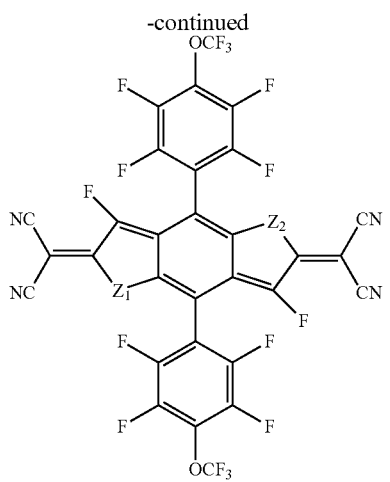

$Z_1 = Z_2 = O$ Compound O-72
$Z_1 = Z_2 = S$ Compound S-72
$Z_1 = Z_2 = Se$ Compound Se-72

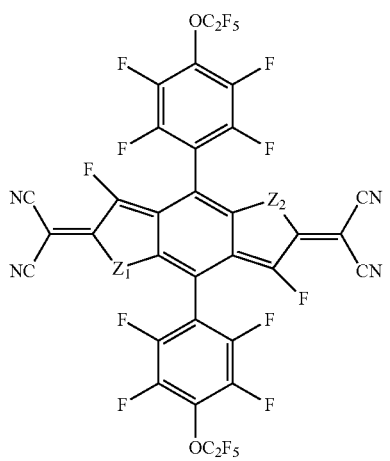

$Z_1 = Z_2 = O$ Compound O-73
$Z_1 = Z_2 = S$ Compound S-73
$Z_1 = Z_2 = Se$ Compound Se-73

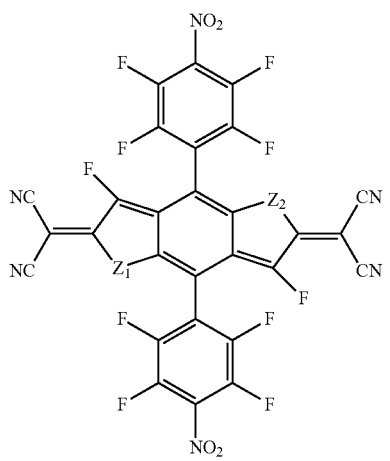

$Z_1 = Z_2 = O$ Compound O-74
$Z_1 = Z_2 = S$ Compound S-74
$Z_1 = Z_2 = Se$ Compound Se-74

-continued

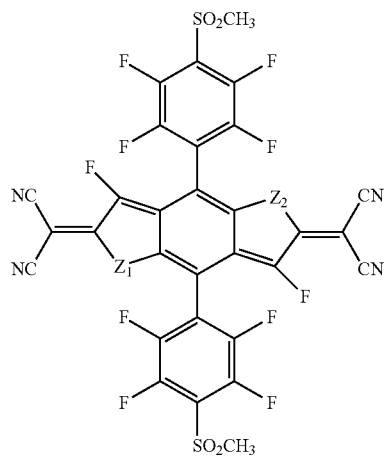

$Z_1 = Z_2 = $ O Compound O-75
$Z_1 = Z_2 = $ S Compound S-75
$Z_1 = Z_2 = $ Se Compound Se-75

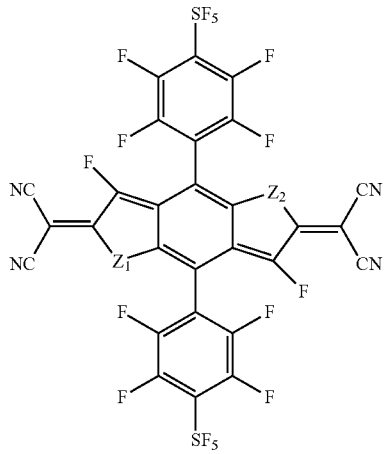

$Z_1 = Z_2 = $ O Compound O-78
$Z_1 = Z_2 = $ S Compound S-78
$Z_1 = Z_2 = $ Se Compound Se-78

-continued

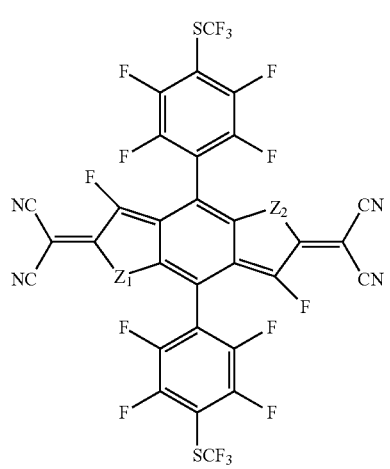

$Z_1 = Z_2 = $ O Compound O-76
$Z_1 = Z_2 = $ S Compound S-76
$Z_1 = Z_2 = $ Se Compound Se-76

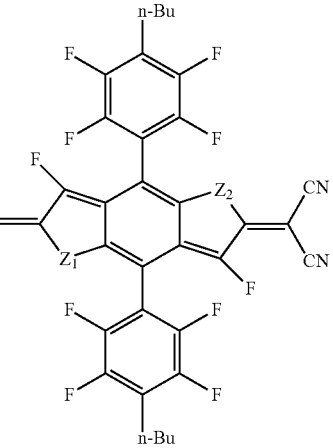

$Z_1 = Z_2 = $ O Compound O-79
$Z_1 = Z_2 = $ S Compound S-79
$Z_1 = Z_2 = $ Se Compound Se-79

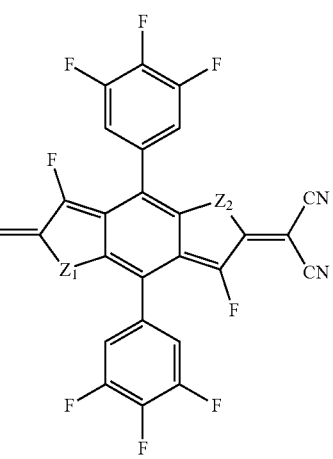

$Z_1 = Z_2 = $ O Compound O-77
$Z_1 = Z_2 = $ S Compound S-77
$Z_1 = Z_2 = $ Se Compound Se-77

$Z_1 = Z_2 = $ O Compound O-80
$Z_1 = Z_2 = $ S Compound S-80
$Z_1 = Z_2 = $ Se Compound Se-80

-continued

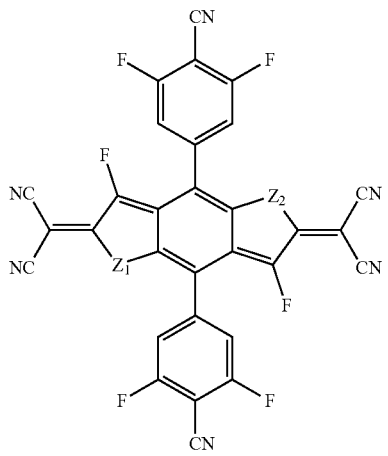

$Z_1 = Z_2 = O$ Compound O-81
$Z_1 = Z_2 = S$ Compound S-81
$Z_1 = Z_2 = Se$ Compound Se-81

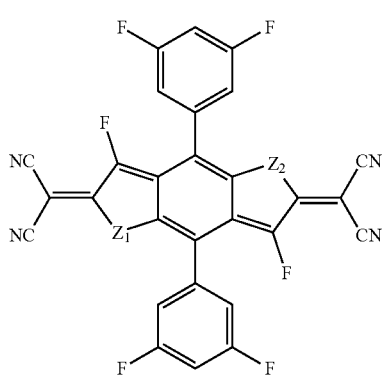

$Z_1 = Z_2 = O$ Compound O-82
$Z_1 = Z_2 = S$ Compound S-82
$Z_1 = Z_2 = Se$ Compound Se-82

$Z_1 = Z_2 = O$ Compound O-83
$Z_1 = Z_2 = S$ Compound S-83
$Z_1 = Z_2 = Se$ Compound Se-83

-continued

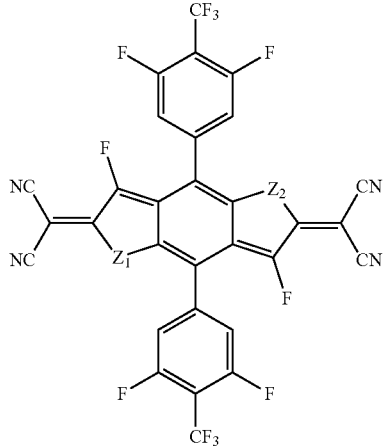

$Z_1 = Z_2 = O$ Compound O-84
$Z_1 = Z_2 = S$ Compound S-84
$Z_1 = Z_2 = Se$ Compound Se-84

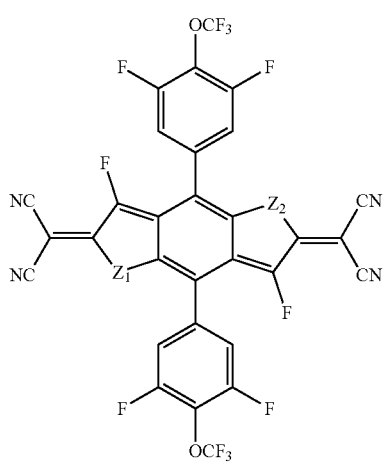

$Z_1 = Z_2 = O$ Compound O-85
$Z_1 = Z_2 = S$ Compound S-85
$Z_1 = Z_2 = Se$ Compound Se-85

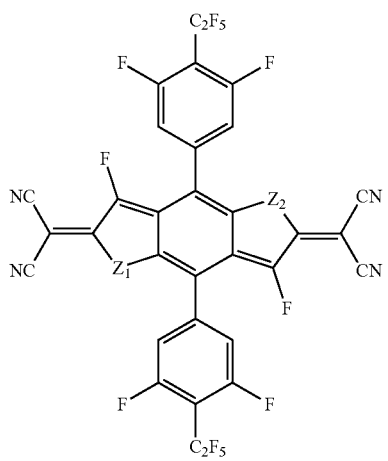

$Z_1 = Z_2 = O$ Compound O-86
$Z_1 = Z_2 = S$ Compound S-86
$Z_1 = Z_2 = Se$ Compound Se-86

-continued


Z₁ = Z₂ = O Compound O-87
Z₁ = Z₂ = S Compound S-87
Z₁ = Z₂ = Se Compound Se-87

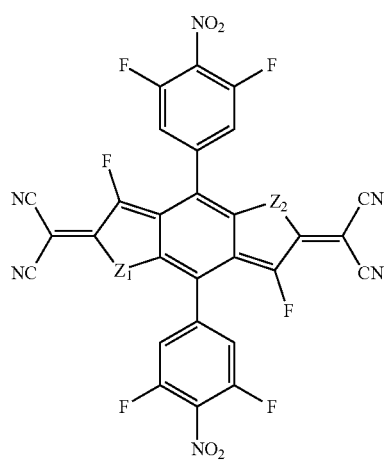

Z₁ = Z₂ = O Compound O-88
Z₁ = Z₂ = S Compound S-88
Z₁ = Z₂ = Se Compound Se-88

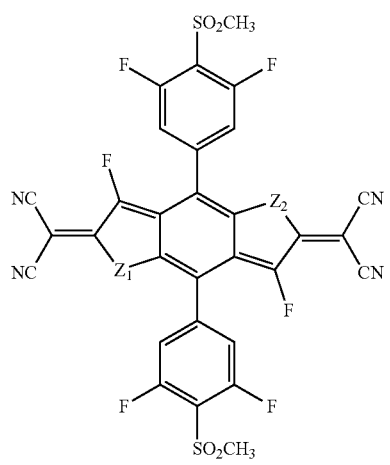

Z₁ = Z₂ = O Compound O-89
Z₁ = Z₂ = S Compound S-89
Z₁ = Z₂ = Se Compound Se-89

-continued


Z₁ = Z₂ = O Compound O-90
Z₁ = Z₂ = S Compound S-90
Z₁ = Z₂ = Se Compound Se-90

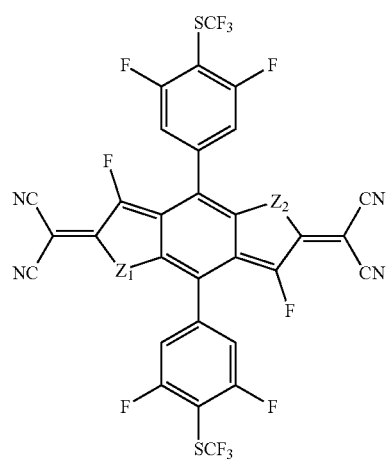

Z₁ = Z₂ = O Compound O-91
Z₁ = Z₂ = S Compound S-91
Z₁ = Z₂ = Se Compound Se-91

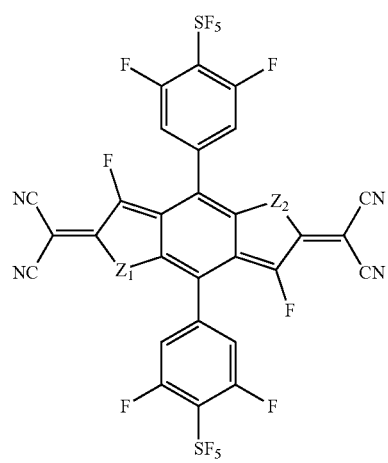

Z₁ = Z₂ = O Compound O-92
Z₁ = Z₂ = S Compound S-92
Z₁ = Z₂ = Se Compound Se-92


$Z_1 = Z_2 = $ O Compound O-93
$Z_1 = Z_2 = $ S Compound S-93
$Z_1 = Z_2 = $ Se Compound Se-93

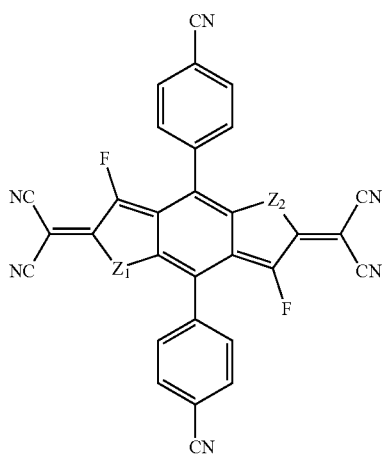

$Z_1 = Z_2 = $ O Compound O-94
$Z_1 = Z_2 = $ S Compound S-94
$Z_1 = Z_2 = $ Se Compound Se-94

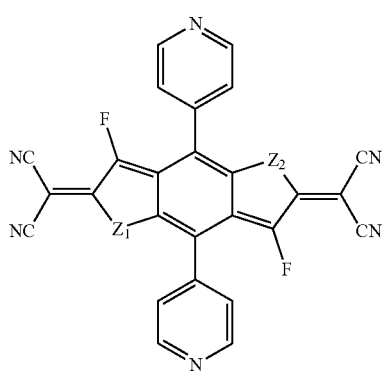

$Z_1 = Z_2 = $ O Compound O-95
$Z_1 = Z_2 = $ S Compound S-95
$Z_1 = Z_2 = $ Se Compound Se-95

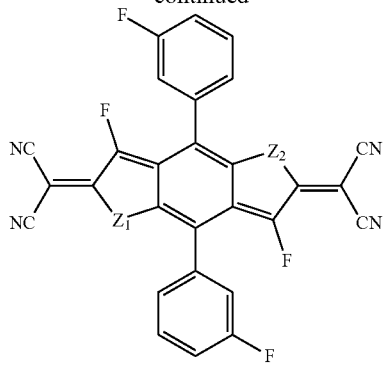

$Z_1 = Z_2 = $ O Compound O-96
$Z_1 = Z_2 = $ S Compound S-96
$Z_1 = Z_2 = $ Se Compound Se-96

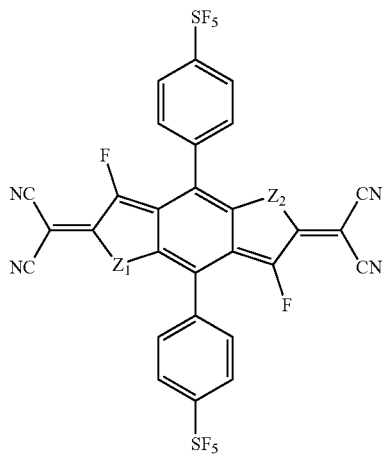

$Z_1 = Z_2 = $ O Compound O-97
$Z_1 = Z_2 = $ S Compound S-97
$Z_1 = Z_2 = $ Se Compound Se-97

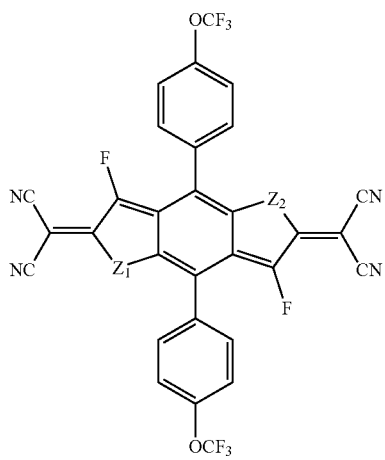

$Z_1 = Z_2 = $ O Compound O-98
$Z_1 = Z_2 = $ S Compound S-98
$Z_1 = Z_2 = $ Se Compound Se-98

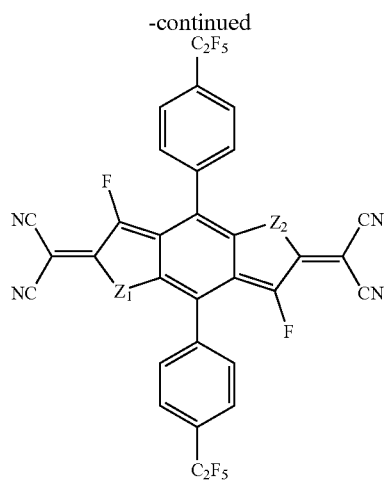

Z₁ = Z₂ = O Compound O-99
Z₁ = Z₂ = S Compound S-99
Z₁ = Z₂ = Se Compound Se-99

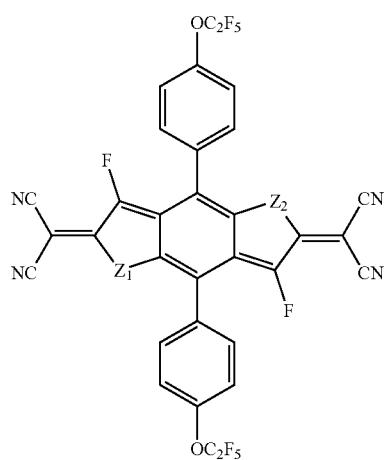

Z₁ = Z₂ = O Compound O-100
Z₁ = Z₂ = S Compound S-100
Z₁ = Z₂ = Se Compound Se-100

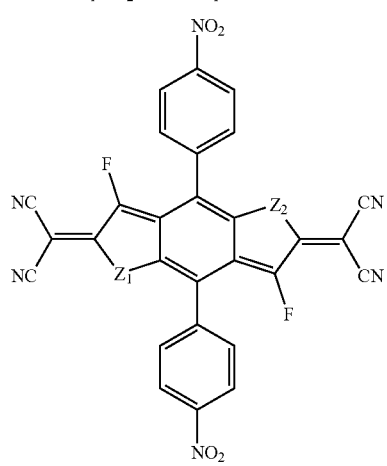

Z₁ = Z₂ = O Compound O-101
Z₁ = Z₂ = S Compound S-101
Z₁ = Z₂ = Se Compound Se-101

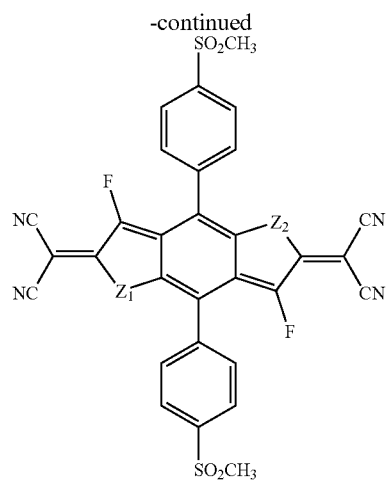

Z₁ = Z₂ = O Compound O-102
Z₁ = Z₂ = S Compound S-102
Z₁ = Z₂ = Se Compound Se-102

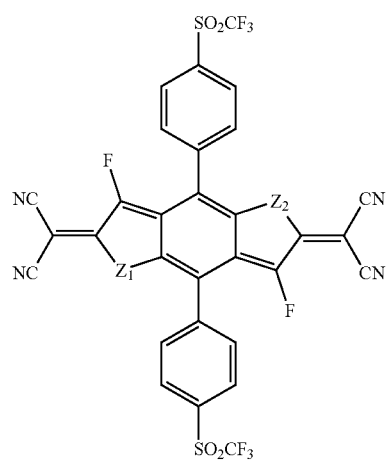

Z₁ = Z₂ = O Compound O-103
Z₁ = Z₂ = S Compound S-103
Z₁ = Z₂ = Se Compound Se-103

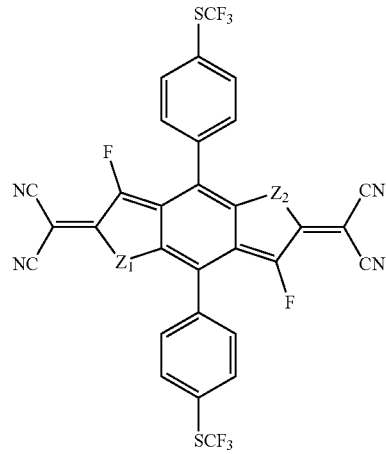

Z₁ = Z₂ = O Compound O-104
Z₁ = Z₂ = S Compound S-104
Z₁ = Z₂ = Se Compound Se-104

-continued

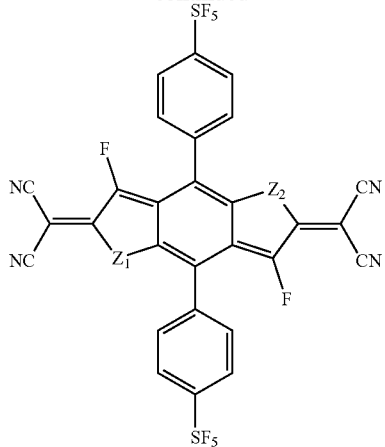

Z₁ = Z₂ = O Compound O-105
Z₁ = Z₂ = S Compound S-105
Z₁ = Z₂ = Se Compound Se-105

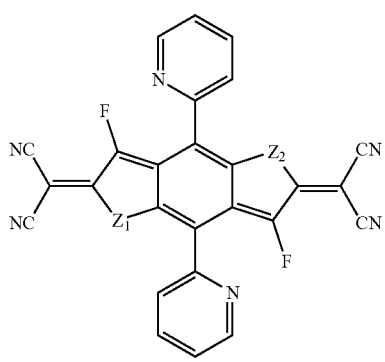

Z₁ = Z₂ = O Compound O-106
Z₁ = Z₂ = S Compound S-106
Z₁ = Z₂ = Se Compound Se-106

Z₁ = Z₂ = O Compound O-107
Z₁ = Z₂ = S Compound S-107
Z₁ = Z₂ = Se Compound Se-107

-continued

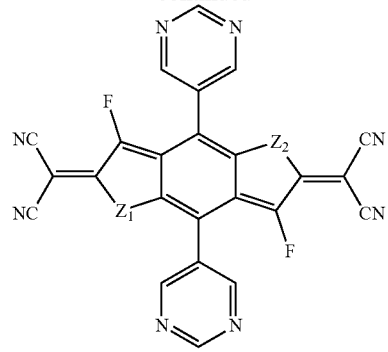

Z₁ = Z₂ = O Compound O-108
Z₁ = Z₂ = S Compound S-108
Z₁ = Z₂ = Se Compound Se-108

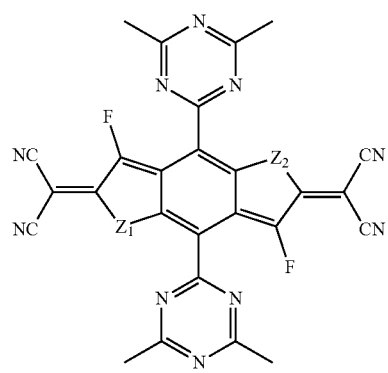

Z₁ = Z₂ = O Compound O-109
Z₁ = Z₂ = S Compound S-109
Z₁ = Z₂ = Se Compound Se-109

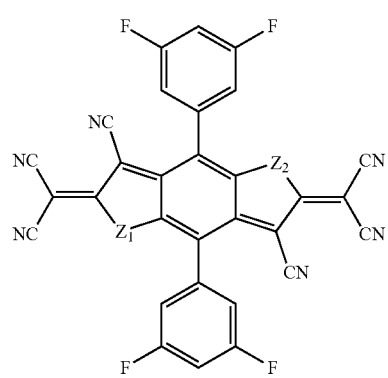

Z₁ = Z₂ = O Compound O-110
Z₁ = Z₂ = S Compound S-110
Z₁ = Z₂ = Se Compound Se-110

-continued

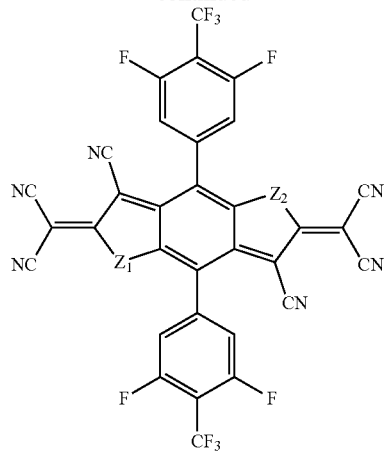

Z₁ = Z₂ = O Compound O-111
Z₁ = Z₂ = S Compound S-111
Z₁ = Z₂ = Se Compound Se-111

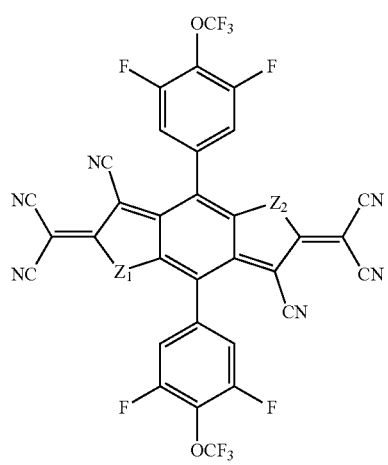

Z₁ = Z₂ = O Compound O-112
Z₁ = Z₂ = S Compound S-112
Z₁ = Z₂ = Se Compound Se-112

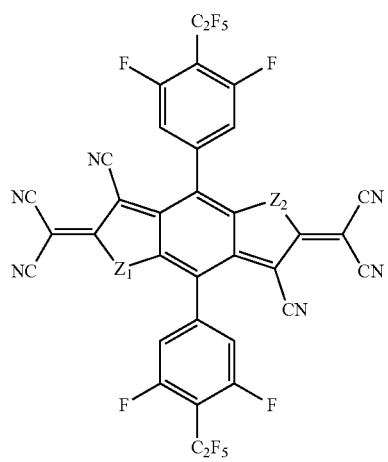

Z₁ = Z₂ = O Compound O-113
Z₁ = Z₂ = S Compound S-113
Z₁ = Z₂ = Se Compound Se-113

-continued

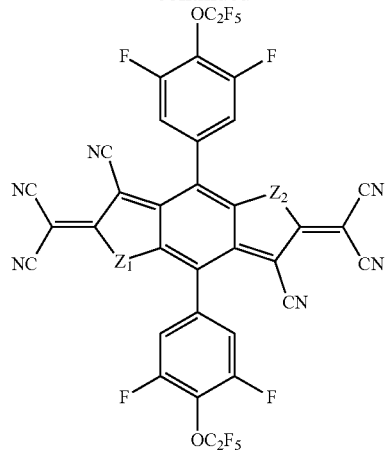

Z₁ = Z₂ = O Compound O-114
Z₁ = Z₂ = S Compound S-114
Z₁ = Z₂ = Se Compound Se-114

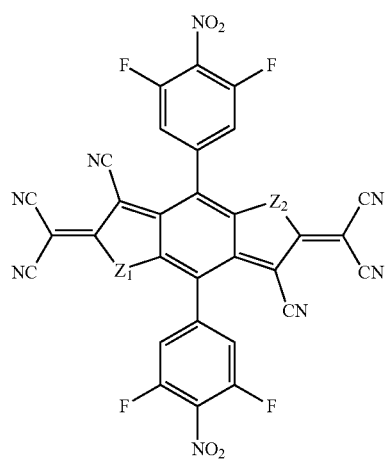

Z₁ = Z₂ = O Compound O-115
Z₁ = Z₂ = S Compound S-115
Z₁ = Z₂ = Se Compound Se-115

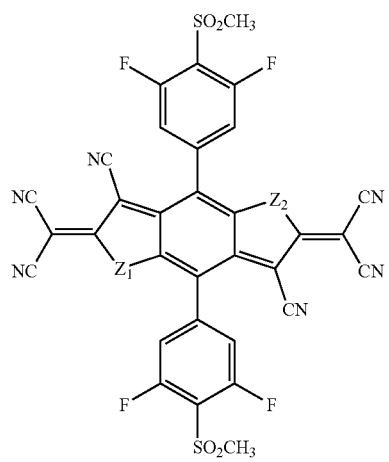

Z₁ = Z₂ = O Compound O-116
Z₁ = Z₂ = S Compound S-116
Z₁ = Z₂ = Se Compound Se-116

-continued

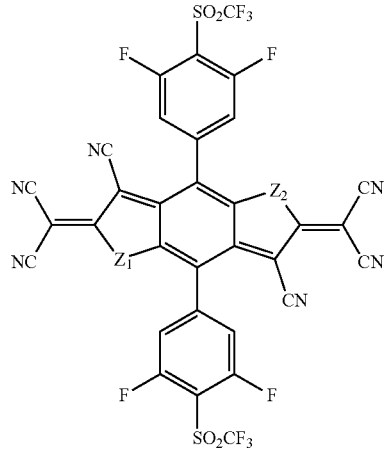

$Z_1 = Z_2 = O$ Compound O-117
$Z_1 = Z_2 = S$ Compound S-117
$Z_1 = Z_2 = Se$ Compound Se-117

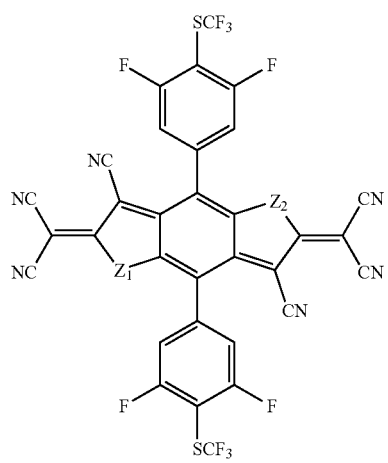

$Z_1 = Z_2 = O$ Compound O-118
$Z_1 = Z_2 = S$ Compound S-118
$Z_1 = Z_2 = Se$ Compound Se-118

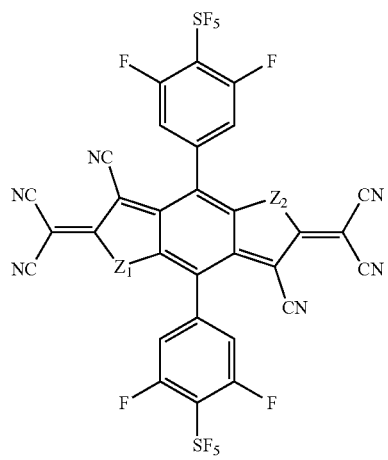

$Z_1 = Z_2 = O$ Compound O-119
$Z_1 = Z_2 = S$ Compound S-119
$Z_1 = Z_2 = Se$ Compound Se-119

-continued

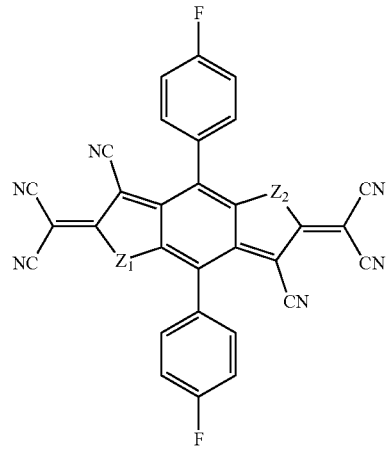

$Z_1 = Z_2 = O$ Compound O-120
$Z_1 = Z_2 = S$ Compound S-120
$Z_1 = Z_2 = Se$ Compound Se-120

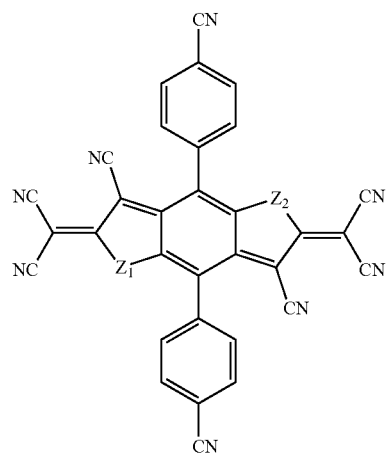

$Z_1 = Z_2 = O$ Compound O-121
$Z_1 = Z_2 = S$ Compound S-121
$Z_1 = Z_2 = Se$ Compound Se-121

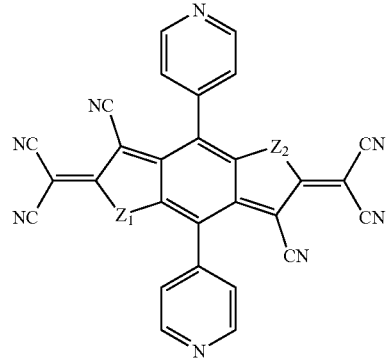

$Z_1 = Z_2 = O$ Compound O-122
$Z_1 = Z_2 = S$ Compound S-122
$Z_1 = Z_2 = Se$ Compound Se-122

-continued

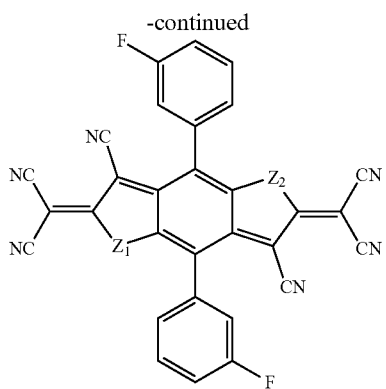

Z₁ = Z₂ = O Compound O-123
Z₁ = Z₂ = S Compound S-123
Z₁ = Z₂ = Se Compound Se-123

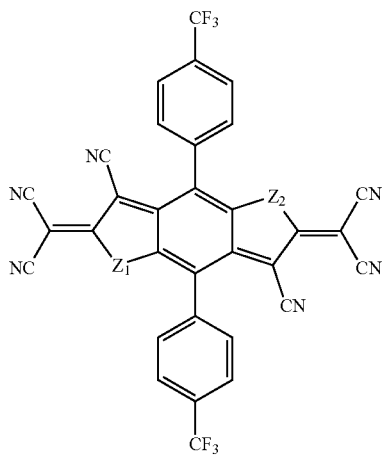

Z₁ = Z₂ = O Compound O-124
Z₁ = Z₂ = S Compound S-124
Z₁ = Z₂ = Se Compound Se-124

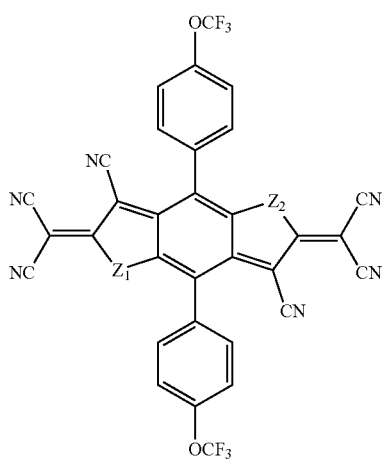

Z₁ = Z₂ = O Compound O-125
Z₁ = Z₂ = S Compound S-125
Z₁ = Z₂ = Se Compound Se-125

-continued

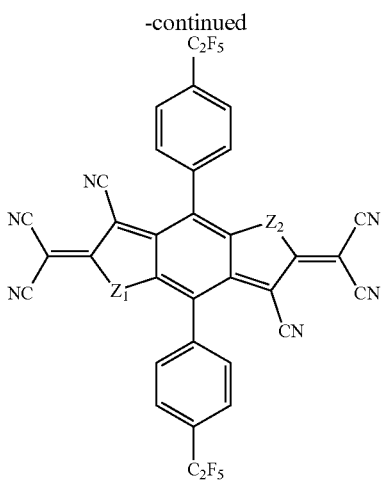

Z₁ = Z₂ = O Compound O-126
Z₁ = Z₂ = S Compound S-126
Z₁ = Z₂ = Se Compound Se-126

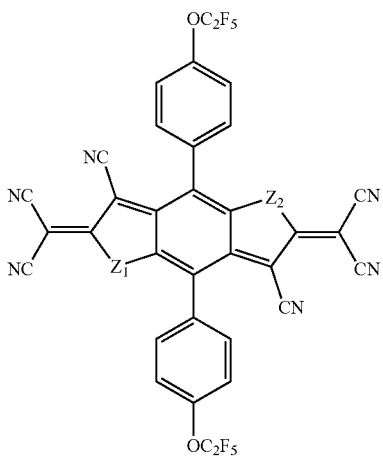

Z₁ = Z₂ = O Compound O-127
Z₁ = Z₂ = S Compound S-127
Z₁ = Z₂ = Se Compound Se-127

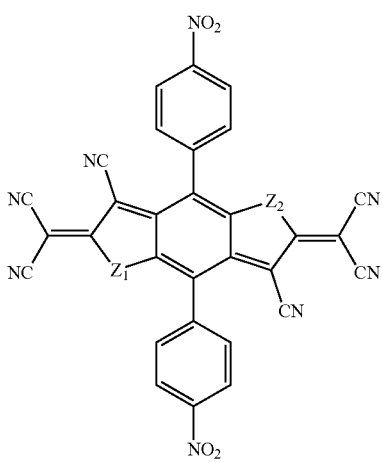

Z₁ = Z₂ = O Compound O-128
Z₁ = Z₂ = S Compound S-128
Z₁ = Z₂ = Se Compound Se-128

-continued

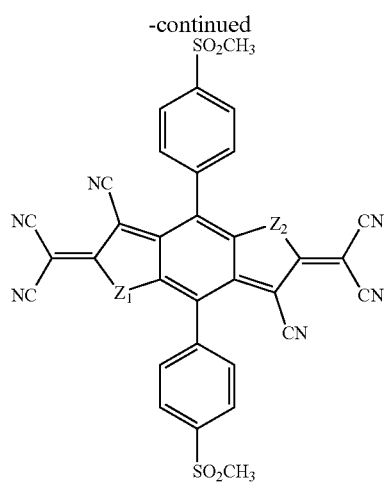

Z₁ = Z₂ = O Compound O-129
Z₁ = Z₂ = S Compound S-129
Z₁ = Z₂ = Se Compound Se-129

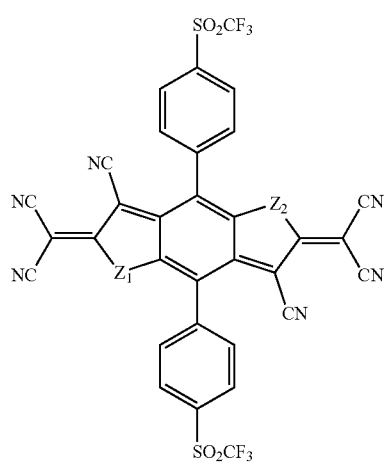

Z₁ = Z₂ = O Compound O-130
Z₁ = Z₂ = S Compound S-130
Z₁ = Z₂ = Se Compound Se-130

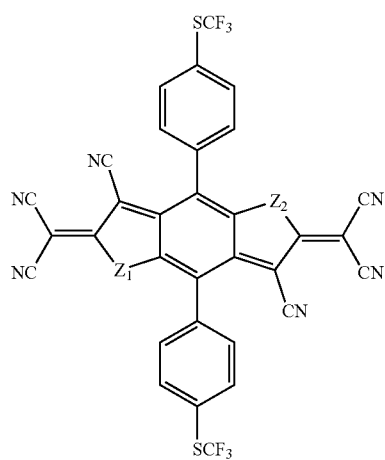

Z₁ = Z₂ = O Compound O-131
Z₁ = Z₂ = S Compound S-131
Z₁ = Z₂ = Se Compound Se-131

-continued

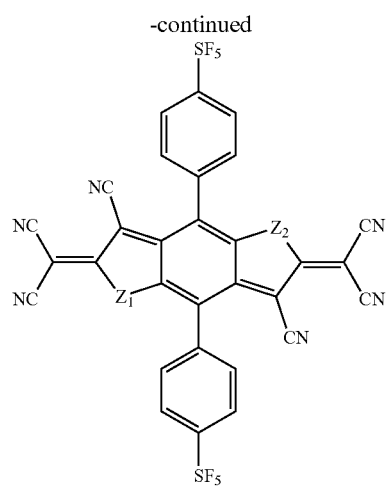

Z₁ = Z₂ = O Compound O-132
Z₁ = Z₂ = S Compound S-132
Z₁ = Z₂ = Se Compound Se-132

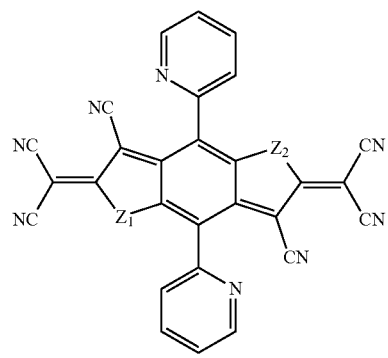

Z₁ = Z₂ = O Compound O-133
Z₁ = Z₂ = S Compound S-133
Z₁ = Z₂ = Se Compound Se-133

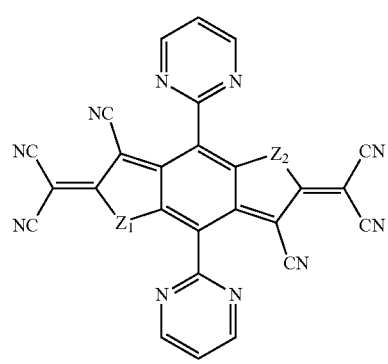

Z₁ = Z₂ = O Compound O-134
Z₁ = Z₂ = S Compound S-134
Z₁ = Z₂ = Se Compound Se-134

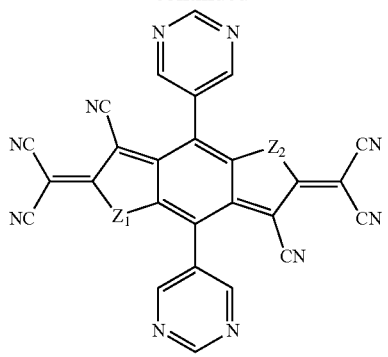

$Z_1 = Z_2 = O$ Compound O-135
$Z_1 = Z_2 = S$ Compound S-135
$Z_1 = Z_2 = Se$ Compound Se-135

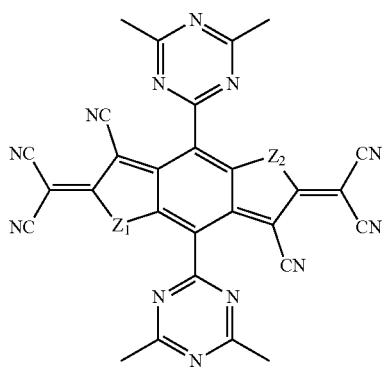

$Z_1 = Z_2 = O$ Compound O-136
$Z_1 = Z_2 = S$ Compound S-136
$Z_1 = Z_2 = Se$ Compound Se-136

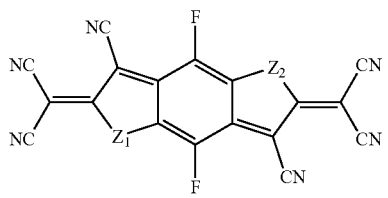

$Z_1 = Z_2 = O$ Compound O-137
$Z_1 = Z_2 = S$ Compound S-137
$Z_1 = Z_2 = Se$ Compound Se-137

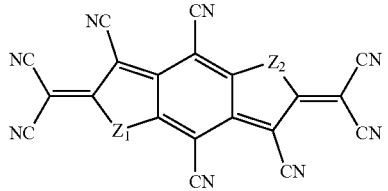

$Z_1 = Z_2 = O$ Compound O-138
$Z_1 = Z_2 = S$ Compound S-138
$Z_1 = Z_2 = Se$ Compound Se-138

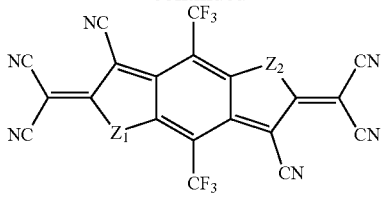

$Z_1 = Z_2 = O$ Compound O-139
$Z_1 = Z_2 = S$ Compound S-139
$Z_1 = Z_2 = Se$ Compound Se-139

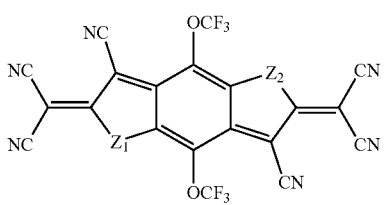

$Z_1 = Z_2 = O$ Compound O-140
$Z_1 = Z_2 = S$ Compound S-140
$Z_1 = Z_2 = Se$ Compound Se-140

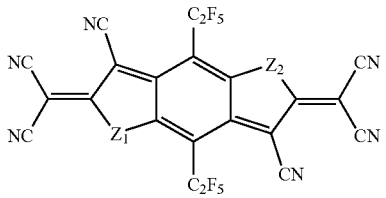

$Z_1 = Z_2 = O$ Compound O-141
$Z_1 = Z_2 = S$ Compound S-141
$Z_1 = Z_2 = Se$ Compound Se-141

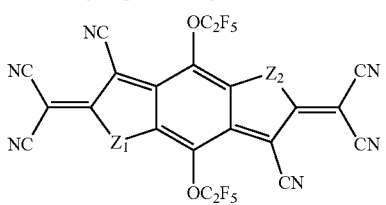

$Z_1 = Z_2 = O$ Compound O-142
$Z_1 = Z_2 = S$ Compound S-142
$Z_1 = Z_2 = Se$ Compound Se-142

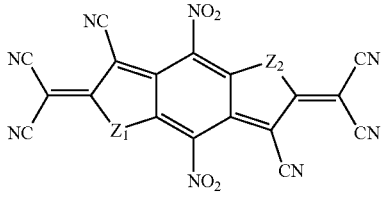

$Z_1 = Z_2 = O$ Compound O-143
$Z_1 = Z_2 = S$ Compound S-143
$Z_1 = Z_2 = Se$ Compound Se-143

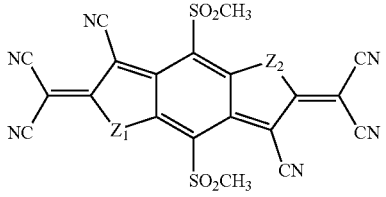

$Z_1 = Z_2 = O$ Compound O-144
$Z_1 = Z_2 = S$ Compound S-144
$Z_1 = Z_2 = Se$ Compound Se-144

-continued

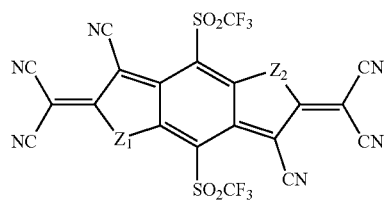

Z₁ = Z₂ = O Compound O-145
Z₁ = Z₂ = S Compound S-145
Z₁ = Z₂ = Se Compound Se-145

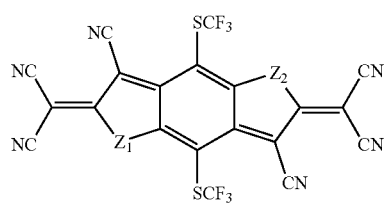

Z₁ = Z₂ = O Compound O-146
Z₁ = Z₂ = S Compound S-146
Z₁ = Z₂ = Se Compound Se-146

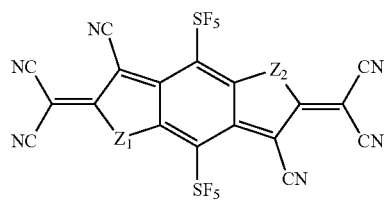

Z₁ = Z₂ = O Compound O-147
Z₁ = Z₂ = S Compound S-147
Z₁ = Z₂ = Se Compound Se-147

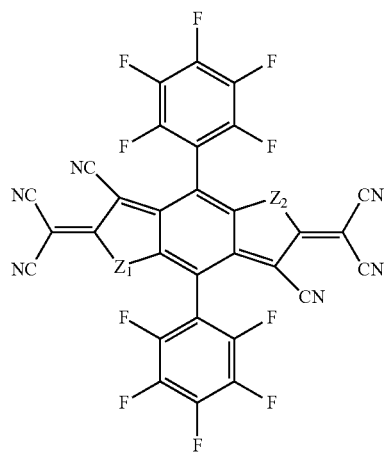

Z₁ = Z₂ = O Compound O-148
Z₁ = Z₂ = S Compound S-148
Z₁ = Z₂ = Se Compound Se-148

-continued

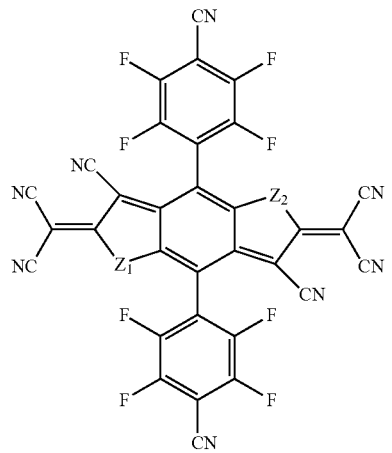

Z₁ = Z₂ = O Compound O-149
Z₁ = Z₂ = S Compound S-149
Z₁ = Z₂ = Se Compound Se-149

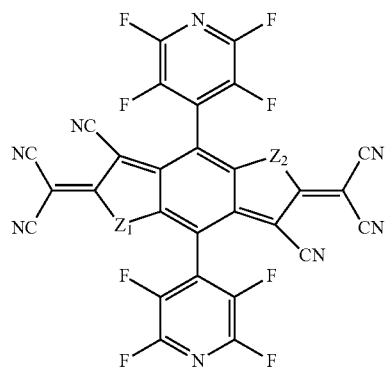

Z₁ = Z₂ = O Compound O-150
Z₁ = Z₂ = S Compound S-150
Z₁ = Z₂ = Se Compound Se-150

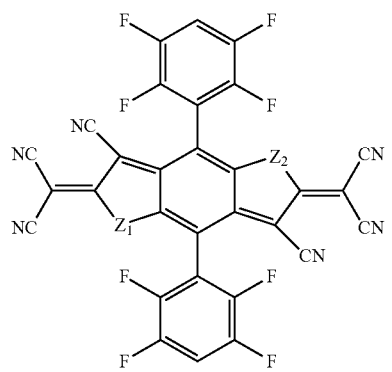

Z₁ = Z₂ = O Compound O-151
Z₁ = Z₂ = S Compound S-151
Z₁ = Z₂ = Se Compound Se-151

-continued

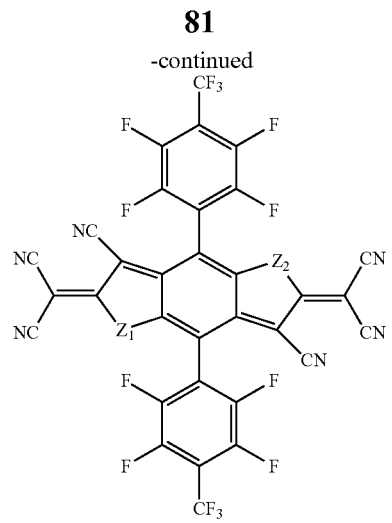

Z₁ = Z₂ = O Compound O-152
Z₁ = Z₂ = S Compound S-152
Z₁ = Z₂ = Se Compound Se-152

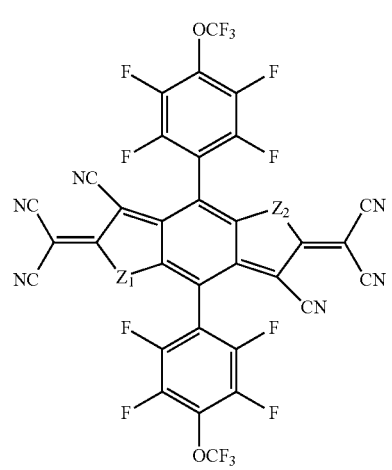

Z₁ = Z₂ = O Compound O-153
Z₁ = Z₂ = S Compound S-153
Z₁ = Z₂ = Se Compound Se-153

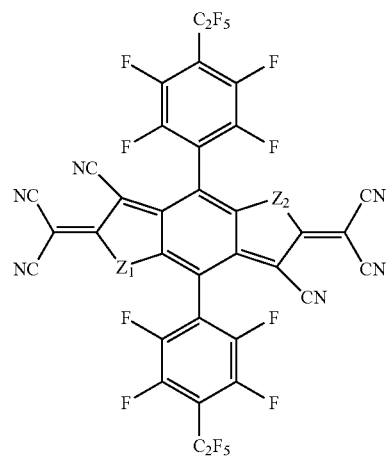

Z₁ = Z₂ = O Compound O-154
Z₁ = Z₂ = S Compound S-154
Z₁ = Z₂ = Se Compound Se-154

-continued

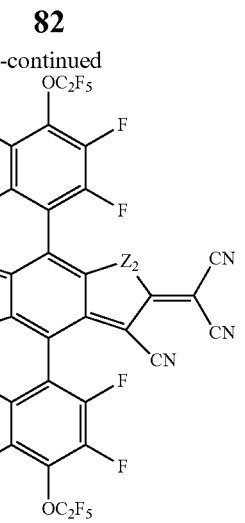

Z₁ = Z₂ = O Compound O-155
Z₁ = Z₂ = S Compound S-155
Z₁ = Z₂ = Se Compound Se-155

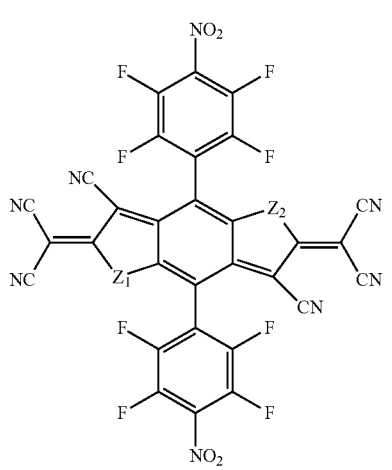

Z₁ = Z₂ = O Compound O-156
Z₁ = Z₂ = S Compound S-156
Z₁ = Z₂ = Se Compound Se-156

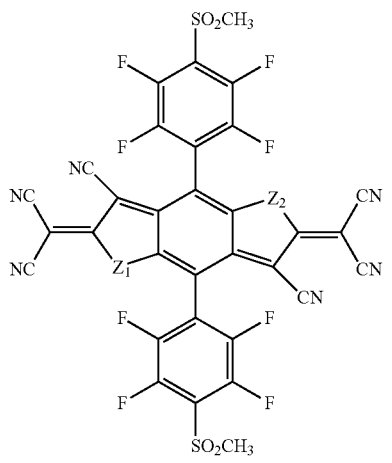

Z₁ = Z₂ = O Compound O-157
Z₁ = Z₂ = S Compound S-157
Z₁ = Z₂ = Se Compound Se-157

-continued

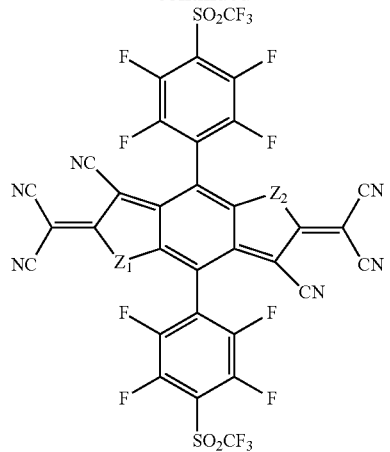

Z₁ = Z₂ = O Compound O-158
Z₁ = Z₂ = S Compound S-158
Z₁ = Z₂ = Se Compound Se-158

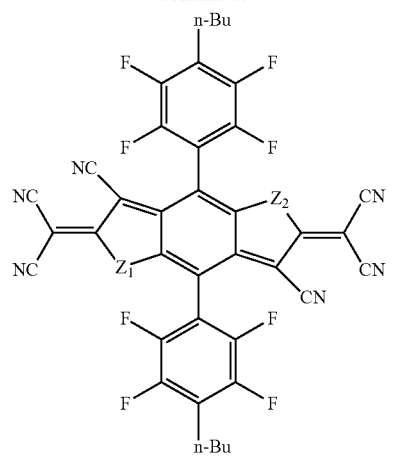

Z₁ = Z₂ = O Compound O-161
Z₁ = Z₂ = S Compound S-161
Z₁ = Z₂ = Se Compound Se-161

Z₁ = Z₂ = O Compound O-159
Z₁ = Z₂ = S Compound S-159
Z₁ = Z₂ = Se Compound Se-159

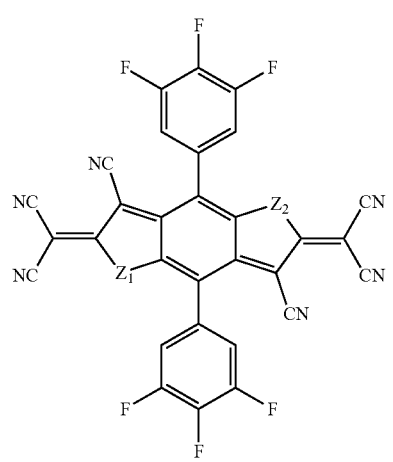

Z₁ = Z₂ = O Compound O-162
Z₁ = Z₂ = S Compound S-162
Z₁ = Z₂ = Se Compound Se-162

Z₁ = Z₂ = O Compound O-160
Z₁ = Z₂ = S Compound S-160
Z₁ = Z₂ = Se Compound Se-160

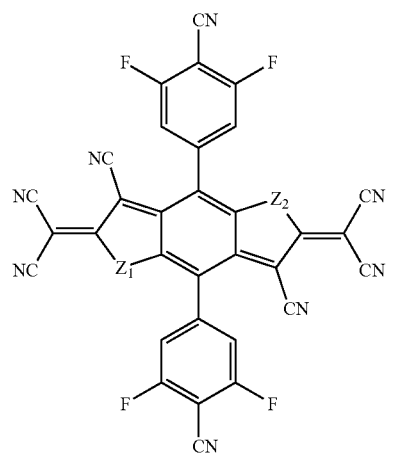

Z₁ = Z₂ = O Compound O-163
Z₁ = Z₂ = S Compound S-163
Z₁ = Z₂ = Se Compound Se-163

-continued

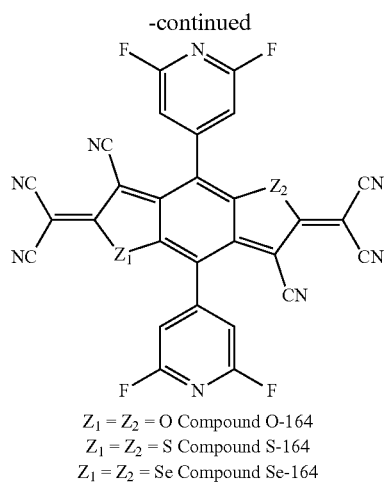

$Z_1 = Z_2 = $ O Compound O-164
$Z_1 = Z_2 = $ S Compound S-164
$Z_1 = Z_2 = $ Se Compound Se-164

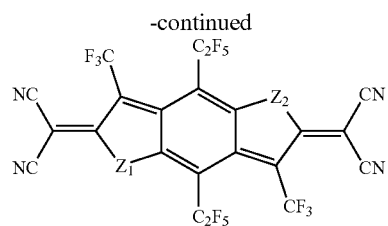

$Z_1 = Z_2 = $ O Compound O-165
$Z_1 = Z_2 = $ S Compound S-165
$Z_1 = Z_2 = $ Se Compound Se-165

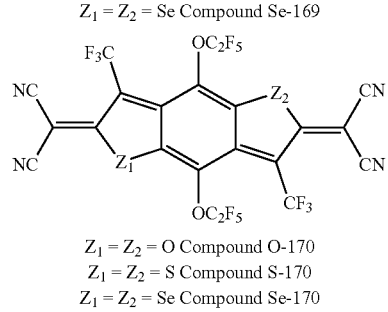

$Z_1 = Z_2 = $ O Compound O-166
$Z_1 = Z_2 = $ S Compound S-166
$Z_1 = Z_2 = $ Se Compound Se-166

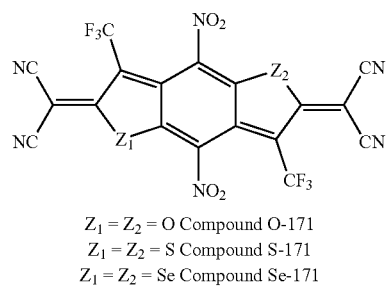

$Z_1 = Z_2 = $ O Compound O-167
$Z_1 = Z_2 = $ S Compound S-167
$Z_1 = Z_2 = $ Se Compound Se-167

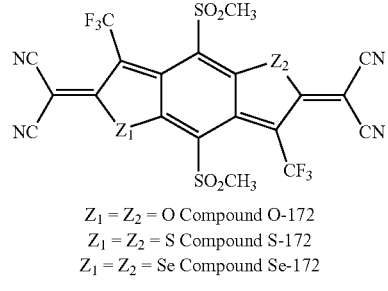

$Z_1 = Z_2 = $ O Compound O-168
$Z_1 = Z_2 = $ S Compound S-168
$Z_1 = Z_2 = $ Se Compound Se-168

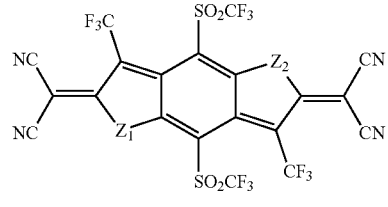

$Z_1 = Z_2 = $ O Compound O-169
$Z_1 = Z_2 = $ S Compound S-169
$Z_1 = Z_2 = $ Se Compound Se-169

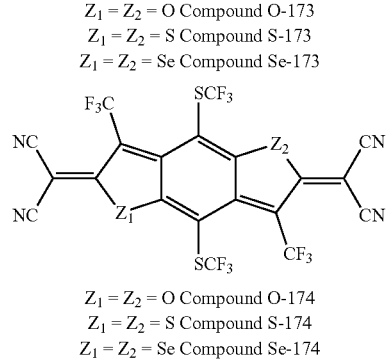

$Z_1 = Z_2 = $ O Compound O-170
$Z_1 = Z_2 = $ S Compound S-170
$Z_1 = Z_2 = $ Se Compound Se-170

$Z_1 = Z_2 = $ O Compound O-171
$Z_1 = Z_2 = $ S Compound S-171
$Z_1 = Z_2 = $ Se Compound Se-171

$Z_1 = Z_2 = $ O Compound O-172
$Z_1 = Z_2 = $ S Compound S-172
$Z_1 = Z_2 = $ Se Compound Se-172

$Z_1 = Z_2 = $ O Compound O-173
$Z_1 = Z_2 = $ S Compound S-173
$Z_1 = Z_2 = $ Se Compound Se-173

$Z_1 = Z_2 = $ O Compound O-174
$Z_1 = Z_2 = $ S Compound S-174
$Z_1 = Z_2 = $ Se Compound Se-174

87
-continued

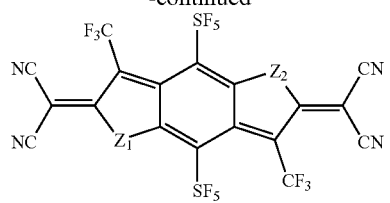

Z₁ = Z₂ = O Compound O-175
Z₁ = Z₂ = S Compound S-175
Z₁ = Z₂ = Se Compound Se-175

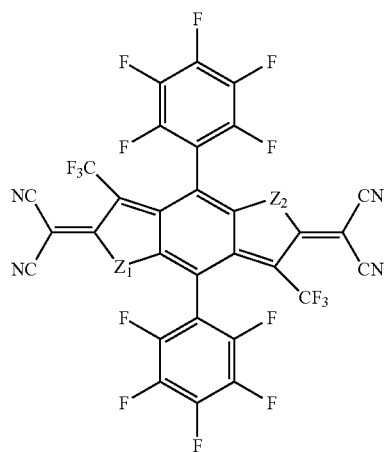

Z₁ = Z₂ = O Compound O-176
Z₁ = Z₂ = S Compound S-176
Z₁ = Z₂ = Se Compound Se-176

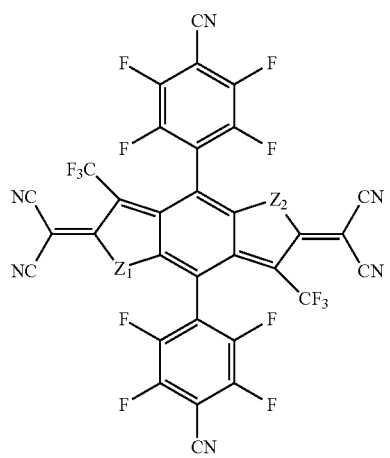

Z₁ = Z₂ = O Compound O-177
Z₁ = Z₂ = S Compound S-177
Z₁ = Z₂ = Se Compound Se-177

88
-continued

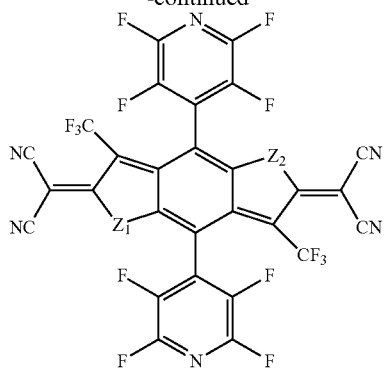

Z₁ = Z₂ = O Compound O-178
Z₁ = Z₂ = S Compound S-178
Z₁ = Z₂ = Se Compound Se-178

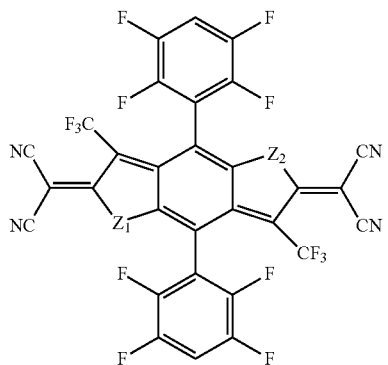

Z₁ = Z₂ = O Compound O-179
Z₁ = Z₂ = S Compound S-179
Z₁ = Z₂ = Se Compound Se-179

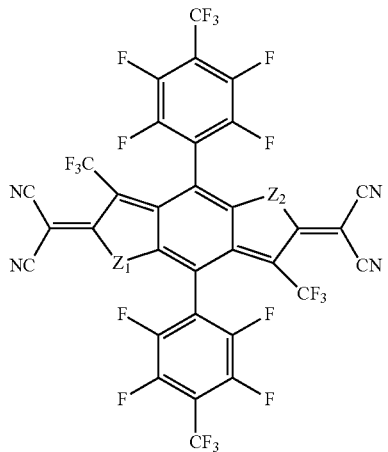

Z₁ = Z₂ = O Compound O-180
Z₁ = Z₂ = S Compound S-180
Z₁ = Z₂ = Se Compound Se-180

-continued

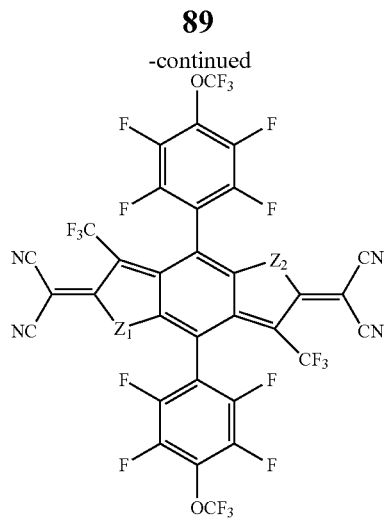

Z₁ = Z₂ = O Compound O-181
Z₁ = Z₂ = S Compound S-181
Z₁ = Z₂ = Se Compound Se-181

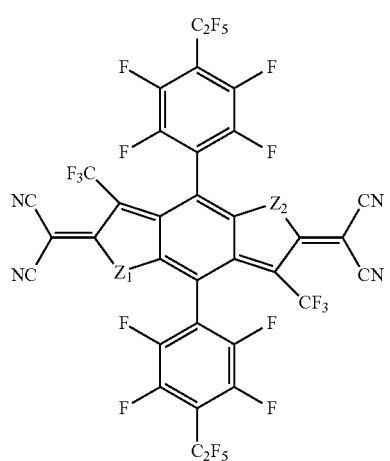

Z₁ = Z₂ = O Compound O-182
Z₁ = Z₂ = S Compound S-182
Z₁ = Z₂ = Se Compound Se-182

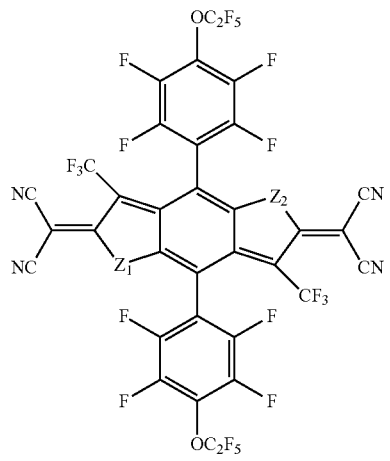

Z₁ = Z₂ = O Compound O-183
Z₁ = Z₂ = S Compound S-183
Z₁ = Z₂ = Se Compound Se-183

-continued

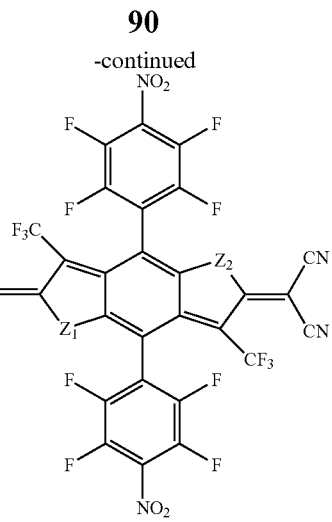

Z₁ = Z₂ = O Compound O-184
Z₁ = Z₂ = S Compound S-184
Z₁ = Z₂ = Se Compound Se-184

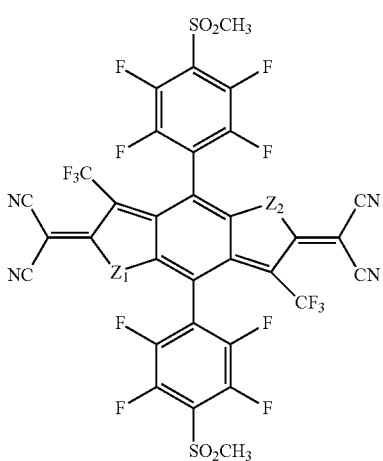

Z₁ = Z₂ = O Compound O-185
Z₁ = Z₂ = S Compound S-185
Z₁ = Z₂ = Se Compound Se-185

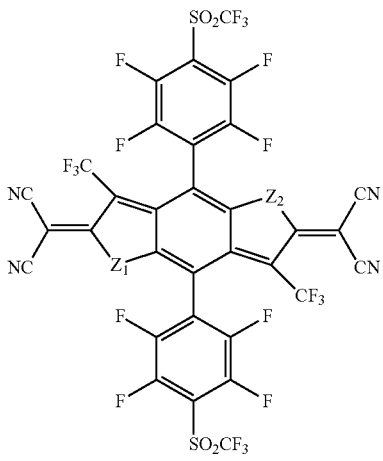

Z₁ = Z₂ = O Compound O-186
Z₁ = Z₂ = S Compound S-186
Z₁ = Z₂ = Se Compound Se-186

-continued

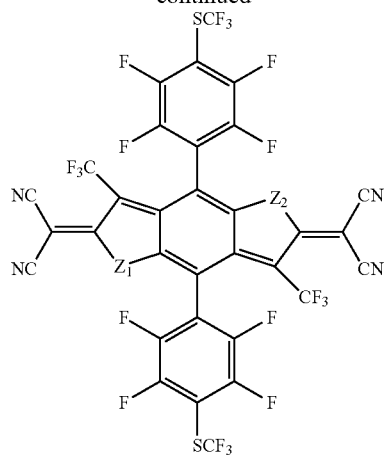

Z₁ = Z₂ = O Compound O-187
Z₁ = Z₂ = S Compound S-187
Z₁ = Z₂ = Se Compound Se-187

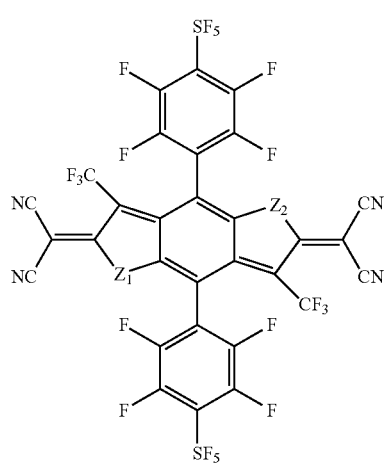

Z₁ = Z₂ = O Compound O-188
Z₁ = Z₂ = S Compound S-188
Z₁ = Z₂ = Se Compound Se-188

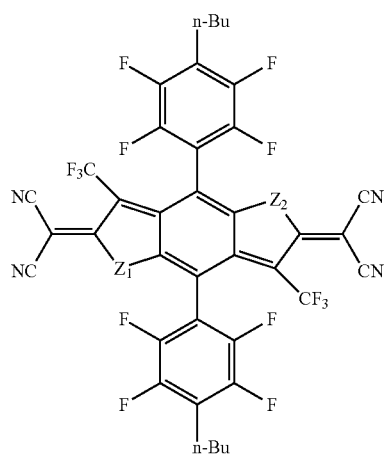

Z₁ = Z₂ = O Compound O-189
Z₁ = Z₂ = S Compound S-189
Z₁ = Z₂ = Se Compound Se-189

-continued

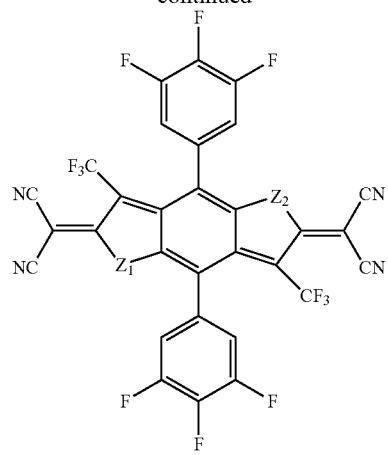

Z₁ = Z₂ = O Compound O-190
Z₁ = Z₂ = S Compound S-190
Z₁ = Z₂ = Se Compound Se-190

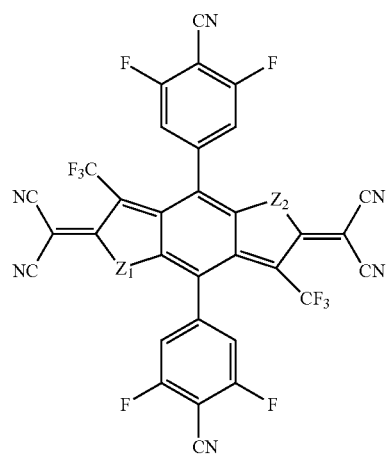

Z₁ = Z₂ = O Compound O-191
Z₁ = Z₂ = S Compound S-191
Z₁ = Z₂ = Se Compound Se-191

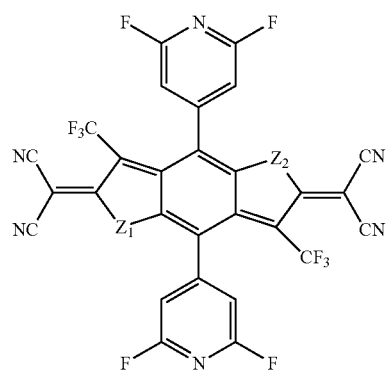

Z₁ = Z₂ = O Compound O-192
Z₁ = Z₂ = S Compound S-192
Z₁ = Z₂ = Se Compound Se-192

-continued

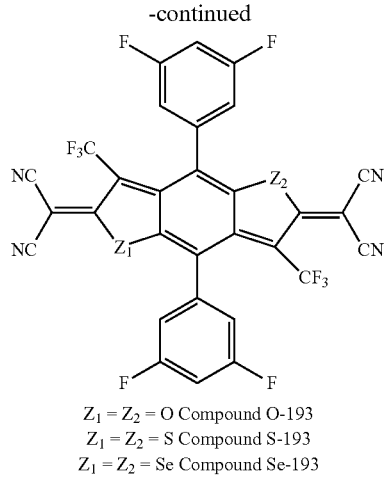

Z₁ = Z₂ = O Compound O-193
Z₁ = Z₂ = S Compound S-193
Z₁ = Z₂ = Se Compound Se-193

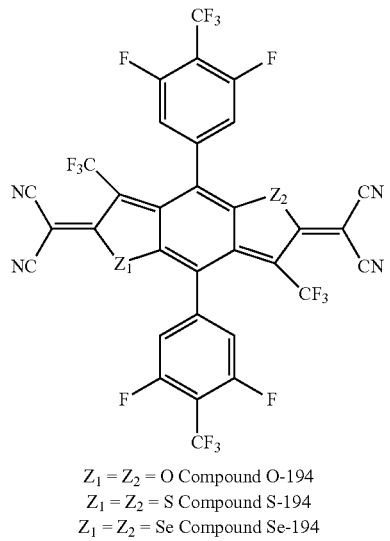

Z₁ = Z₂ = O Compound O-194
Z₁ = Z₂ = S Compound S-194
Z₁ = Z₂ = Se Compound Se-194

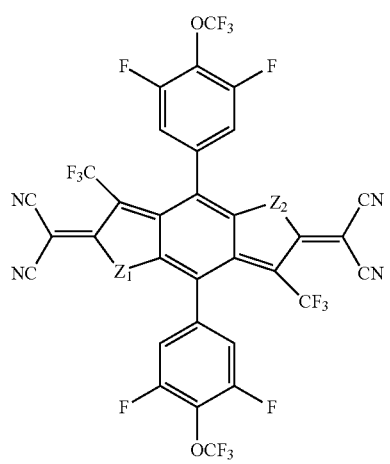

Z₁ = Z₂ = O Compound O-195
Z₁ = Z₂ = S Compound S-195
Z₁ = Z₂ = Se Compound Se-195

-continued

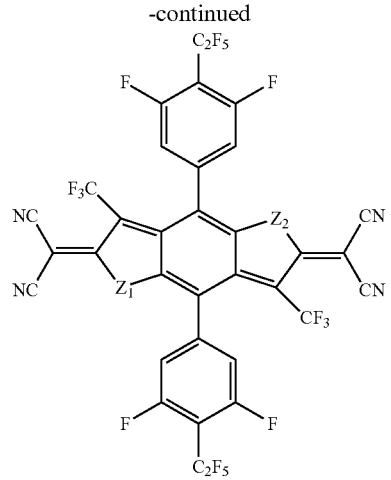

Z₁ = Z₂ = O Compound O-196
Z₁ = Z₂ = S Compound S-196
Z₁ = Z₂ = Se Compound Se-196

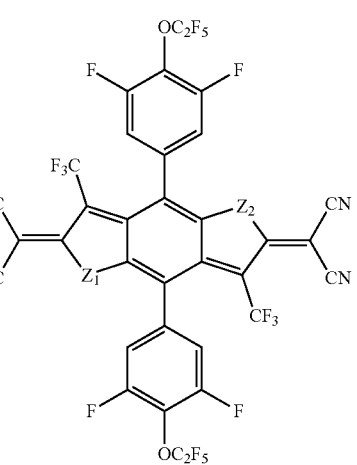

Z₁ = Z₂ = O Compound O-197
Z₁ = Z₂ = S Compound S-197
Z₁ = Z₂ = Se Compound Se-197

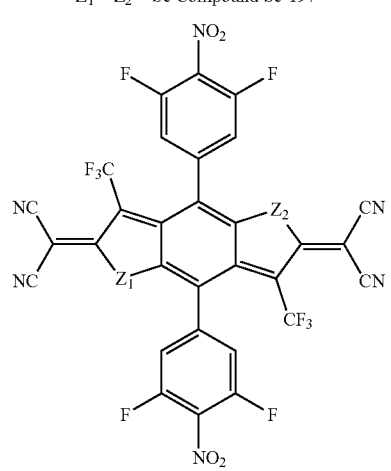

Z₁ = Z₂ = O Compound O-198
Z₁ = Z₂ = S Compound S-198
Z₁ = Z₂ = Se Compound Se-198

-continued

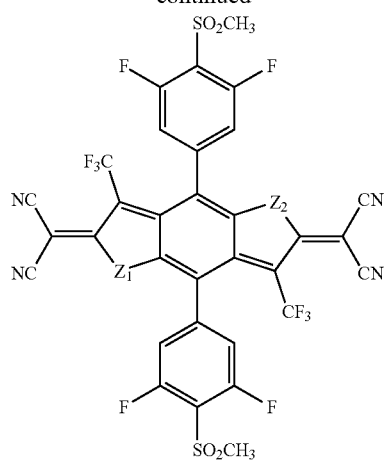

Z₁ = Z₂ = O Compound O-199
Z₁ = Z₂ = S Compound S-199
Z₁ = Z₂ = Se Compound Se-199

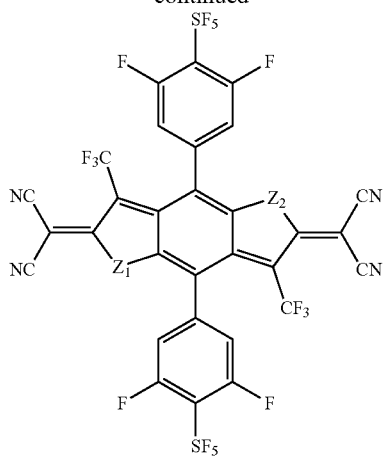

Z₁ = Z₂ = O Compound O-202
Z₁ = Z₂ = S Compound S-202
Z₁ = Z₂ = Se Compound Se-202

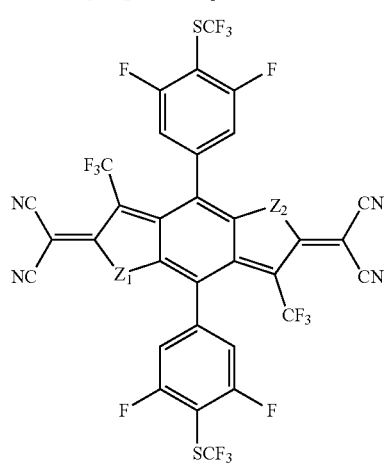

Z₁ = Z₂ = O Compound O-200
Z₁ = Z₂ = S Compound S-200
Z₁ = Z₂ = Se Compound Se-200

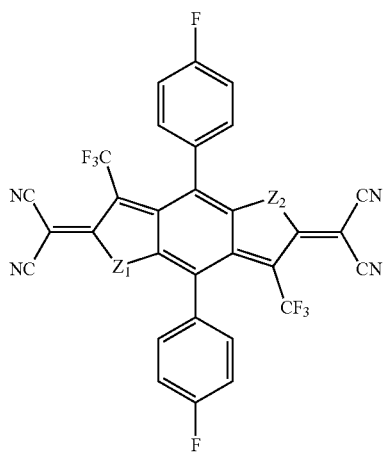

Z₁ = Z₂ = O Compound O-203
Z₁ = Z₂ = S Compound S-203
Z₁ = Z₂ = Se Compound Se-203

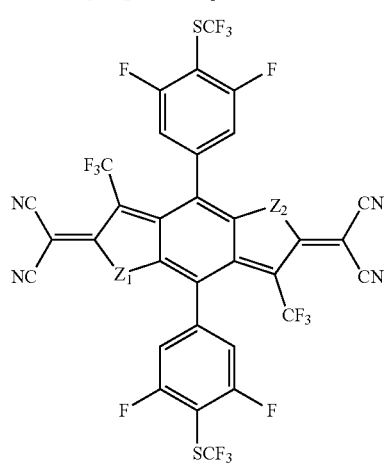

Z₁ = Z₂ = O Compound O-201
Z₁ = Z₂ = S Compound S-201
Z₁ = Z₂ = Se Compound Se-201

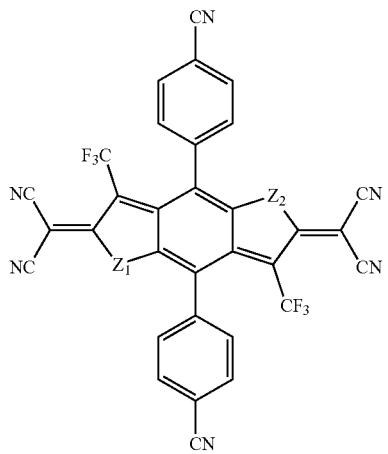

Z₁ = Z₂ = O Compound O-204
Z₁ = Z₂ = S Compound S-204
Z₁ = Z₂ = Se Compound Se-204

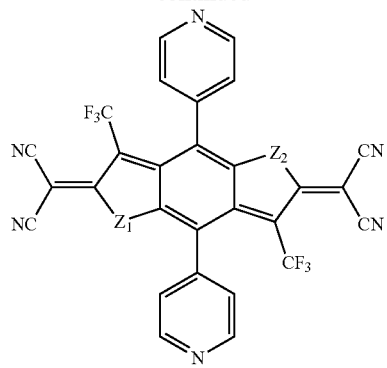

Z₁ = Z₂ = O Compound O-205
Z₁ = Z₂ = S Compound S-205
Z₁ = Z₂ = Se Compound Se-205

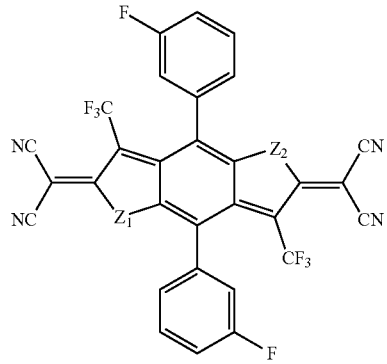

Z₁ = Z₂ = O Compound O-206
Z₁ = Z₂ = S Compound S-206
Z₁ = Z₂ = Se Compound Se-206

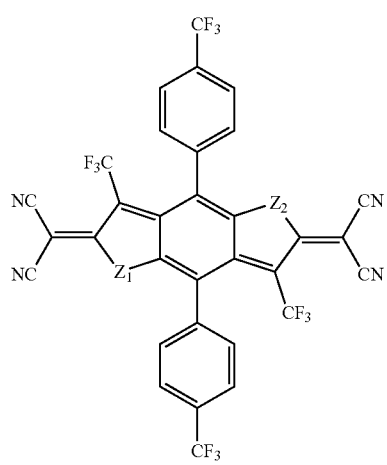

Z₁ = Z₂ = O Compound O-207
Z₁ = Z₂ = S Compound S-207
Z₁ = Z₂ = Se Compound Se-207

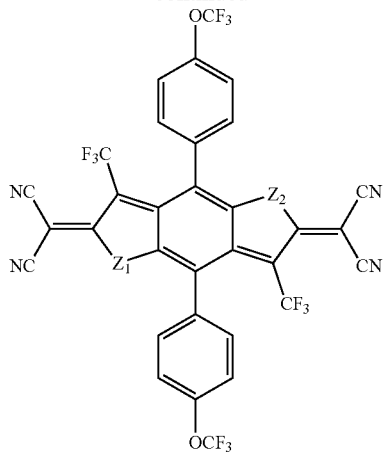

Z₁ = Z₂ = O Compound O-208
Z₁ = Z₂ = S Compound S-208
Z₁ = Z₂ = Se Compound Se-208

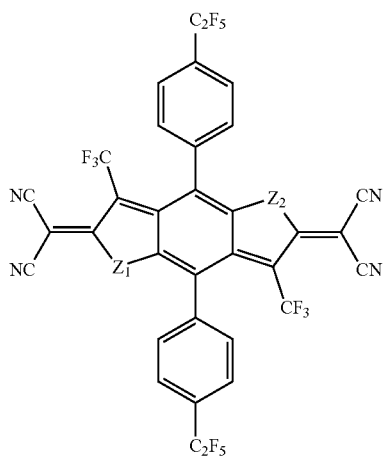

Z₁ = Z₂ = O Compound O-209
Z₁ = Z₂ = S Compound S-209
Z₁ = Z₂ = Se Compound Se-209

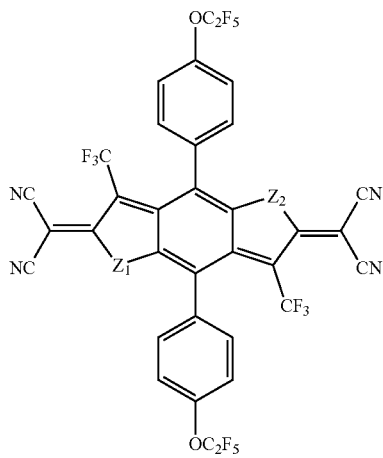

Z₁ = Z₂ = O Compound O-210
Z₁ = Z₂ = S Compound S-210
Z₁ = Z₂ = Se Compound Se-210

-continued

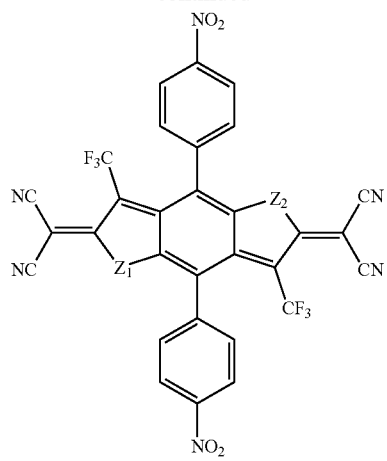

Z₁ = Z₂ = O Compound O-211
Z₁ = Z₂ = S Compound S-211
Z₁ = Z₂ = Se Compound Se-211

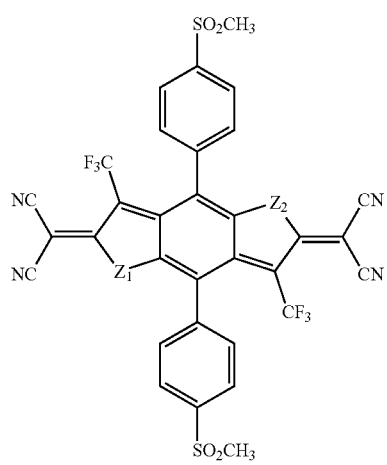

Z₁ = Z₂ = O Compound O-212
Z₁ = Z₂ = S Compound S-212
Z₁ = Z₂ = Se Compound Se-212

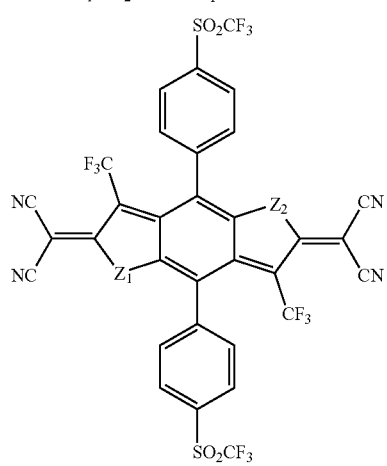

Z₁ = Z₂ = O Compound O-213
Z₁ = Z₂ = S Compound S-213
Z₁ = Z₂ = Se Compound Se-213

-continued

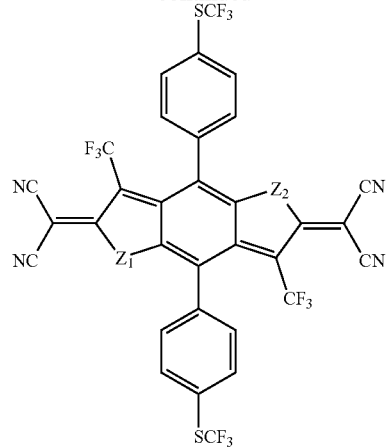

Z₁ = Z₂ = O Compound O-214
Z₁ = Z₂ = S Compound S-214
Z₁ = Z₂ = Se Compound Se-214

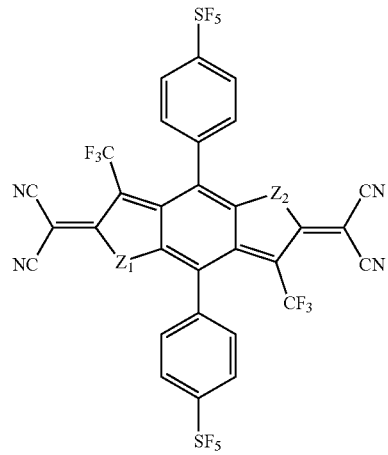

Z₁ = Z₂ = O Compound O-215
Z₁ = Z₂ = S Compound S-215
Z₁ = Z₂ = Se Compound Se-215

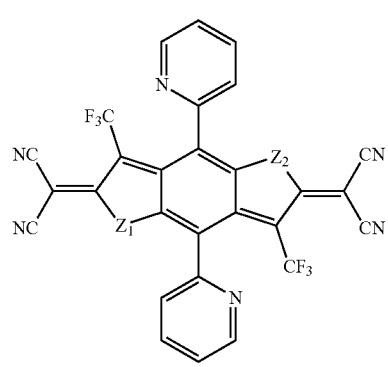

Z₁ = Z₂ = O Compound O-216
Z₁ = Z₂ = S Compound S-216
Z₁ = Z₂ = Se Compound Se-216

-continued

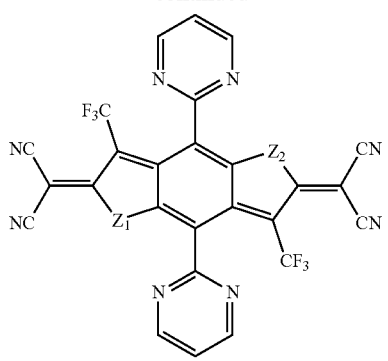

Z₁ = Z₂ = O Compound O-217
Z₁ = Z₂ = S Compound S-217
Z₁ = Z₂ = Se Compound Se-217

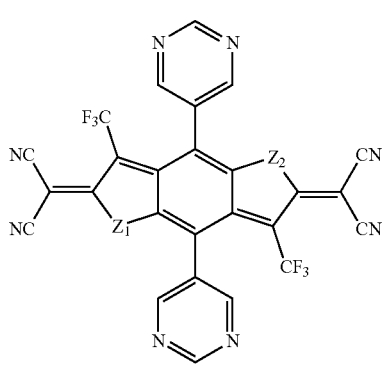

Z₁ = Z₂ = O Compound O-218
Z₁ = Z₂ = S Compound S-218
Z₁ = Z₂ = Se Compound Se-218

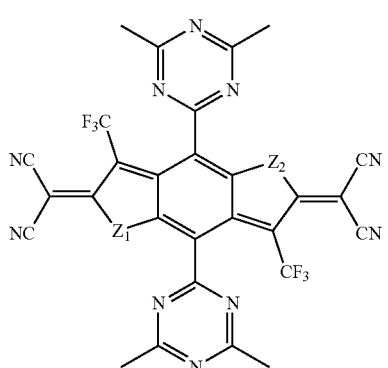

Z₁ = Z₂ = O Compound O-219
Z₁ = Z₂ = S Compound S-219
Z₁ = Z₂ = Se Compound Se-219

-continued

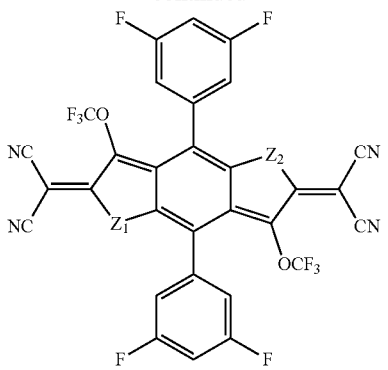

Z₁ = Z₂ = O Compound O-220
Z₁ = Z₂ = S Compound S-220
Z₁ = Z₂ = Se Compound Se-220

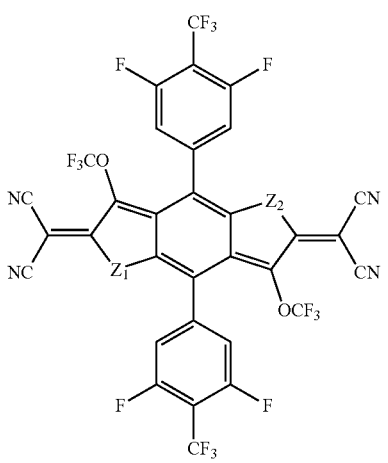

Z₁ = Z₂ = O Compound O-221
Z₁ = Z₂ = S Compound S-221
Z₁ = Z₂ = Se Compound Se-221

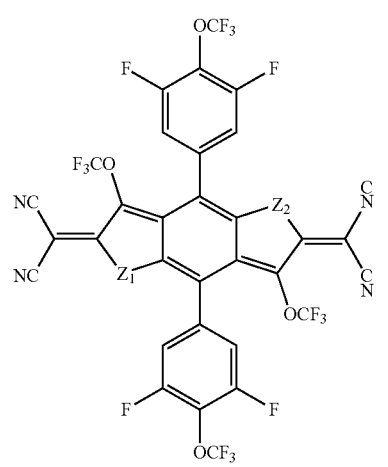

Z₁ = Z₂ = O Compound O-222
Z₁ = Z₂ = S Compound S-222
Z₁ = Z₂ = Se Compound Se-222

-continued

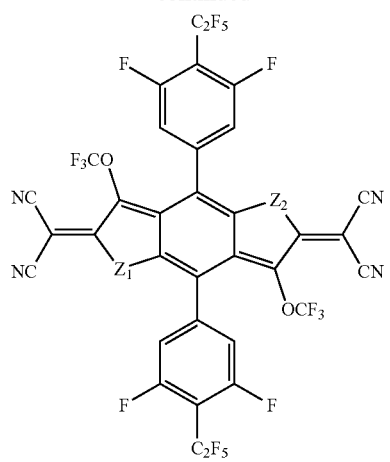

Z$_1$ = Z$_2$ = O Compound O-223
Z$_1$ = Z$_2$ = S Compound S-223
Z$_1$ = Z$_2$ = Se Compound Se-223

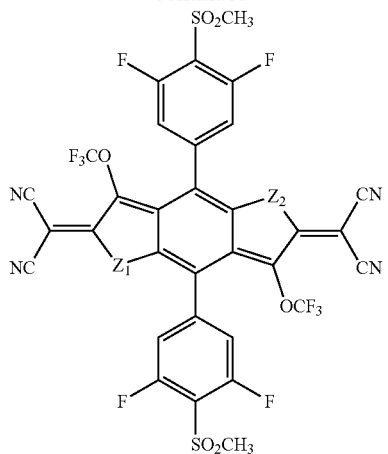

Z$_1$ = Z$_2$ = O Compound O-226
Z$_1$ = Z$_2$ = S Compound S-226
Z$_1$ = Z$_2$ = Se Compound Se-226

-continued

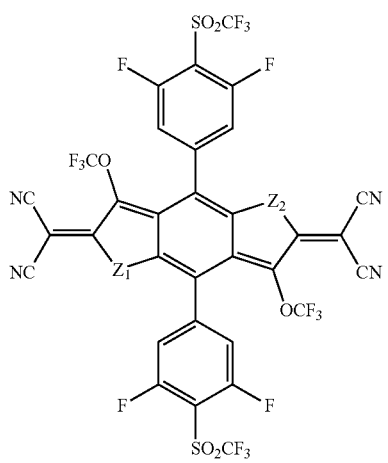

Z$_1$ = Z$_2$ = O Compound O-224
Z$_1$ = Z$_2$ = S Compound S-224
Z$_1$ = Z$_2$ = Se Compound Se-224

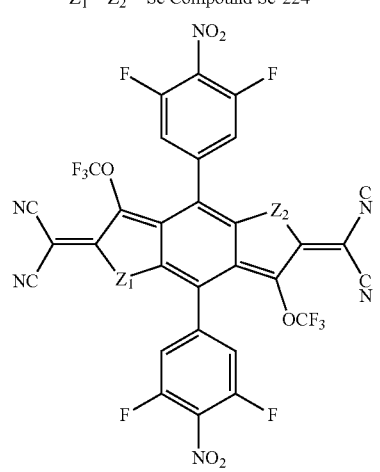

Z$_1$ = Z$_2$ = O Compound O-227
Z$_1$ = Z$_2$ = S Compound S-227
Z$_1$ = Z$_2$ = Se Compound Se-227

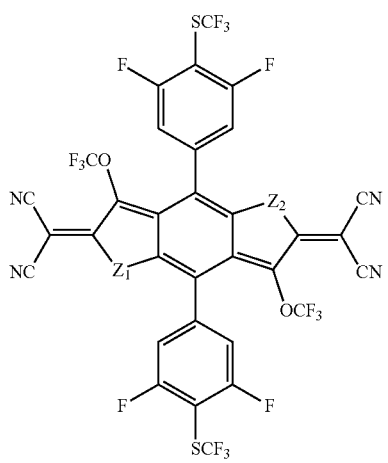

Z$_1$ = Z$_2$ = O Compound O-225
Z$_1$ = Z$_2$ = S Compound S-225
Z$_1$ = Z$_2$ = Se Compound Se-225

Z$_1$ = Z$_2$ = O Compound O-228
Z$_1$ = Z$_2$ = S Compound S-228
Z$_1$ = Z$_2$ = Se Compound Se-228

-continued

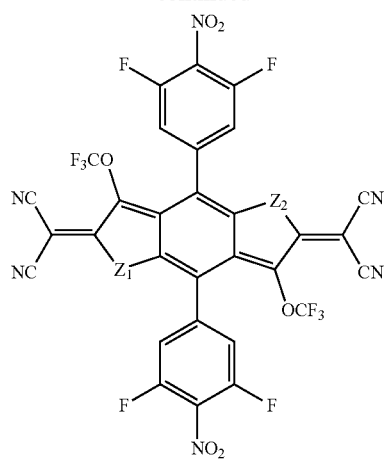

$Z_1 = Z_2 = O$ Compound O-229
$Z_1 = Z_2 = S$ Compound S-229
$Z_1 = Z_2 = Se$ Compound Se-229

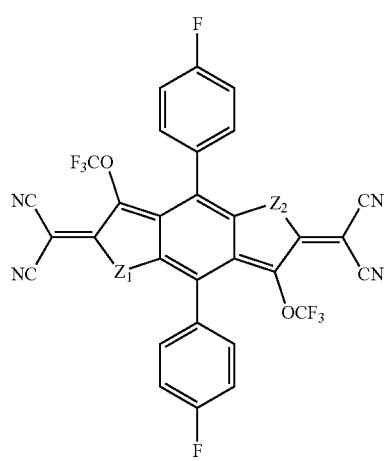

$Z_1 = Z_2 = O$ Compound O-230
$Z_1 = Z_2 = S$ Compound S-230
$Z_1 = Z_2 = Se$ Compound Se-230

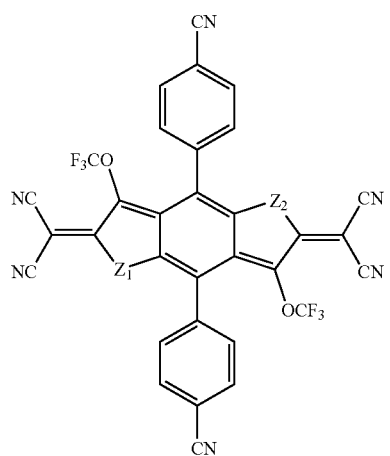

$Z_1 = Z_2 = O$ Compound O-231
$Z_1 = Z_2 = S$ Compound S-231
$Z_1 = Z_2 = Se$ Compound Se-231

-continued

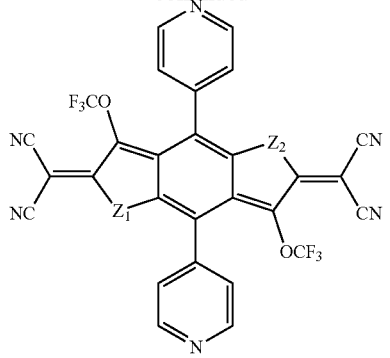

$Z_1 = Z_2 = O$ Compound O-232
$Z_1 = Z_2 = S$ Compound S-232
$Z_1 = Z_2 = Se$ Compound Se-232

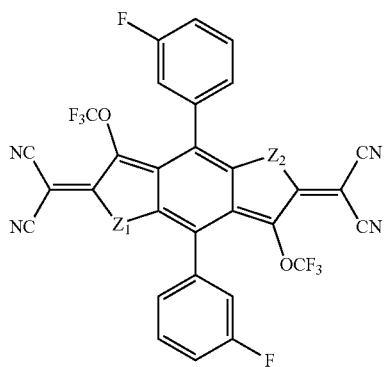

$Z_1 = Z_2 = O$ Compound O-233
$Z_1 = Z_2 = S$ Compound S-233
$Z_1 = Z_2 = Se$ Compound Se-233

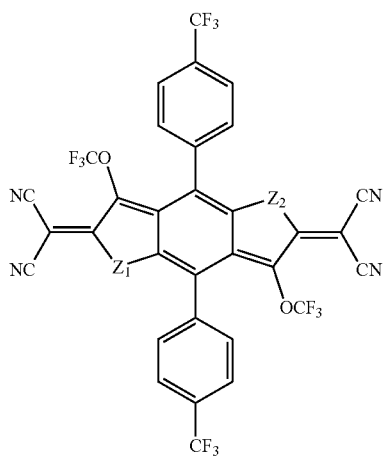

$Z_1 = Z_2 = O$ Compound O-234
$Z_1 = Z_2 = S$ Compound S-234
$Z_1 = Z_2 = Se$ Compound Se-234

107
-continued

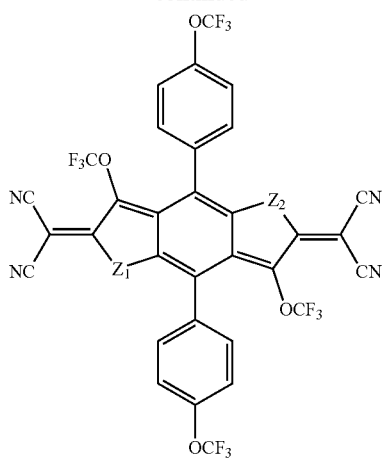

Z₁ = Z₂ = O Compound O-235
Z₁ = Z₂ = S Compound S-235
Z₁ = Z₂ = Se Compound Se-235

108
-continued

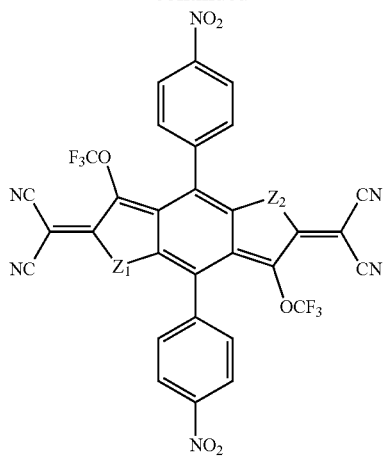

Z₁ = Z₂ = O Compound O-238
Z₁ = Z₂ = S Compound S-238
Z₁ = Z₂ = Se Compound Se-238

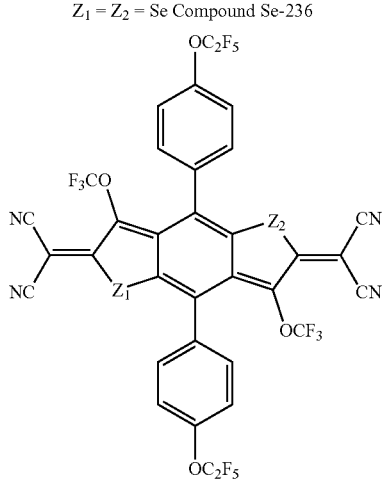

Z₁ = Z₂ = O Compound O-236
Z₁ = Z₂ = S Compound S-236
Z₁ = Z₂ = Se Compound Se-236

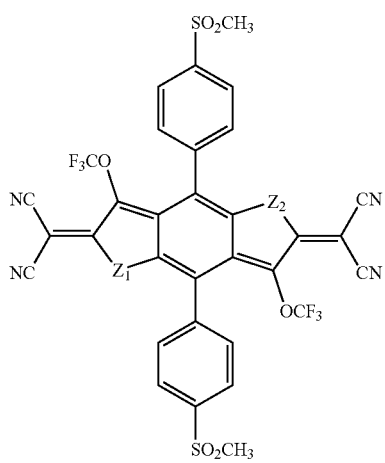

Z₁ = Z₂ = O Compound O-239
Z₁ = Z₂ = S Compound S-239
Z₁ = Z₂ = Se Compound Se-239

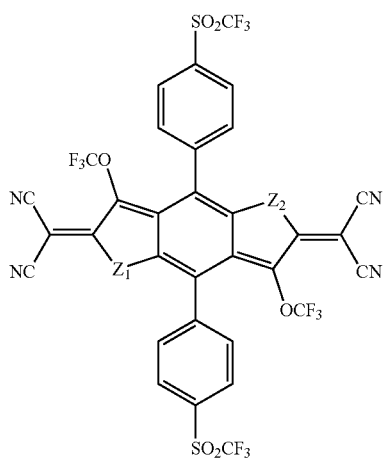

Z₁ = Z₂ = O Compound O-237
Z₁ = Z₂ = S Compound S-237
Z₁ = Z₂ = Se Compound Se-237

Z₁ = Z₂ = O Compound O-240
Z₁ = Z₂ = S Compound S-240
Z₁ = Z₂ = Se Compound Se-240

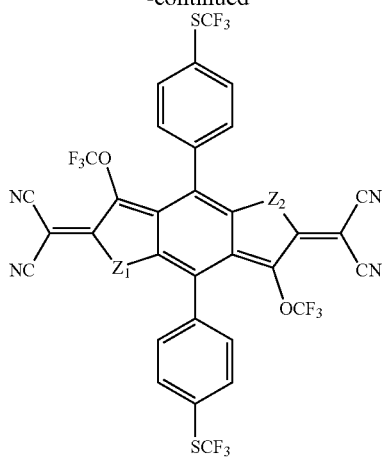

Z₁ = Z₂ = O Compound O-241
Z₁ = Z₂ = S Compound S-241
Z₁ = Z₂ = Se Compound Se-241

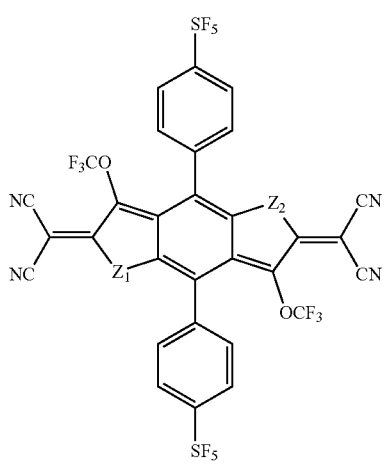

Z₁ = Z₂ = O Compound O-242
Z₁ = Z₂ = S Compound S-242
Z₁ = Z₂ = Se Compound Se-242

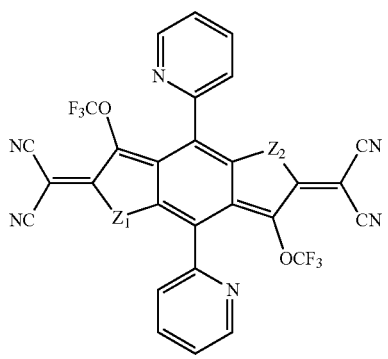

Z₁ = Z₂ = O Compound O-243
Z₁ = Z₂ = S Compound S-243
Z₁ = Z₂ = Se Compound Se-243

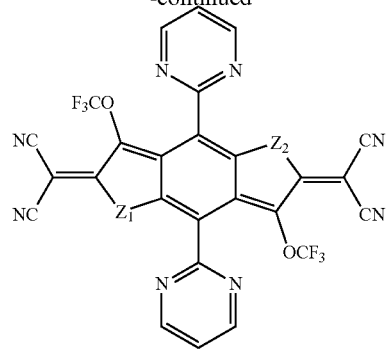

Z₁ = Z₂ = O Compound O-244
Z₁ = Z₂ = S Compound S-244
Z₁ = Z₂ = Se Compound Se-244

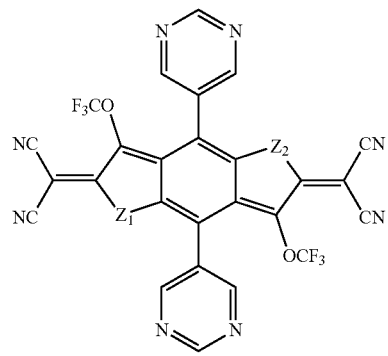

Z₁ = Z₂ = O Compound O-245
Z₁ = Z₂ = S Compound S-245
Z₁ = Z₂ = Se Compound Se-245

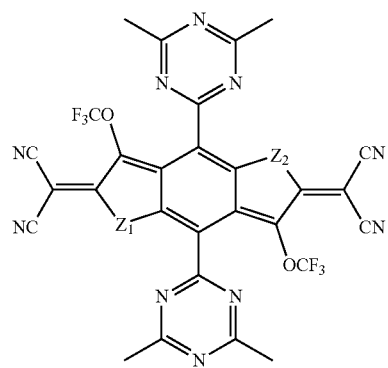

Z₁ = Z₂ = O Compound O-246
Z₁ = Z₂ = S Compound S-246
Z₁ = Z₂ = Se Compound Se-246

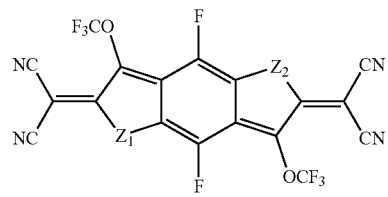

Z₁ = Z₂ = O Compound O-247
Z₁ = Z₂ = S Compound S-247
Z₁ = Z₂ = Se Compound Se-247

-continued

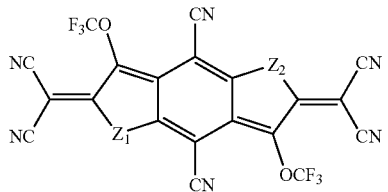

$Z_1 = Z_2 = O$ Compound O-248
$Z_1 = Z_2 = S$ Compound S-248
$Z_1 = Z_2 = Se$ Compound Se-248

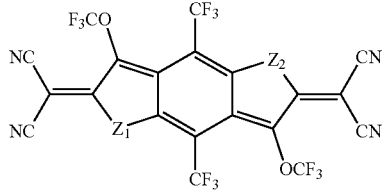

$Z_1 = Z_2 = O$ Compound O-249
$Z_1 = Z_2 = S$ Compound S-249
$Z_1 = Z_2 = Se$ Compound Se-249

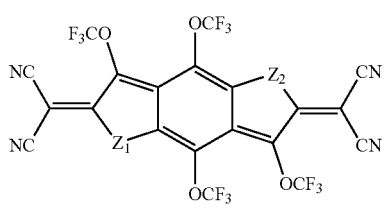

$Z_1 = Z_2 = O$ Compound O-250
$Z_1 = Z_2 = S$ Compound S-250
$Z_1 = Z_2 = Se$ Compound Se-250

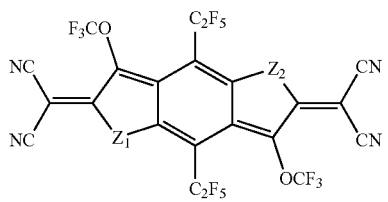

$Z_1 = Z_2 = O$ Compound O-251
$Z_1 = Z_2 = S$ Compound S-251
$Z_1 = Z_2 = Se$ Compound Se-251

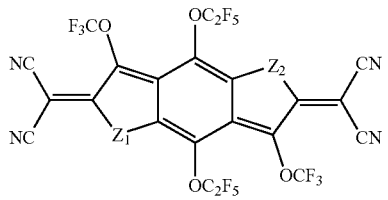

$Z_1 = Z_2 = O$ Compound O-252
$Z_1 = Z_2 = S$ Compound S-252
$Z_1 = Z_2 = Se$ Compound Se-252

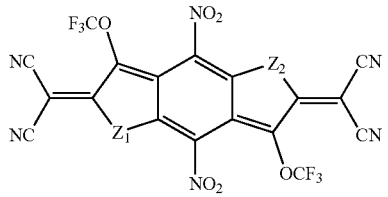

$Z_1 = Z_2 = O$ Compound O-253
$Z_1 = Z_2 = S$ Compound S-253
$Z_1 = Z_2 = Se$ Compound Se-253

-continued

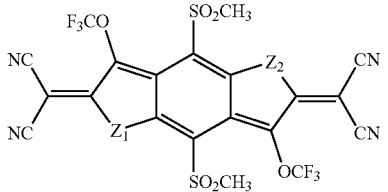

$Z_1 = Z_2 = O$ Compound O-254
$Z_1 = Z_2 = S$ Compound S-254
$Z_1 = Z_2 = Se$ Compound Se-254

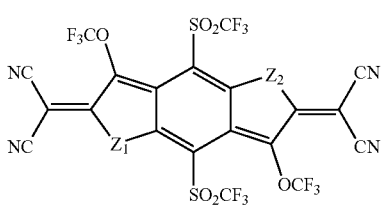

$Z_1 = Z_2 = O$ Compound O-255
$Z_1 = Z_2 = S$ Compound S-255
$Z_1 = Z_2 = Se$ Compound Se-255

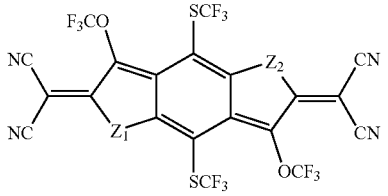

$Z_1 = Z_2 = O$ Compound O-256
$Z_1 = Z_2 = S$ Compound S-256
$Z_1 = Z_2 = Se$ Compound Se-256

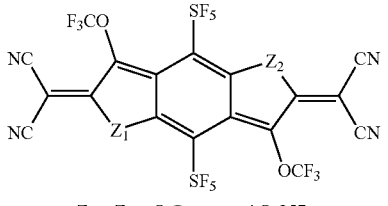

$Z_1 = Z_2 = O$ Compound O-257
$Z_1 = Z_2 = S$ Compound S-257
$Z_1 = Z_2 = Se$ Compound Se-257

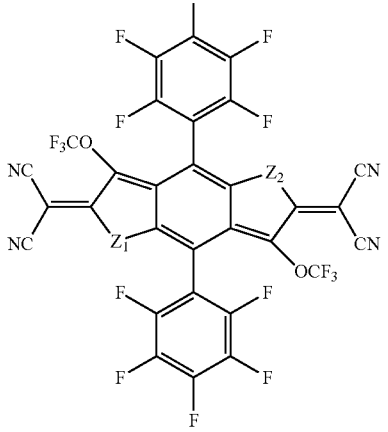

$Z_1 = Z_2 = O$ Compound O-258
$Z_1 = Z_2 = S$ Compound S-258
$Z_1 = Z_2 = Se$ Compound Se-258

-continued

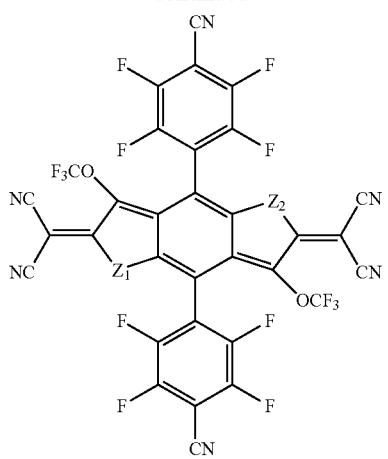

Z₁ = Z₂ = O Compound O-259
Z₁ = Z₂ = S Compound S-259
Z₁ = Z₂ = Se Compound Se-259

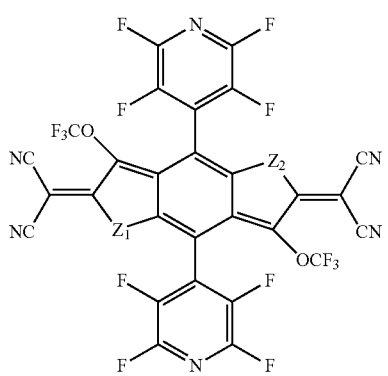

Z₁ = Z₂ = O Compound O-260
Z₁ = Z₂ = S Compound S-260
Z₁ = Z₂ = Se Compound Se-260

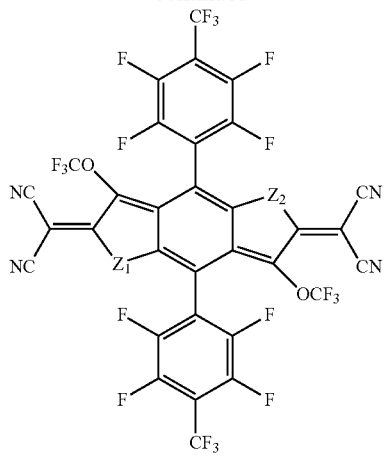

Z₁ = Z₂ = O Compound O-261
Z₁ = Z₂ = S Compound S-261
Z₁ = Z₂ = Se Compound Se-261

-continued

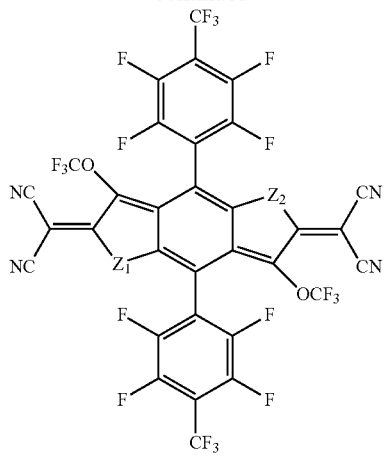

Z₁ = Z₂ = O Compound O-262
Z₁ = Z₂ = S Compound S-262
Z₁ = Z₂ = Se Compound Se-262

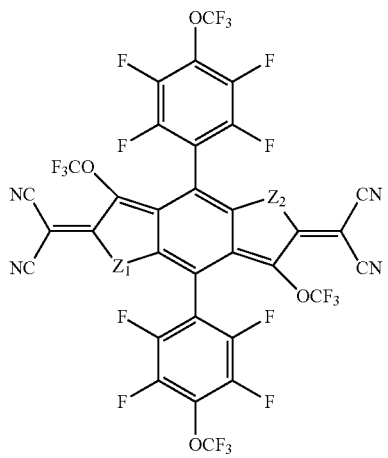

Z₁ = Z₂ = O Compound O-263
Z₁ = Z₂ = S Compound S-263
Z₁ = Z₂ = Se Compound Se-263

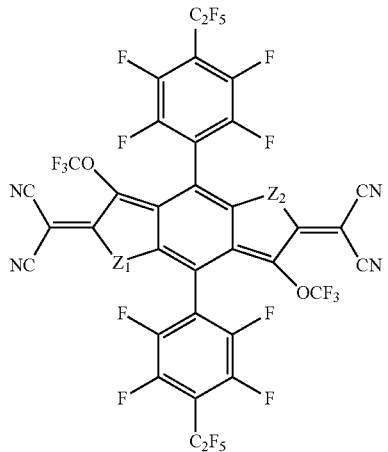

Z₁ = Z₂ = O Compound O-264
Z₁ = Z₂ = S Compound S-264
Z₁ = Z₂ = Se Compound Se-264

-continued

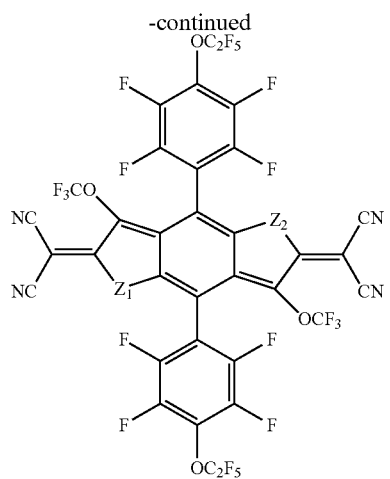

Z₁ = Z₂ = O Compound O-265
Z₁ = Z₂ = S Compound S-265
Z₁ = Z₂ = Se Compound Se-265

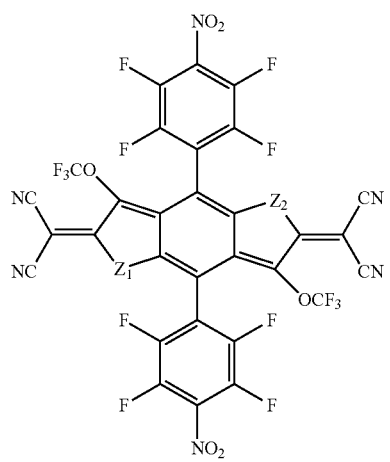

Z₁ = Z₂ = O Compound O-266
Z₁ = Z₂ = S Compound S-266
Z₁ = Z₂ = Se Compound Se-266

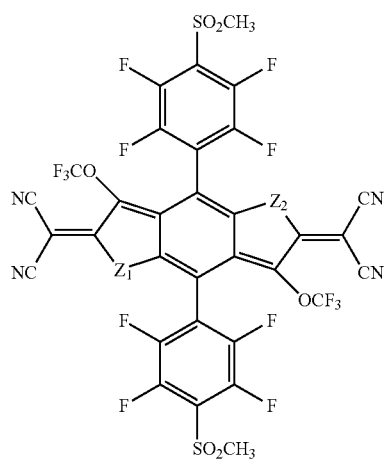

Z₁ = Z₂ = O Compound O-267
Z₁ = Z₂ = S Compound S-267
Z₁ = Z₂ = Se Compound Se-267

-continued

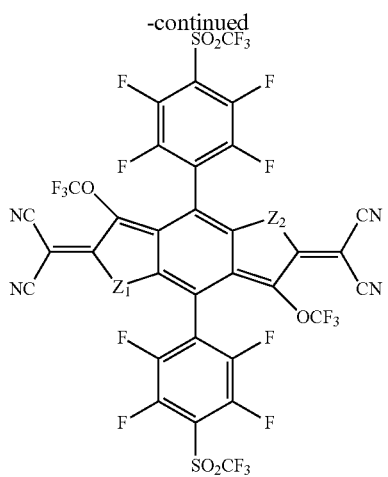

Z₁ = Z₂ = O Compound O-268
Z₁ = Z₂ = S Compound S-268
Z₁ = Z₂ = Se Compound Se-268

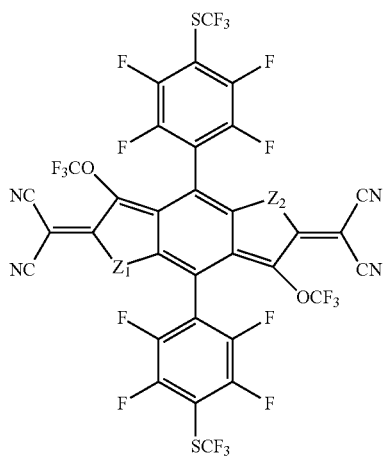

Z₁ = Z₂ = O Compound O-269
Z₁ = Z₂ = S Compound S-269
Z₁ = Z₂ = Se Compound Se-269

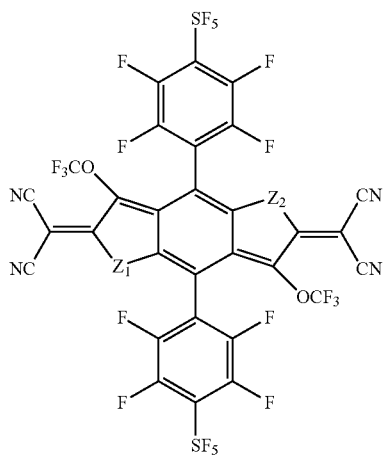

Z₁ = Z₂ = O Compound O-270
Z₁ = Z₂ = S Compound S-270
Z₁ = Z₂ = Se Compound Se-270

-continued

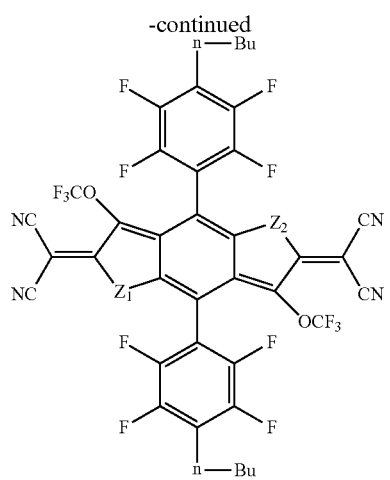

Z₁ = Z₂ = O Compound O-271
Z₁ = Z₂ = S Compound S-271
Z₁ = Z₂ = Se Compound Se-271

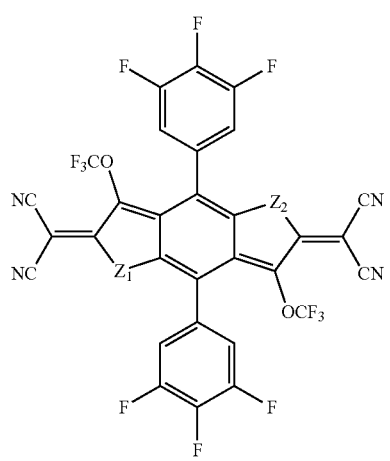

Z₁ = Z₂ = O Compound O-272
Z₁ = Z₂ = S Compound S-272
Z₁ = Z₂ = Se Compound Se-272

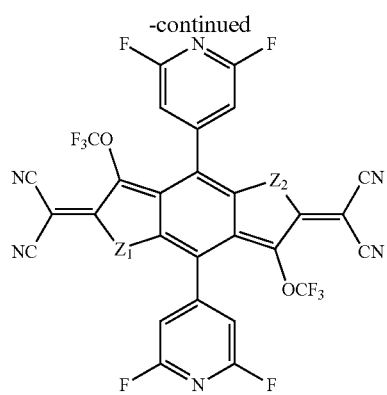

Z₁ = Z₂ = O Compound O-273
Z₁ = Z₂ = S Compound S-273
Z₁ = Z₂ = Se Compound Se-273

-continued

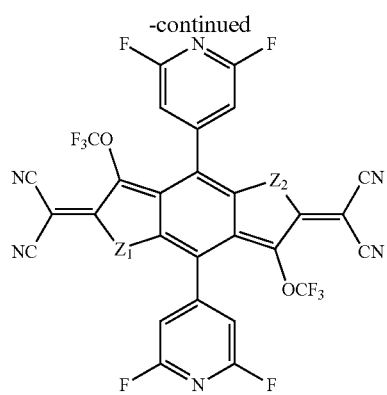

Z₁ = Z₂ = O Compound O-274
Z₁ = Z₂ = S Compound S-274
Z₁ = Z₂ = Se Compound Se-274

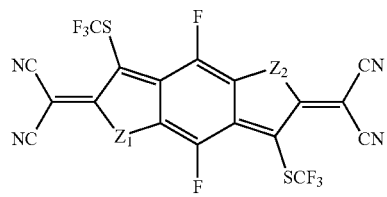

Z₁ = Z₂ = O Compound O-275
Z₁ = Z₂ = S Compound S-275
Z₁ = Z₂ = Se Compound Se-275

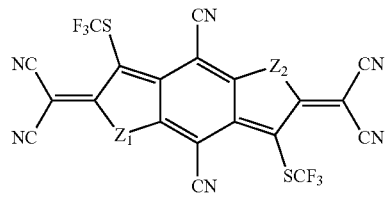

Z₁ = Z₂ = O Compound O-276
Z₁ = Z₂ = S Compound S-276
Z₁ = Z₂ = Se Compound Se-276

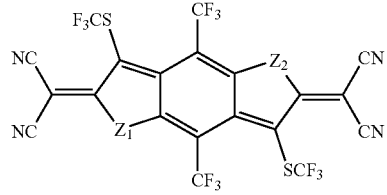

Z₁ = Z₂ = O Compound O-277
Z₁ = Z₂ = S Compound S-277
Z₁ = Z₂ = Se Compound Se-277

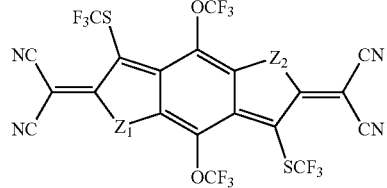

Z₁ = Z₂ = O Compound O-278
Z₁ = Z₂ = S Compound S-278
Z₁ = Z₂ = Se Compound Se-278

-continued

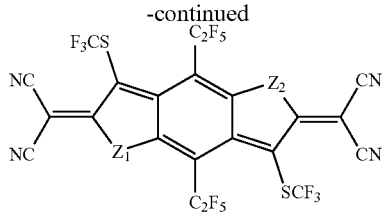

Z₁ = Z₂ = O Compound O-279
Z₁ = Z₂ = S Compound S-279
Z₁ = Z₂ = Se Compound Se-279

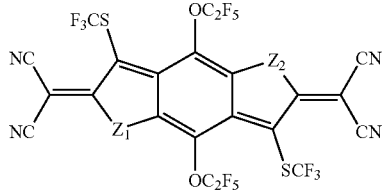

Z₁ = Z₂ = O Compound O-280
Z₁ = Z₂ = S Compound S-280
Z₁ = Z₂ = Se Compound Se-280

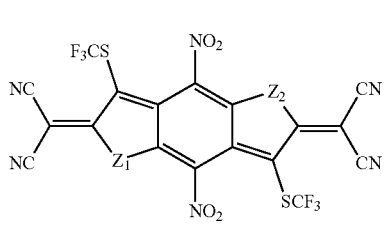

Z₁ = Z₂ = O Compound O-281
Z₁ = Z₂ = S Compound S-281
Z₁ = Z₂ = Se Compound Se-281

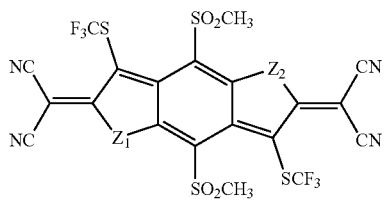

Z₁ = Z₂ = O Compound O-282
Z₁ = Z₂ = S Compound S-282
Z₁ = Z₂ = Se Compound Se-282

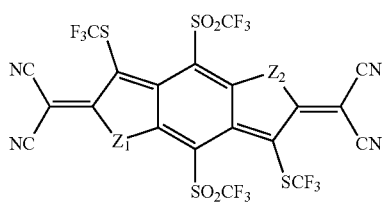

Z₁ = Z₂ = O Compound O-283
Z₁ = Z₂ = S Compound S-283
Z₁ = Z₂ = Se Compound Se-283

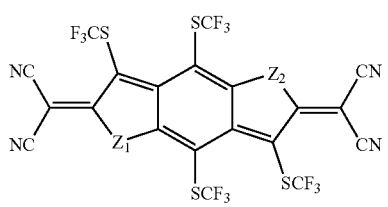

Z₁ = Z₂ = O Compound O-284
Z₁ = Z₂ = S Compound S-284
Z₁ = Z₂ = Se Compound Se-284

-continued

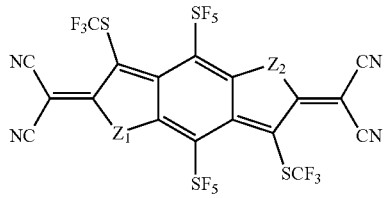

Z₁ = Z₂ = O Compound O-285
Z₁ = Z₂ = S Compound S-285
Z₁ = Z₂ = Se Compound Se-285

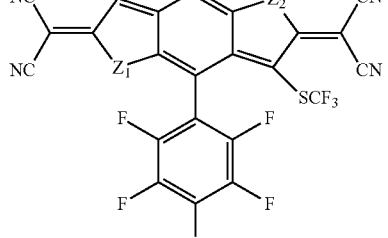

Z₁ = Z₂ = O Compound O-286
Z₁ = Z₂ = S Compound S-286
Z₁ = Z₂ = Se Compound Se-286

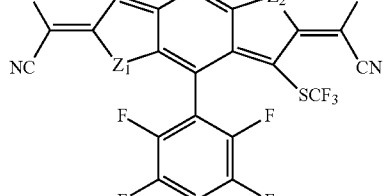

Z₁ = Z₂ = O Compound O-287
Z₁ = Z₂ = S Compound S-287
Z₁ = Z₂ = Se Compound Se-287

121
-continued

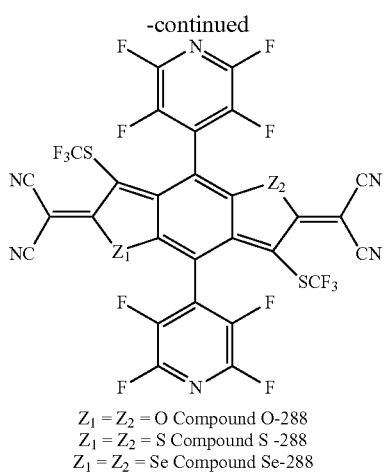

Z₁ = Z₂ = O Compound O-288
Z₁ = Z₂ = S Compound S-288
Z₁ = Z₂ = Se Compound Se-288

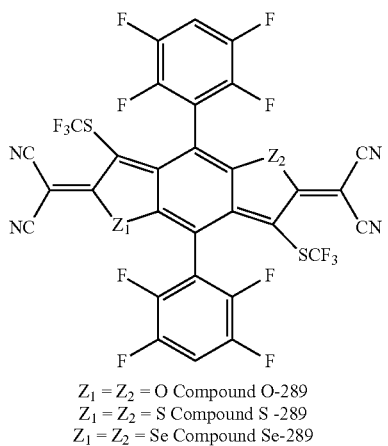

Z₁ = Z₂ = O Compound O-289
Z₁ = Z₂ = S Compound S-289
Z₁ = Z₂ = Se Compound Se-289

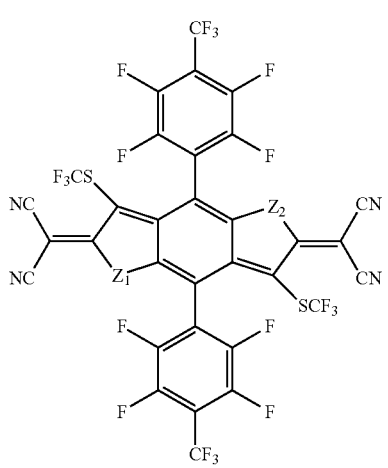

Z₁ = Z₂ = O Compound O-290
Z₁ = Z₂ = S Compound S-290
Z₁ = Z₂ = Se Compound Se-290

122
-continued

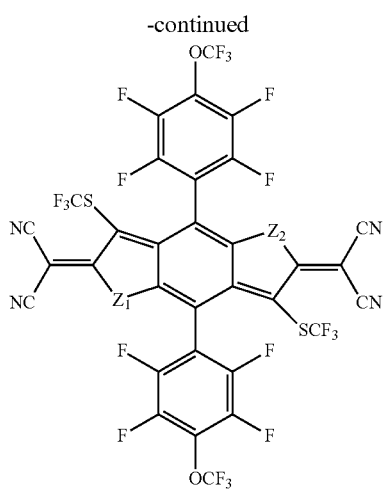

Z₁ = Z₂ = O Compound O-291
Z₁ = Z₂ = S Compound S-291
Z₁ = Z₂ = Se Compound Se-291

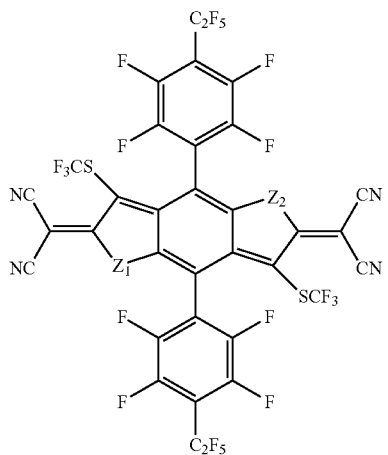

Z₁ = Z₂ = O Compound O-292
Z₁ = Z₂ = S Compound S-292
Z₁ = Z₂ = Se Compound Se-292

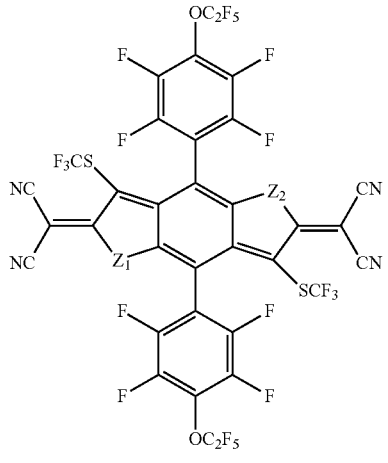

Z₁ = Z₂ = O Compound O-293
Z₁ = Z₂ = S Compound S-293
Z₁ = Z₂ = Se Compound Se-293

-continued

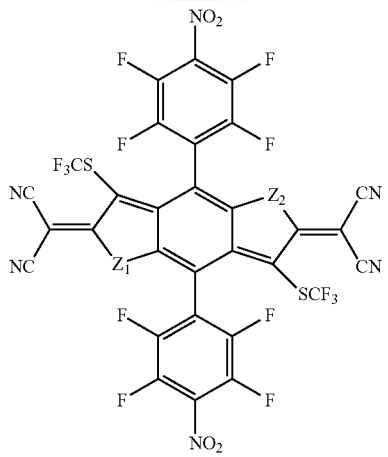

Z₁ = Z₂ = O Compound O-294
Z₁ = Z₂ = S Compound S-294
Z₁ = Z₂ = Se Compound Se-294

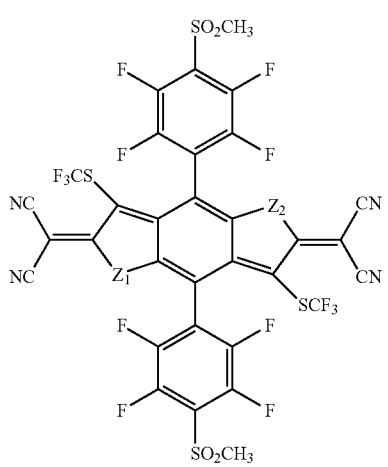

Z₁ = Z₂ = O Compound O-295
Z₁ = Z₂ = S Compound S-295
Z₁ = Z₂ = Se Compound Se-295

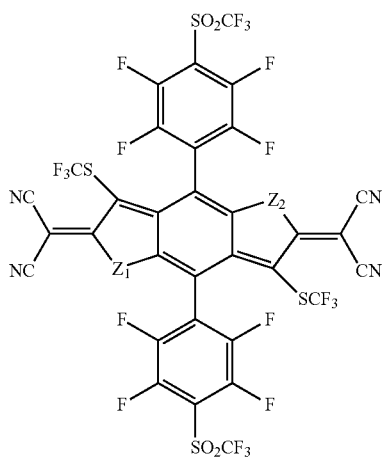

Z₁ = Z₂ = O Compound O-296
Z₁ = Z₂ = S Compound S-296
Z₁ = Z₂ = Se Compound Se-296

-continued

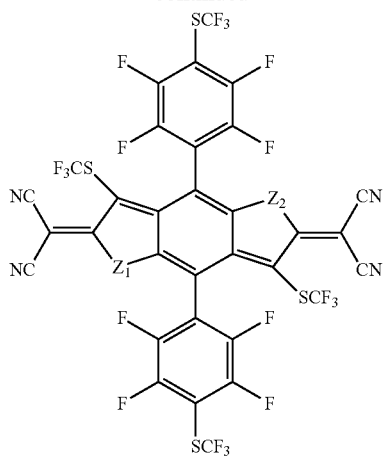

Z₁ = Z₂ = O Compound O-297
Z₁ = Z₂ = S Compound S-297
Z₁ = Z₂ = Se Compound Se-297

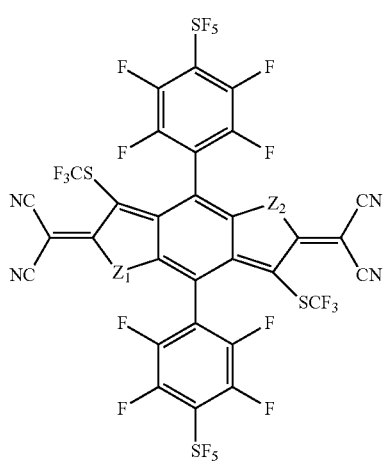

Z₁ = Z₂ = O Compound O-298
Z₁ = Z₂ = S Compound S-298
Z₁ = Z₂ = Se Compound Se-298

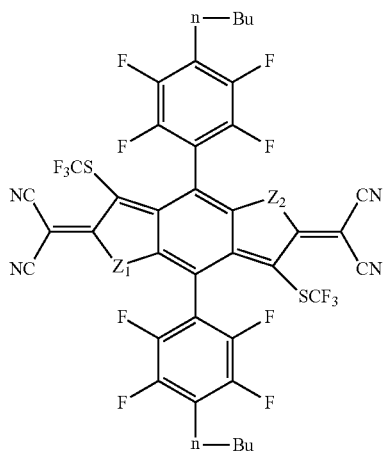

Z₁ = Z₂ = O Compound O-299
Z₁ = Z₂ = S Compound S-299
Z₁ = Z₂ = Se Compound Se-299

125
-continued

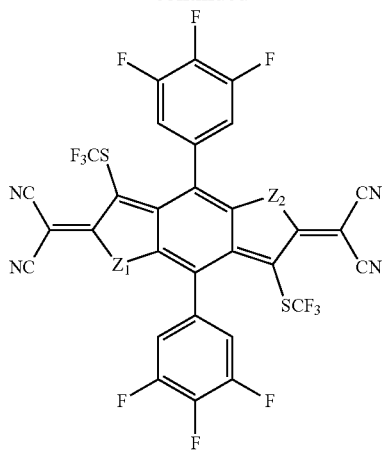

Z₁ = Z₂ = O Compound O-300
Z₁ = Z₂ = S Compound S-300
Z₁ = Z₂ = Se Compound Se-300

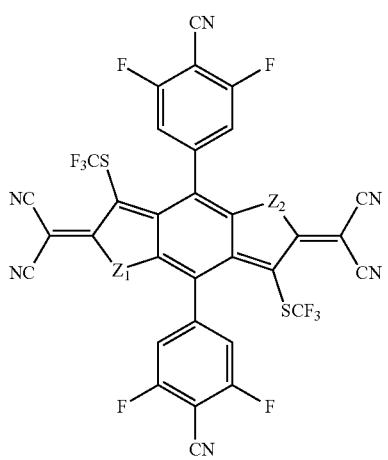

Z₁ = Z₂ = O Compound O-301
Z₁ = Z₂ = S Compound S-301
Z₁ = Z₂ = Se Compound Se-301

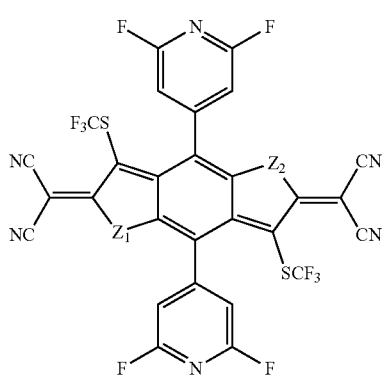

Z₁ = Z₂ = O Compound O-302
Z₁ = Z₂ = S Compound S-302
Z₁ = Z₂ = Se Compound Se-302

126
-continued

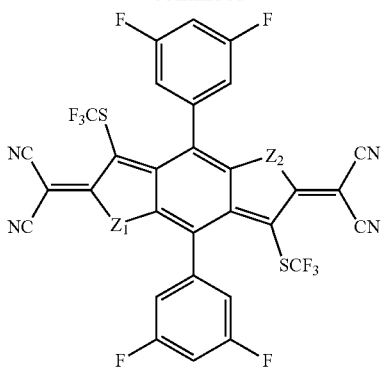

Z₁ = Z₂ = O Compound O-303
Z₁ = Z₂ = S Compound S-303
Z₁ = Z₂ = Se Compound Se-303

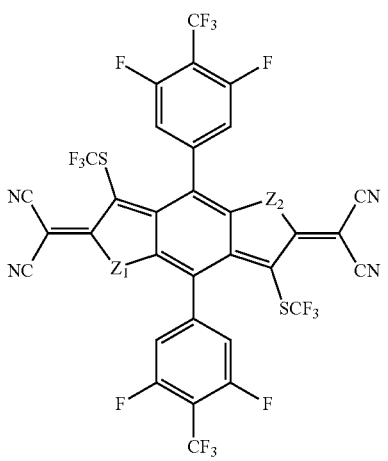

Z₁ = Z₂ = O Compound O-304
Z₁ = Z₂ = S Compound S-304
Z₁ = Z₂ = Se Compound Se-304

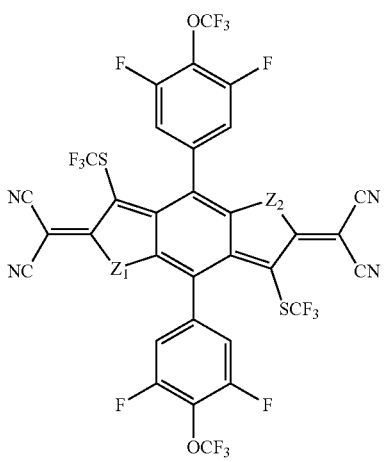

Z₁ = Z₂ = O Compound O-305
Z₁ = Z₂ = S Compound S-305
Z₁ = Z₂ = Se Compound Se-305

-continued

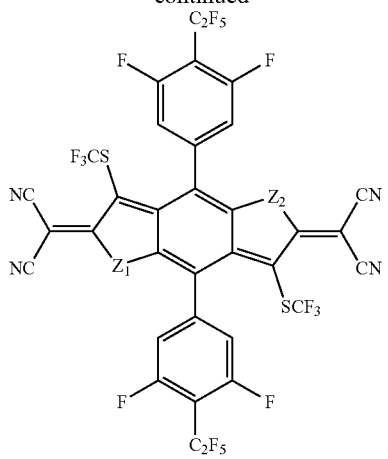

Z₁ = Z₂ = O Compound O-306
Z₁ = Z₂ = S Compound S-306
Z₁ = Z₂ = Se Compound Se-306

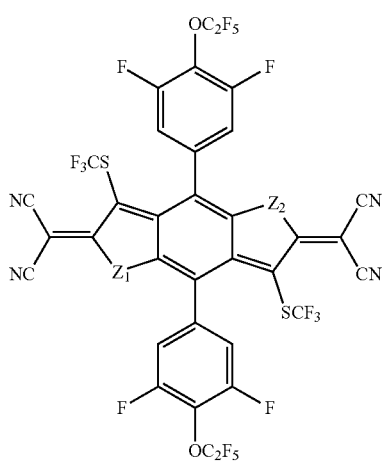

Z₁ = Z₂ = O Compound O-307
Z₁ = Z₂ = S Compound S-307
Z₁ = Z₂ = Se Compound Se-307

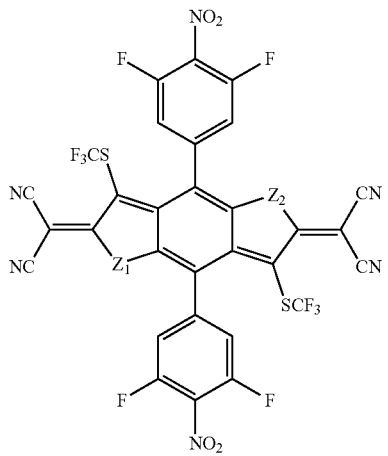

Z₁ = Z₂ = O Compound O-308
Z₁ = Z₂ = S Compound S-308
Z₁ = Z₂ = Se Compound Se-308

-continued

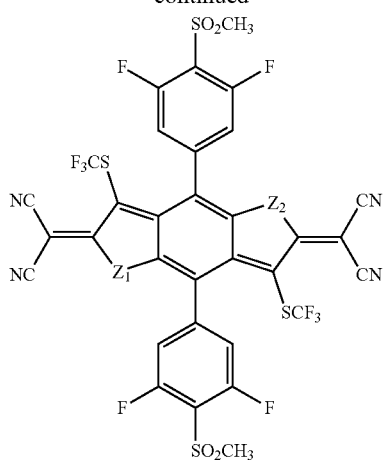

Z₁ = Z₂ = O Compound O-309
Z₁ = Z₂ = S Compound S-309
Z₁ = Z₂ = Se Compound Se-309

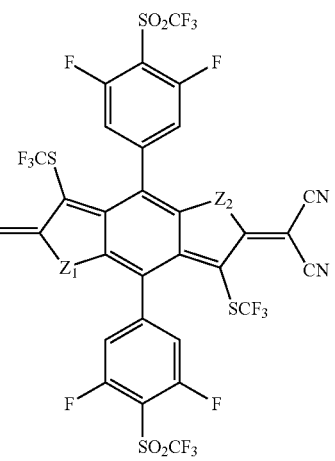

Z₁ = Z₂ = O Compound O-310
Z₁ = Z₂ = S Compound S-310
Z₁ = Z₂ = Se Compound Se-310

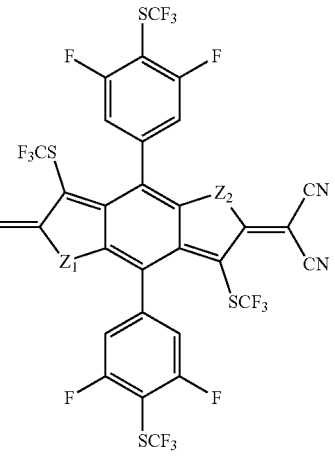

Z₁ = Z₂ = O Compound O-311
Z₁ = Z₂ = S Compound S-311
Z₁ = Z₂ = Se Compound Se-311

-continued

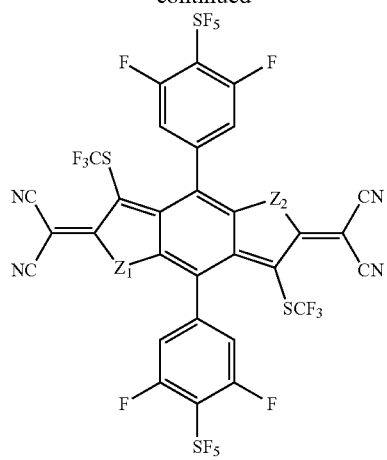

Z₁ = Z₂ = O Compound O-312
Z₁ = Z₂ = S Compound S-312
Z₁ = Z₂ = Se Compound Se-312

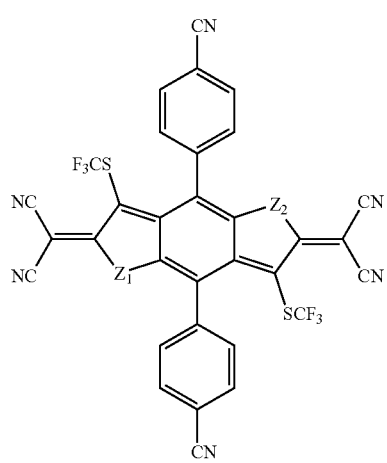

Z₁ = Z₂ = O Compound O-313
Z₁ = Z₂ = S Compound S-313
Z₁ = Z₂ = Se Compound Se-313

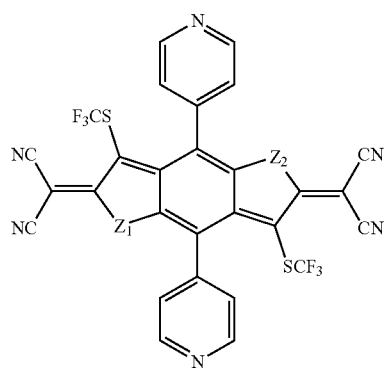

Z₁ = Z₂ = O Compound O-314
Z₁ = Z₂ = S Compound S-314
Z₁ = Z₂ = Se Compound Se-314

-continued

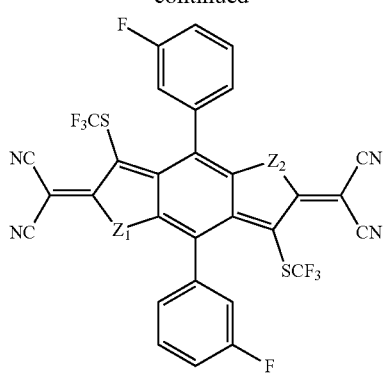

Z₁ = Z₂ = O Compound O-315
Z₁ = Z₂ = S Compound S-315
Z₁ = Z₂ = Se Compound Se-315

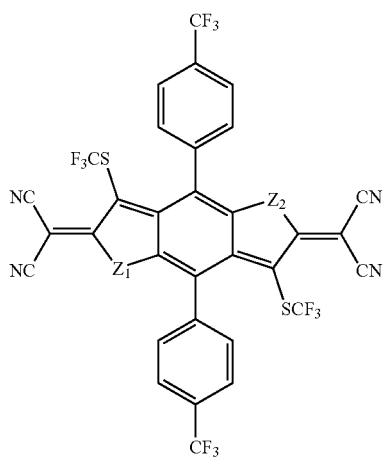

Z₁ = Z₂ = O Compound O-316
Z₁ = Z₂ = S Compound S-316
Z₁ = Z₂ = Se Compound Se-316

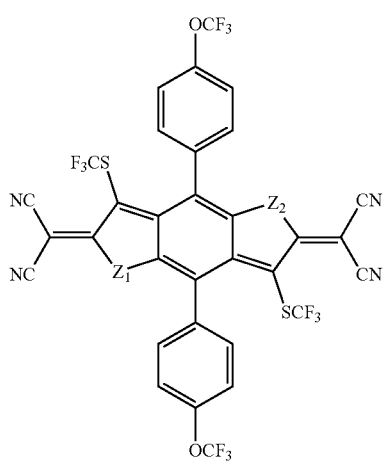

Z₁ = Z₂ = O Compound O-317
Z₁ = Z₂ = S Compound S-317
Z₁ = Z₂ = Se Compound Se-317

-continued

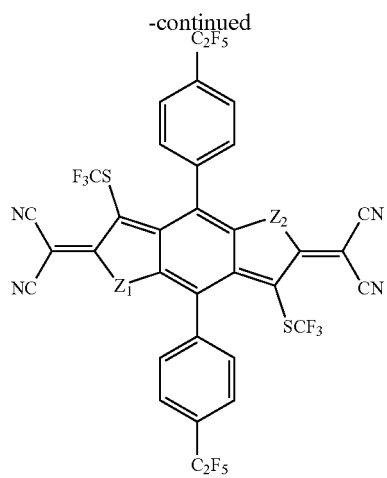

Z₁ = Z₂ = O Compound O-318
Z₁ = Z₂ = S Compound S-318
Z₁ = Z₂ = Se Compound Se-318

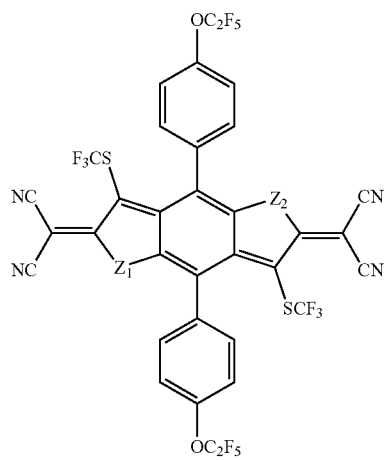

Z₁ = Z₂ = O Compound O-319
Z₁ = Z₂ = S Compound S-319
Z₁ = Z₂ = Se Compound Se-319

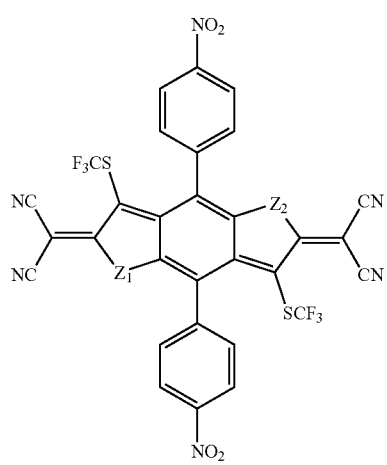

Z₁ = Z₂ = O Compound O-320
Z₁ = Z₂ = S Compound S-320
Z₁ = Z₂ = Se Compound Se-320

-continued

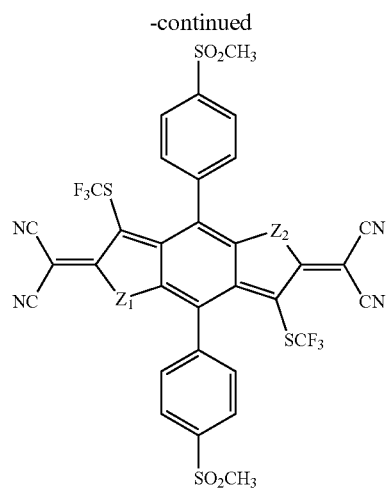

Z₁ = Z₂ = O Compound O-321
Z₁ = Z₂ = S Compound S-321
Z₁ = Z₂ = Se Compound Se-321

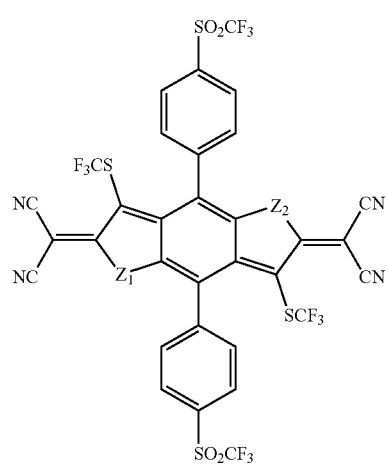

Z₁ = Z₂ = O Compound O-322
Z₁ = Z₂ = S Compound S-322
Z₁ = Z₂ = Se Compound Se-322

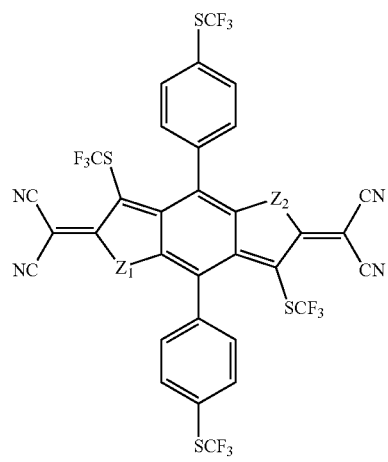

Z₁ = Z₂ = O Compound O-323
Z₁ = Z₂ = S Compound S-323
Z₁ = Z₂ = Se Compound Se-323

-continued

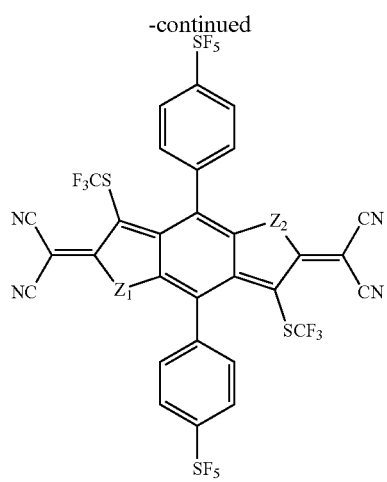

Z₁ = Z₂ = O Compound O-324
Z₁ = Z₂ = S Compound S-324
Z₁ = Z₂ = Se Compound Se-324

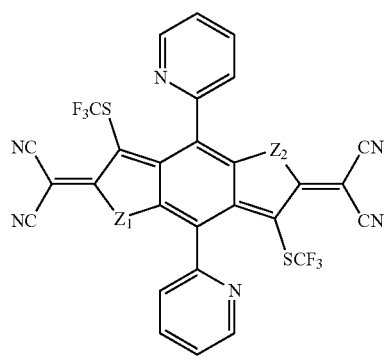

Z₁ = Z₂ = O Compound O-325
Z₁ = Z₂ = S Compound S-325
Z₁ = Z₂ = Se Compound Se-325

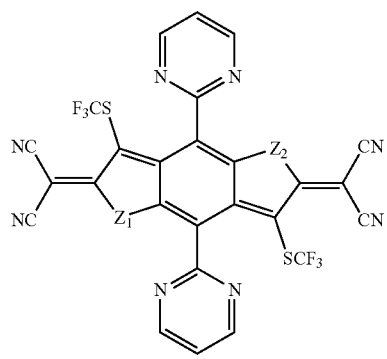

Z₁ = Z₂ = O Compound O-326
Z₁ = Z₂ = S Compound S-326
Z₁ = Z₂ = Se Compound Se-326

-continued

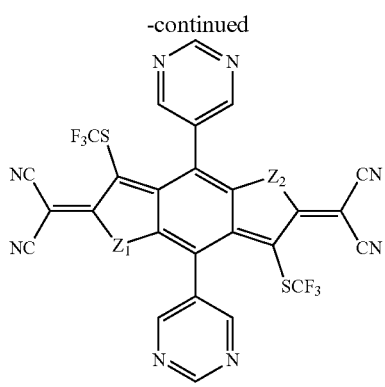

Z₁ = Z₂ = O Compound O-327
Z₁ = Z₂ = S Compound S-327
Z₁ = Z₂ = Se Compound Se-327

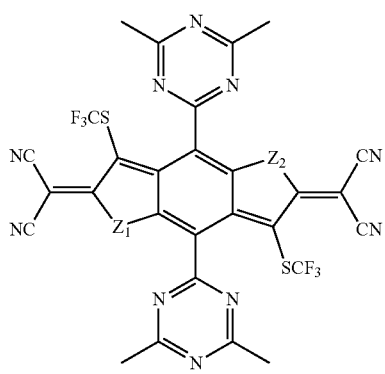

Z₁ = Z₂ = O Compound O-328
Z₁ = Z₂ = S Compound S-328
Z₁ = Z₂ = Se Compound Se-328

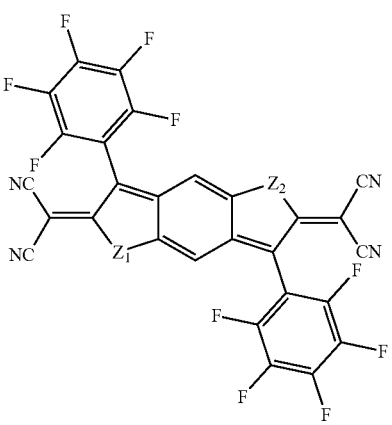

Z₁ = Z₂ = O Compound O-329
Z₁ = Z₂ = S Compound S-329
Z₁ = Z₂ = Se Compound Se-329

-continued

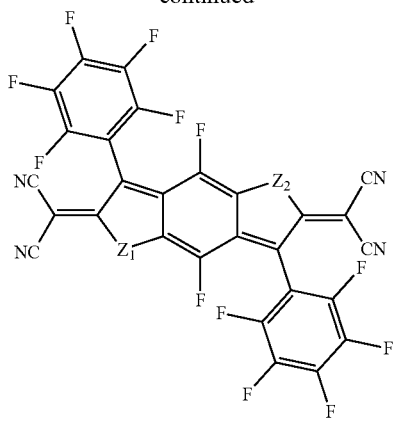

Z₁ = Z₂ = O Compound O-330
Z₁ = Z₂ = S Compound S-330
Z₁ = Z₂ = Se Compound Se-330

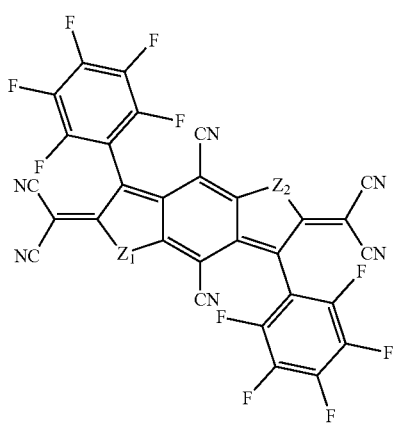

Z₁ = Z₂ = O Compound O-331
Z₁ = Z₂ = S Compound S-331
Z₁ = Z₂ = Se Compound Se-331

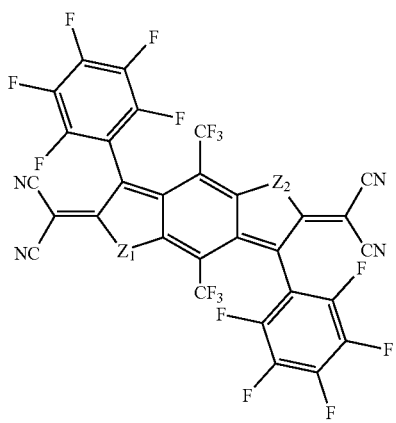

Z₁ = Z₂ = O Compound O-332
Z₁ = Z₂ = S Compound S-332
Z₁ = Z₂ = Se Compound Se-332

-continued

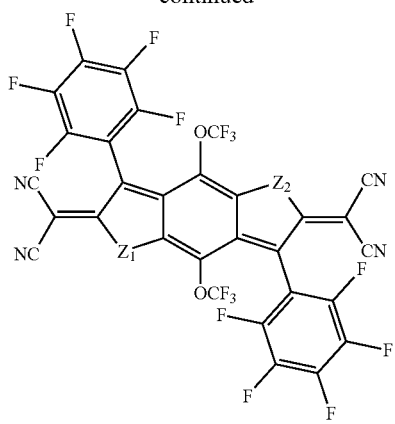

Z₁ = Z₂ = O Compound O-333
Z₁ = Z₂ = S Compound S-333
Z₁ = Z₂ = Se Compound Se-333

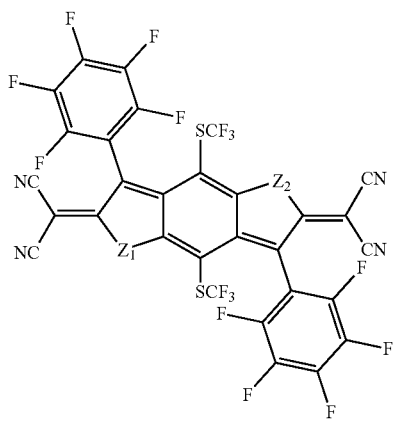

Z₁ = Z₂ = O Compound O-334
Z₁ = Z₂ = S Compound S-334
Z₁ = Z₂ = Se Compound Se-334

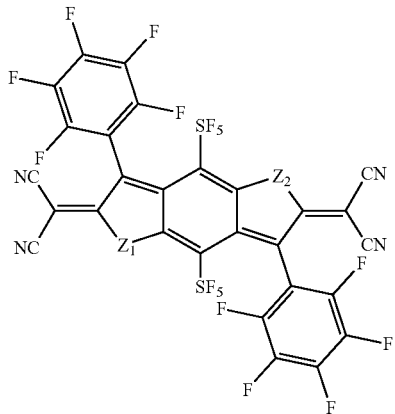

Z₁ = Z₂ = O Compound O-335
Z₁ = Z₂ = S Compound S-335
Z₁ = Z₂ = Se Compound Se-335

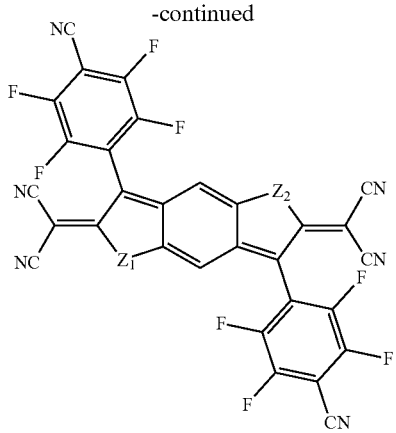

Z₁ = Z₂ = O Compound O-336
Z₁ = Z₂ = S Compound S-336
Z₁ = Z₂ = Se Compound Se-336

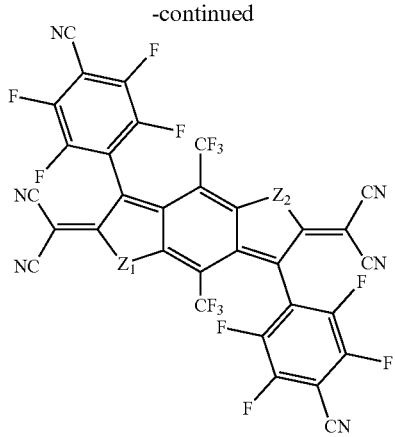

Z₁ = Z₂ = O Compound O-339
Z₁ = Z₂ = S Compound S-339
Z₁ = Z₂ = Se Compound Se-339

Z₁ = Z₂ = O Compound O-337
Z₁ = Z₂ = S Compound S-337
Z₁ = Z₂ = Se Compound Se-337

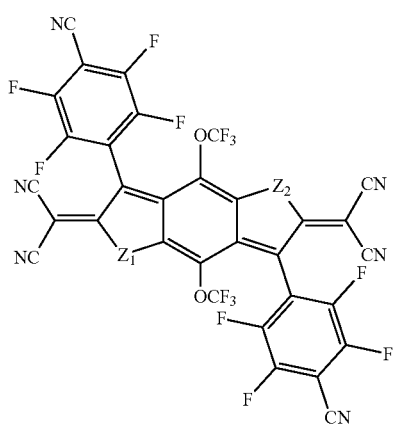

Z₁ = Z₂ = O Compound O-340
Z₁ = Z₂ = S Compound S-340
Z₁ = Z₂ = Se Compound Se-340

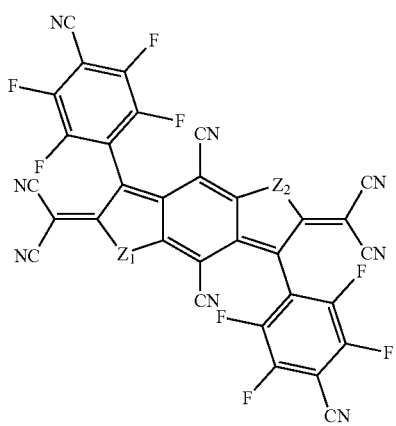

Z₁ = Z₂ = O Compound O-338
Z₁ = Z₂ = S Compound S-338
Z₁ = Z₂ = Se Compound Se-338

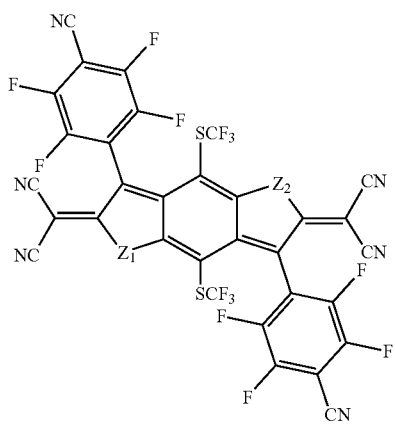

Z₁ = Z₂ = O Compound O-341
Z₁ = Z₂ = S Compound S-341
Z₁ = Z₂ = Se Compound Se-341

-continued

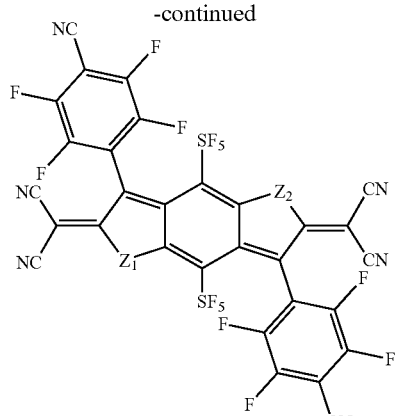

Z₁ = Z₂ = O Compound O-342
Z₁ = Z₂ = S Compound S-342
Z₁ = Z₂ = Se Compound Se-342

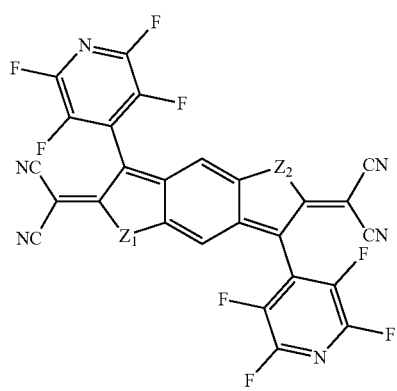

Z₁ = Z₂ = O Compound O-343
Z₁ = Z₂ = S Compound S-343
Z₁ = Z₂ = Se Compound Se-343

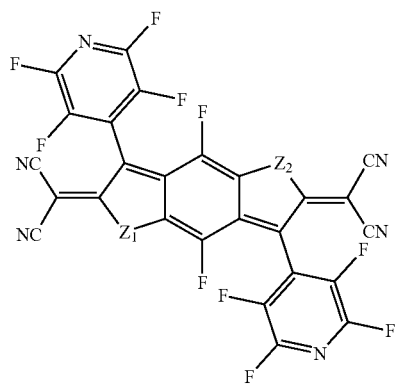

Z₁ = Z₂ = O Compound O-344
Z₁ = Z₂ = S Compound S-344
Z₁ = Z₂ = Se Compound Se-344

-continued

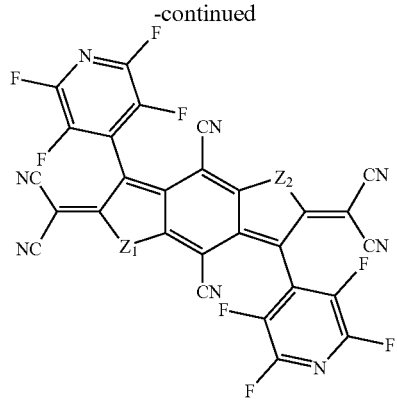

Z₁ = Z₂ = O Compound O-345
Z₁ = Z₂ = S Compound S-345
Z₁ = Z₂ = Se Compound Se-345

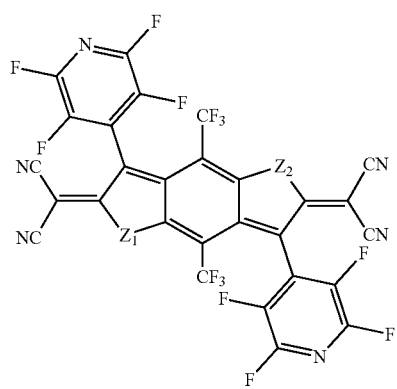

Z₁ = Z₂ = O Compound O-346
Z₁ = Z₂ = S Compound S-346
Z₁ = Z₂ = Se Compound Se-346

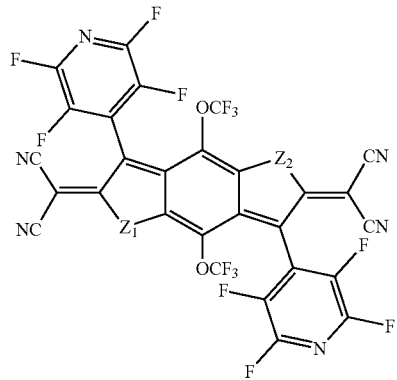

Z₁ = Z₂ = O Compound O-347
Z₁ = Z₂ = S Compound S-347
Z₁ = Z₂ = Se Compound Se-347

-continued

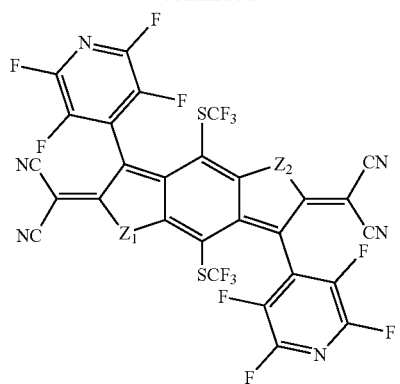

Z₁ = Z₂ = O Compound O-348
Z₁ = Z₂ = S Compound S-348
Z₁ = Z₂ = Se Compound Se-348

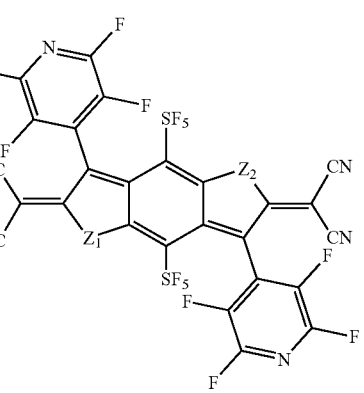

Z₁ = Z₂ = O Compound O-349
Z₁ = Z₂ = S Compound S-349
Z₁ = Z₂ = Se Compound Se-349

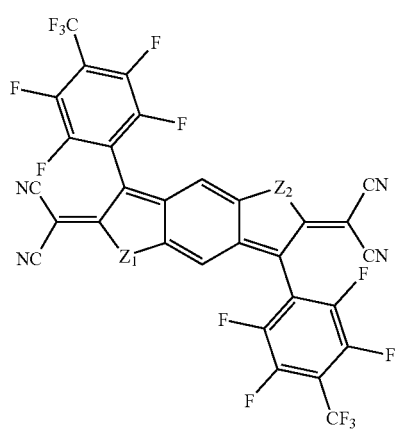

Z₁ = Z₂ = O Compound O-350
Z₁ = Z₂ = S Compound S-350
Z₁ = Z₂ = Se Compound Se-350

-continued

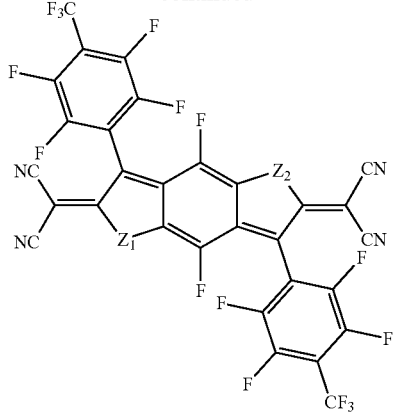

Z₁ = Z₂ = O Compound O-351
Z₁ = Z₂ = S Compound S-351
Z₁ = Z₂ = Se Compound Se-351

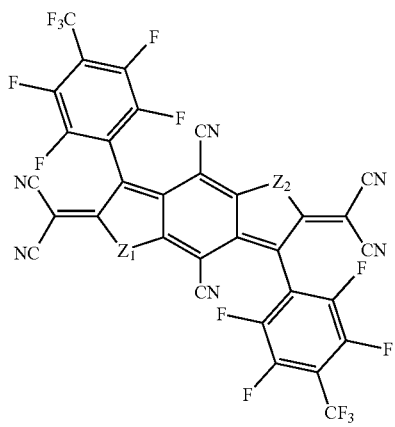

Z₁ = Z₂ = O Compound O-352
Z₁ = Z₂ = S Compound S-352
Z₁ = Z₂ = Se Compound Se-352

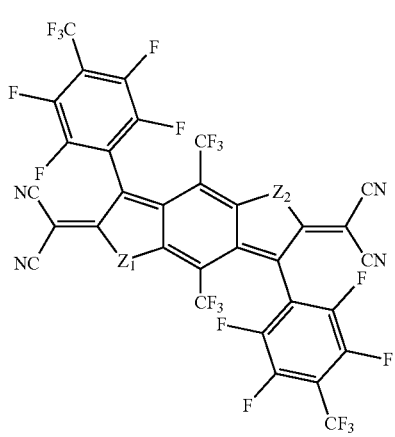

Z₁ = Z₂ = O Compound O-353
Z₁ = Z₂ = S Compound S-353
Z₁ = Z₂ = Se Compound Se-353

-continued

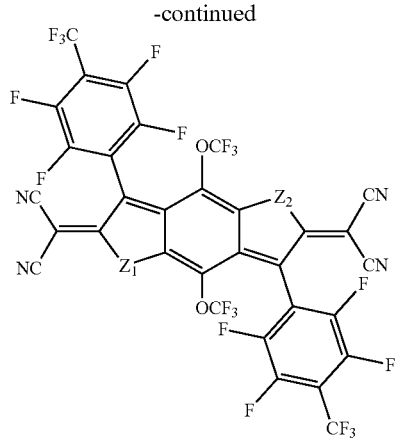

Z₁ = Z₂ = O Compound O-354
Z₁ = Z₂ = S Compound S-354
Z₁ = Z₂ = Se Compound Se-354

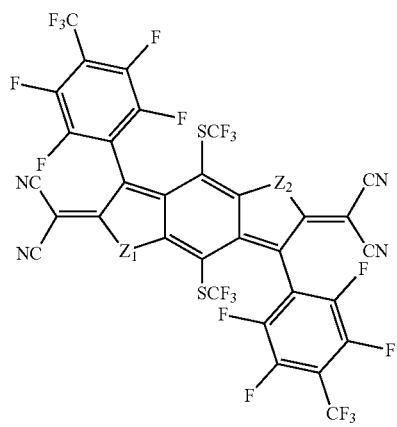

Z₁ = Z₂ = O Compound O-355
Z₁ = Z₂ = S Compound S-355
Z₁ = Z₂ = Se Compound Se-355

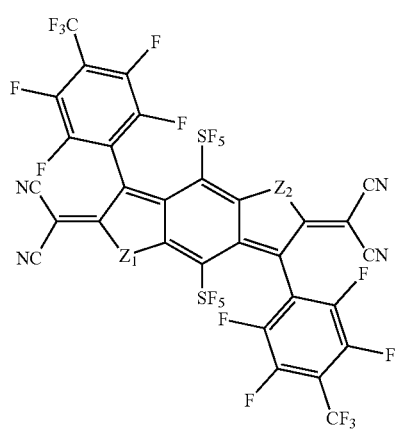

Z₁ = Z₂ = O Compound O-356
Z₁ = Z₂ = S Compound S-356
Z₁ = Z₂ = Se Compound Se-356

-continued

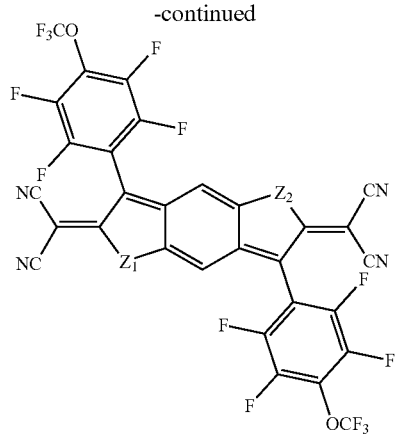

Z₁ = Z₂ = O Compound O-357
Z₁ = Z₂ = S Compound S-357
Z₁ = Z₂ = Se Compound Se-357

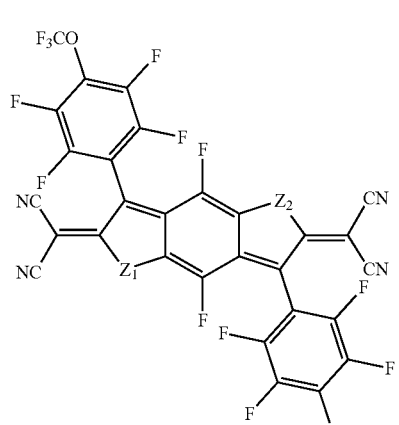

Z₁ = Z₂ = O Compound O-358
Z₁ = Z₂ = S Compound S-358
Z₁ = Z₂ = Se Compound Se-358

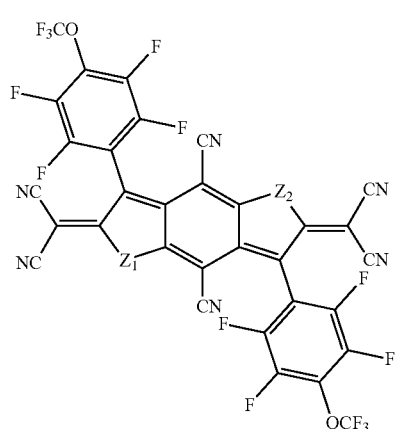

Z₁ = Z₂ = O Compound O-359
Z₁ = Z₂ = S Compound S-359
Z₁ = Z₂ = Se Compound Se-359

-continued

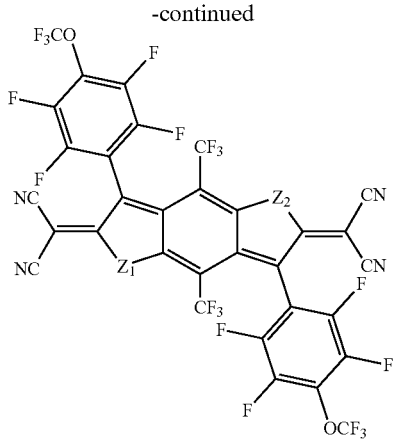

Z₁ = Z₂ = O Compound O-360
Z₁ = Z₂ = S Compound S-360
Z₁ = Z₂ = Se Compound Se-360

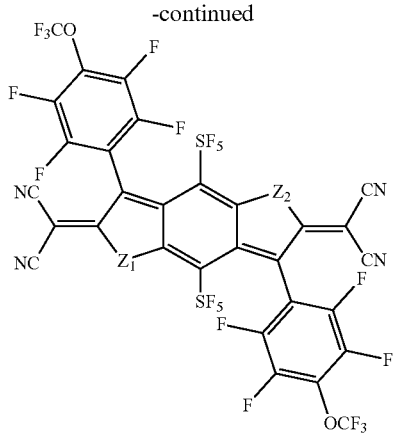

Z₁ = Z₂ = O Compound O-363
Z₁ = Z₂ = S Compound S-363
Z₁ = Z₂ = Se Compound Se-363

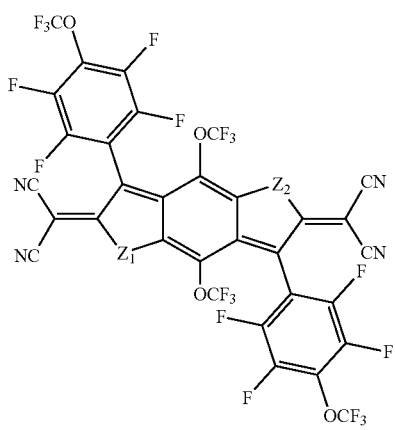

Z₁ = Z₂ = O Compound O-361
Z₁ = Z₂ = S Compound S-361
Z₁ = Z₂ = Se Compound Se-361

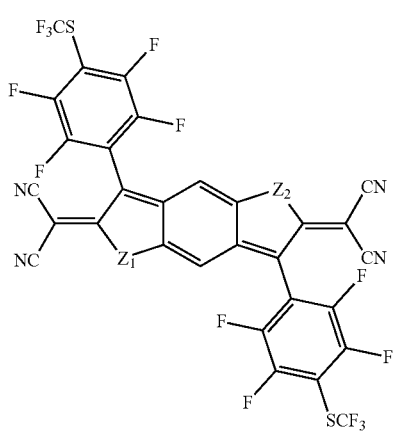

Z₁ = Z₂ = O Compound O-364
Z₁ = Z₂ = S Compound S-364
Z₁ = Z₂ = Se Compound Se-364

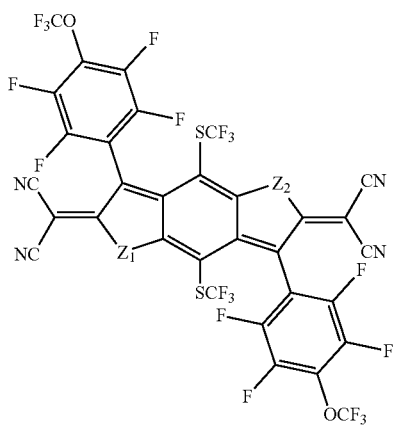

Z₁ = Z₂ = O Compound O-362
Z₁ = Z₂ = S Compound S-362
Z₁ = Z₂ = Se Compound Se-362

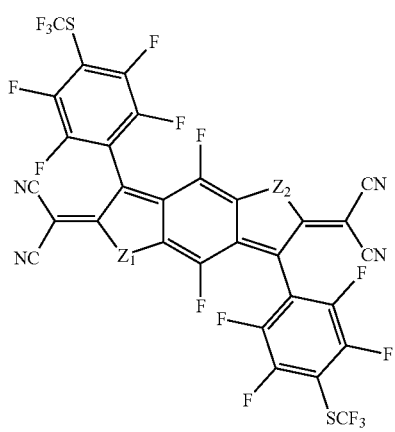

Z₁ = Z₂ = O Compound O-365
Z₁ = Z₂ = S Compound S-365
Z₁ = Z₂ = Se Compound Se-365

-continued

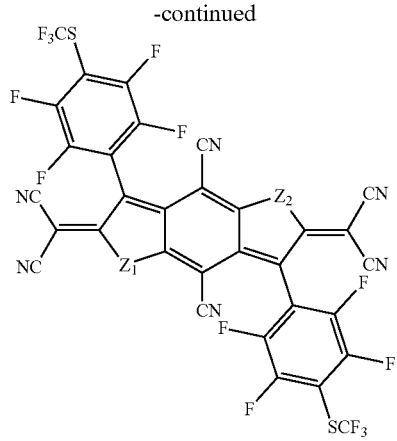

Z₁ = Z₂ = O Compound O-366
Z₁ = Z₂ = S Compound S-366
Z₁ = Z₂ = Se Compound Se-366

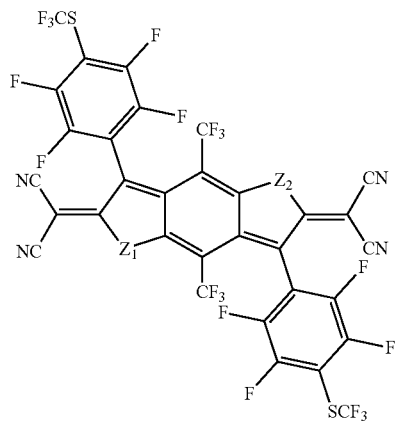

Z₁ = Z₂ = O Compound O-367
Z₁ = Z₂ = S Compound S-367
Z₁ = Z₂ = Se Compound Se-367

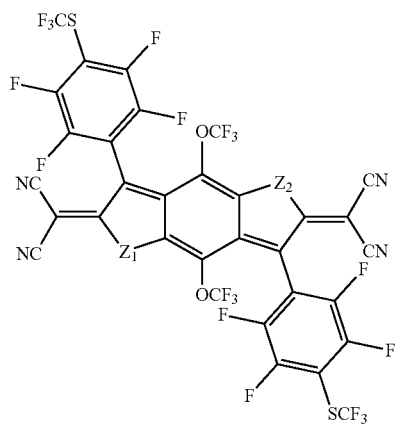

Z₁ = Z₂ = O Compound O-368
Z₁ = Z₂ = S Compound S-368
Z₁ = Z₂ = Se Compound Se-368

-continued

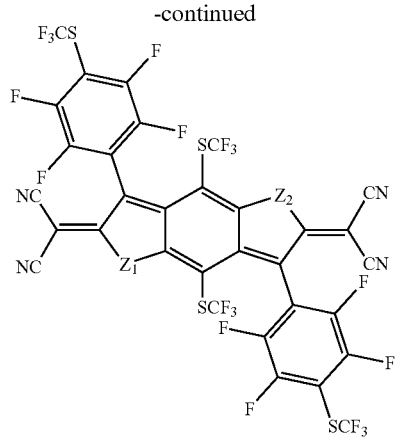

Z₁ = Z₂ = O Compound O-369
Z₁ = Z₂ = S Compound S-369
Z₁ = Z₂ = Se Compound Se-369

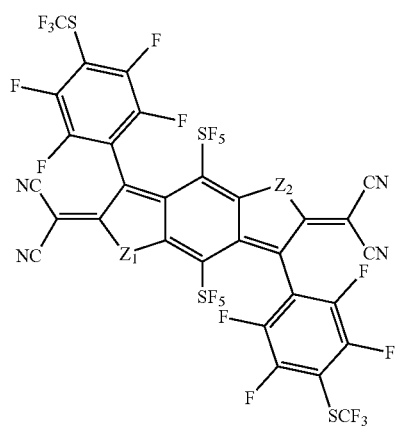

Z₁ = Z₂ = O Compound O-370
Z₁ = Z₂ = S Compound S-370
Z₁ = Z₂ = Se Compound Se-370

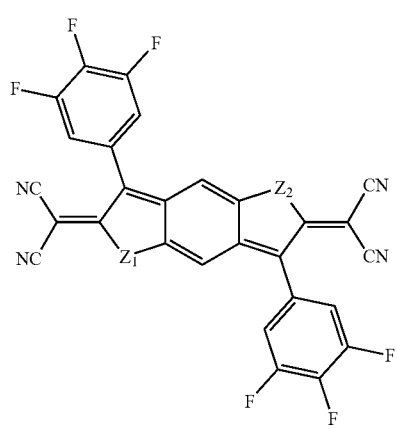

Z₁ = Z₂ = O Compound O-371
Z₁ = Z₂ = S Compound S-371
Z₁ = Z₂ = Se Compound Se-371

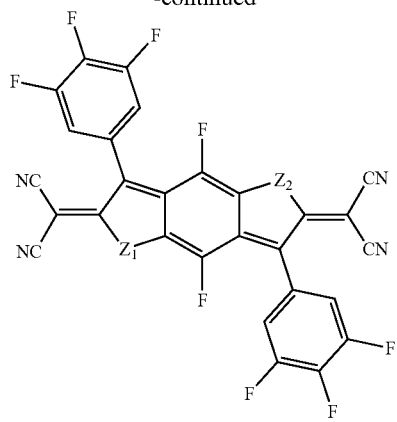

Z₁ = Z₂ = O Compound O-372
Z₁ = Z₂ = S Compound S-372
Z₁ = Z₂ = Se Compound Se-372

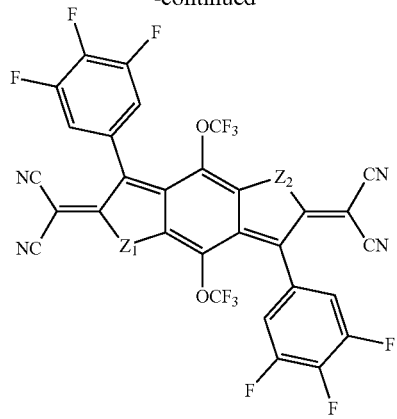

Z₁ = Z₂ = O Compound O-375
Z₁ = Z₂ = S Compound S-375
Z₁ = Z₂ = Se Compound Se-375

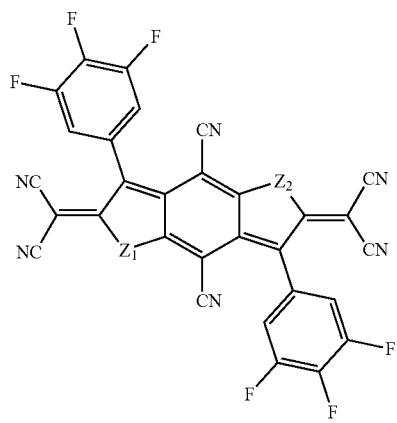

Z₁ = Z₂ = O Compound O-373
Z₁ = Z₂ = S Compound S-373
Z₁ = Z₂ = Se Compound Se-373

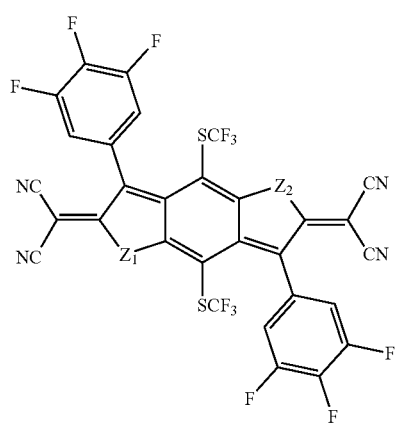

Z₁ = Z₂ = O Compound O-376
Z₁ = Z₂ = S Compound S-376
Z₁ = Z₂ = Se Compound Se-376

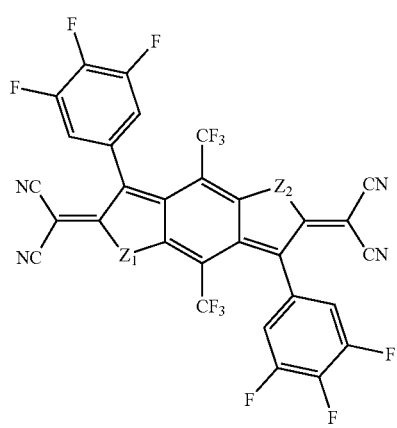

Z₁ = Z₂ = O Compound O-374
Z₁ = Z₂ = S Compound S-374
Z₁ = Z₂ = Se Compound Se-374

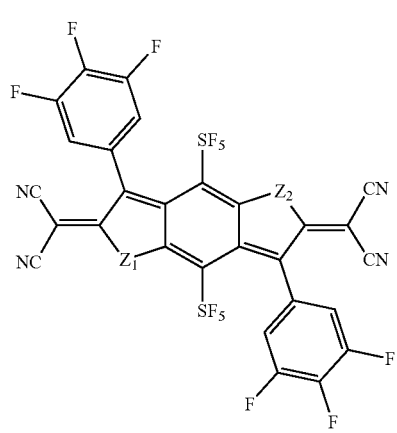

Z₁ = Z₂ = O Compound O-377
Z₁ = Z₂ = S Compound S-377
Z₁ = Z₂ = Se Compound Se-377

151
-continued

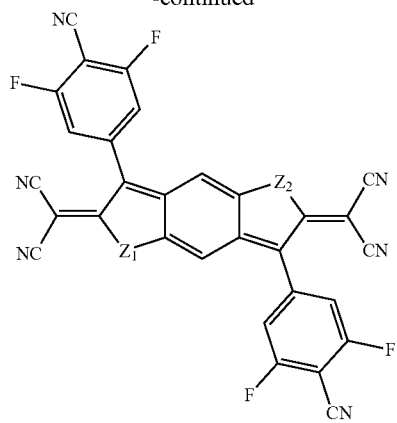

Z₁ = Z₂ = O Compound O-378
Z₁ = Z₂ = S Compound S-378
Z₁ = Z₂ = Se Compound Se-378

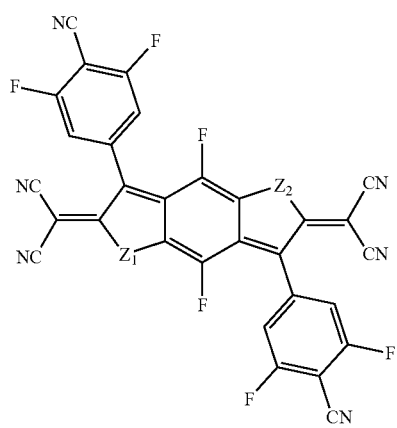

Z₁ = Z₂ = O Compound O-379
Z₁ = Z₂ = S Compound S-379
Z₁ = Z₂ = Se Compound Se-379

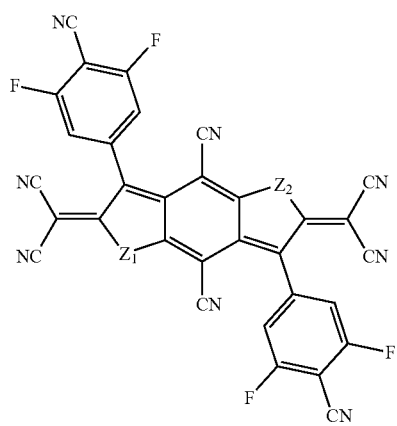

Z₁ = Z₂ = O Compound O-380
Z₁ = Z₂ = S Compound S-380
Z₁ = Z₂ = Se Compound Se-380

152
-continued

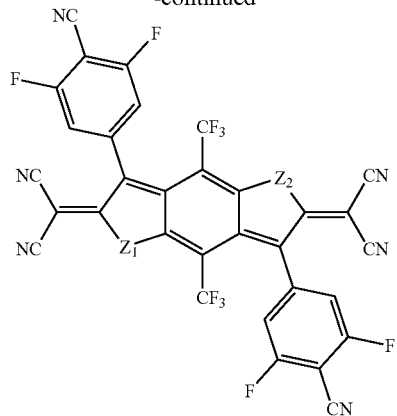

Z₁ = Z₂ = O Compound O-381
Z₁ = Z₂ = S Compound S-381
Z₁ = Z₂ = Se Compound Se-381

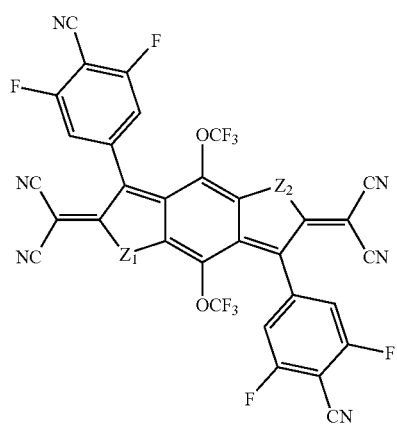

Z₁ = Z₂ = O Compound O-382
Z₁ = Z₂ = S Compound S-382
Z₁ = Z₂ = Se Compound Se-382

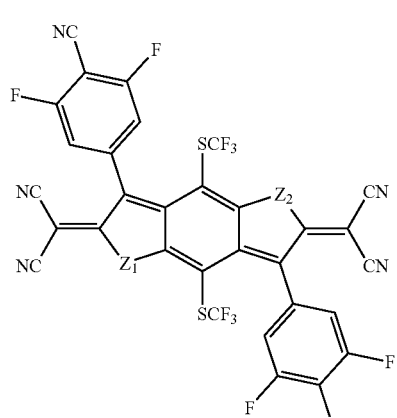

Z₁ = Z₂ = O Compound O-383
Z₁ = Z₂ = S Compound S-383
Z₁ = Z₂ = Se Compound Se-383

-continued

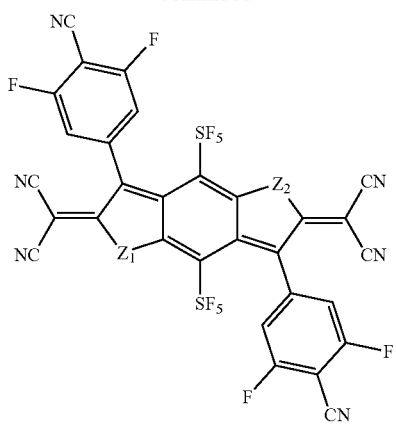

Z₁ = Z₂ = O Compound O-384
Z₁ = Z₂ = S Compound S-384
Z₁ = Z₂ = Se Compound Se-384

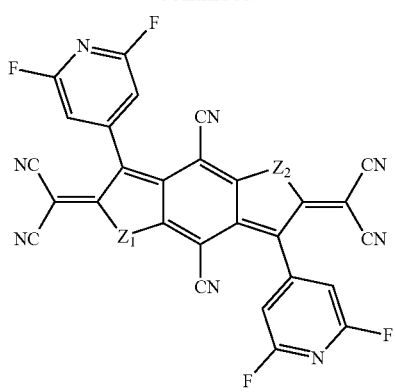

Z₁ = Z₂ = O Compound O-387
Z₁ = Z₂ = S Compound S-387
Z₁ = Z₂ = Se Compound Se-387

-continued

Z₁ = Z₂ = O Compound O-385
Z₁ = Z₂ = S Compound S-385
Z₁ = Z₂ = Se Compound Se-385

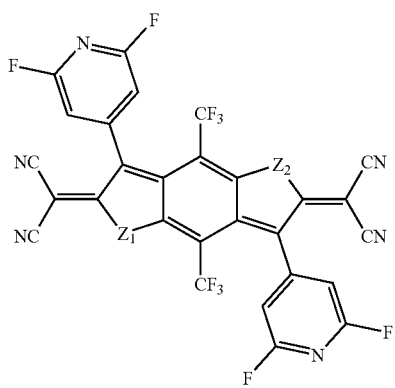

Z₁ = Z₂ = O Compound O-388
Z₁ = Z₂ = S Compound S-388
Z₁ = Z₂ = Se Compound Se-388

Z₁ = Z₂ = O Compound O-386
Z₁ = Z₂ = S Compound S-386
Z₁ = Z₂ = Se Compound Se-386

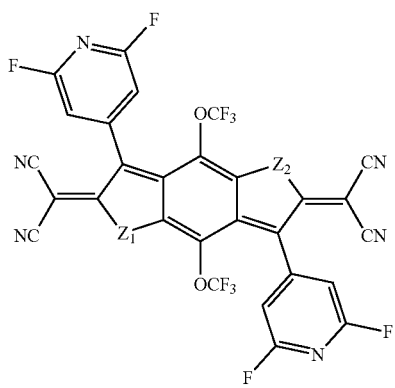

Z₁ = Z₂ = O Compound O-389
Z₁ = Z₂ = S Compound S-389
Z₁ = Z₂ = Se Compound Se-389

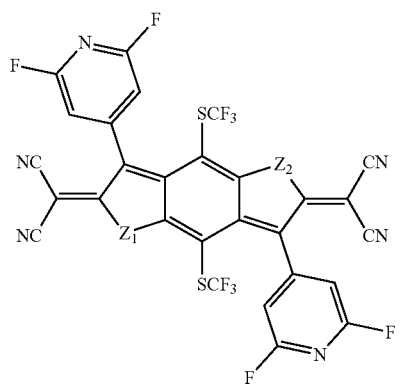

Z₁ = Z₂ = O Compound O-390
Z₁ = Z₂ = S Compound S-390
Z₁ = Z₂ = Se Compound Se-390

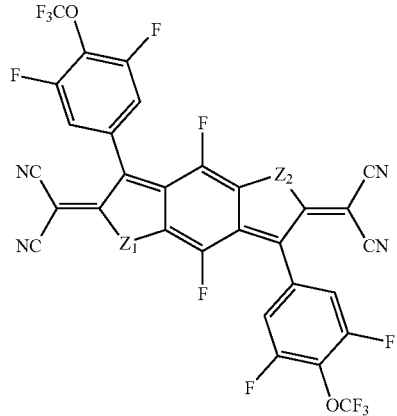

Z₁ = Z₂ = O Compound O-393
Z₁ = Z₂ = S Compound S-393
Z₁ = Z₂ = Se Compound Se-393

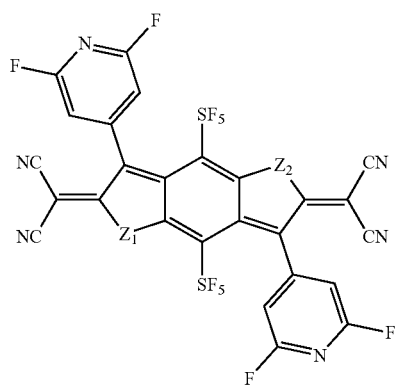

Z₁ = Z₂ = O Compound O-391
Z₁ = Z₂ = S Compound S-391
Z₁ = Z₂ = Se Compound Se-391

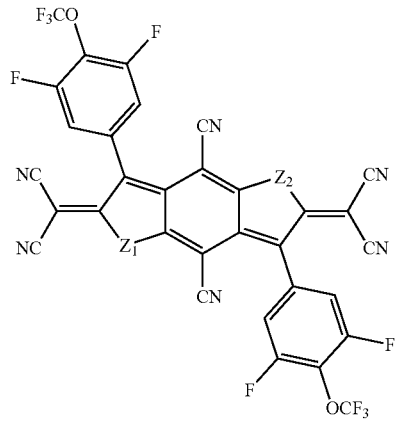

Z₁ = Z₂ = O Compound O-394
Z₁ = Z₂ = S Compound S-394
Z₁ = Z₂ = Se Compound Se-394

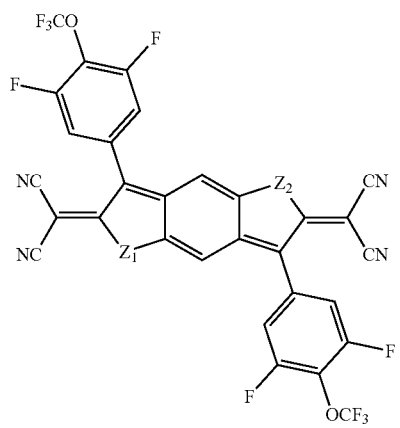

Z₁ = Z₂ = O Compound O-392
Z₁ = Z₂ = S Compound S-392
Z₁ = Z₂ = Se Compound Se-392

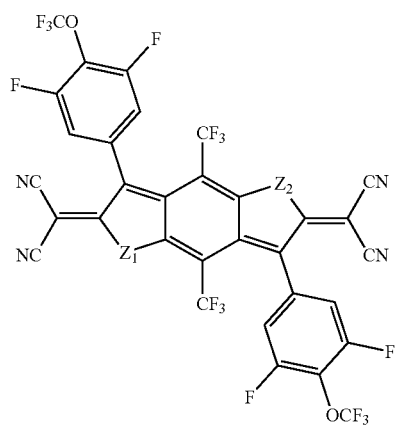

Z₁ = Z₂ = O Compound O-395
Z₁ = Z₂ = S Compound S-395
Z₁ = Z₂ = Se Compound Se-395

-continued

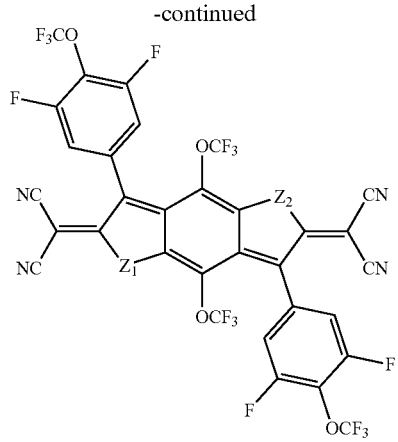

Z₁ = Z₂ = O Compound O-396
Z₁ = Z₂ = S Compound S-396
Z₁ = Z₂ = Se Compound Se-396

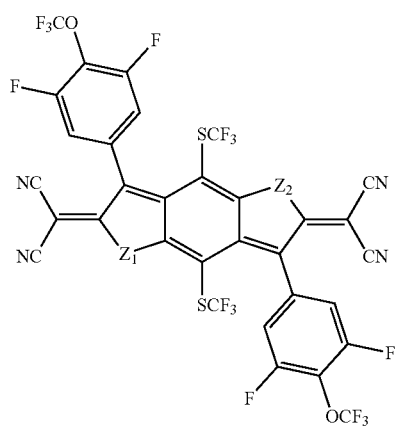

Z₁ = Z₂ = O Compound O-397
Z₁ = Z₂ = S Compound S-397
Z₁ = Z₂ = Se Compound Se-397

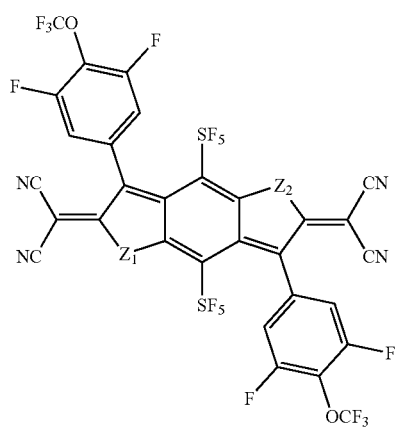

Z₁ = Z₂ = O Compound O-398
Z₁ = Z₂ = S Compound S-398
Z₁ = Z₂ = Se Compound Se-398

-continued

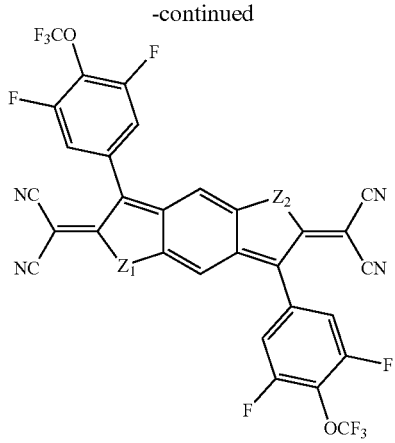

Z₁ = Z₂ = O Compound O-399
Z₁ = Z₂ = S Compound S-399
Z₁ = Z₂ = Se Compound Se-399

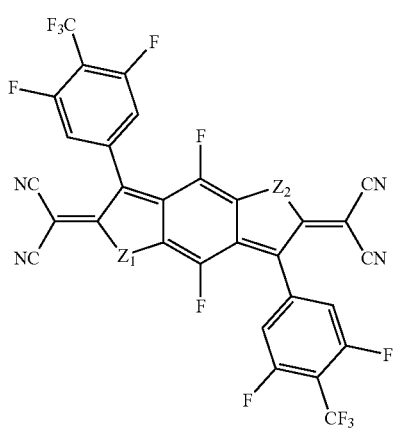

Z₁ = Z₂ = O Compound O-400
Z₁ = Z₂ = S Compound S-400
Z₁ = Z₂ = Se Compound Se-400

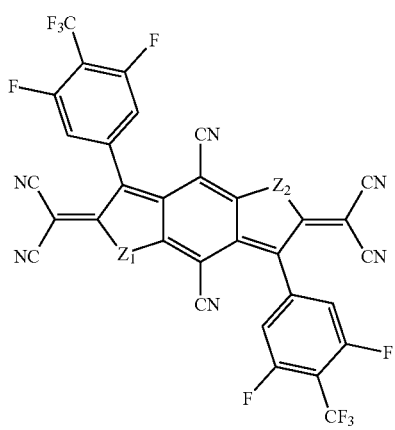

Z₁ = Z₂ = O Compound O-401
Z₁ = Z₂ = S Compound S-401
Z₁ = Z₂ = Se Compound Se-401

-continued

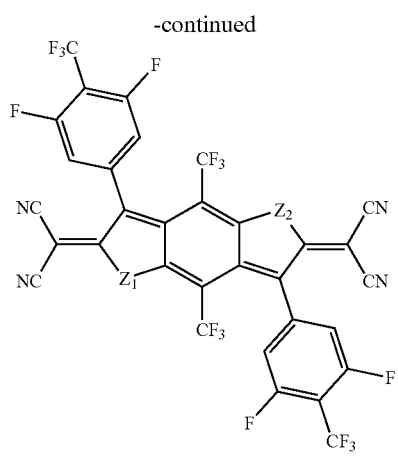

Z₁ = Z₂ = O Compound O-402
Z₁ = Z₂ = S Compound S-402
Z₁ = Z₂ = Se Compound Se-402

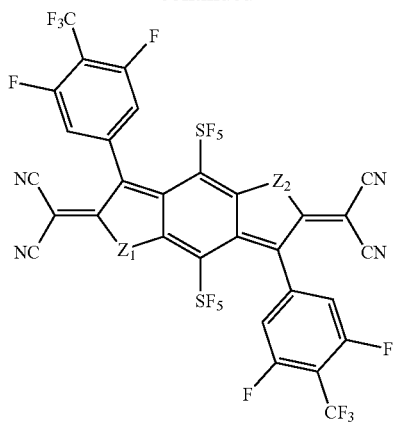

Z₁ = Z₂ = O Compound O-405
Z₁ = Z₂ = S Compound S-405
Z₁ = Z₂ = Se Compound Se-405

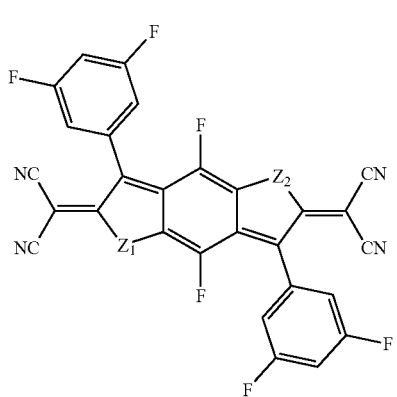

Z₁ = Z₂ = O Compound O-403
Z₁ = Z₂ = S Compound S-403
Z₁ = Z₂ = Se Compound Se-403

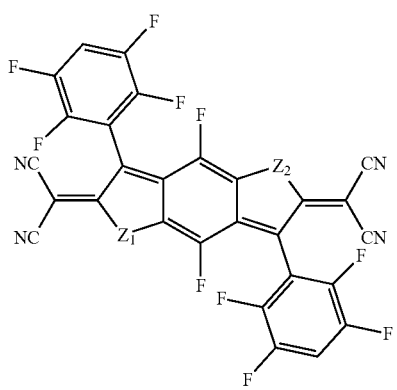

Z₁ = Z₂ = O Compound O-406
Z₁ = Z₂ = S Compound S-406
Z₁ = Z₂ = Se Compound Se-406

Z₁ = Z₂ = O Compound O-404
Z₁ = Z₂ = S Compound S-404
Z₁ = Z₂ = Se Compound Se-404

Z₁ = Z₂ = O Compound O-407
Z₁ = Z₂ = S Compound S-407
Z₁ = Z₂ = Se Compound Se-407

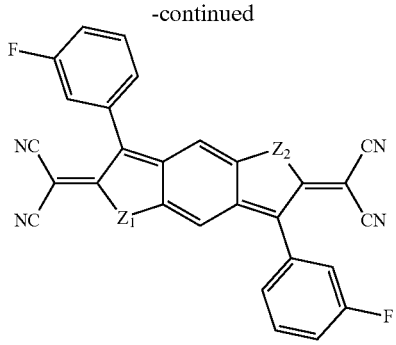

Z₁ = Z₂ = O Compound O-408
Z₁ = Z₂ = S Compound S-408
Z₁ = Z₂ = Se Compound Se-408

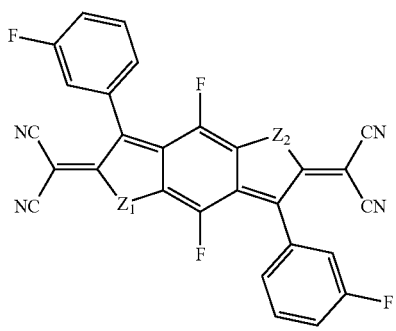

Z₁ = Z₂ = O Compound O-409
Z₁ = Z₂ = S Compound S-409
Z₁ = Z₂ = Se Compound Se-409

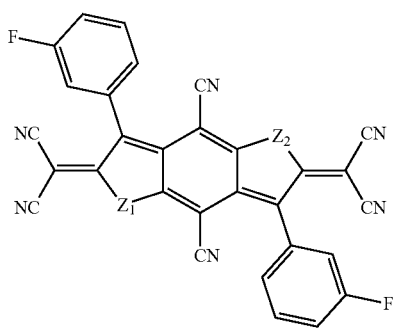

Z₁ = Z₂ = O Compound O-410
Z₁ = Z₂ = S Compound S-410
Z₁ = Z₂ = Se Compound Se-410

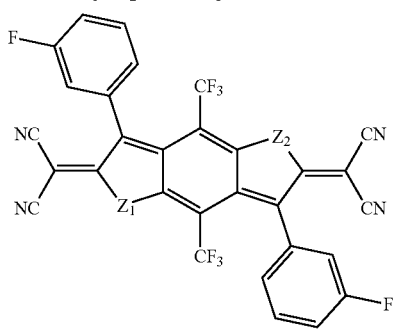

Z₁ = Z₂ = O Compound O-411
Z₁ = Z₂ = S Compound S-411
Z₁ = Z₂ = Se Compound Se-411

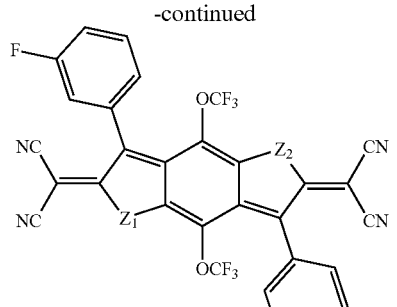

Z₁ = Z₂ = O Compound O-412
Z₁ = Z₂ = S Compound S-412
Z₁ = Z₂ = Se Compound Se-412

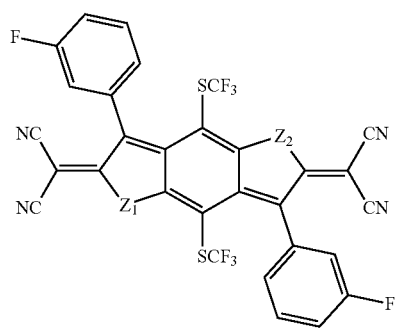

Z₁ = Z₂ = O Compound O-413
Z₁ = Z₂ = S Compound S-413
Z₁ = Z₂ = Se Compound Se-413

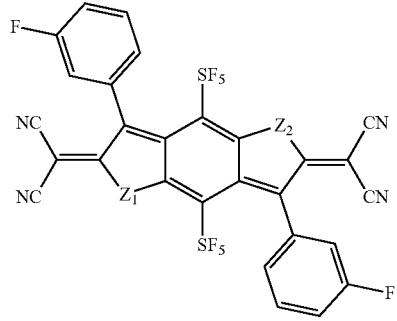

Z₁ = Z₂ = O Compound O-414
Z₁ = Z₂ = S Compound S-414
Z₁ = Z₂ = Se Compound Se-414

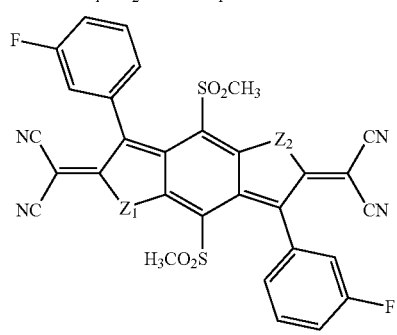

Z₁ = Z₂ = O Compound O-415
Z₁ = Z₂ = S Compound S-415
Z₁ = Z₂ = Se Compound Se-415

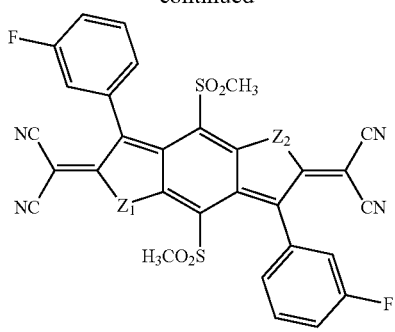

Z₁ = Z₂ = O Compound O-416
Z₁ = Z₂ = S Compound S-416
Z₁ = Z₂ = Se Compound Se-416

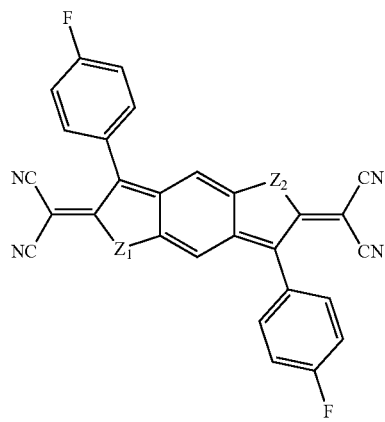

Z₁ = Z₂ = O Compound O-417
Z₁ = Z₂ = S Compound S-417
Z₁ = Z₂ = Se Compound Se-417

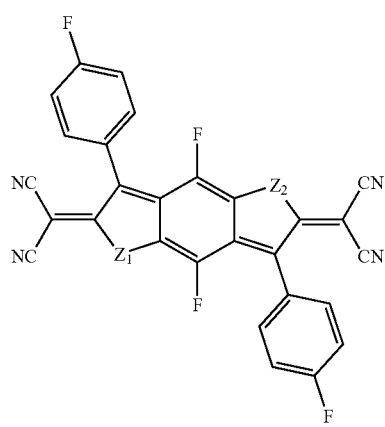

Z₁ = Z₂ = O Compound O-418
Z₁ = Z₂ = S Compound S-418
Z₁ = Z₂ = Se Compound Se-418

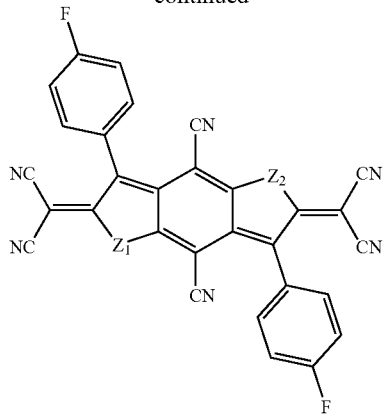

Z₁ = Z₂ = O Compound O-419
Z₁ = Z₂ = S Compound S-419
Z₁ = Z₂ = Se Compound Se-419

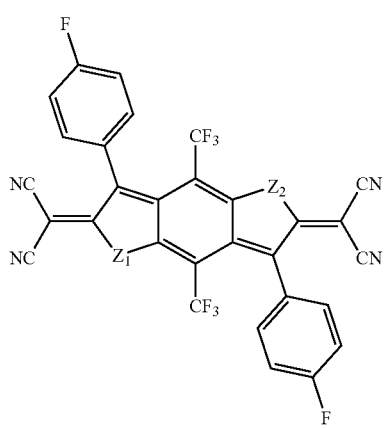

Z₁ = Z₂ = O Compound O-420
Z₁ = Z₂ = S Compound S-420
Z₁ = Z₂ = Se Compound Se-420

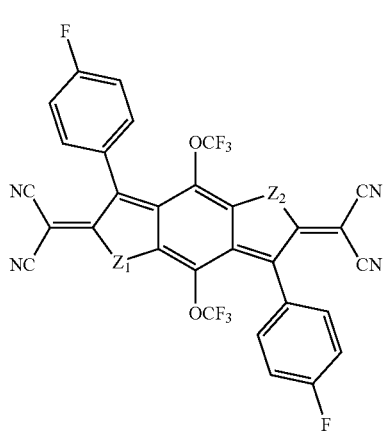

Z₁ = Z₂ = O Compound O-421
Z₁ = Z₂ = S Compound S-421
Z₁ = Z₂ = Se Compound Se-421

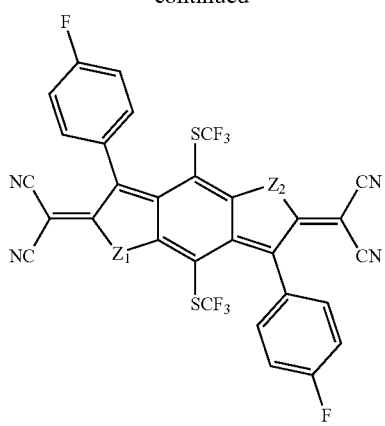

Z₁ = Z₂ = O Compound O-422
Z₁ = Z₂ = S Compound S-422
Z₁ = Z₂ = Se Compound Se-422

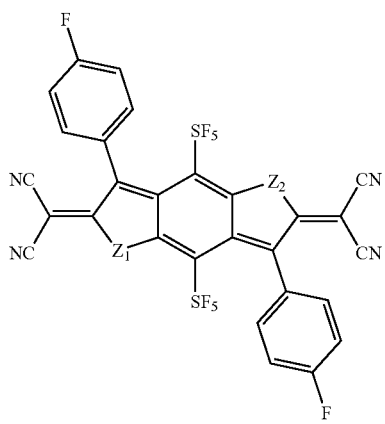

Z₁ = Z₂ = O Compound O-423
Z₁ = Z₂ = S Compound S-423
Z₁ = Z₂ = Se Compound Se-423

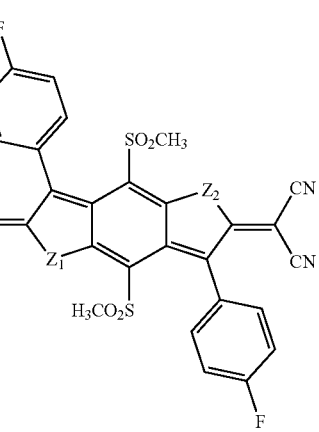

Z₁ = Z₂ = O Compound O-424
Z₁ = Z₂ = S Compound S-424
Z₁ = Z₂ = Se Compound Se-424

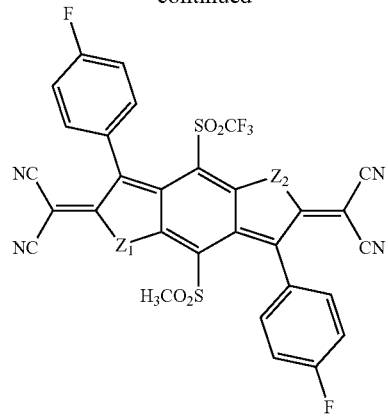

Z₁ = Z₂ = O Compound O-425
Z₁ = Z₂ = S Compound S-425
Z₁ = Z₂ = Se Compound Se-425

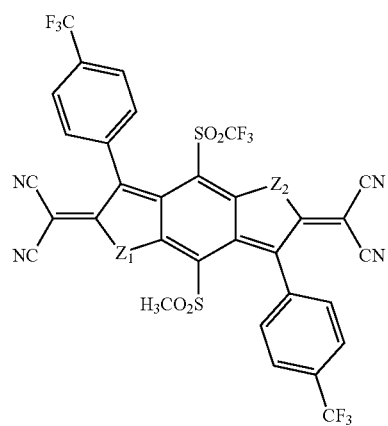

Z₁ = Z₂ = O Compound O-426
Z₁ = Z₂ = S Compound S-426
Z₁ = Z₂ = Se Compound Se-426

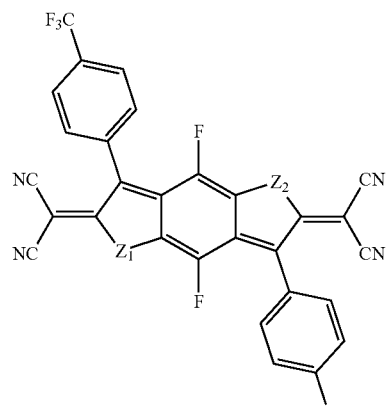

Z₁ = Z₂ = O Compound O-427
Z₁ = Z₂ = S Compound S-427
Z₁ = Z₂ = Se Compound Se-427

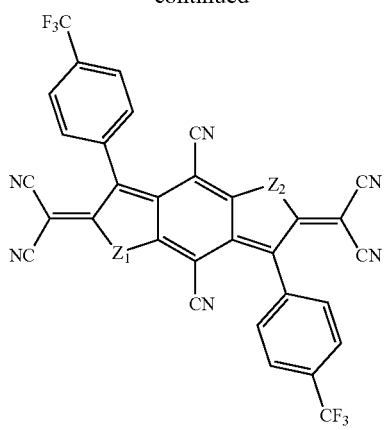

Z₁ = Z₂ = O Compound O-428
Z₁ = Z₂ = S Compound S-428
Z₁ = Z₂ = Se Compound Se-428

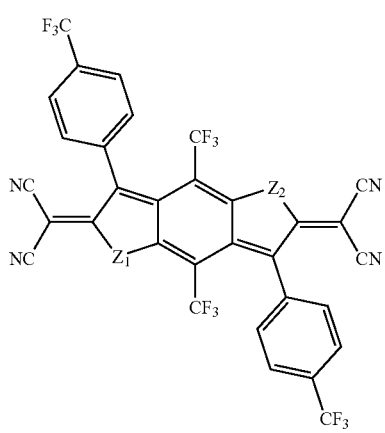

Z₁ = Z₂ = O Compound O-429
Z₁ = Z₂ = S Compound S-429
Z₁ = Z₂ = Se Compound Se-429

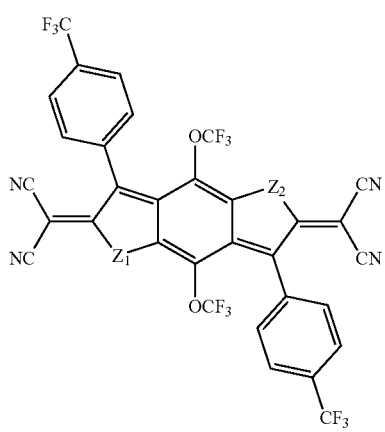

Z₁ = Z₂ = O Compound O-430
Z₁ = Z₂ = S Compound S-430
Z₁ = Z₂ = Se Compound Se-430

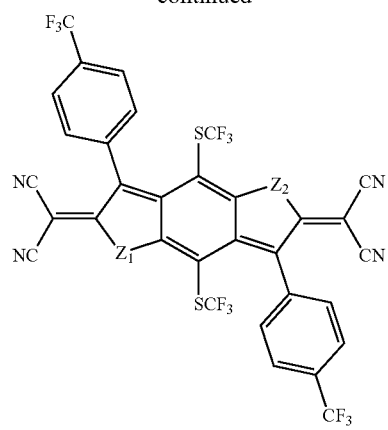

Z₁ = Z₂ = O Compound O-431
Z₁ = Z₂ = S Compound S-431
Z₁ = Z₂ = Se Compound Se-431

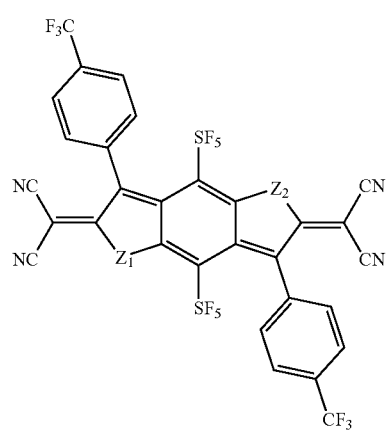

Z₁ = Z₂ = O Compound O-432
Z₁ = Z₂ = S Compound S-432
Z₁ = Z₂ = Se Compound Se-432

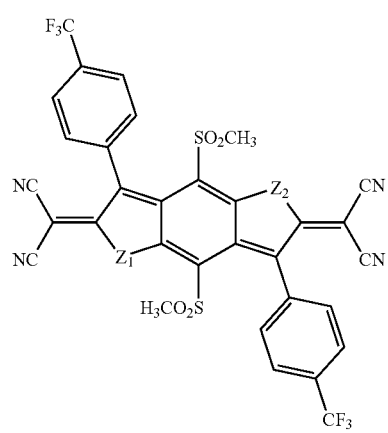

Z₁ = Z₂ = O Compound O-433
Z₁ = Z₂ = S Compound S-433
Z₁ = Z₂ = Se Compound Se-433

-continued

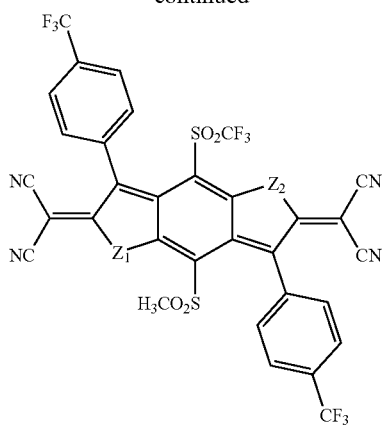

$Z_1 = Z_2 = O$ Compound O-434
$Z_1 = Z_2 = S$ Compound S-434
$Z_1 = Z_2 = Se$ Compound Se-434

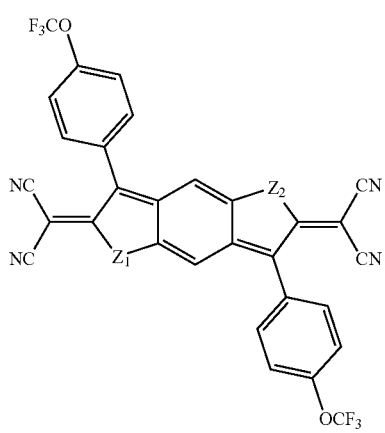

$Z_1 = Z_2 = O$ Compound O-435
$Z_1 = Z_2 = S$ Compound S-435
$Z_1 = Z_2 = Se$ Compound Se-435

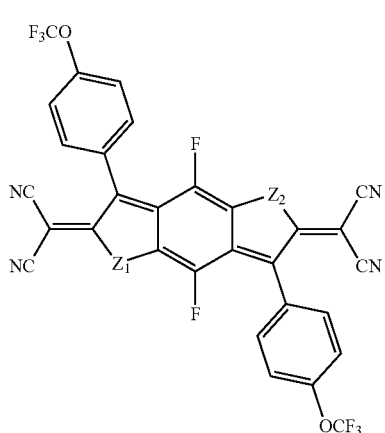

$Z_1 = Z_2 = O$ Compound O-436
$Z_1 = Z_2 = S$ Compound S-436
$Z_1 = Z_2 = Se$ Compound Se-436

-continued

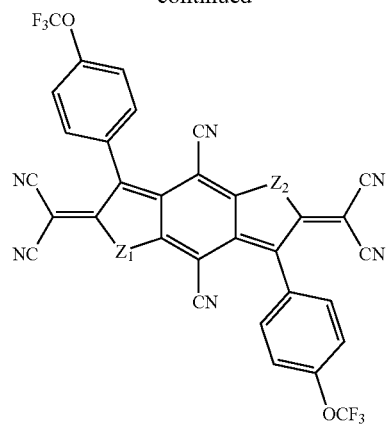

$Z_1 = Z_2 = O$ Compound O-437
$Z_1 = Z_2 = S$ Compound S-437
$Z_1 = Z_2 = Se$ Compound Se-437

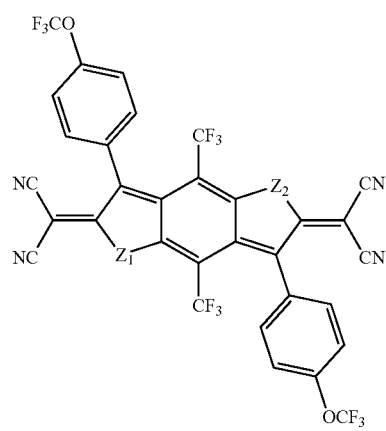

$Z_1 = Z_2 = O$ Compound O-438
$Z_1 = Z_2 = S$ Compound S-438
$Z_1 = Z_2 = Se$ Compound Se-438

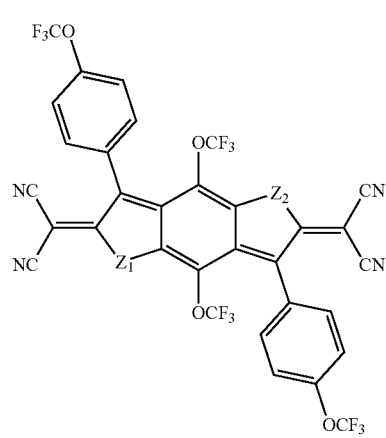

$Z_1 = Z_2 = O$ Compound O-439
$Z_1 = Z_2 = S$ Compound S-439
$Z_1 = Z_2 = Se$ Compound Se-439

-continued

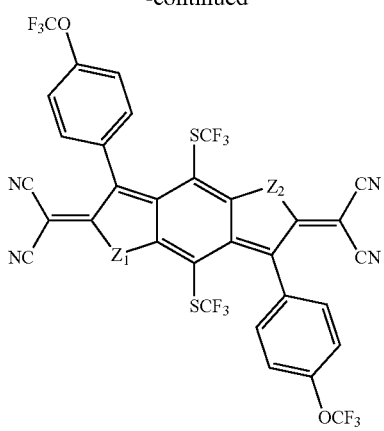

Z₁ = Z₂ = O Compound O-440
Z₁ = Z₂ = S Compound S-440
Z₁ = Z₂ = Se Compound Se-440

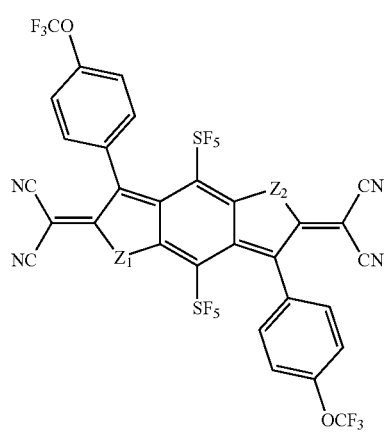

Z₁ = Z₂ = O Compound O-441
Z₁ = Z₂ = S Compound S-441
Z₁ = Z₂ = Se Compound Se-441

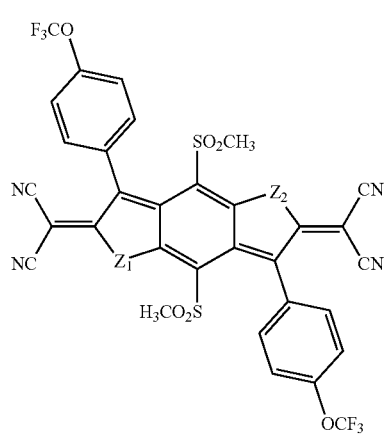

Z₁ = Z₂ = O Compound O-442
Z₁ = Z₂ = S Compound S-442
Z₁ = Z₂ = Se Compound Se-442

-continued

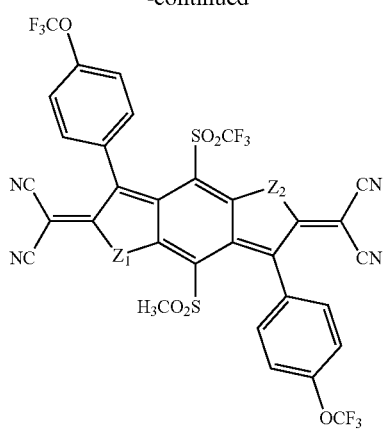

Z₁ = Z₂ = O Compound O-443
Z₁ = Z₂ = S Compound S-443
Z₁ = Z₂ = Se Compound Se-443

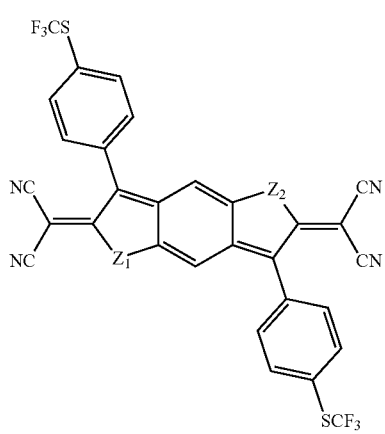

Z₁ = Z₂ = O Compound O-444
Z₁ = Z₂ = S Compound S-444
Z₁ = Z₂ = Se Compound Se-444

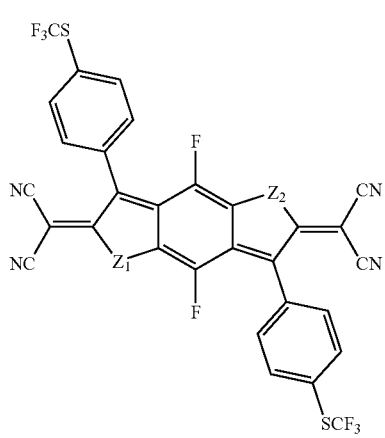

Z₁ = Z₂ = O Compound O-445
Z₁ = Z₂ = S Compound S-445
Z₁ = Z₂ = Se Compound Se-445

-continued

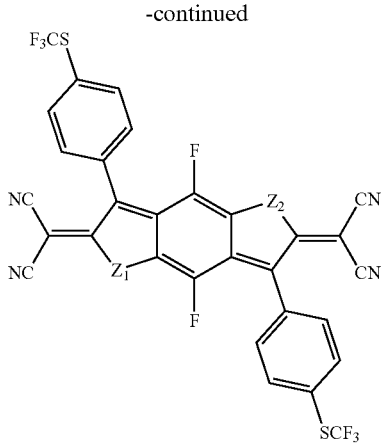

Z₁ = Z₂ = O Compound O-446
Z₁ = Z₂ = S Compound S-446
Z₁ = Z₂ = Se Compound Se-446

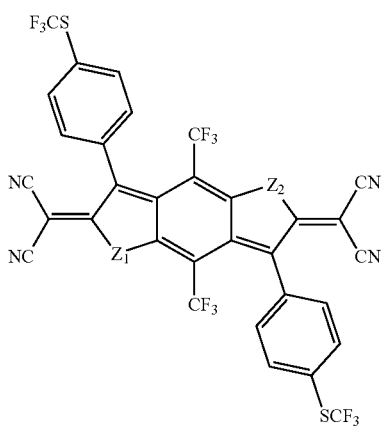

Z₁ = Z₂ = O Compound O-447
Z₁ = Z₂ = S Compound S-447
Z₁ = Z₂ = Se Compound Se-447

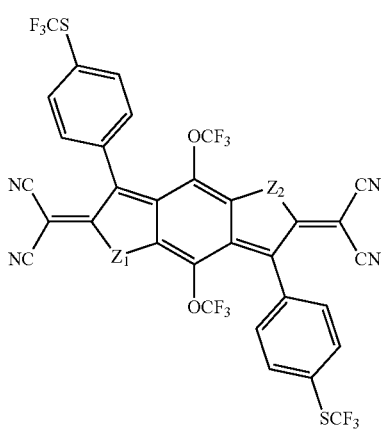

Z₁ = Z₂ = O Compound O-448
Z₁ = Z₂ = S Compound S-448
Z₁ = Z₂ = Se Compound Se-448

-continued

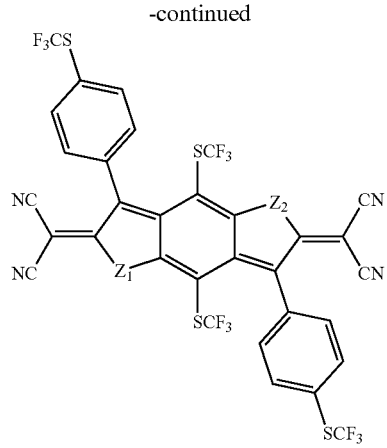

Z₁ = Z₂ = O Compound O-449
Z₁ = Z₂ = S Compound S-449
Z₁ = Z₂ = Se Compound Se-449

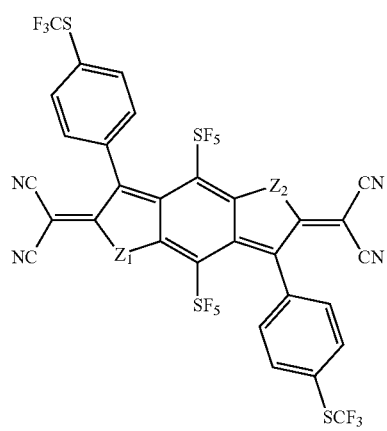

Z₁ = Z₂ = O Compound O-450
Z₁ = Z₂ = S Compound S-450
Z₁ = Z₂ = Se Compound Se-450

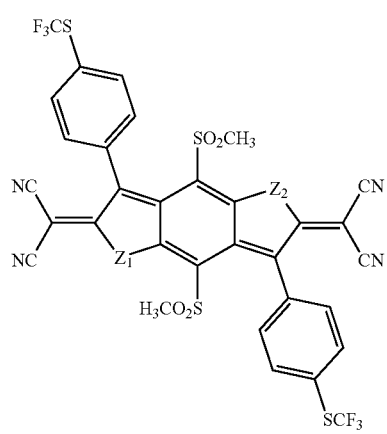

Z₁ = Z₂ = O Compound O-451
Z₁ = Z₂ = S Compound S-451
Z₁ = Z₂ = Se Compound Se-451

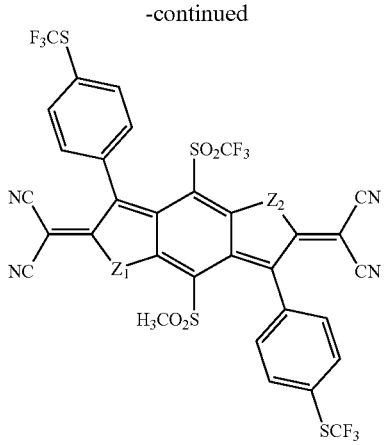

Z₁ = Z₂ = O Compound O-452
Z₁ = Z₂ = S Compound S-452
Z₁ = Z₂ = Se Compound Se-452

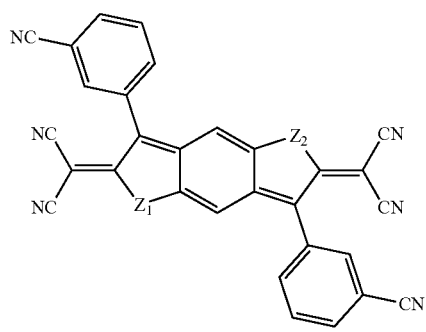

Z₁ = Z₂ = O Compound O-453
Z₁ = Z₂ = S Compound S-453
Z₁ = Z₂ = Se Compound Se-453

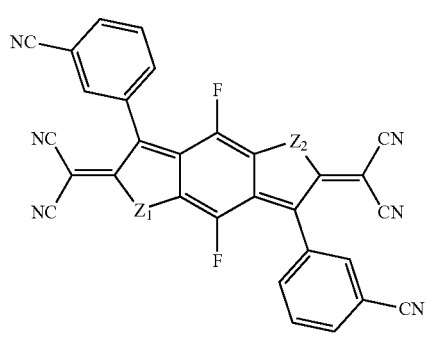

Z₁ = Z₂ = O Compound O-454
Z₁ = Z₂ = S Compound S-454
Z₁ = Z₂ = Se Compound Se-454

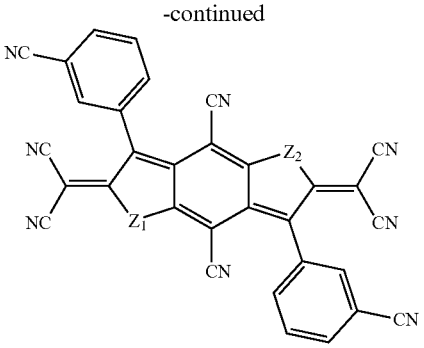

Z₁ = Z₂ = O Compound O-455
Z₁ = Z₂ = S Compound S-455
Z₁ = Z₂ = Se Compound Se-455

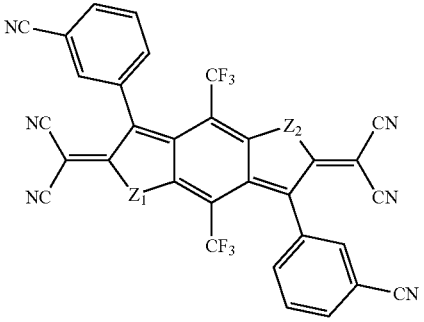

Z₁ = Z₂ = O Compound O-456
Z₁ = Z₂ = S Compound S-456
Z₁ = Z₂ = Se Compound Se-456

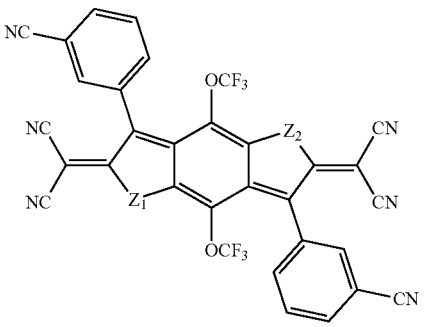

Z₁ = Z₂ = O Compound O-457
Z₁ = Z₂ = S Compound S-457
Z₁ = Z₂ = Se Compound Se-457

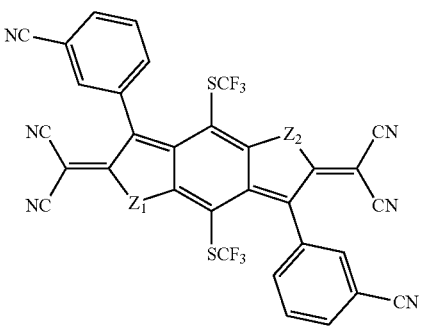

Z₁ = Z₂ = O Compound O-458
Z₁ = Z₂ = S Compound S-458
Z₁ = Z₂ = Se Compound Se-458

-continued

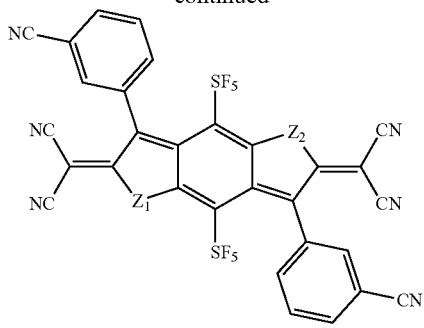

Z₁ = Z₂ = O Compound O-459
Z₁ = Z₂ = S Compound S-459
Z₁ = Z₂ = Se Compound Se-459

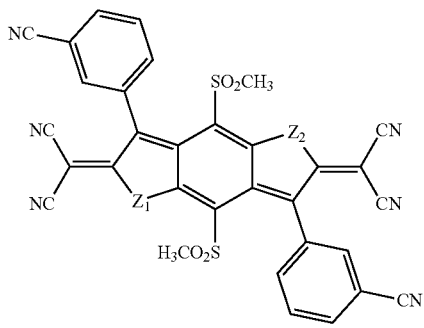

Z₁ = Z₂ = O Compound O-460
Z₁ = Z₂ = S Compound S-460
Z₁ = Z₂ = Se Compound Se-460

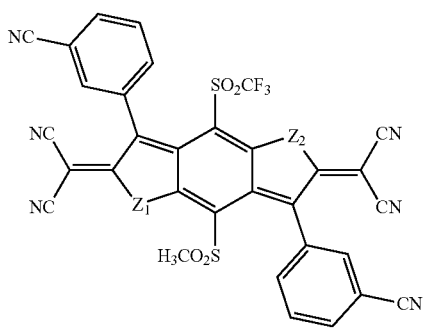

Z₁ = Z₂ = O Compound O-461
Z₁ = Z₂ = S Compound S-461
Z₁ = Z₂ = Se Compound Se-461

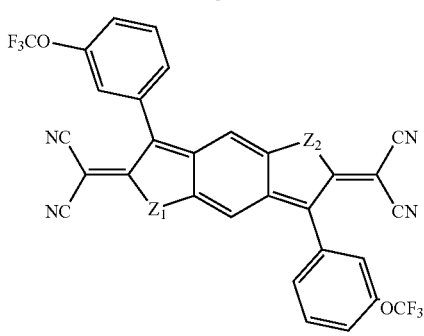

Z₁ = Z₂ = O Compound O-462
Z₁ = Z₂ = S Compound S-462
Z₁ = Z₂ = Se Compound Se-462

-continued

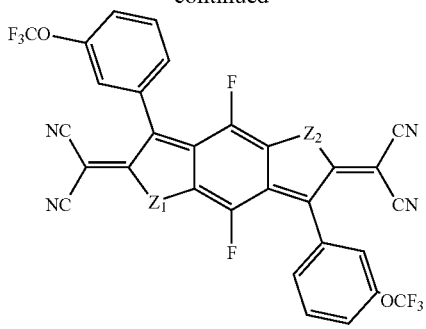

Z₁ = Z₂ = O Compound O-463
Z₁ = Z₂ = S Compound S-463
Z₁ = Z₂ = Se Compound Se-463

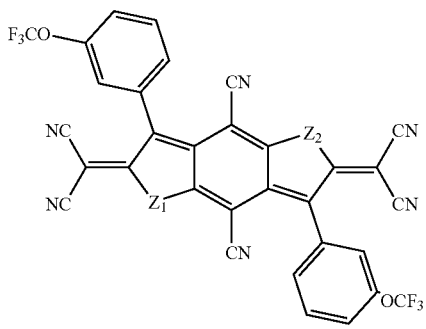

Z₁ = Z₂ = O Compound O-464
Z₁ = Z₂ = S Compound S-464
Z₁ = Z₂ = Se Compound Se-464

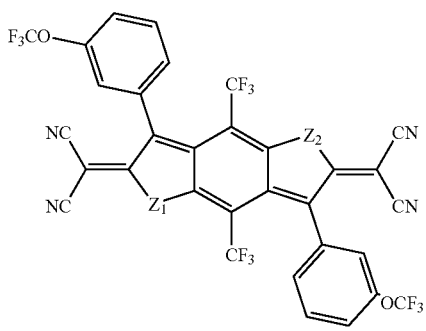

Z₁ = Z₂ = O Compound O-465
Z₁ = Z₂ = S Compound S-465
Z₁ = Z₂ = Se Compound Se-465

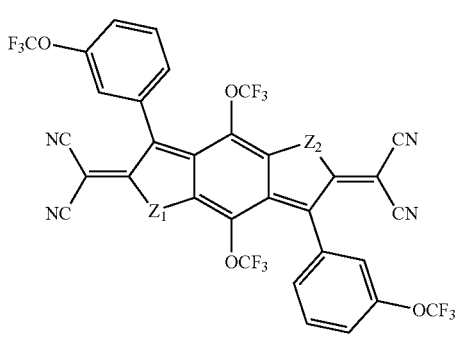

Z₁ = Z₂ = O Compound O-466
Z₁ = Z₂ = S Compound S-466
Z₁ = Z₂ = Se Compound Se-466

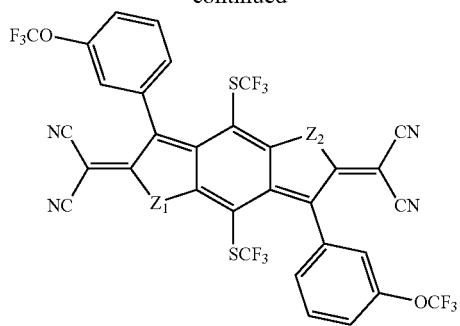

Z₁ = Z₂ = O Compound O-467
Z₁ = Z₂ = S Compound S-467
Z₁ = Z₂ = Se Compound Se-467

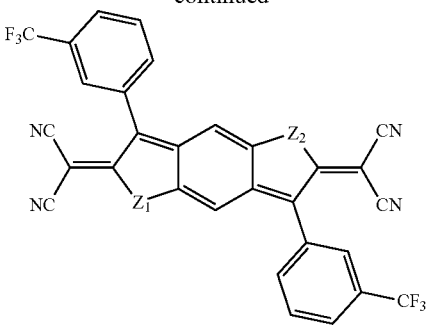

Z₁ = Z₂ = O Compound O-471
Z₁ = Z₂ = S Compound S-471
Z₁ = Z₂ = Se Compound Se-471

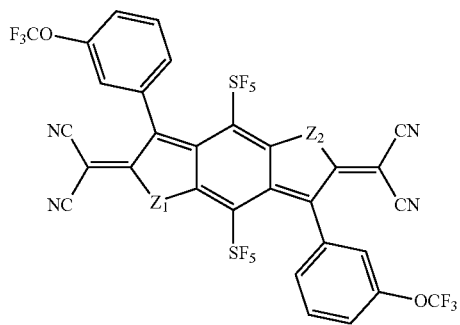

Z₁ = Z₂ = O Compound O-468
Z₁ = Z₂ = S Compound S-468
Z₁ = Z₂ = Se Compound Se-468

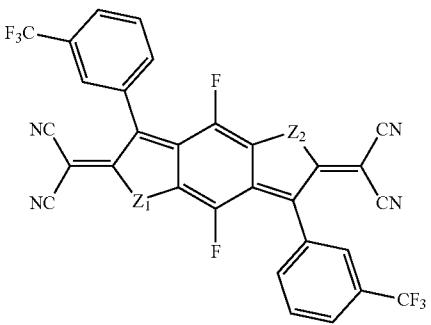

Z₁ = Z₂ = O Compound O-472
Z₁ = Z₂ = S Compound S-472
Z₁ = Z₂ = Se Compound Se-472

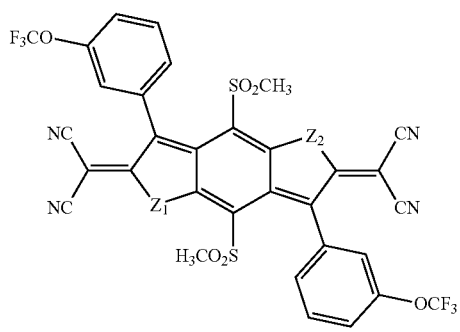

Z₁ = Z₂ = O Compound O-469
Z₁ = Z₂ = S Compound S-469
Z₁ = Z₂ = Se Compound Se-469

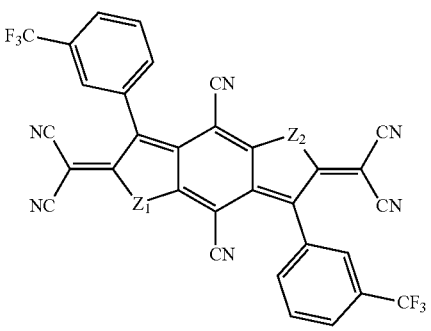

Z₁ = Z₂ = O Compound O-473
Z₁ = Z₂ = S Compound S-473
Z₁ = Z₂ = Se Compound Se-473

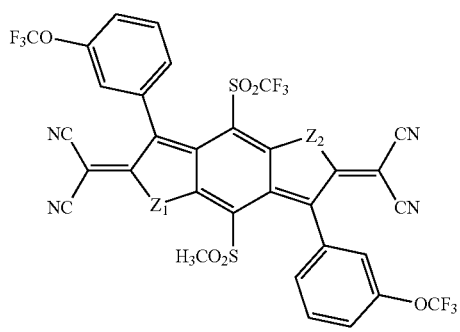

Z₁ = Z₂ = O Compound O-470
Z₁ = Z₂ = S Compound S-470
Z₁ = Z₂ = Se Compound Se-470

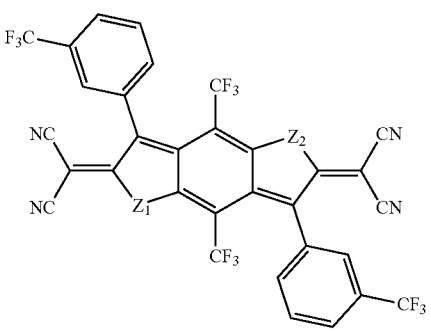

Z₁ = Z₂ = O Compound O-474
Z₁ = Z₂ = S Compound S-474
Z₁ = Z₂ = Se Compound Se-474

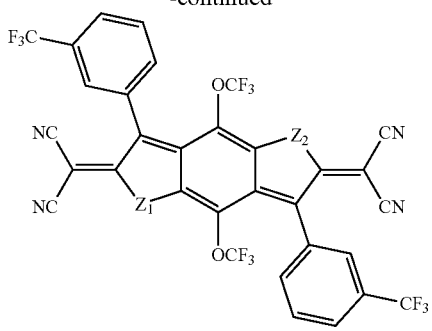

Z₁ = Z₂ = O Compound O-475
Z₁ = Z₂ = S Compound S-475
Z₁ = Z₂ = Se Compound Se-475

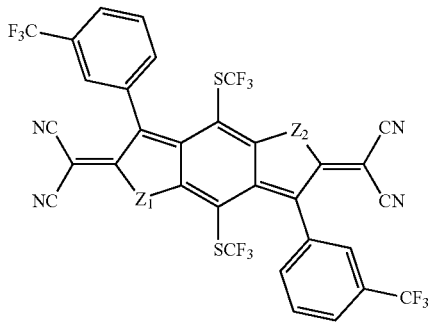

Z₁ = Z₂ = O Compound O-476
Z₁ = Z₂ = S Compound S-476
Z₁ = Z₂ = Se Compound Se-476

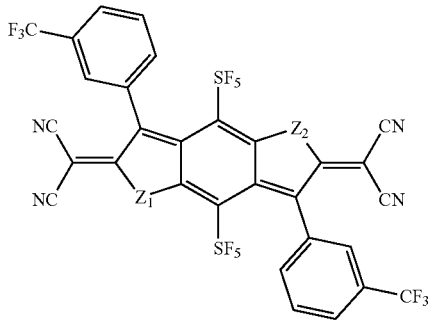

Z₁ = Z₂ = O Compound O-477
Z₁ = Z₂ = S Compound S-477
Z₁ = Z₂ = Se Compound Se-477

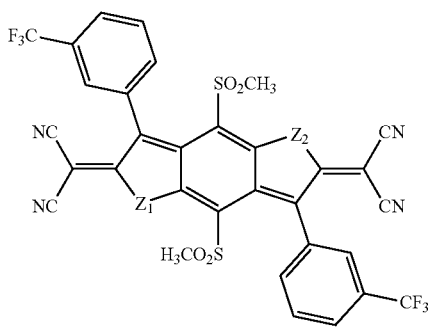

Z₁ = Z₂ = O Compound O-478
Z₁ = Z₂ = S Compound S-478
Z₁ = Z₂ = Se Compound Se-478

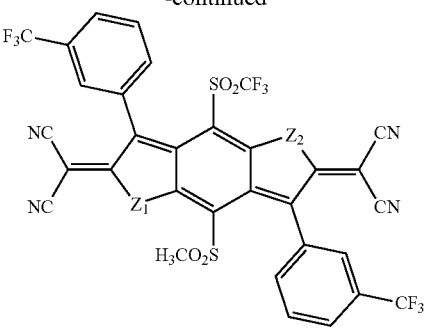

Z₁ = Z₂ = O Compound O-479
Z₁ = Z₂ = S Compound S-479
Z₁ = Z₂ = Se Compound Se-479

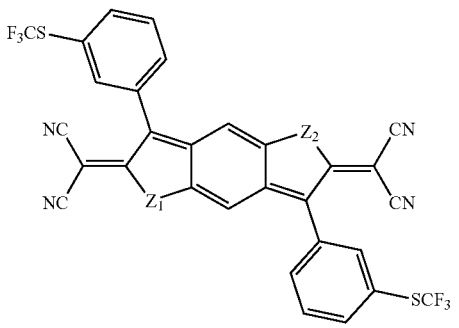

Z₁ = Z₂ = O Compound O-480
Z₁ = Z₂ = S Compound S-480
Z₁ = Z₂ = Se Compound Se-480

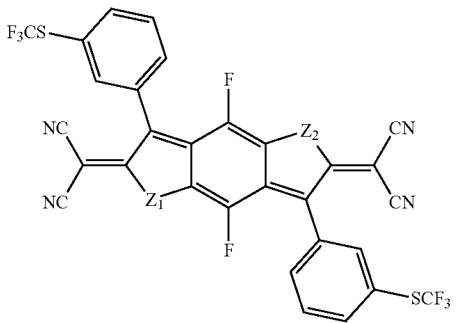

Z₁ = Z₂ = O Compound O-481
Z₁ = Z₂ = S Compound S-481
Z₁ = Z₂ = Se Compound Se-481

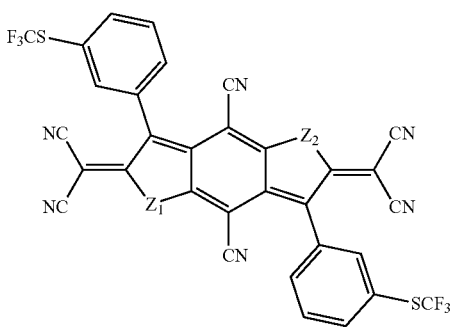

Z₁ = Z₂ = O Compound O-482
Z₁ = Z₂ = S Compound S-482
Z₁ = Z₂ = Se Compound Se-482

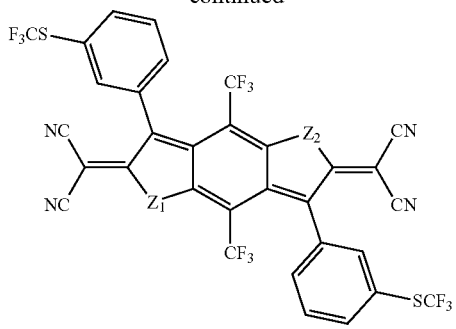

$Z_1 = Z_2 = $ O Compound O-483
$Z_1 = Z_2 = $ S Compound S-483
$Z_1 = Z_2 = $ Se Compound Se-483

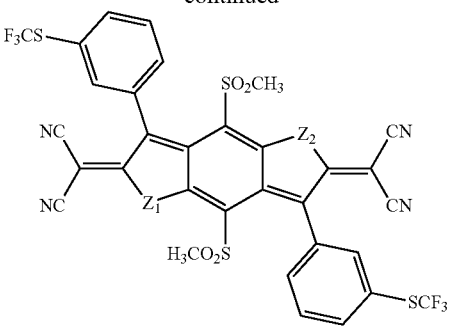

$Z_1 = Z_2 = $ O Compound O-487
$Z_1 = Z_2 = $ S Compound S-487
$Z_1 = Z_2 = $ Se Compound Se-487

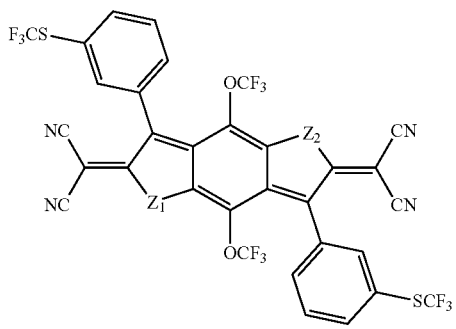

$Z_1 = Z_2 = $ O Compound O-484
$Z_1 = Z_2 = $ S Compound S-484
$Z_1 = Z_2 = $ Se Compound Se-484

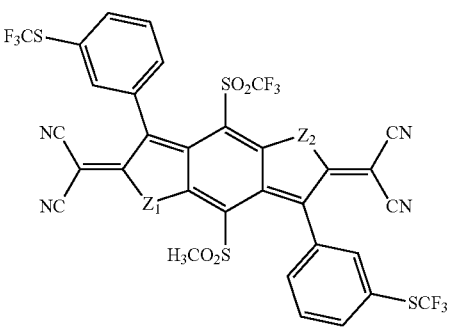

$Z_1 = Z_2 = $ O Compound O-488
$Z_1 = Z_2 = $ S Compound S-488
$Z_1 = Z_2 = $ Se Compound Se-488

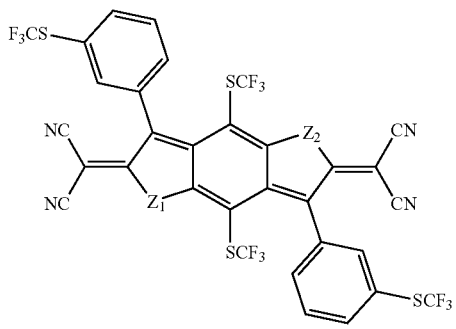

$Z_1 = Z_2 = $ O Compound O-485
$Z_1 = Z_2 = $ S Compound S-485
$Z_1 = Z_2 = $ Se Compound Se-485

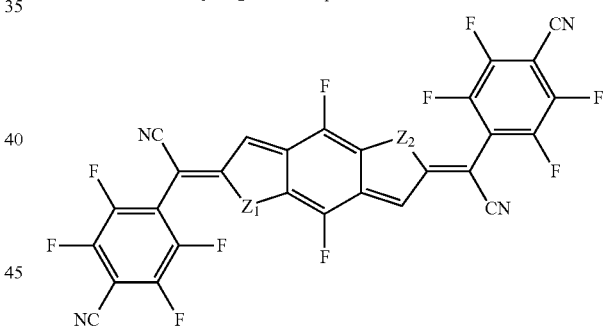

$Z_1 = Z_2 = $ O Compound O-489
$Z_1 = Z_2 = $ S Compound S-489
$Z_1 = Z_2 = $ Se Compound Se-489

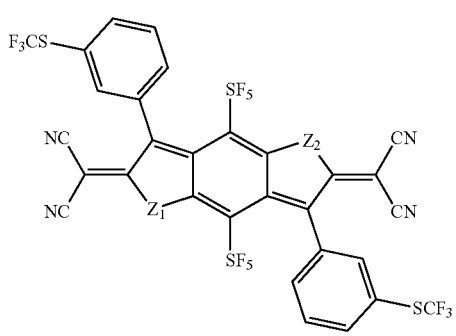

$Z_1 = Z_2 = $ O Compound O-486
$Z_1 = Z_2 = $ S Compound S-486
$Z_1 = Z_2 = $ Se Compound Se-486

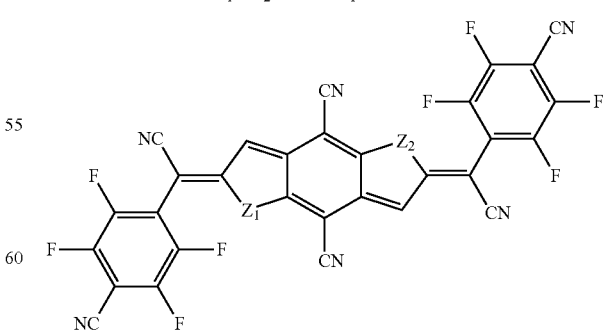

$Z_1 = Z_2 = $ O Compound O-490
$Z_1 = Z_2 = $ S Compound S-490
$Z_1 = Z_2 = $ Se Compound Se-490

-continued

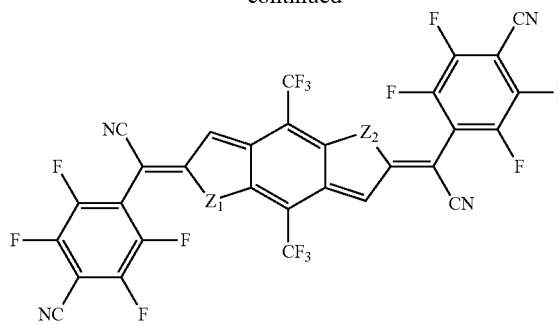

Z₁ = Z₂ = O Compound O-491
Z₁ = Z₂ = S Compound S-491
Z₁ = Z₂ = Se Compound Se-491

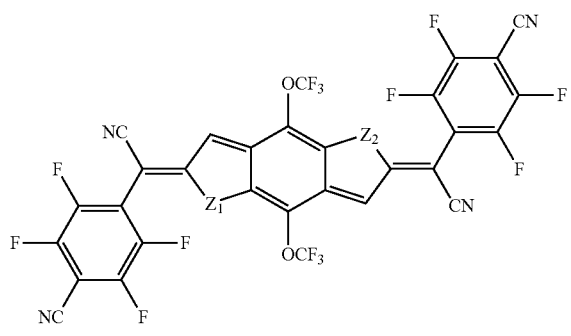

Z₁ = Z₂ = O Compound O-492
Z₁ = Z₂ = S Compound S-492
Z₁ = Z₂ = Se Compound Se-492

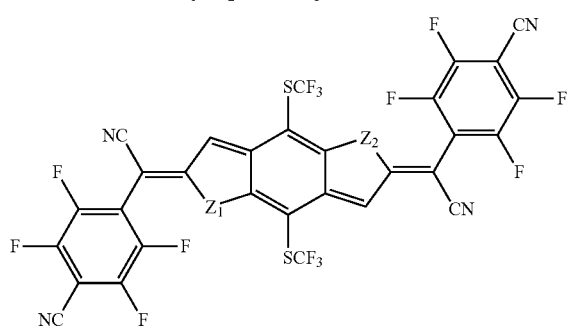

Z₁ = Z₂ = O Compound O-493
Z₁ = Z₂ = S Compound S-493
Z₁ = Z₂ = Se Compound Se-493

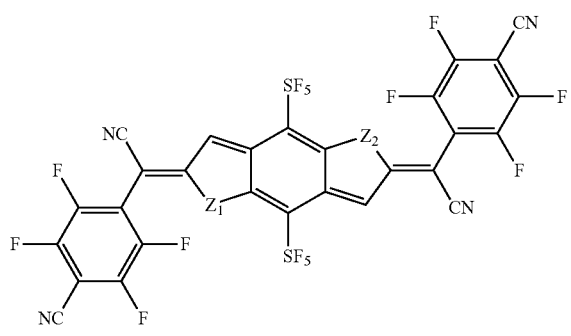

Z₁ = Z₂ = O Compound O-494
Z₁ = Z₂ = S Compound S-494
Z₁ = Z₂ = Se Compound Se-494

-continued

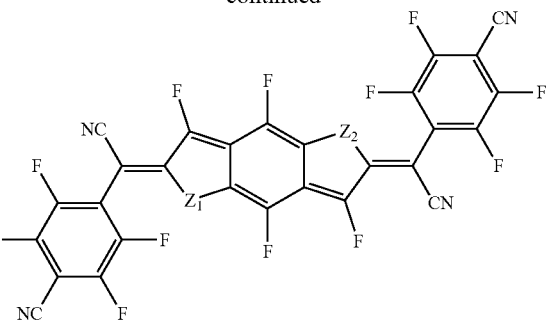

Z₁ = Z₂ = O Compound O-495
Z₁ = Z₂ = S Compound S-495
Z₁ = Z₂ = Se Compound Se-495

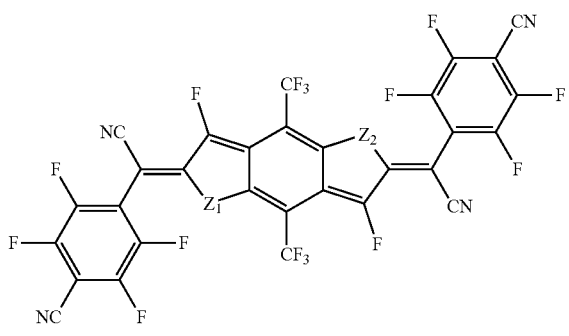

Z₁ = Z₂ = O Compound O-496
Z₁ = Z₂ = S Compound S-496
Z₁ = Z₂ = Se Compound Se-496

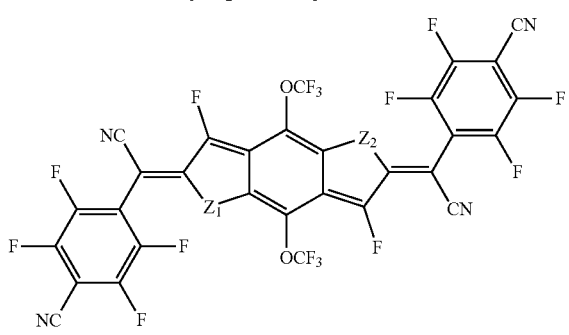

Z₁ = Z₂ = O Compound O-497
Z₁ = Z₂ = S Compound S-497
Z₁ = Z₂ = Se Compound Se-497

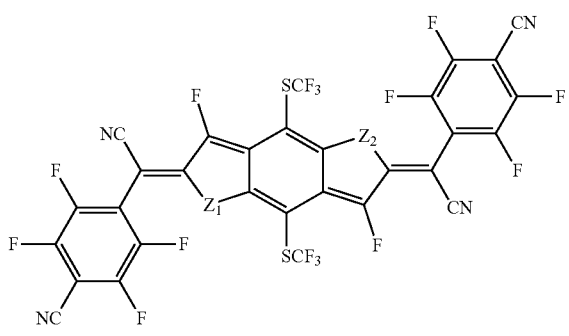

Z₁ = Z₂ = O Compound O-498
Z₁ = Z₂ = S Compound S-498
Z₁ = Z₂ = Se Compound Se-498

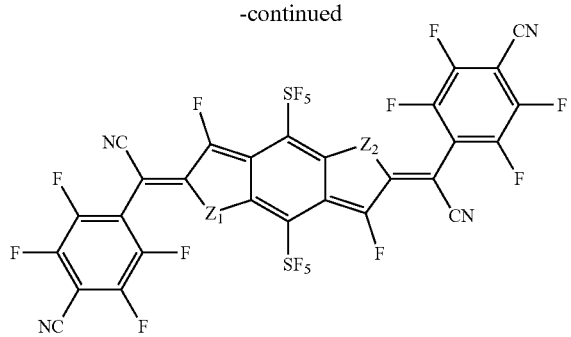

Z₁ = Z₂ = O Compound O-499
Z₁ = Z₂ = S Compound S-499
Z₁ = Z₂ = Se Compound Se-499

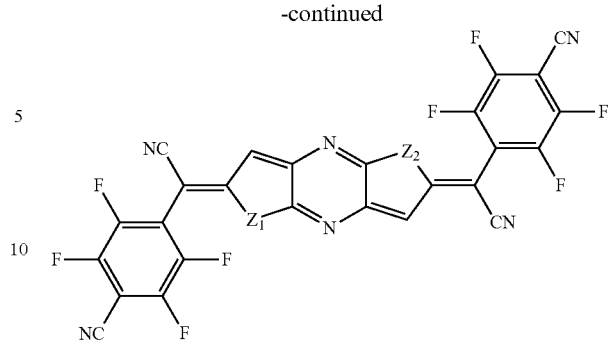

Z₁ = Z₂ = O Compound O-503
Z₁ = Z₂ = S Compound S-503
Z₁ = Z₂ = Se Compound Se-503

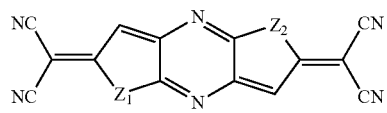

Z₁ = Z₂ = O Compound O-500
Z₁ = Z₂ = S Compound S-500
Z₁ = Z₂ = Se Compound Se-500

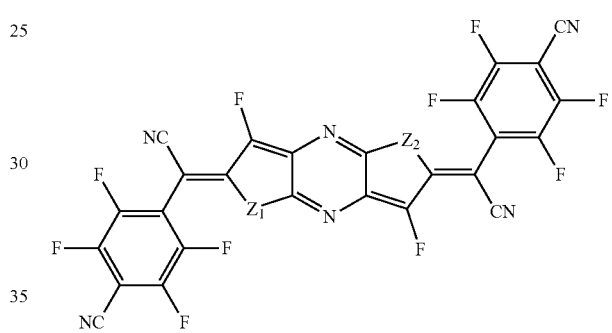

Z₁ = Z₂ = O Compound O-504
Z₁ = Z₂ = S Compound S-504
Z₁ = Z₂ = Se Compound Se-504

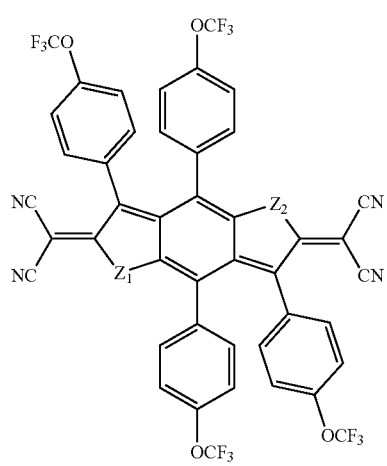

Z₁ = Z₂ = O Compound O-501
Z₁ = Z₂ = S Compound S-501
Z₁ = Z₂ = Se Compound Se-501

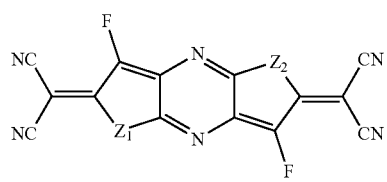

Z₁ = Z₂ = O Compound O-502
Z₁ = Z₂ = S Compound S-502
Z₁ = Z₂ = Se Compound Se-502

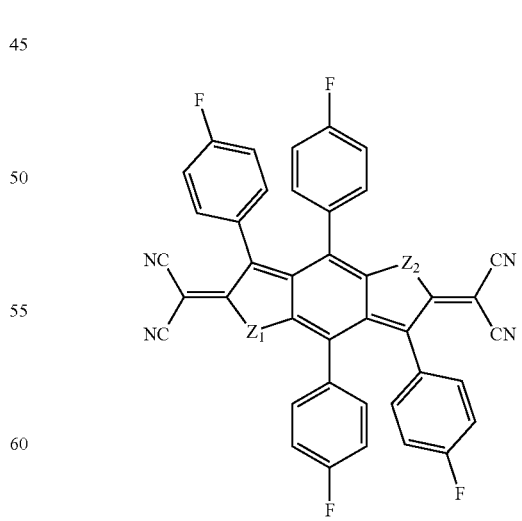

Z₁ = Z₂ = O Compound O-505
Z₁ = Z₂ = S Compound S-505
Z₁ = Z₂ = Se Compound Se-505

-continued

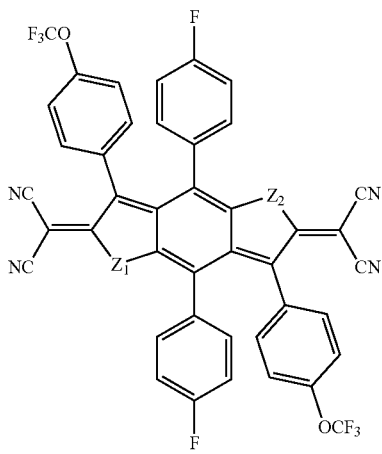

Z₁ = Z₂ = O Compound O-506
Z₁ = Z₂ = S Compound S-506
Z₁ = Z₂ = Se Compound Se-506

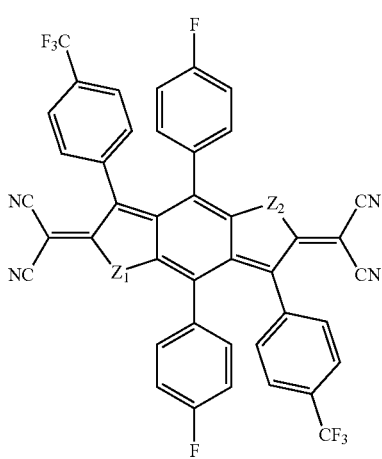

Z₁ = Z₂ = O Compound O-507
Z₁ = Z₂ = S Compound S-507
Z₁ = Z₂ = Se Compound Se-507

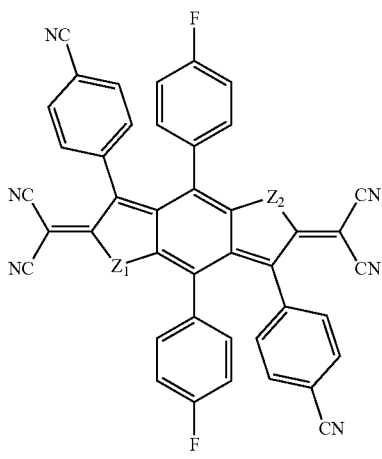

Z₁ = Z₂ = O Compound O-508
Z₁ = Z₂ = S Compound S-508
Z₁ = Z₂ = Se Compound Se-508

-continued

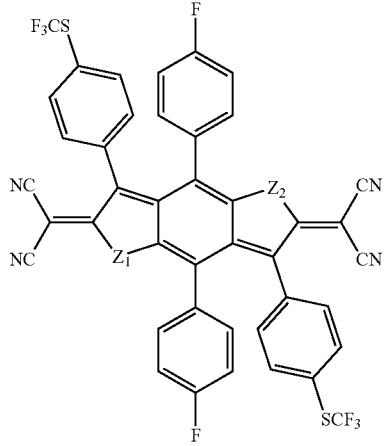

Z₁ = Z₂ = O Compound O-509
Z₁ = Z₂ = S Compound S-509
Z₁ = Z₂ = Se Compound Se-509

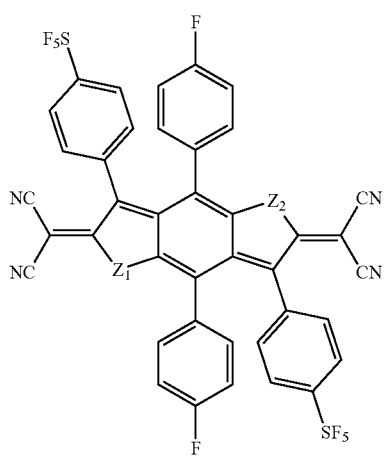

Z₁ = Z₂ = O Compound O-510
Z₁ = Z₂ = S Compound S-510
Z₁ = Z₂ = Se Compound Se-510

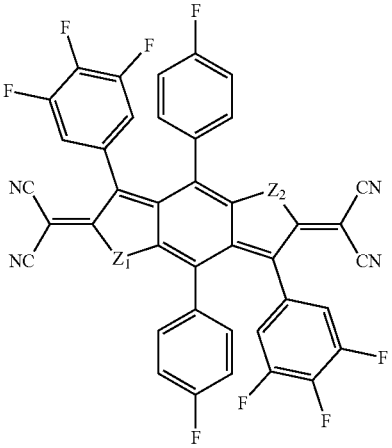

Z₁ = Z₂ = O Compound O-511
Z₁ = Z₂ = S Compound S-511
Z₁ = Z₂ = Se Compound Se-511

-continued

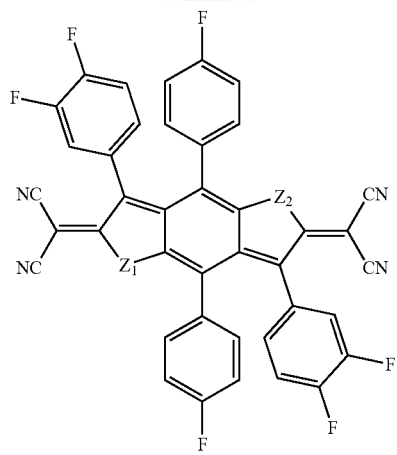

Z₁ = Z₂ = O Compound O-512
Z₁ = Z₂ = S Compound S-512
Z₁ = Z₂ = Se Compound Se-512

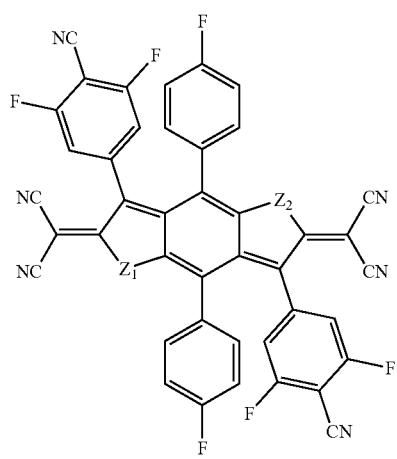

Z₁ = Z₂ = O Compound O-513
Z₁ = Z₂ = S Compound S-513
Z₁ = Z₂ = Se Compound Se-513

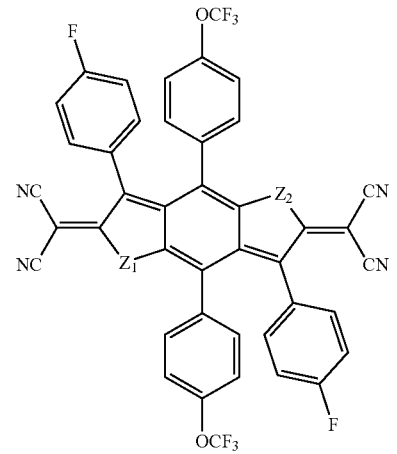

Z₁ = Z₂ = O Compound O-514
Z₁ = Z₂ = S Compound S-514
Z₁ = Z₂ = Se Compound Se-514

-continued

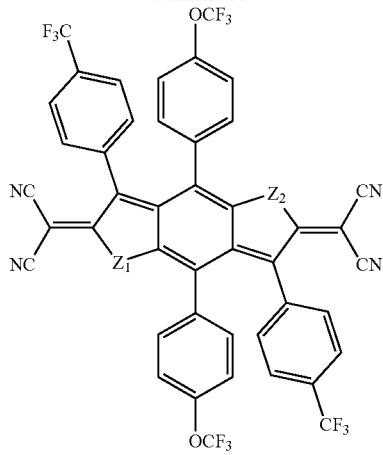

Z₁ = Z₂ = O Compound O-515
Z₁ = Z₂ = S Compound S-515
Z₁ = Z₂ = Se Compound Se-515

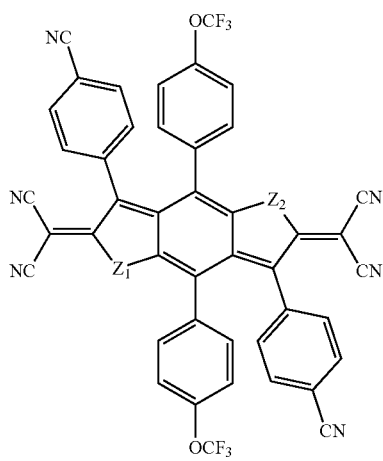

Z₁ = Z₂ = O Compound O-516
Z₁ = Z₂ = S Compound S-516
Z₁ = Z₂ = Se Compound Se-516

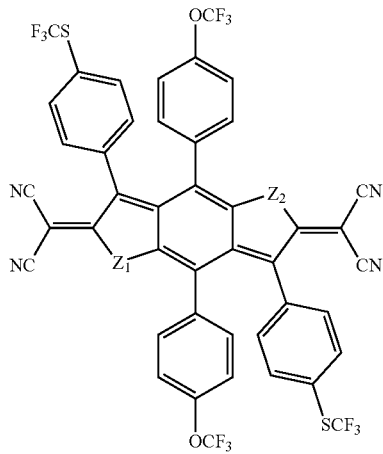

Z₁ = Z₂ = O Compound O-517
Z₁ = Z₂ = S Compound S-517
Z₁ = Z₂ = Se Compound Se-517

-continued

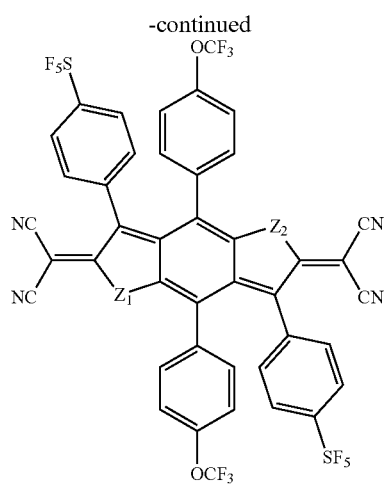

Z₁ = Z₂ = O Compound O-518
Z₁ = Z₂ = S Compound S-518
Z₁ = Z₂ = Se Compound Se-518

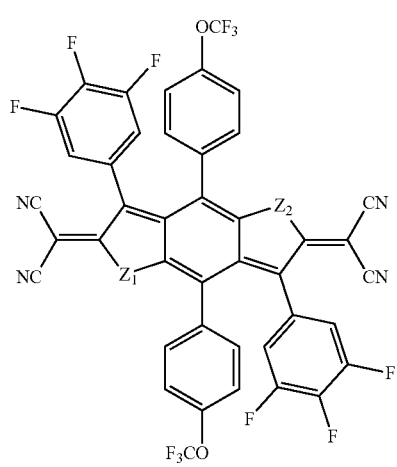

Z₁ = Z₂ = O Compound O-519
Z₁ = Z₂ = S Compound S-519
Z₁ = Z₂ = Se Compound Se-519

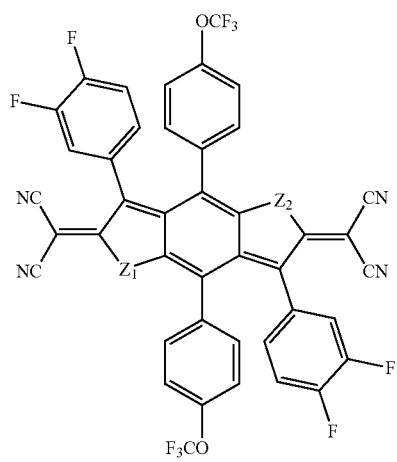

Z₁ = Z₂ = O Compound O-520
Z₁ = Z₂ = S Compound S-520
Z₁ = Z₂ = Se Compound Se-520

-continued

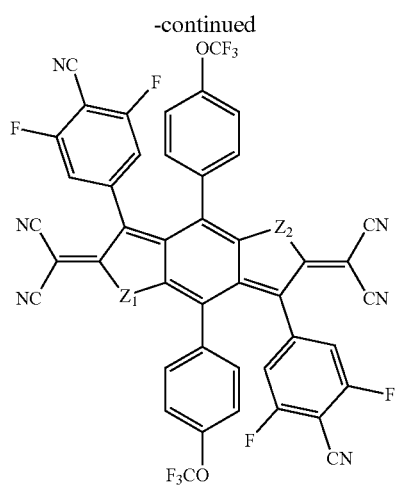

Z₁ = Z₂ = O Compound O-521
Z₁ = Z₂ = S Compound S-521
Z₁ = Z₂ = Se Compound Se-521

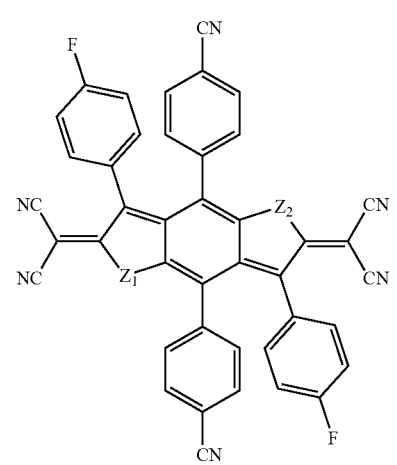

Z₁ = Z₂ = O Compound O-522
Z₁ = Z₂ = S Compound S-522
Z₁ = Z₂ = Se Compound Se-522

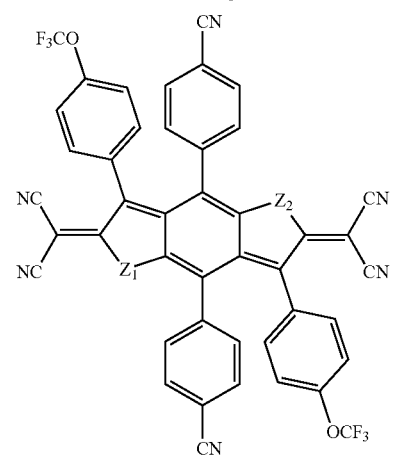

Z₁ = Z₂ = O Compound O-523
Z₁ = Z₂ = S Compound S-523
Z₁ = Z₂ = Se Compound Se-523

-continued

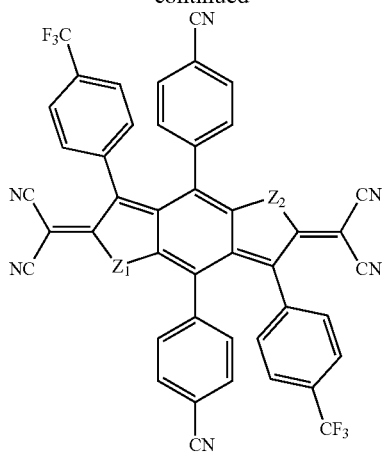

Z₁ = Z₂ = O Compound O-524
Z₁ = Z₂ = S Compound S-524
Z₁ = Z₂ = Se Compound Se-524

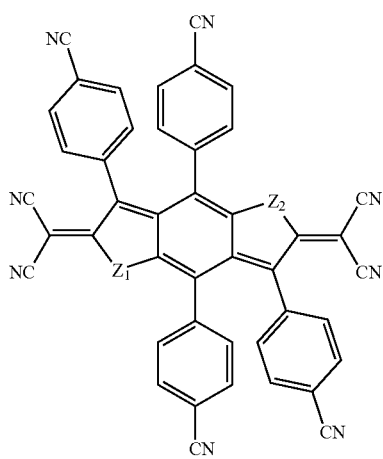

Z₁ = Z₂ = O Compound O-525
Z₁ = Z₂ = S Compound S-525
Z₁ = Z₂ = Se Compound Se-525

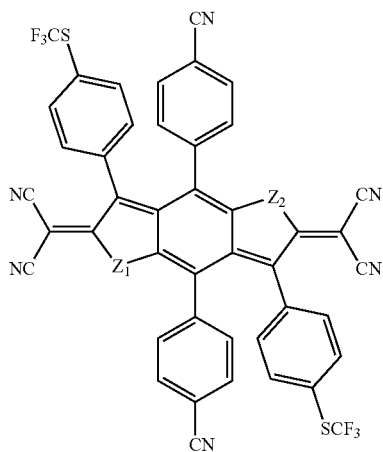

Z₁ = Z₂ = O Compound O-526
Z₁ = Z₂ = S Compound S-526
Z₁ = Z₂ = Se Compound Se-526

-continued

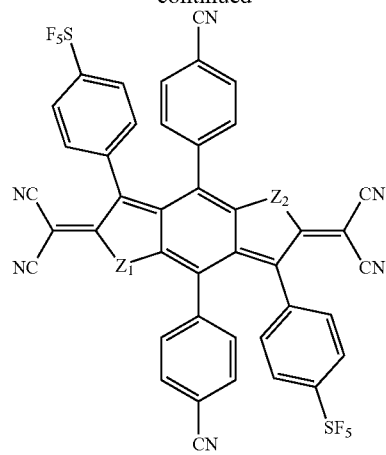

Z₁ = Z₂ = O Compound O-527
Z₁ = Z₂ = S Compound S-527
Z₁ = Z₂ = Se Compound Se-527

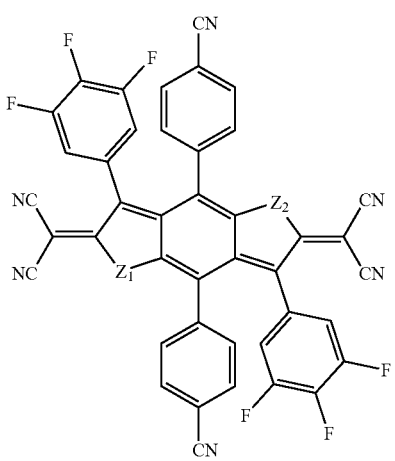

Z₁ = Z₂ = O Compound O-528
Z₁ = Z₂ = S Compound S-528
Z₁ = Z₂ = Se Compound Se-528

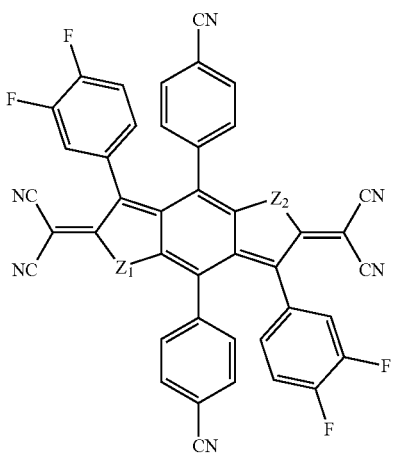

Z₁ = Z₂ = O Compound O-529
Z₁ = Z₂ = S Compound S-529
Z₁ = Z₂ = Se Compound Se-529

-continued

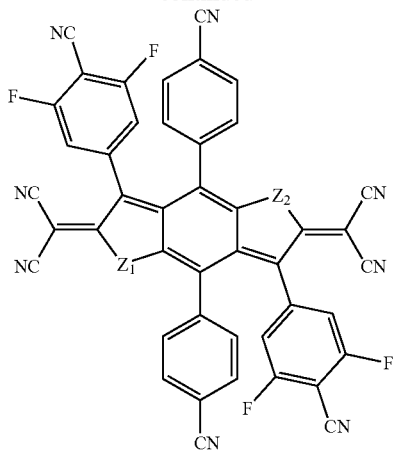

Z₁ = Z₂ = O Compound O-530
Z₁ = Z₂ = S Compound S-530
Z₁ = Z₂ = Se Compound Se-530

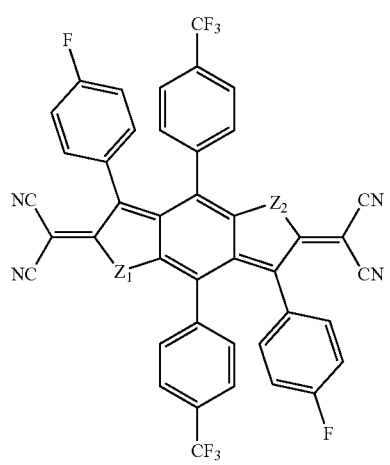

Z₁ = Z₂ = O Compound O-531
Z₁ = Z₂ = S Compound S-531
Z₁ = Z₂ = Se Compound Se-531

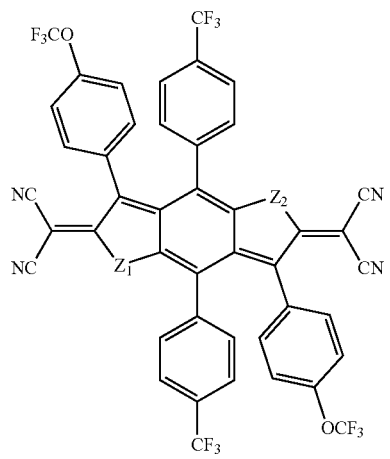

Z₁ = Z₂ = O Compound O-532
Z₁ = Z₂ = S Compound S-532
Z₁ = Z₂ = Se Compound Se-532

-continued

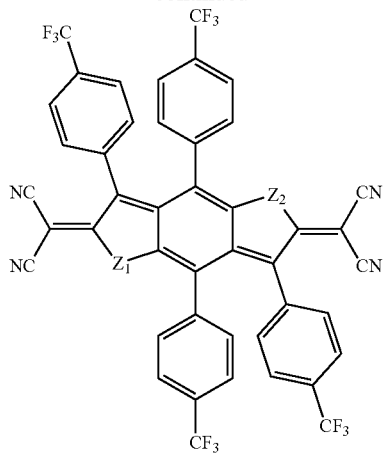

Z₁ = Z₂ = O Compound O-533
Z₁ = Z₂ = S Compound S-533
Z₁ = Z₂ = Se Compound Se-533

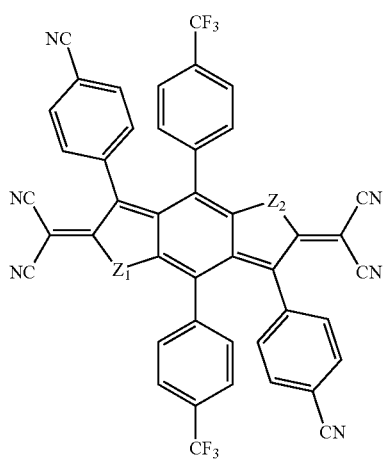

Z₁ = Z₂ = O Compound O-534
Z₁ = Z₂ = S Compound S-534
Z₁ = Z₂ = Se Compound Se-534

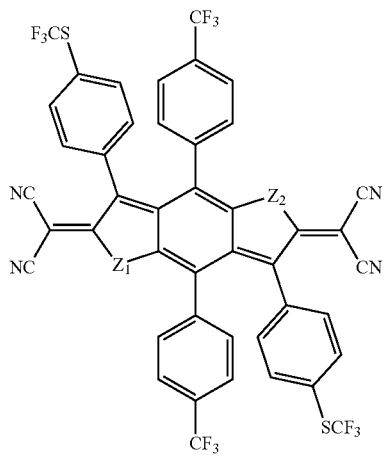

Z₁ = Z₂ = O Compound O-535
Z₁ = Z₂ = S Compound S-535
Z₁ = Z₂ = Se Compound Se-535

-continued

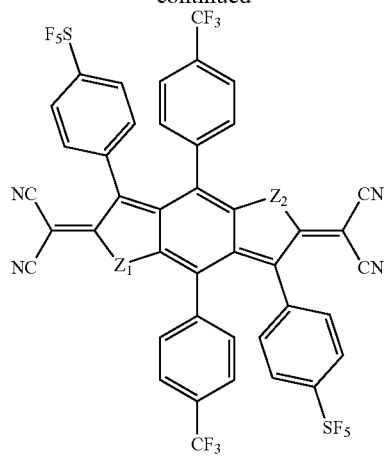

Z₁ = Z₂ = O Compound O-536
Z₁ = Z₂ = S Compound S-536
Z₁ = Z₂ = Se Compound Se-536

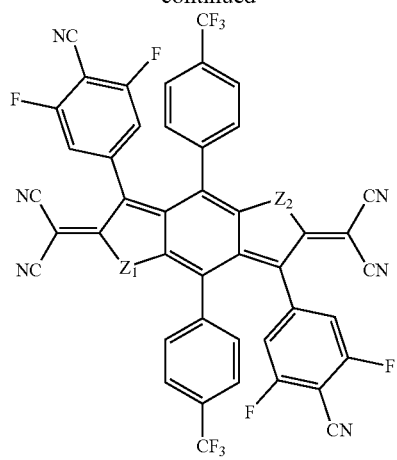

Z₁ = Z₂ = O Compound O-539
Z₁ = Z₂ = S Compound S-539
Z₁ = Z₂ = Se Compound Se-539

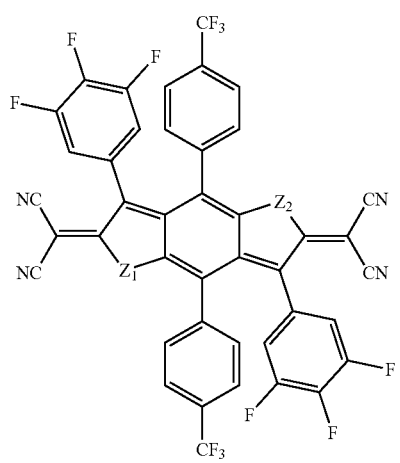

Z₁ = Z₂ = O Compound O-537
Z₁ = Z₂ = S Compound S-537
Z₁ = Z₂ = Se Compound Se-537

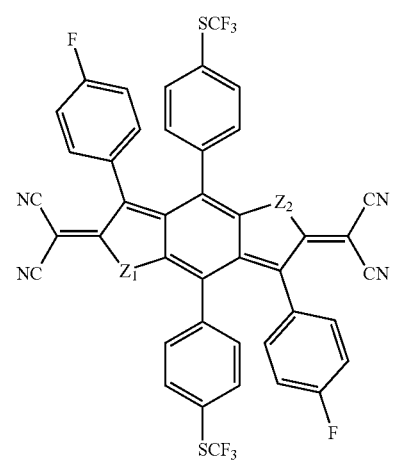

Z₁ = Z₂ = O Compound O-540
Z₁ = Z₂ = S Compound S-540
Z₁ = Z₂ = Se Compound Se-540

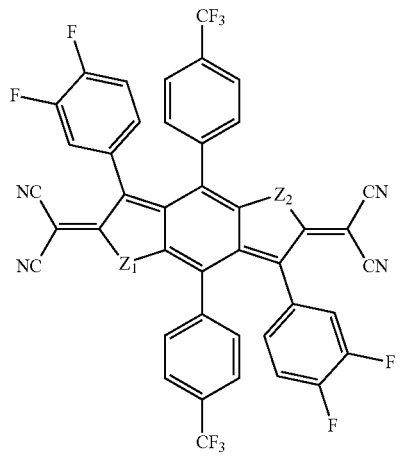

Z₁ = Z₂ = O Compound O-538
Z₁ = Z₂ = S Compound S-538
Z₁ = Z₂ = Se Compound Se-538

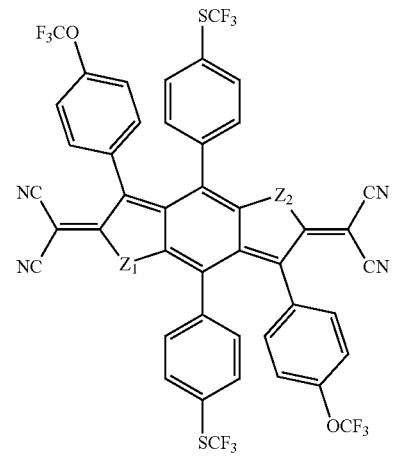

Z₁ = Z₂ = O Compound O-541
Z₁ = Z₂ = S Compound S-541
Z₁ = Z₂ = Se Compound Se-541

-continued

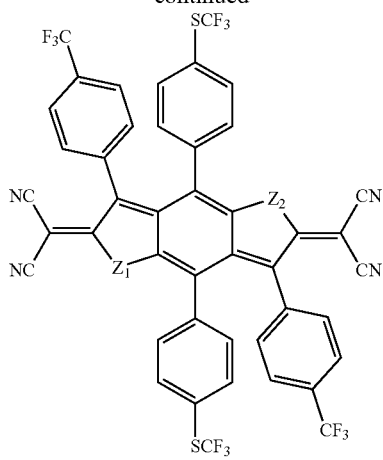

Z₁ = Z₂ = O Compound O-542
Z₁ = Z₂ = S Compound S-542
Z₁ = Z₂ = Se Compound Se-542

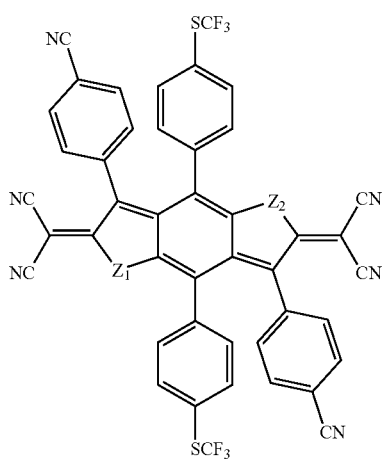

Z₁ = Z₂ = O Compound O-543
Z₁ = Z₂ = S Compound S-543
Z₁ = Z₂ = Se Compound Se-543

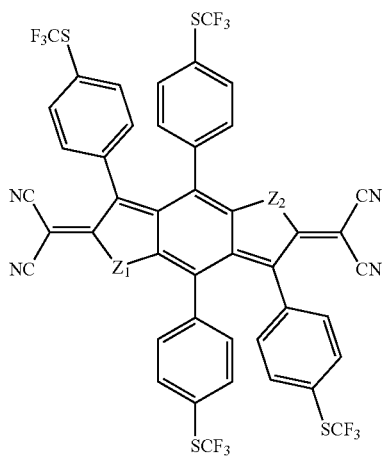

Z₁ = Z₂ = O Compound O-544
Z₁ = Z₂ = S Compound S-544
Z₁ = Z₂ = Se Compound Se-544

-continued

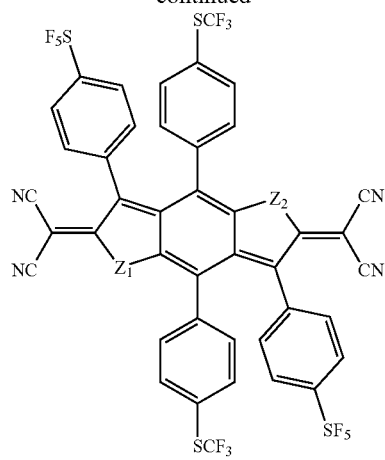

Z₁ = Z₂ = O Compound O-545
Z₁ = Z₂ = S Compound S-545
Z₁ = Z₂ = Se Compound Se-545

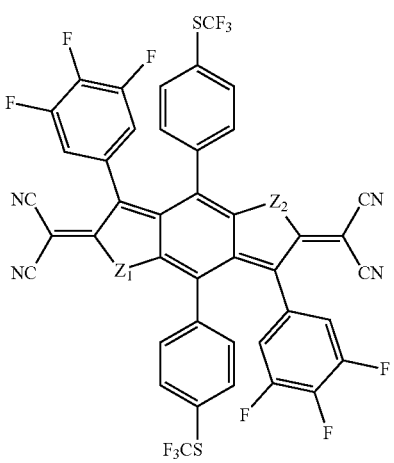

Z₁ = Z₂ = O Compound O-546
Z₁ = Z₂ = S Compound S-546
Z₁ = Z₂ = Se Compound Se-546

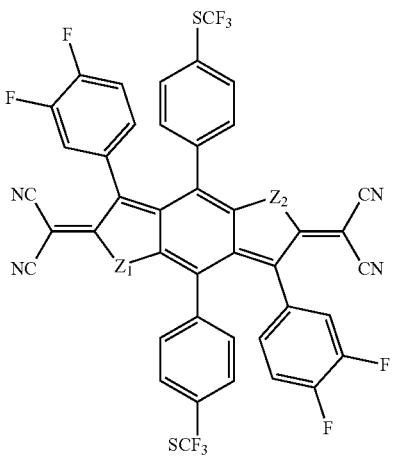

Z₁ = Z₂ = O Compound O-547
Z₁ = Z₂ = S Compound S-547
Z₁ = Z₂ = Se Compound Se-547

203
-continued

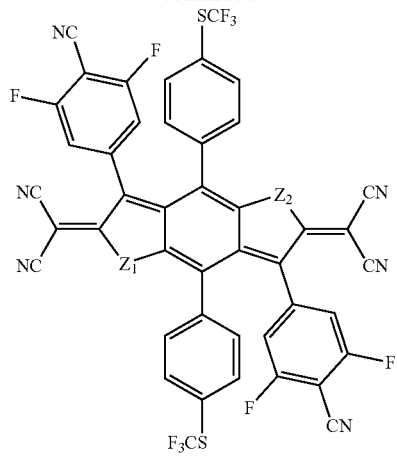

$Z_1 = Z_2 = $ O Compound O-548
$Z_1 = Z_2 = $ S Compound S-548
$Z_1 = Z_2 = $ Se Compound Se-548

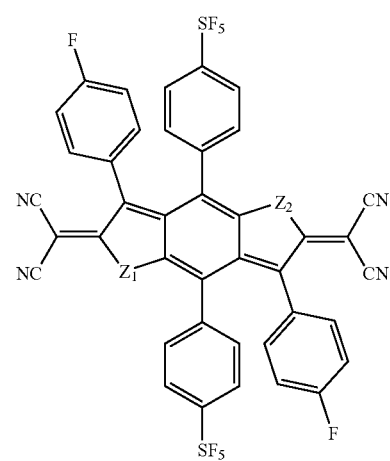

$Z_1 = Z_2 = $ O Compound O-549
$Z_1 = Z_2 = $ S Compound S-549
$Z_1 = Z_2 = $ Se Compound Se-549

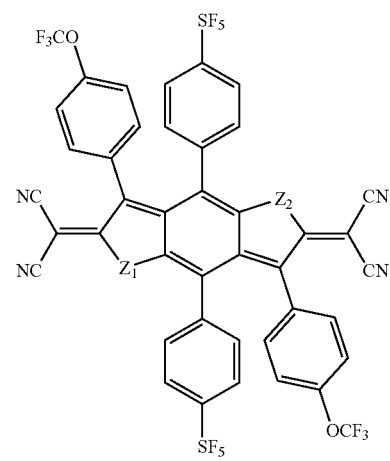

$Z_1 = Z_2 = $ O Compound O-550
$Z_1 = Z_2 = $ S Compound S-550
$Z_1 = Z_2 = $ Se Compound Se-550

204
-continued

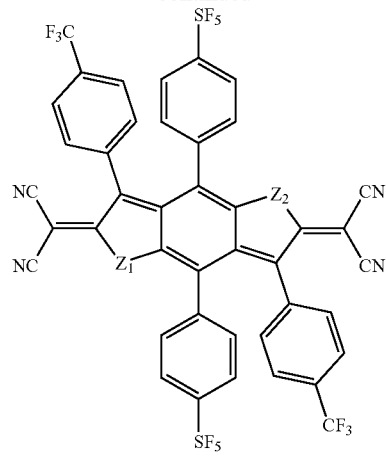

$Z_1 = Z_2 = $ O Compound O-551
$Z_1 = Z_2 = $ S Compound S-551
$Z_1 = Z_2 = $ Se Compound Se-551

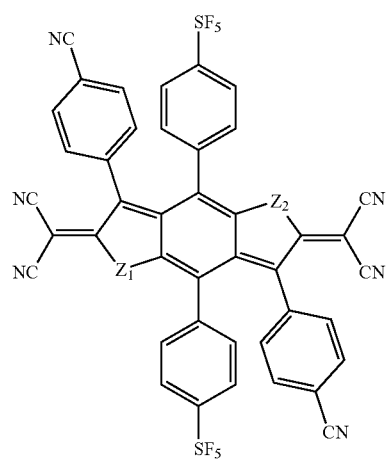

$Z_1 = Z_2 = $ O Compound O-552
$Z_1 = Z_2 = $ S Compound S-552
$Z_1 = Z_2 = $ Se Compound Se-552

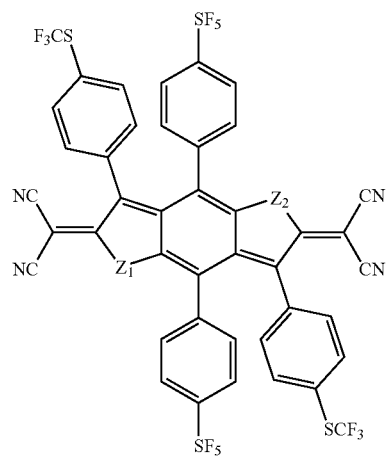

$Z_1 = Z_2 = $ O Compound O-553
$Z_1 = Z_2 = $ S Compound S-553
$Z_1 = Z_2 = $ Se Compound Se-553

-continued

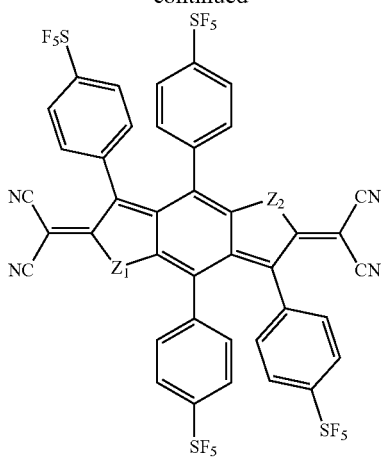

Z₁ = Z₂ = O Compound O-554
Z₁ = Z₂ = S Compound S-554
Z₁ = Z₂ = Se Compound Se-554

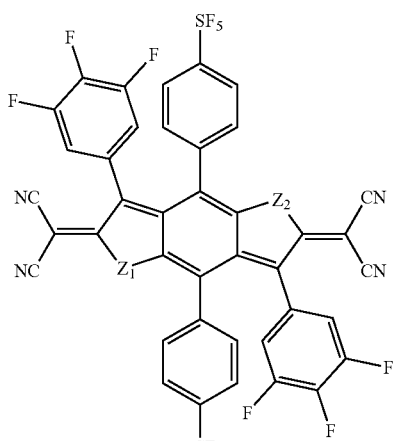

Z₁ = Z₂ = O Compound O-555
Z₁ = Z₂ = S Compound S-555
Z₁ = Z₂ = Se Compound Se-555

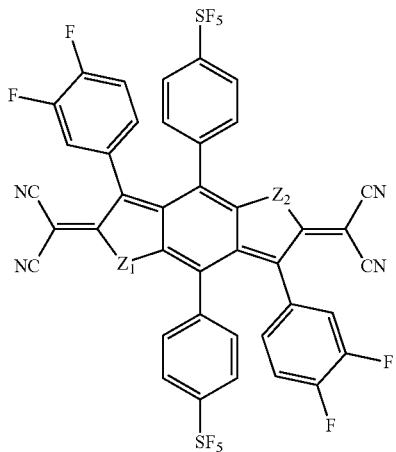

Z₁ = Z₂ = O Compound O-556
Z₁ = Z₂ = S Compound S-556
Z₁ = Z₂ = Se Compound Se-556

-continued

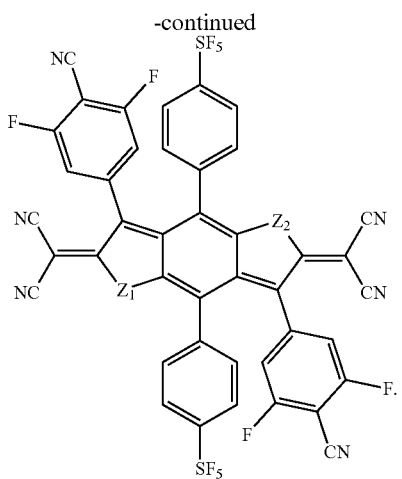

Z₁ = Z₂ = O Compound O-557
Z₁ = Z₂ = S Compound S-557
Z₁ = Z₂ = Se Compound Se-557

In one embodiment of the present invention, an electroluminescent device is disclosed, which comprises:
an anode,
a cathode,
and an organic layer disposed between the anode and the cathode, wherein comprising a compound having Formula 1:

Formula 1

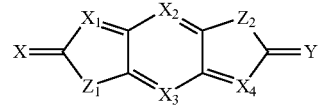

wherein
$X_1$, $X_2$, $X_3$, and $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;
$Z_1$ and $Z_2$ are each independently selected from the group consisting of O, S, Se, S=O, and SO₂;
X and Y are each independently selected from the group consisting of S, Se, NR', or CR"R'";
R, R', R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring or fused structure.

In one embodiment of the present invention, wherein the organic layer is a charge transporting layer.

In one embodiment of the present invention, wherein the organic layer is a hole injection layer.

In one embodiment of the present invention, wherein the organic layer is a charge transporting layer, and the organic layer further comprises an arylarmine compound.

In one embodiment of the present invention, wherein the organic layer is a hole injection layer, and the organic layer further comprises an arylamine compound.

In one embodiment of the present invention, wherein the device further comprises a light emitting layer.

In yet another embodiment of the present invention, an organic light-emitting device is also disclosed. The organic light-emitting device comprises a plurality of stacks between an anode and a cathode is disclosed, the stacks comprise a first light-emitting layer and a second light-emitting layer, wherein the first stack comprises a first light-emitting layer, the second stack comprises a second light-emitting layer, and a charge generation layer is disposed between the first stack and the second stack, wherein the charge generation layer comprises a p type charge generation layer and an n type charge generation layer, wherein the p type charge generation layer comprises a compound according to Formula 1:

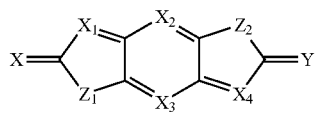

Formula 1 wherein $X_1$, $X_2$, $X_3$, and $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, Se, S=O, and $SO_2$;

X and Y are each independently selected from the group consisting of S, Se, NR', or CR"R'";

R, R', R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphine group, and combinations thereof;

Any adjacent substitution can be optionally joined to form a ring or fused structure.

Combination with Other Materials

The materials described herein as useful for a particular layer in an organic light emitting device may be used in combination with a wide variety of other materials present in the device. The combinations of these materials are described in more detail in U.S. Pat. App. No. 20160359122. at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, materials disclosed herein may be used in combination with a wide variety of emitters, hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH, electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

SYNTHESIS EXAMPLES

The method for preparing the compounds of the present invention is not limited. The following compounds are exemplified as a typical but non-limiting example, and the synthesis route and preparation method are as follows:

Synthesis Example 1

Synthesis of S-1

Step 1: Synthesis of S-1-1

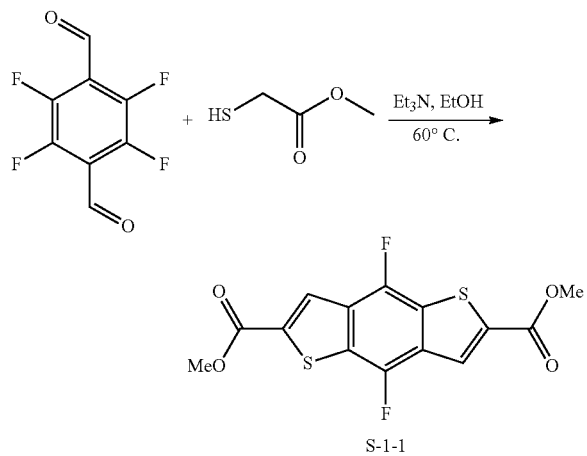

S-1-1

To a solution of 2,3,5,6-tetrafluoroterephthalaldehyde (15.6 g, 75.7 mmol) and triethylamine (42 mL, 303 mmol) in ethanol (300 mL) was added methyl 2-mercaptoacetate (14 mL, 159 mmol) dropwise at room temperature, then stirred at 60° C. for 12 hours. The solution was cooled to room temperature and filtered, the solid was washed with small amount of ethanol to obtain intermediate S-1-1 as yellow solid (20 g, 77% yield).

Step 2: Synthesis of S-1-2

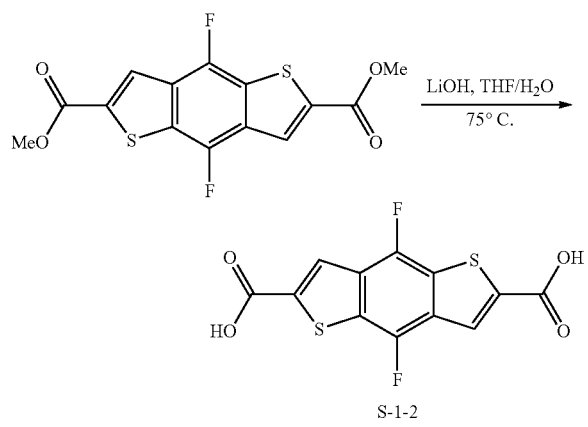

S-1-2

To a suspension of dimethyl 4,8-difluorobenzo[1,2-b:4,5-b']dithiophene-2,6-dicarboxylate (20 g, 58.5 mmol) in THF (200 mL) was added aqueous lithium hydroxide (234 mL, 1N), then stirred at 75° C. for 12 hours. The solution was cooled to room temperature and HCl (500 mL, 2 N) was added, the solid was collected by filtration and washed with small amount of water, vacuum dried to obtain intermediate S-1-2 as yellow solid (19 g, 99% yield).

Step 3: Synthesis of S-1-3

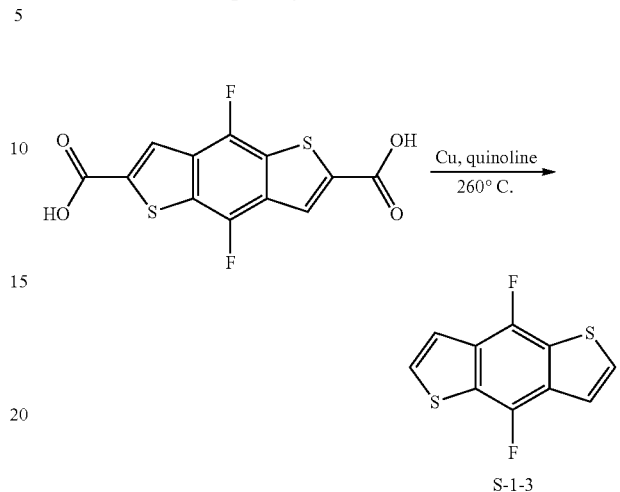

S-1-3

To a suspension of 4,8-difluorobenzo[1,1-b:4,5-b']dithiophene-2,6-dicarboxylic acid (20 g, 58.5 mmol) in quinoline (100 mL) was added copper powder (750 mg, 11.7 mmol), then stirred at 260° C. for 3 hours. The solution was cooled to room temperature and added HCl (500 mL, 3N), the mixture was extracted with EA (200 mL*3), organic phase was combined and washed with HCl (300 mL, 3N) and brine successively and dried using magnesium sulfate. A column-chromatography was performed onto the resultant and then recrystallized from n-hexane and DCM to obtain intermediate S-1-3 as white solid (6 g, 45% yield).

Step 4: Synthesis of S-1-4

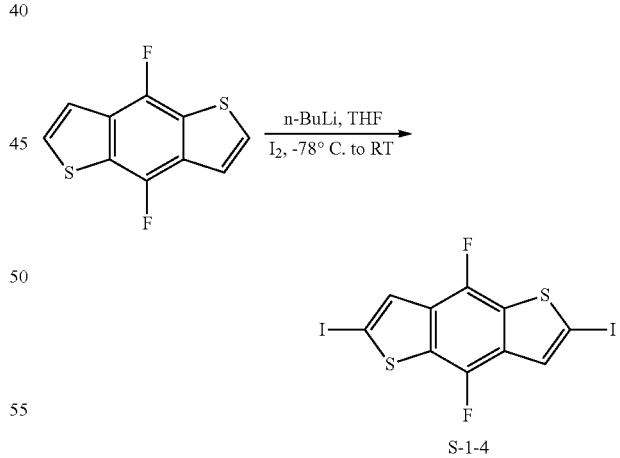

S-1-4

To a solution of 4,8-difluorobenzo[1,2-b:4,5-b']dithiophene (3 g, 13.27 mmol) in THF (130 mL) was n-BuLi (16 mL, 2.5 M) dropwise at −78° C. with stirring, after 1 hour at the same temperature, the reaction temperature was risen to room temperature slowly and stayed at room temperature for 10 minutes. Then the reaction was cooled back to −78° C. with cooling bath and kept for 30 minutes. A solution of iodine (10 g, 39.8 mmol) in THF (20 mL) was added, the cooling bath was removed and stirred overnight. The reaction was quenched with saturated aqueous ammonia chloride (100 mL), the aqueous layer was extracted with DCM (100 mL×3), the organic phase was combined and washed with aqueous sodium thiosulfate (100 mL, 1N) and brine successively and dried using magnesium sulfate. Removed of solvent and recrystallized from DCM to obtain intermediate S-1-4 as white solid (5.3 g, 90% yield), Step 5: Synthesis of S-1-5

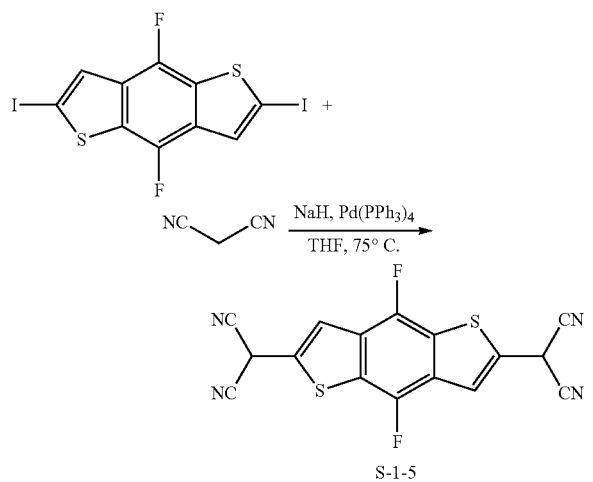

S-1-5

To a solution of malononitrile (1.84 g, 29.5 mmol) in THF (100 mL) was added NaH (2.33 g, 59 mmol) carefully at 0° C. with stirring. After 0.5 hour at the same temperature, 4,8-difluoro-2,6-diiodobenzo[1,2-b:4,5-b']dithiophene (5.3 g, 11.7 mmol) and Tetrakis(triphenylphosphine)palladium (645 mg, 0.59 mmol) was added with bubbling of nitrogen. After 20 minutes, the mixture was heated at 75° C. for 12. hours. The solvent was removed and HCl (100 mL, 2 N) was added, the yellow precipitates was collected by filtration and washed with small amount of water, ethanol and PE, vacuum dried to obtain intermediate S-1-5 as yellow solid (3.4 g, 86% yield).

Step 6: Synthesis of S-1

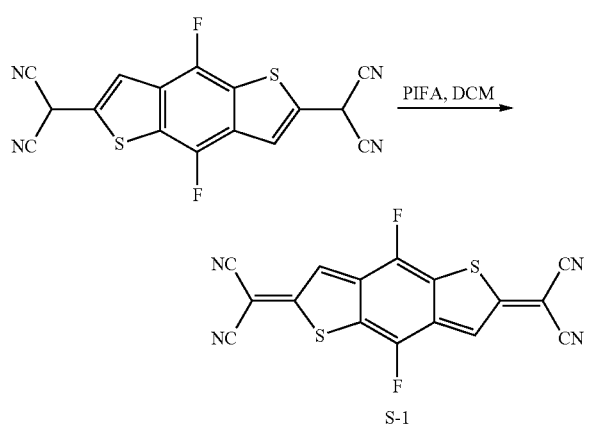

S-1

To a suspension of 2,2'-(4,8-difluorobenzo[1,2-b:4,5-b']dithiophene-2,6-diyl)dimalononitrile (3.4 g, 9 mmol) in DCM (100 mL) was added [Bis(trifluoroacetoxy)iodo]benzene (PIFA, 4.3 g, 9.9 mmol), then stirred for 12 hours at room temperature. The volume of solvent was reduced to approximate 50 mL by vacuum evaporation and the residue mixture was cooled to 0° C., the dark precipitates were collected by filtration and washed with DCM to obtain Compound S-1 as black solid (2.1 g, 65% yield). Further purification was carried out by vacuum sublimation. The product was confirmed as the target product, with a molecular weight of 352.

Synthesis Example 2

Synthesis of S-44

Step 1: Synthesis of S-44-1

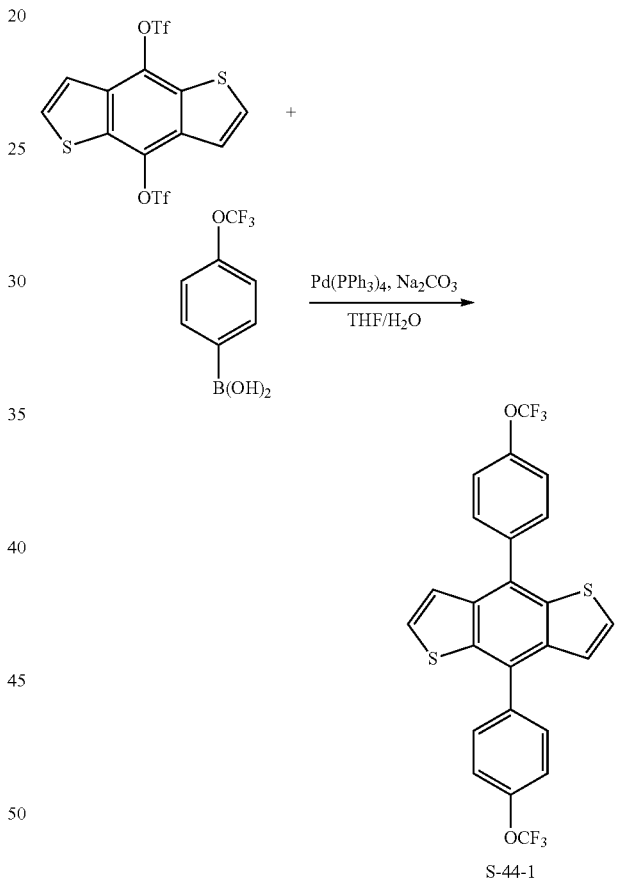

S-44-1

In a 500 mL three-necked round-bottomed flask benzo[1,2-b:4,5-b']dithiophene-4,8-diylbis(trifluoromethanesulfonate) (13 g, 27 mmol) and (4-(trifluoromethoxy)phenyl)boronic acid (13.9 g, 67.5 mmol) were dissolved in THF (200 mL). Tetrakis(triphenylphosphine)palladium(0) (1.55 g, 1.35 mmol) and sodium carbonate solution (135 mL, 1M) were added to the reaction mixture. The reaction mixture was heated at 75° C. for 12 hours. Water was added to the reaction mixture followed by extraction with DCM and washed with brine. The combined organic layers were concentrated. The crude product was purified by column-chromatography to obtain S-44-1 as white solid (11 g, 80% yield),

Step 2: Synthesis of S-44-2
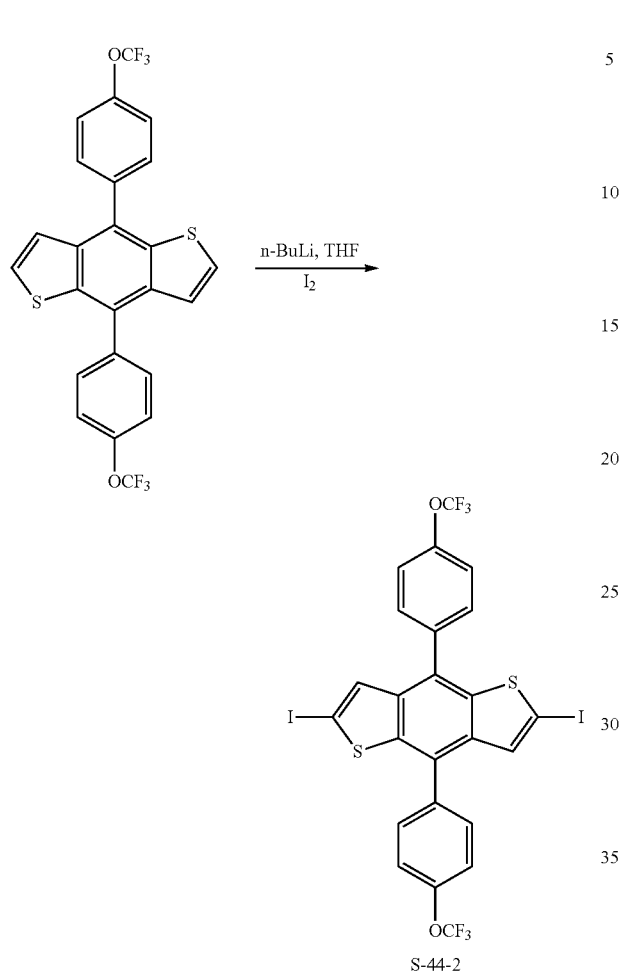
S-44-2
The procedure of the synthesis of S-44-2 was repeated as the synthesis of S-1-4 except for using S-44-1 in place of S-1-3. S-44-2 was obtained as white solid (7.3 g, 80% yield),
Step 3: Synthesis of S-44-3
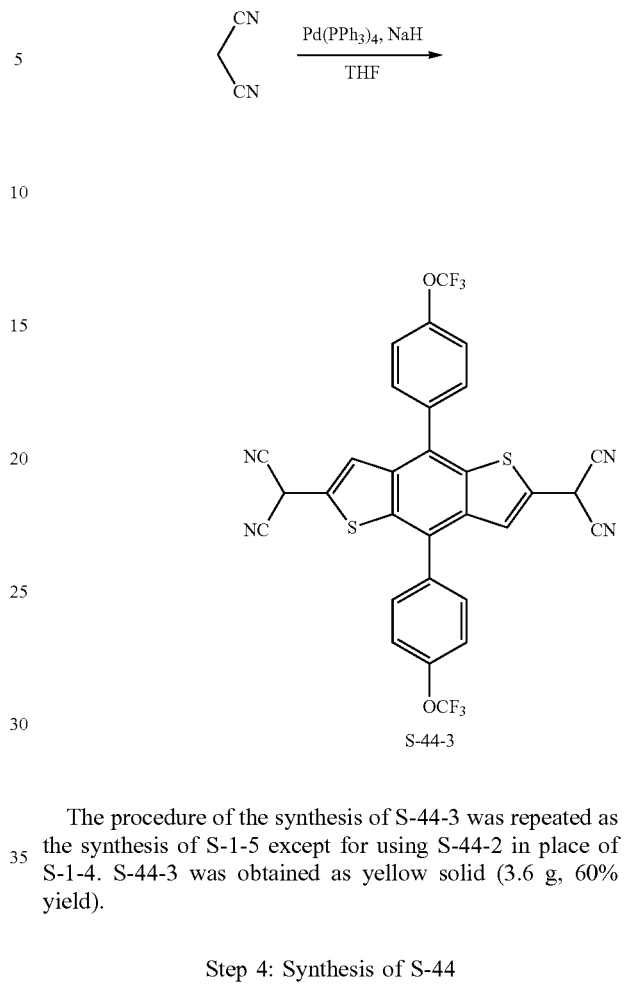
S-44-3
The procedure of the synthesis of S-44-3 was repeated as the synthesis of S-1-5 except for using S-44-2 in place of S-1-4. S-44-3 was obtained as yellow solid (3.6 g, 60% yield).
Step 4: Synthesis of S-44
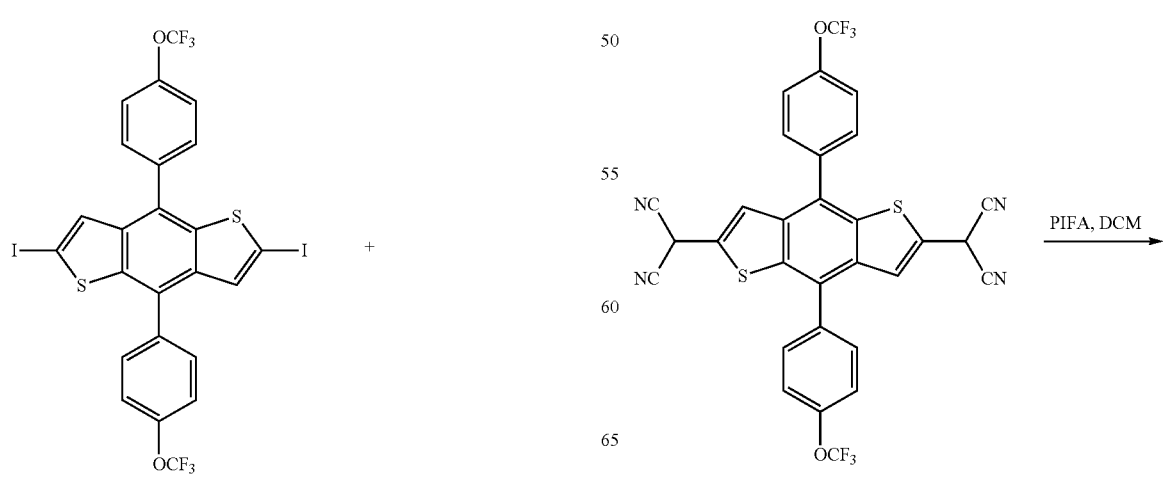

-continued

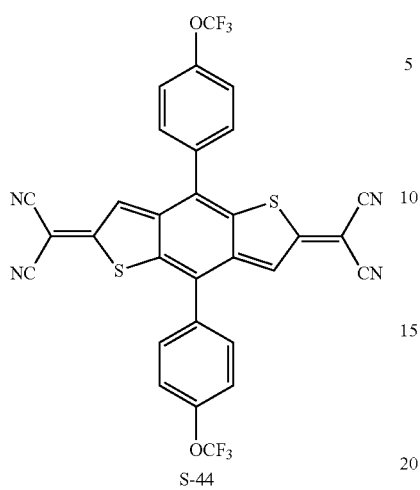

S-44

The procedure of the synthesis of S-44 was repeated as the synthesis of S-1 except for using S-44-3 in place of S-1-5. S-44 was obtained as violet solid (1.7 g, 45% yield). The product was confirmed as the target product, with a molecular weight of 637.

Synthesis Example 3

Synthesis of S-26

Step 1: Synthesis of S-26-1

-continued

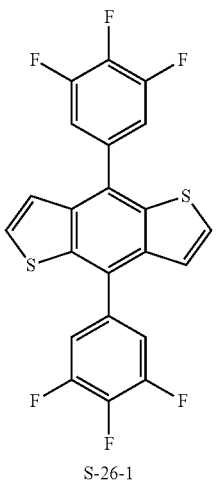

S-26-1

The procedure of the synthesis of S-26-1 was repeated as the synthesis of S-44-1 except for using (3,4,5-trifluorophenyl)boronic acid in place of (4-(trifluoromethoxy)phenyl)boronic acid. S-26-1 was obtained as white solid (10 g, 60% yield).

Step 2: Synthesis of S-26-2

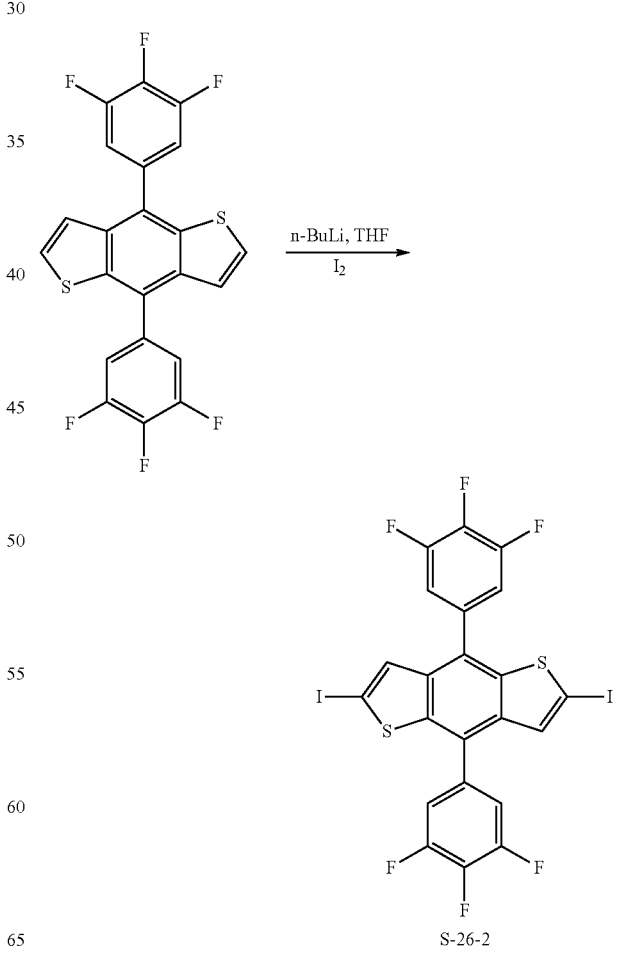

S-26-2

The procedure of the synthesis of S-26-2 was repeated as the synthesis of S-1-4 except for using S-26-1 in place of S-1-3. S-26-2 was obtained as white solid (6.8 g, 80% yield), Step 3: Synthesis of S-26-3

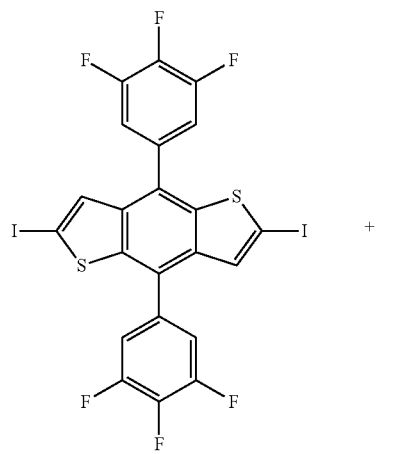

Step 4: Synthesis of S-26

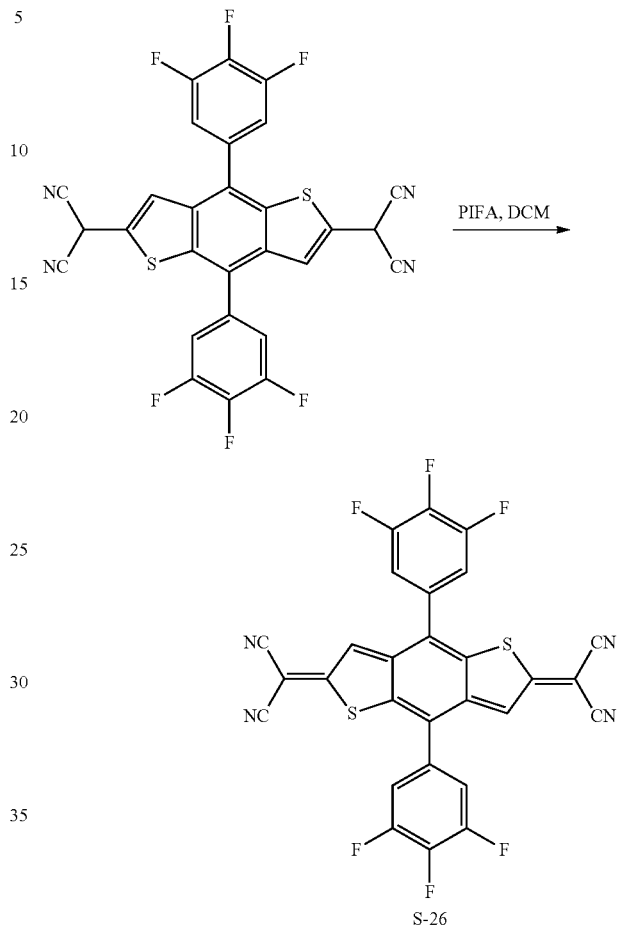

The procedure of the synthesis of S-26-3 was repeated as the synthesis of S-1-5 except for using S-26-2 in place of S-1-4. S-26-3 was obtained as yellow solid (3.2. g, 60% yield).

The procedure of the synthesis of S-26 was repeated as the synthesis of S-1 except for using S-26-3 in place of S-1-5. S-26 was obtained as violet solid (1.3 g, 47% yield). The product was confirmed as the target product, with a molecular weight of 576.

The persons skilled in the art should know that the above preparation method is only an illustrative example, and the persons skilled in the art can obtain the structure of other compounds of the present invention by modifying the above preparation method.

Synthesis Comparative Example 1

Synthesis of A-1

Step 1: Synthesis of A-1-1

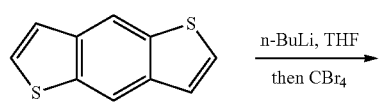

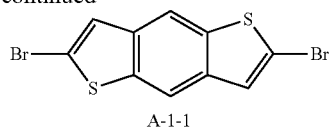

A-1-1

The procedure of the synthesis of A-1-1 was repeated as the synthesis of S-1-4 except for using benzo[1,2-b:4,5-b']dithiophene and carbon tetrabromide in place of S-1-3 and iodine respectively. A-1-1 was obtained as light yellow solid (3.2 g, 80% yield).

Step 2: Synthesis of A-1-2

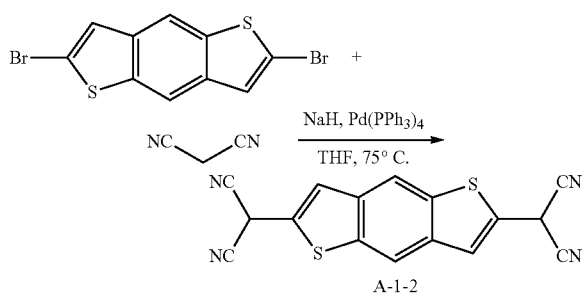

The procedure of the synthesis of A-1-2 was repeated as the synthesis of S-1-5 except for using A-1-1 in place of S-1-4. A-1-2 was obtained as yellow solid (2.8 g, 97% yield).

Step 3: Synthesis of A-1

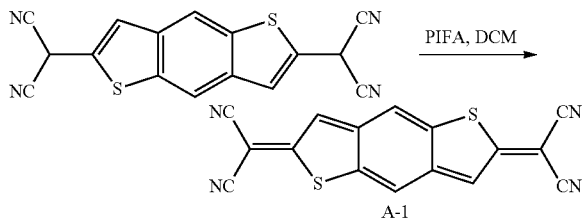

The procedure of the synthesis of A-1 was repeated as the synthesis of S-1 except for using A-1-2 in place of S-1-5. A-1 was obtained as black solid (2.1 g, 75% yield). The product was confirmed as the target product, with a molecular weight of 316.

The above synthesized compounds of the present invention all can keep stable during sublimation, proving that they are suitable for the vacuum deposition fabrication of OLED. Otherwise, the comparative compound A-1 degrades during sublimation, proving that it is not suitable for the vacuum deposition fabrication of OLED. And also, the solubility of comparative compound A-1 in organic solvents is very low, so it is also not suitable for the printing fabrication of OLED.

These above synthesized compounds of the present invention are more electron deficient than the comparative compound A-1. Measuring with Cyclic voltammetry test, the LUMO of compound S-1 and S-44 are −4.74 eV and −4.67 eV, respectively, while which of comparative compound A-1 is only −4.30 eV, and the difference is more than 0.3 eV. This suggests that compound S-1 and S-44 are more easily to reduce than comparative compound A-1, more effectively to obtain p type conductive doped triarylamine compounds in HIL, and/or HTL, and can improve performance of OLED, for example, longer device lifetime, higher efficiency and/or lower voltage. And this proves that the compounds having Formula 1, one feature of which is having electron withdrawing group at the $X_1$ and $X_4$ position of the five-membered ring and/or $X_2$ and $X_3$ position of the six-membered ring, can effectively improve the electron deficiency of the molecules, reduce LUMO, match with HOMO of triarylamine compounds, and form p-type conduction of HIL and/or HTL. The compound of Formula 1 can obtain similar effects when the five-membered ring and/or six-membered ring of Formula 1 are aza-heterocycles, for the electron withdrawing effects of the nitrogen on the heterocycles.

DEVICE EXAMPLES

Example 1

A glass substrate with 120 nm thick of ITO transparent electrode was subjected to oxygen plasma and UV ozone treatment. The cleaned glass substrate was dried on a hotplate in a glovebox before deposition. The following materials were deposited onto the surface of the glass at the rate of 0.02-0.2 nm/s under the pressure of $10^{-8}$ torr. First, Compound HI was deposited onto the surface of the glass to form a 10 nm-thick film as a hole-injecting layer (HIL). Subsequently, Compound HT and Compound S-1 (weight ratio 97:3) was codeposited onto on the above obtained film to form a 20 nm-thick film which served as the first hole-transporting layer (HTL1). Further, Compound HT was deposited onto on the above obtained film to form a 20 nm-thick film which served as the second hole-transporting layer (HTL2). Further, Compound H1, Compound H2 and Compound GD (weight ratio 45:45:10) was codeposited onto on the above obtained film to form a 40 nm-thick film which served as the emitting layer (EML). Further, Compound H2 was deposited onto on the above obtained film to form a 10 nm-thick film which served as the hole-blocking layer (HBL). Then, 8-Hydroxyquinolinolato-lithium (Liq) and Compound ET (weight ratio 60:40) was codeposited onto on the above obtained film to form a 35 nm-thick film which served as the electron-transporting layer (ETL). Finally, Liq was deposited to form a 1 nm-thick film which served as the electron-injecting layer (EIL) and 120 nm-thick of Al was deposited to form the cathode.

Example 2 was fabricated in the same manner as in Example 1, except that Compound HT and Compound S-1 with a weight ratio of 91:9 (10 nm) was used as the HIL and Compound HT and Compound S-1 with a weight ratio of 91:9 (20 nm) was used as the MIL Example 3 was fabricated in the same manner as in Example 1, except that in the HTL1, Compound HT and Compound S-44 with a weight ratio 97:3 was used.

Example 4 was fabricated in the same manner as in Example 2, except that Compound HT and Compound S-44 with a weight ratio of 97:3 (10 nm) was used as the HIL, and Compound HT and Compound S-44 with a weight ratio of 97:3 (20 nm) was used as the HTL1.

Comparative Example 1 was fabricated in the same manner as in Example 1, except that Compound HT (20 nm) was used in the HTL1.

The partial structures of devices are shown in Table 1:

TABLE I

| Device ID | HIL (10 nm) | HTL1 (20 nm) | HTL2 (20 nm) |
|---|---|---|---|
| Example 1 | HI | HT:S-1 (97:3) | HT |
| Example 2 | HT:S-1 (91:9) | HT:S-1 (91:9) | |
| Example 3 | HI | HT:S-44 (97:3) | |
| Example 4 | HT:S-44 (97:3) | HT:S-44 (97:3) | |
| Comparative Example 1 | HI | HT | |

Structure of the materials used in the devices are shown as below:

Compound HI

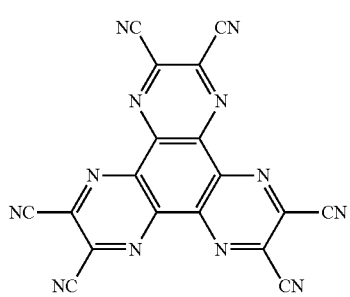

Compound HT

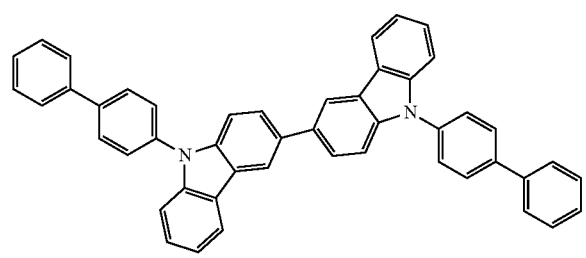

Compound H1

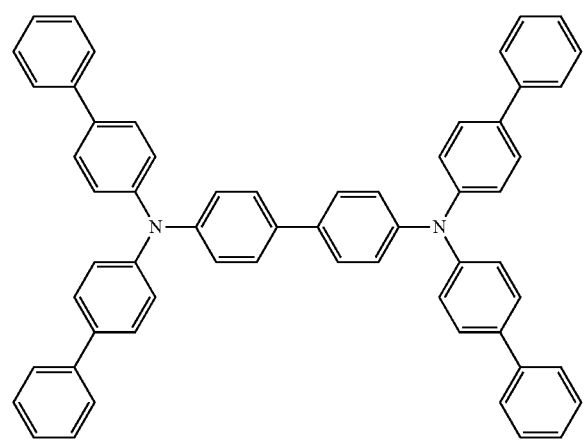

Compound H2

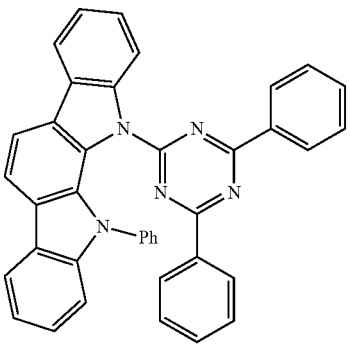

Compound GD

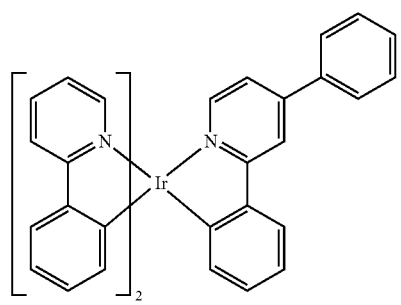

Compound ET

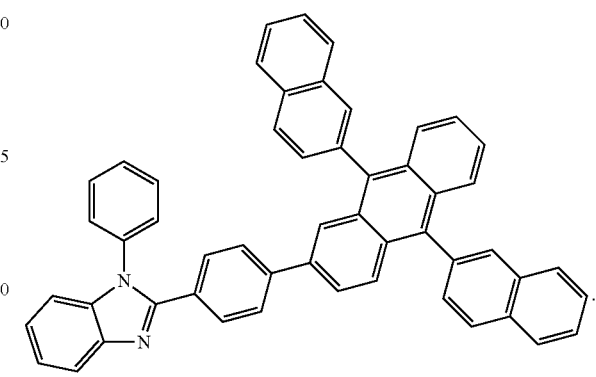

The devices were evaluated by measuring the External Quantum Efficiency (EQE), current efficiency (CE) and CIE at 1000 cd/m² and LT97 from an initial luminance of 21750 cd/m². The results obtained are shown in Table 2.

TABLE 2

| Device ID | EQE (%) | CE (cd/A) | CIE (x, y) | | LT97 (h) |
|---|---|---|---|---|---|
| Example 1 | 19.37 | 66.09 | 0.435 | 0.553 | 196 |
| Example 2 | 20.17 | 69.27 | 0.427 | 0.560 | 202 |
| Example 3 | 20.71 | 70.79 | 0.437 | 0.552 | 264 |
| Example 4 | 27.18 | 90.35 | 0.438 | 0.550 | 171 |
| Comparative Example 1 | 22.06 | 75.25 | 0.439 | 0.549 | 174 |

Discussion:

As shown in Table 2, Device Example 1 using Compound S-1 as a dopant in the HTL1 has better lifetime than Comparative Example 1 using only representative HTL material of the art (196 h vs 174 h). Device Example 2 using Compound S-1 as a dopant in both the HIL and HTL1 has a better lifetime than Comparative Example 1 using only representative HIL, HTL materials of the art (202 h vs 174 h). Device Example 3 using Compound S-44 as a dopant in the HTL1 has much better lifetime than Comparative Example 1 using only representative HTL material of the art (264 h vs 174 h). Remarkably, Device Example 4 using Compound S-44 as a dopant in both the HIL and HTL1 has a much higher efficiency than Comparative Example 1 using only representative HIL, HTL materials of the art (27.18% vs 22.06%, 90.35 cd/A vs 75.25 cd/A), while maintaining a similar lifetime as Comparative Example 1 (171 h vs 174 h). The result conclusively proves that compounds of Formula 1 in the present invention can offer similar or even better performance of devices than the representative materials of the art, especially in terms of device lifetime and/or efficiency, when used in the HIL or HTL layers.

Additional Material Synthesis Examples:

Without intending to limit the method for preparing the compounds of the present invention, the following compounds are exemplified as a typical but non-limiting example, and the synthesis route and preparation method are as follows:

Synthesis Example 4

Synthesis of Compound 56

Step 1: Synthesis of [Intermediate 1-a]

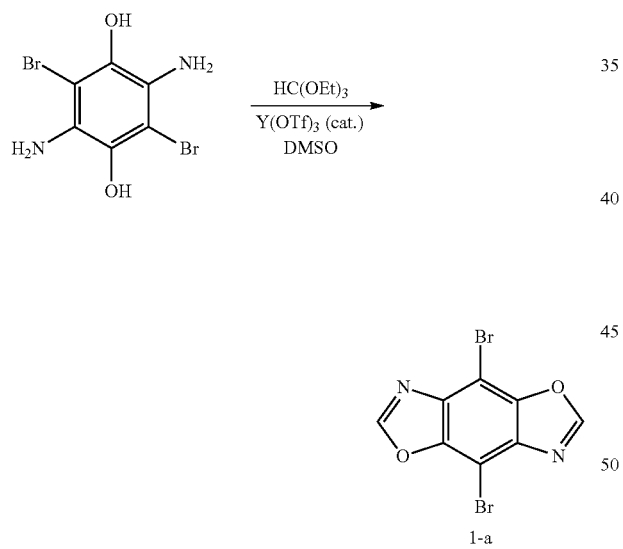

To a 500 mL three-necked flask, DMSO (150 mL) was added, and nitrogen was bubbled for half an hour. HC(OEt)$_3$ (22.2 g, 150 mmol) and Y(OTf)$_3$ (2.15 g, 4 mmol) were added successively and further bubbled for 5 minutes. 2,5-diamino-3,6-dibromobenzene-1,4-diol (894 g, 30 mmol) was added and the mixture was warmed to 60° C. After 20 minutes, the solution turned brown or khaki and stirred overnight. After completion of the reaction, DCM/PE (1:1, 500 mL) was added. A solid was collected by filtration and it was washed with acetone and filtered to obtain 1-a as an off-white solid (7.2 g, 75% yield). $^1$HNMR (400 MHz, d$_6$-DMSO) δ=9.03 (s, 2H).

Step 2: Synthesis of [Intermediate 1-b]

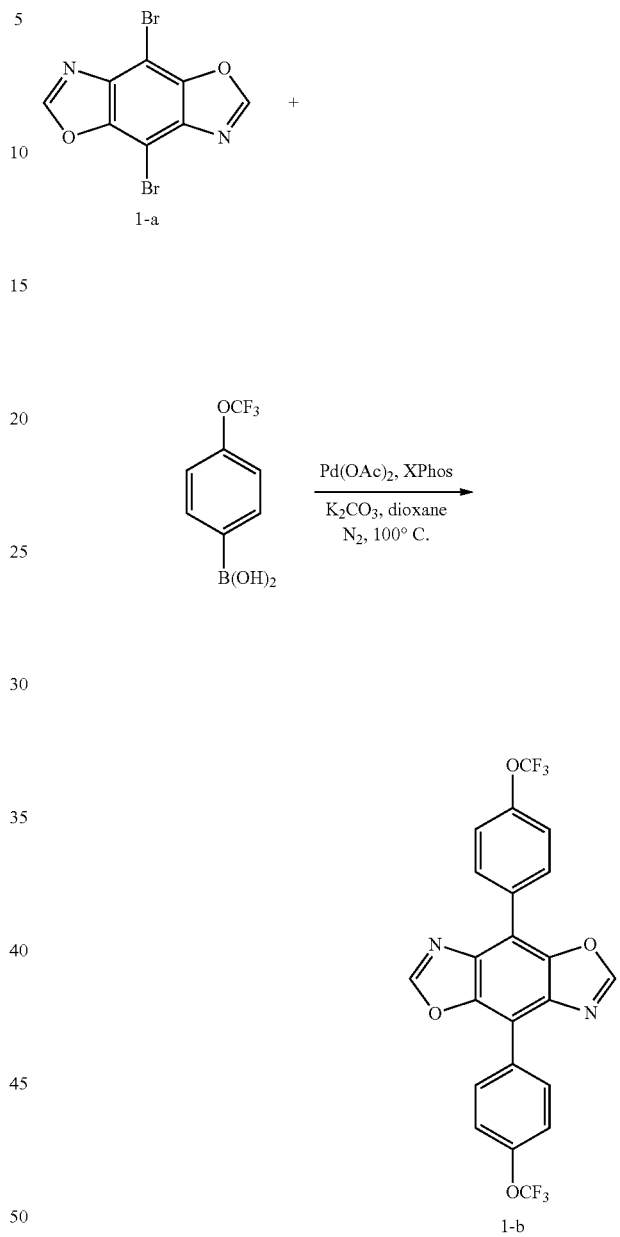

To a 250 mL two-necked flask, dioxane (50 mL) was added, and nitrogen was bubbled for 15 minutes. Pd(OAc)$_2$ (225 mg, 10 mol %, 1.0 mmol) and XPhos (1.0 g, 2.1 mmol) were added under stirring. After stirring for 10 minutes, 1-a (3.18 g, 10 mmol), p-trifluoromethoxyphenylboronic acid (8.24 g, 40 mmol), and potassium carbonate (8.34 g, 60 mmol) were added successively. The reaction was warmed to 110° C., refluxed, and stirred overnight under nitrogen atmosphere. After completion, the reaction mixture was cooled, filtered through celite, washed with dichloromethane, and isolated via silica gel column chromatography to obtain 1-b as a white solid (4.36 g, 91% yield). $^1$HNMR (400 MHz, d$_6$-DMSO) δ=9.00 (s, 2H), 8.33 (d, J=8.8 Hz, 4H), 7.63 (d, J=8.8 Hz, 4H).

Step 3: Synthesis of [Intermediate 1-c]

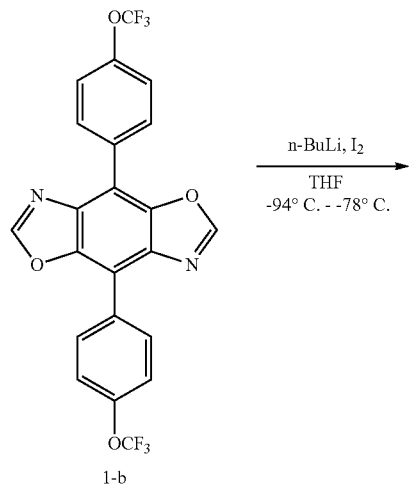

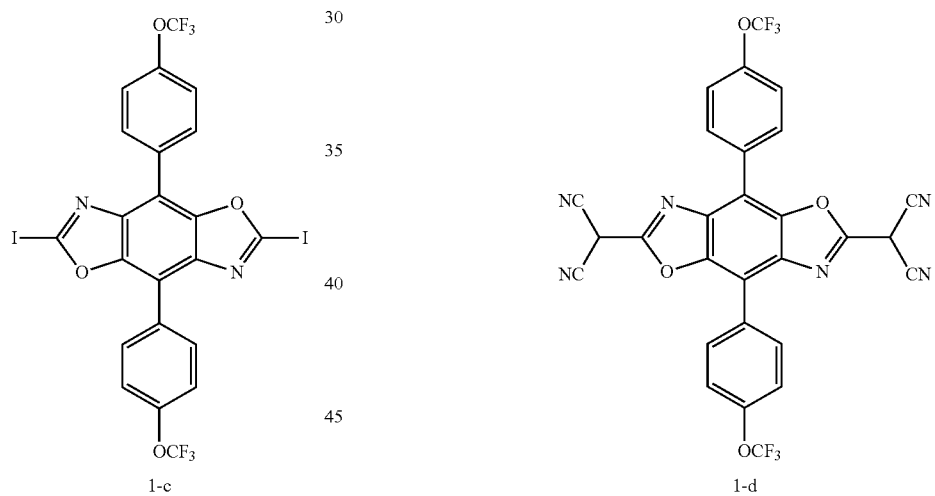

Under nitrogen atmosphere, Intermediate 1-b (4.36 g, 9.1 mmol) was added to THF (114 mL, 0.08 M). The mixture was cooled to −94° C. (in an acetone/liquid nitrogen cooling bath). n-Butyllithium (13.8 mL, 20.93 mmol, 1.6 M in n-hexane) was slowly added dropwise. The reaction was held at this temperature for 1 h, then slowly warmed to −78° C. (in an acetone/dry ice cooling bath) and reacted for 8 h. A solution of elemental iodine (6.93 g, 27.3 mmol) in THF (15 mL) was added. After the addition, the mixture was slowly warmed to room temperature and reacted overnight. The reaction was quenched with a small amount of saturated aqueous ammonium chloride solution, and celite was directly added. The mixture was purified by silica gel column chromatography (PE: DCM 3: 1-1:1) to obtain product 1-c as a white solid (4.0 g, 60% yield). $^1$HNMR (400 MHz, d$_6$-DMSO) δ =8.16 (d, J=8.8 Hz, 4H), 7.62 (d, J=8.8 Hz, 4H).

Step 4: Synthesis of [Intermediate 1-d]

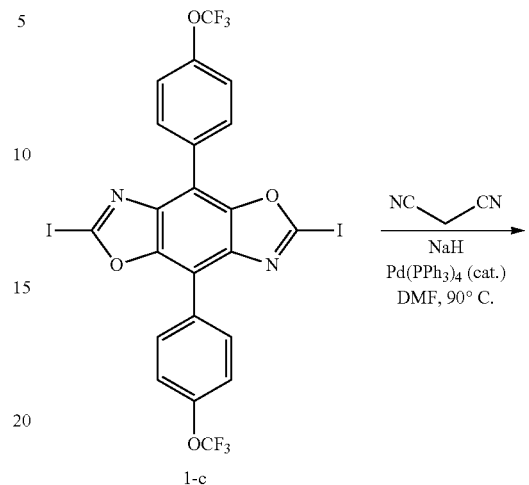

Under nitrogen atmosphere, malononitrile (2.78 g, 42 mmol) was added to anhydrous DMF (70 mL). NaH (1.67 g, 42 mmol, 60% content) was added in portions at 0° C. The mixture was stirred at 0° C. for 10 minutes and at room temperature for 20 minutes. 1-c (5.08 g, 7 mmol) and Pd(PPh$_4$)$_3$ (1.62 g, 1.4 mmol) were then added, and the mixture was warmed to 90° C. and reacted for 24-36 h. After completion of the conversion, the reaction mixture was poured into ice water, and the pH was adjusted to <1 with 4 N diluted hydrochloric acid. After stirring well, a large amount of yellow solid was precipitated. The mixture was filtered to collect a solid. The solid was washed with dichloromethane to give 4.38 g of yellow solid. The solid was then washed twice with dichloromethane and filtered to obtain 1-d as a yellow solid (4.2 g, 98% yield). $^1$HNMR (400 MHz, d$_6$-DMSO) δ=8.08 (d, J=8.8 Hz, 4H), 7.56 (d, J=8.8 Hz, 4H).

Step 5: Synthesis of Compound 56

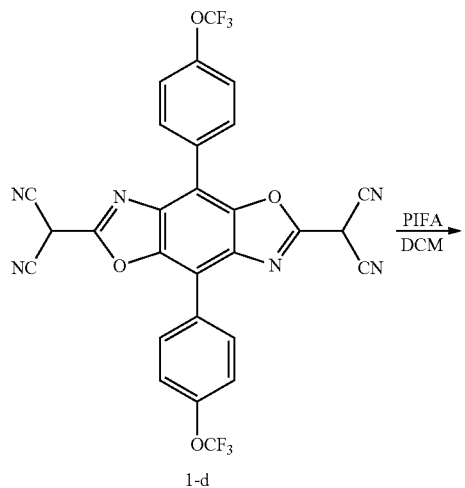

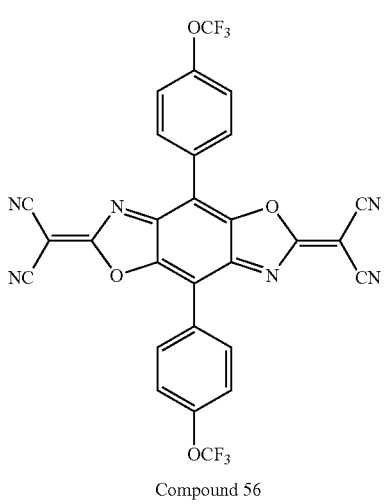

Under nitrogen atmosphere, 1-d (3.04 g, 5 mmol) was added to DCM (150 mL). The mixture was cooled to 0° C., and PIFA (6.45 g, 15 mmol) was added in portions. After stirring at room temperature for 3 days, the solution was purple-black. n-Hexane (450 mL) was added to the reaction solution, and the mixture was stirred for 10 minutes and then filtered to give a dark green solid. The solid was washed twice with DCM/PE (2: 1-1:1) to give Compound 56 as a dark green solid (2.5 g, 83% yield). $^1$HNMR (400 MHz, $d_6$-acetone) δ=8.30 (d, J=8.4 Hz, 4H), 7.73 (d, J=8.4 Hz, 4H).

Synthesis Example 5

Synthesis of Compound 68

Step 1: Synthesis of [Intermediate 2-a]

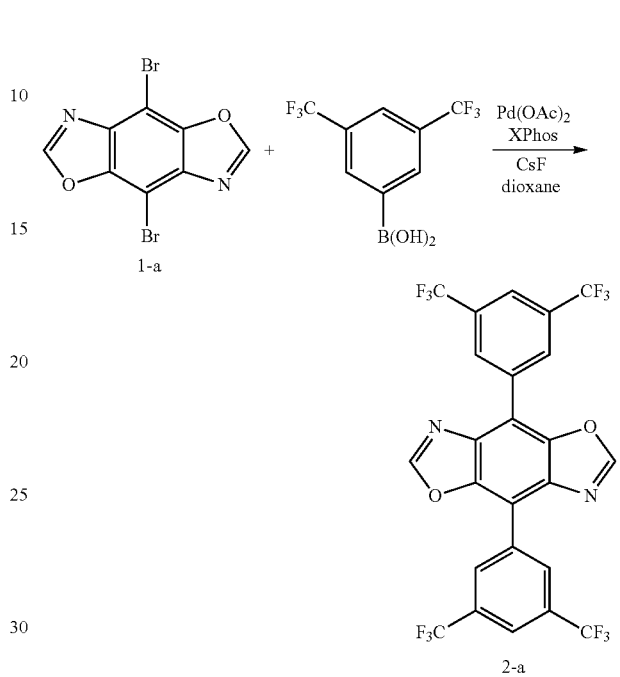

To a 250 mL two-necked flask, dioxane (80 mL) was added, and nitrogen was bubbled for 15 minutes. Pd(OAc)$_2$ (360 mg, 1.6 mmol) and XPhos (1.53 g, 3.2 mmol) were added with stirring. After stirring for 10 minutes, 1-a (4.1 g, 13 mmol), 3,5-bis(trifluoromethyl)phenylboronic acid (14.0 g, 54 mmol) and cesium fluoride (9.12 g, 60 mmol) were added successively. The mixture was warmed to 110° C., refluxed, and stirred overnight under nitrogen atmosphere. After completion of the reaction, the mixture was cooled, filtered through celite, washed with dichloromethane, and isolated via silica gel column chromatography to obtain 2-a as a white solid (6.7 g, 88% yield). $^1$HNMR (400 MHz, CDCl$_3$) δ=8.87 (s, 4H), 8.41 (s, 2H), 8.00 (s, 2H).

Step 2: Synthesis of [Intermediate 2-b]

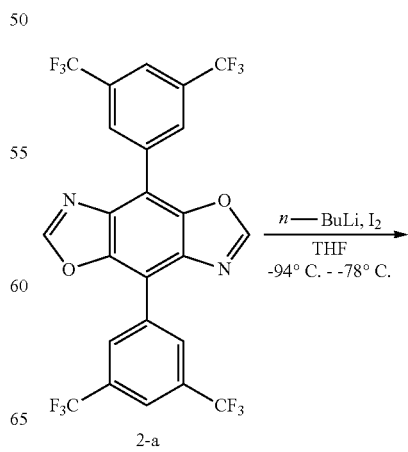

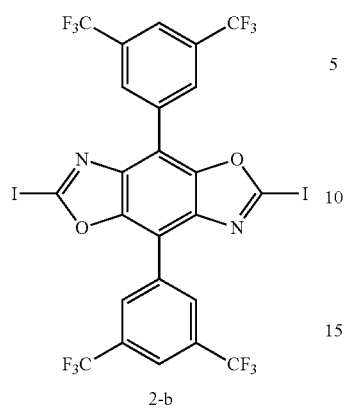

2-b

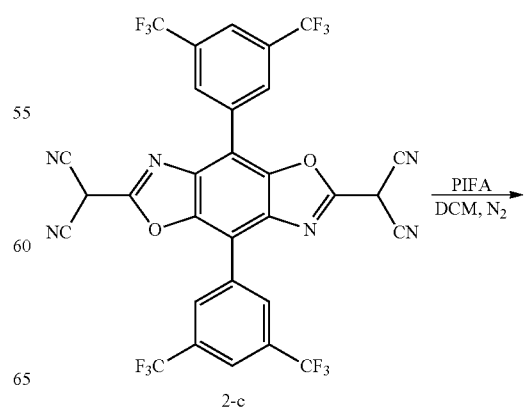

2-c

Under nitrogen atmosphere, 2-a (6.2 g, 10.6 mmol) was added to THF (212 mL, 0.05 M). The mixture was cooled to −94° C. (in an acetone/liquid nitrogen cooling bath). n-Butyllithium (15.2 mL, 24.4 mmol, 1.6 M in n-hexane) was slowly added dropwise. The reaction was held at this temperature for 1 h, then slowly warmed to −78° C. (in an acetone/dry ice cooling bath) and reacted for 8 h. A solution of elemental iodine (8.07 g, 31.8 mmol) in THF (20 mL) was added. After the addition, the reaction was slowly warmed to room temperature and reacted overnight. The reaction was quenched with a small amount of saturated aqueous ammonium chloride solution, and celite was directly added. The mixture was purified by silica gel column chromatography (PE: DCM 6: 1-2:1) to obtain product 2-b as a white solid (4.7 g, 53% yield). $^1$HNMR (400 MHz, CDCl$_3$) δ=8.69 (s, 4H), 8.01 (s, 2H).

Step 3: Synthesis of [Intermediate 2-c]

Under nitrogen atmosphere, malononitrile (1.56 g, 23.7 mmol) was added to anhydrous DMF (55 mL, 0.1 NaH (948 mg, 23.7 mmol, 60% content) was added in portions at 0° C. The mixture was stirred at 0° C. for 10 minutes and at room temperature for 20 minutes. 2-b (3.3 g, 3.95 mmol) and Pd(PPh$_4$)$_3$ (456 mg, 0.39 mmol) were then added, and the mixture was warmed to 90° C. and reacted for 24-36 h, After completion of the conversion, the reaction mixture was poured into ice water, and the pH was adjusted to <1 with 4 N diluted hydrochloric acid. After stirring well, a large amount of yellow solid was precipitated. The mixture was filtered to collect a solid. The solid was washed with dichloromethane to give 2.98 g of yellow solid. The solid was then washed twice with solvent (DCM/PE=2:1, 200 mL) and filtered to obtain 2-c as a yellow solid (2.81 g, 99% yield), $^1$HNMR (400 MHz, d$_6$-acetone) δ=8.57 (s, 4H), 8.33 (s, 2H).

Step 4: Synthesis of Compound 68

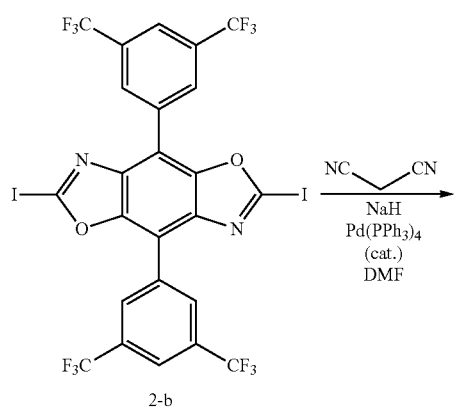

2-b

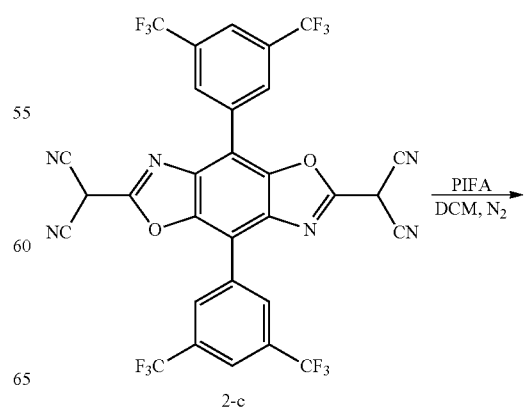

2-c

231
-continued

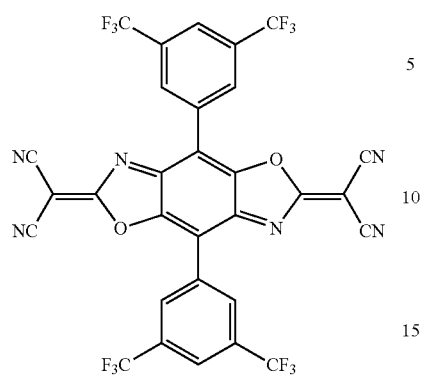

Compound 68

Under nitrogen atmosphere, 2-c (2.85 g, 4.0 mmol) was divided into 3 portions (0.95 g/portion), and placed in three two-necked flasks, and DCM (200 mL) was added, respectively. Cooled to 0° C., and then PIFA (1.73 g, 4.0 mmol) was added in portions. After stirring at room temperature for 3 days, the solution was purple-black. Then, the solution in the three flasks was collected into a 1 L single-necked flask and the solution was evaporated by rotary evaporation to about 50 mL. n-Hexane (450 mL) was added therein, and the mixture was stirred for 10 minutes and then filtered to give a dark green solid. The solid was washed twice with DCM/PE (2:1, 200 mL) to give Compound 68 as a dark green solid (2.4 g, 85% yield). $^1$HNMR (400 MHz, d$_6$-acetone) δ=8.86 (s, 4H), 8.37 (s, 2H).

Synthesis Example 6

Synthesis of Compound 70

Step 1: Synthesis of [Intermediate 4-a]

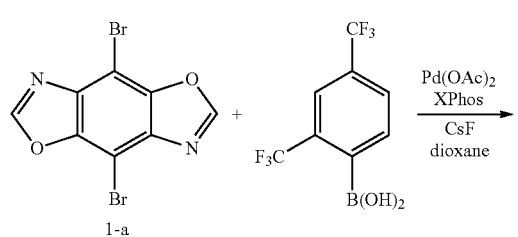

232
-continued

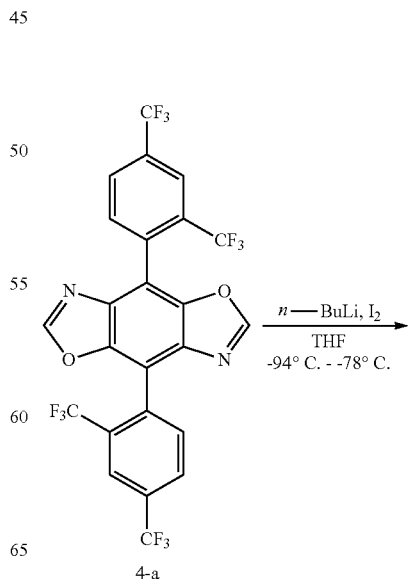

4-a

In a 250 mL two-necked flask, dioxane (80 mL) was added, and nitrogen was bubbled for 15 minutes. Pd(OAc)$_2$ (360 mg, 1.6 mmol) and XPhos (1.53 g, 3.2 mmol) were added under stirring. After stirring for 10 minutes, 1-a (4.1 g, 13 mmol), 2,4-bis(trifluoromethyl)phenylboronic acid (14.0 g, 54 mmol) and cesium fluoride (9.12 g, 60 mmol) were added successively. The reaction was warmed to 110° C., refluxed, and stirred overnight under nitrogen. After completion of the reaction, the reaction mixture was cooled, filtered through celite, washed with dichloromethane, and isolated via silica gel column chromatography to obtain 4-a as a white solid (6.83 g, 90% yield). $^1$HNMR (400 MHz, CDCl$_3$) δ=8.19 (s, 2H), 8.12 (s, 2H), 8.02 (d, J=8.0 Hz, 2H), 7.77 (d, J=8.0 Hz, 2H), Step 2: Synthesis of [Intermediate 4-b]

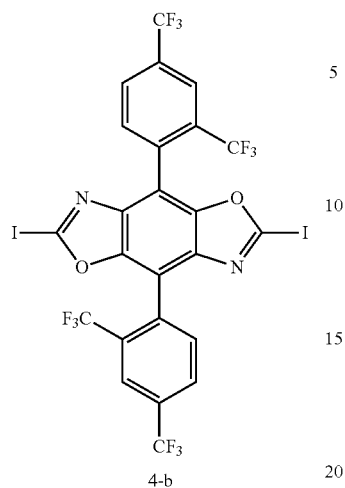

4-b

Under nitrogen atmosphere, 4-a (6.4 g, 11 mmol) was added to THF (150 mL). The mixture was cooled to −94° C. (in an acetone/liquid nitrogen cooling bath). n-Butyllithium (15.8 mL, 25.3 mmol, 1.6 M in n-hexane) was slowly added dropwise. The reaction was held at this temperature for 1 h, then slowly warmed to −78° C. (in an acetone/dry ice cooling bath) and reacted for 8 h. A solution of elemental iodine (8.4 g, 33 mmol) in THF (20 mL) was added. After the addition, the reaction was slowly warmed to room temperature and reacted overnight. The reaction was quenched with a small amount of saturated aqueous ammonium chloride solution, and celite was directly added. The mixture was purified by silica gel column chromatography (PE: DCM 10: 1-2:1) to obtain product 4-b as a white solid (6.89 g, 75% yield). $^1$HNMR (400 MHz, CDCl$_3$) δ=8.16 (s, 2H), 8.01 (d, J=7.6 Hz, 2H) 7.73 (d, J=7.6 Hz, 2H).

Step 3: Synthesis of [Intermediate 4-c]

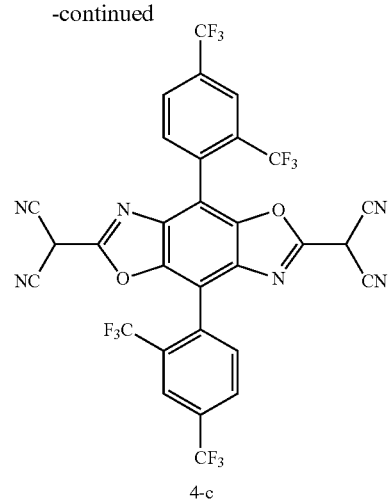

4-c

Under nitrogen atmosphere, malononitrile (2.14 g, 32 mmol) was added to anhydrous DMF (60 mL). NaH (1.40 g, 35 mmol, 60% content) was added in portions at 0° C. The mixture was stirred at 0° C. for 10 minutes and at room temperature for 20 minutes. 4-b (4.51 g, 5.4 mmol) and Pd(PPh$_4$)$_3$ (1.15 g, 1.0 mmol) were then added, and the mixture was warmed to 90° C. and reacted for 24-36 h. After the completion of the conversion, the reaction mixture was poured into ice water, and the pH was adjusted to <1 with 4 N diluted hydrochloric acid. After stirring well, a large amount of yellow solid was precipitated. The mixture was filtered to collect a solid. The solid was washed with dichloromethane to give 2.98 g of yellow solid. The solid was then washed twice with dichloromethane and filtered to obtain 4-c as a yellow solid (2.92 g, 76% yield). $^1$HNMR (400 MHz, d$_6$-acetone) δ=8.35 (m, 4H), 8.16 (d, j=7.6 Hz, 2H).

Step 4: Synthesis of Compound 70

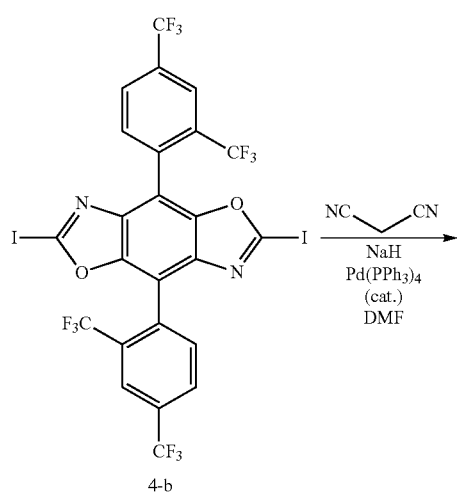

4-b

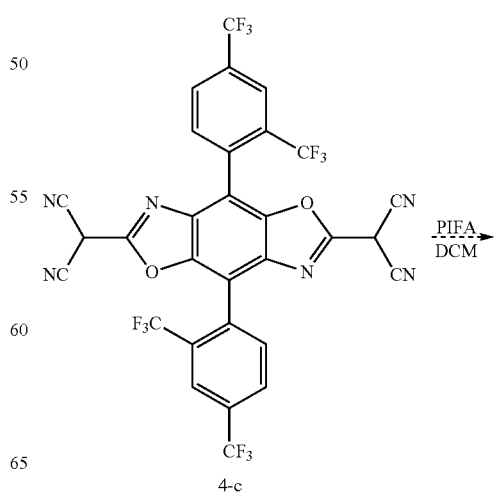

4-c

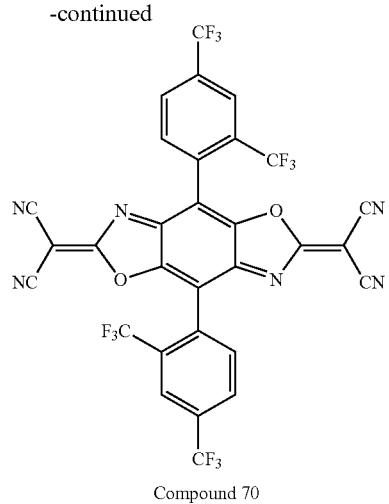

Compound 70

Under nitrogen atmosphere, 4-c (2.92 g, 4.1 mmol) was divided into 3 portions (1 g/portion), and placed in three two-necked flasks, and DCM (100 mL) was added, respectively. Cooled to 0° C., and then PIFA (1.8 g, 4.2 mmol) was added in portions. After stirred at room temperature for 3 days, the solution was purple-black. Then, the solution in the three flasks was collected into a 1 L single-necked flask and the solution was concentrated to about 50 mL. n-Hexane (450 mL) was added therein, and the mixture was stirred for 10 minutes and then filtered to give a purple solid. The solid was washed twice with DCM/PE (2:1, 200 mL) to give Compound 70 as a purple solid (2.0 g, 70% yield). $^1$HNMR (400 MHz, CD$_2$Cl$_2$) δ=8.22. (s, 2H), 8.11(d, J=8.4 Hz, 2H), 7.75 (d, J=8.0 Hz, 2H).

Synthesis Example 7

Synthesis of Compound 101

Step 1: Synthesis of [Intermediate 5-a]

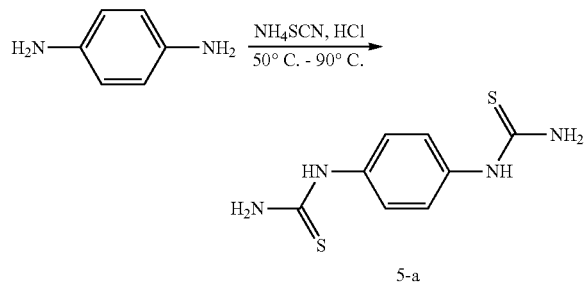

In a 500 mL two-necked flask, distilled water (50 mL), 1,4-phenylenediamine (17.0 g, 157 mmol) and hydrochloric acid (30.7 mL, 125 mmol) were added. The mixture was warmed to 50° C., and NH$_4$SCN (48.4 g, 636 mmol) was added. The mixture was further warmed to 95° C., and stirred for 24 h. After completion of the reaction, the reaction mixture was cooled, filtered, and washed with ethanol to obtain Compound 5-a as a gray solid (31.5 g, 90% yield). $^1$HNMR (400 MHz, d$_6$-DMSO) δ=9.69 (s, 2H), 7.32 (s, 4H).

Step 2: Synthesis of [Intermediate 5-b]

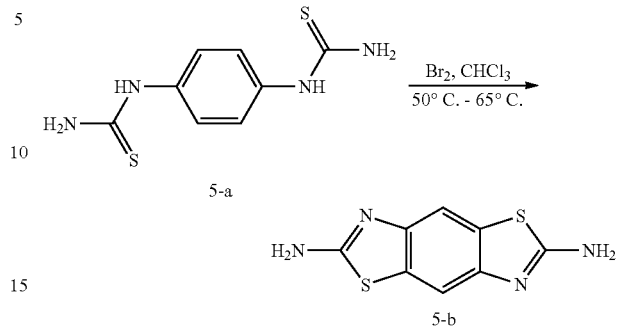

To a 500 mL, three-necked flask, Compound 5-a (15 g, 66.5 mmol) and chloroform (100 mL) were sequentially added. The mixture was warmed to 50° C., and a solution of bromine (8 mL, 309 mmol) in chloroform (100 mL) was added dropwise very slowly. After the addition, the mixture was refluxed for 24-36 h. After completion of the reaction, it was cooled to 0° C. and filtered. The filter cake was washed three times with chloroform. A solid was collected, washed with saturated sodium thiosulfate solution, and filtered. A solid was collected, washed with methanol and dichloromethane separately, and then filtered to obtain 5-b as a brown solid (12.5 g, 83% yield). $^1$HNMR (400 MHz, d$_6$-DMSO) δ=8.56 (bs, 4H), 7.83 (s, 2H).

Step 3: Synthesis of [Intermediate 5-c]

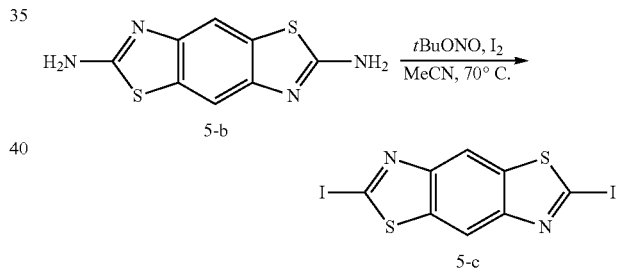

To a 1 L three-necked flask, acetonitrile (500 mL) was added, and nitrogen was bubbled for 20 minutes. Compound 5-b (11 g, 50 mmol), iodine (76 g, 300 mmol) and tBuONO (20.6 g, 200 mmol) were then sequentially added. The mixture was reacted at 70° C. for 24 h. After completion of the reaction, the reaction mixture was cooled, and evaporated under reduced pressure to remove acetonitrile. 200 mL of dichloromethane was then added. The mixture was filtered and washed with petroleum ether to obtain 5-c as a brick red solid (11 g, 50% yield). $^1$HNMR (400 MHz, d$_6$-DMSO) δ=8.74 (s, 2H).

Step 4: Synthesis of [Intermediate 5-d]

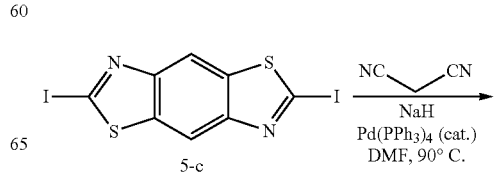

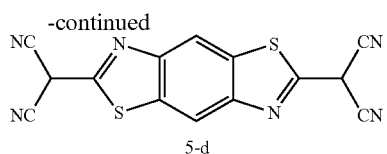

5-d

Under nitrogen atmosphere, malononitrile (5.35 g, 81 mmol) was added to anhydrous DMF (135 mL). NaH (3.24 g, 81 mmol, 60% content) was added in portions at 0° C. The mixture was stirred at 0° C. for 10 minutes and at room temperature for 20 minutes. Compound 5-c (6.08 g, 13.5 mmol) and Pd(PPh$_4$)$_3$ (3.12 g, 2.7 mmol) were then added, and the mixture was warmed to 90° C. and reacted for 24-36 h. After the completion of the conversion, the reaction mixture was poured into ice water, and the pH was adjusted to <1 with 4 N diluted hydrochloric acid. After stirring well, a large amount of brown solid was precipitated. The mixture was filtered to collect a solid. The solid was washed with dichloromethane to give a brown solid (4.2 g). The solid was then washed twice with dichloromethane and filtered to obtain 5-d as a brown solid (4.02 g, 93% yield), LCMS (ESI): m/z 319 [M-H]$^-$.

Step 5: Synthesis of Compound 101

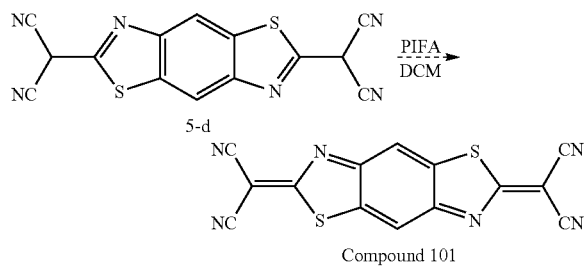

Compound 101

Under nitrogen atmosphere, the compound (3.2.0 g, 10 mmol) was added to DCM (1 L). The mixture was cooled to 0° C., and PIFA (12.9 g, 30 mmol) was added in portions. After stirring at room temperature for 3 days, the solution was purple-black. After completion of the reaction, the solution was evaporated by rotary evaporation to about 100 mL. n-Hexane (450 mL) was then added to the reaction solution, and the mixture was stirred for 10 minutes and filtered to give a purple-black solid. The solid was washed twice with dichloromethane to give Compound 101 as a purple-black solid (3.0 g, 94% yield). LCMS(ESI): m/z 317 [M-H]$^-$.

The persons skilled in the art should know that the above preparation method is only an illustrative example, and the persons skilled in the art can obtain the structure of other compounds of the present invention by modifying the above preparation method.

Additional Device Examples

Device Example 5

Device Example 5.1

A glass substrate with a 80 nm-thick indium tin oxide (ITO) transparent electrode was subjected to oxygen plasma and UV ozone treatment. The cleaned glass substrate was dried on a hotplate in a glovebox before deposition. The following materials were deposited in sequence onto the surface of the glass at the rate of 0.02-0.2 angstrom/s under the vacuum of around 10$^{-8}$ torr. First, Compound 56 of the present invention was deposited onto the surface of the glass substrate to form a 10 nm-thick film which served as a hole injection layer (HIL). Next, Compound HT1 was deposited on the above obtained film to form a 120 nm-thick film which served as a hole transporting layer (HTL). Next, Compound EB1 was deposited on the above obtained film to form a 5 nm-thick film which served as an electron blocking layer (EBL). Next, Compound BH and Compound BD (in a weight ratio of 96:4) were co-deposited on the above obtained film to form a 25 nm-thick film which served as an emitting layer (EML). Next, Compound. HB1 was deposited on the above obtained film to form a 5 nm-thick film which served as a hole blocking layer (HBL). Then, 8-hydroxy-quinolinolato-lithium (Liq) and Compound ET1 (in a weight ratio of 60:40) were co-deposited on the above obtained film to form a 30 nm-thick film which served as an electron transporting layer (ETL). Finally, Liq was deposited to form a 1 nm-thick film which served as an electron injection layer (EIL) and 120 nm-thick of Al was deposited to form a cathode. The device was then transferred back to the glove box and encapsulated with a glass lid and a moisture absorbent to complete the device.

Device Example 5.2

Device Example 5.2 was fabricated in the same manner as in Device Example 5.1, except that Compound 68 was used instead of Compound 56 to serve as an HIL.

Device Example 5.3

Device Example 5.3 was fabricated in the same manner as in Device Example 5.1, except that Compound 70 was used instead of Compound 56 to serve as an HIL.

Device Example 5.4

Device Example 5.4 was fabricated in the same manner as in Device Example 5.3, except that Compound 70 was used to form a 5 nm-thick film to serve as an HIL.

Device Example 5.5

Device Example 5.5 was fabricated in the same manner as in Device Example 5.3, except that Compound 70 was used to form a 2 nm-thick film to serve as an HIL.

Device Example 5.6

Device Example 5.6 was fabricated in the same manner as in Device Example 5.3, except that Compound HT2 was used instead of Compound HT1 to serve as an HTL.

Device Example 5.7

Device Example 5.7 was fabricated in the same manner as in Device Example 5.6, except that Compound 70 was used to form a 2 inn-thick film to serve as an HIL.

Device Example 5.8

Device Example 5.8 was fabricated in the same manner as in Device Example 5.6, except that Compound 70 was used to form a 1 nm-thick film to serve as an HIL.

Device Comparative Example 5.1

Device Comparative Example 5.1 was fabricated in the same manner as in Device Example 5.6, except that Compound 70 was not used and there was no hole injection layer.

Detailed layer structure and thickness of the devices are shown in the table below. Layers in which more than one material is used are obtained by doping different compounds in the weight ratio as described therein.

TABLE 3

Device Structures of Device Examples and Comparative Example

| Device ID | HIL | HTL | EBL | EML | HBL | ETL |
|---|---|---|---|---|---|---|
| Device Example 5.1 | Compound 56 (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.2 | Compound 68 (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.3 | Compound 70 (10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.4 | Compound 70 (5 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.5 | Compound 70 (2 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.6 | Compound 70 (10 nm) | Compound HT2 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.7 | Compound 70 (2 nm) | Compound HT2 (120 nm) | Compound EB1 (5 nm) | Compound BH:Compound BD (96:4, 25 nm) | Compound HB1 (5 nm) | Compound ET1:Liq (40:60, 30 nm) |
| Device Example 5.8 | Compound 70 (1 nm) | Compound HT2 (120 nm) | Compound EB1 (5 nm) | Compound BH:Compound BD (96:4, 25 nm) | Compound HB1 (5 nm) | Compound ET1:Liq (40:60, 30 nm) |
| Device Comparative Example 5.1 | None | Compound HT2 (120 nm) | Compound EB1 (5 nm) | Compound BH:Compound BD (96:4, 25 nm) | Compound HB1 (5 nm) | Compound ET1:Liq (40:60, 30 nm) |

Structure of the materials used in the devices is shown as below:

-continued

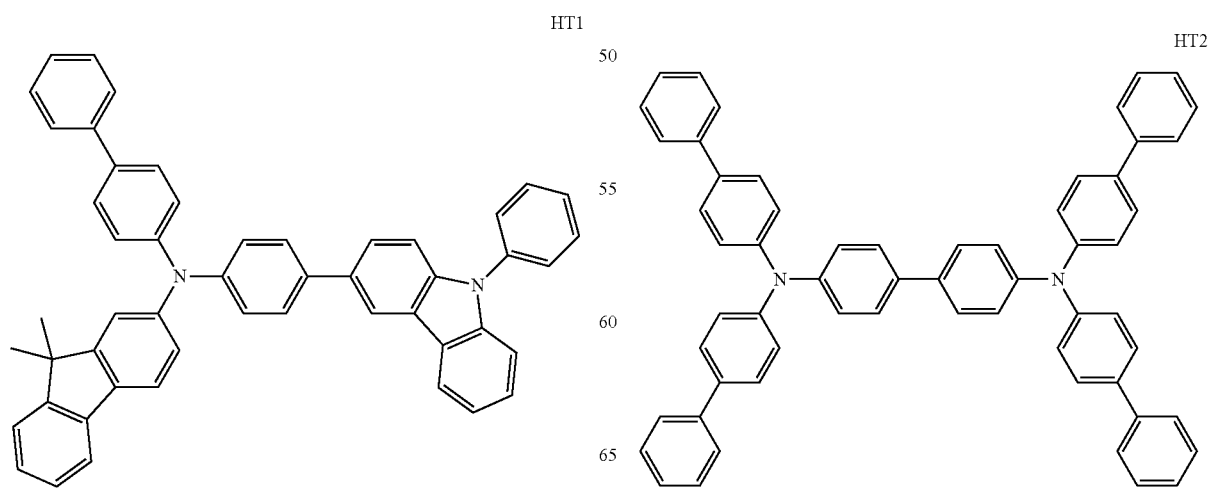

-continued

EB1
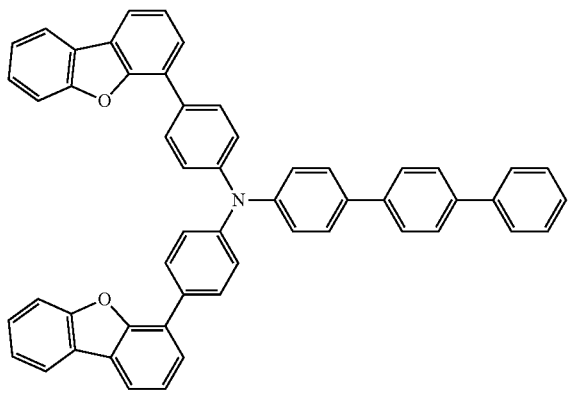

BH
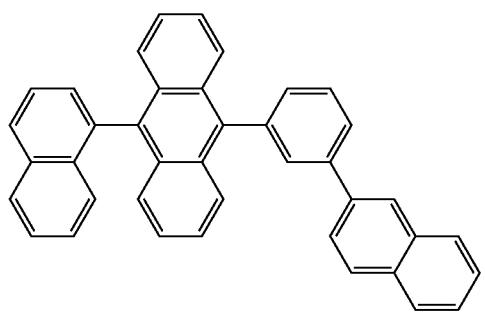

BD
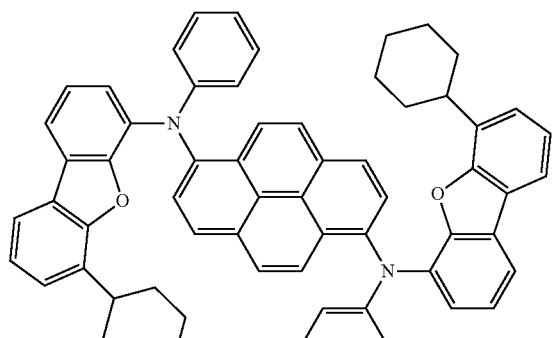

HB1
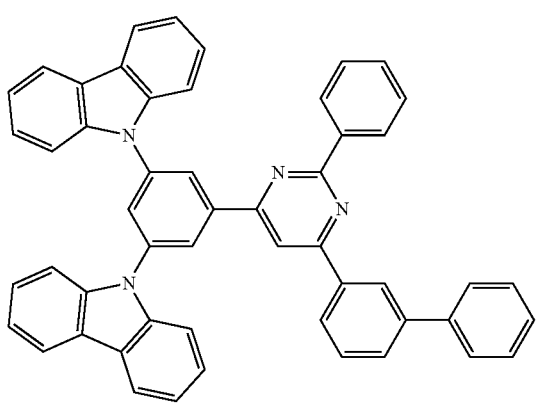

-continued

ET1
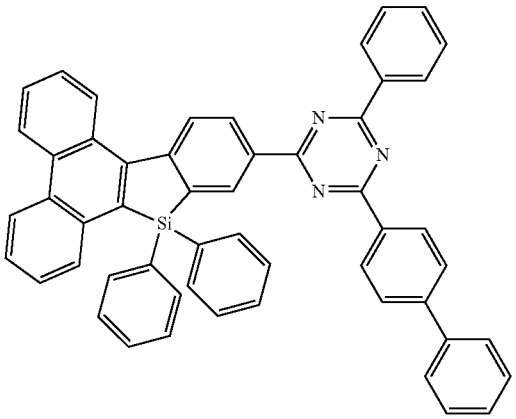

The above devices were measured for IVL characteristics at 10 mA/cm², and their voltage (V), power efficiency (PE), and lifetime (LT95) were recorded and shown in Table 4.

TABLE 4

Device Data

| Device Number | Voltage (V) | PE (lm/W) | LT95 (h) |
|---|---|---|---|
| Device Example 5.1 | 4.22 | 4.64 | 183 |
| Device Example 5.2 | 4.56 | 4.87 | 1204 |
| Device Example 5.3 | 4.18 | 4.70 | 292 |
| Device Example 5.4 | 4.08 | 4.97 | 601 |
| Device Example 5.5 | 4.07 | 5.25 | 643 |
| Device Example 5.6 | 4.12 | 4.49 | 1572 |
| Device Example 5.7 | 4.11 | 5.15 | 1615 |
| Device Example 5.8 | 4.12 | 5.25 | 1596 |
| Device Comparative Example 5.1 | 8.34 | 4.02 | 93 |

Discussion 1:

As can be seen from the above table, when a single material was used as a hole injection layer in 8 preferred Examples of the present invention and the Comparative Example 5.1, the preferred Examples were superior to the Comparative Example 5.1 in terms of voltage, power efficiency, and lifetime. The voltage was greatly reduced, the power efficiency was improved, and in terms of the lifetime, there was fold improvement. Even when the thickness of the hole injection layer was reduced to 5 nm and 2 nm, even to 1 nm, the voltage, efficiency, and lifetime were still excellent. Especially in the absence of a hole injection layer, the voltage of the device was as high as 8.34 V, and the power efficiency and lifetime were also inferior to those of devices having a hole injection layer. From this, it can be seen that when used alone as a hole injection layer, the compounds of the present invention were better choice and brought unexpected improvement.

Device Example 6

Device Example 6.1

A glass substrate with a 80 nm-thick indium tin oxide (ITO) transparent electrode was subjected to oxygen plasma and UV ozone treatment. The cleaned glass substrate was dried on a hotplate in a glovebox before deposition. The following materials were deposited in sequence onto the surface of the glass at a rate of 0.02-0.2 angstrom/s under a vacuum of around $10^{-8}$ torr. First, Compound 56 (as a dopant) of the present invention and Compound HT1 (in a weight ratio of 3:97) were co-deposited on the surface of the glass substrate to form a 10 nm-thick film which served as a hole injection layer (HIL). Next, Compound HT1 was deposited on the above obtained film to form a 120 nm-thick film which served as a hole transporting layer (HTL). Next, Compound EB1 was deposited on the above obtained film to form a 5 nm-thick film which served as an electron blocking layer (EBL). Next, Compound BH and Compound BD (in a weight ratio of 96:4) were co-deposited on the above obtained film to form a 25 nm-thick film which served as an emitting layer (EML). Next, Compound HB1 was deposited on the above obtained film to form a 5 nm-thick film which served as a hole blocking layer (HBL). Next, 8-hydroxyquinolinolato-lithium (Liq) and Compound ET1 (in a weight ratio of 60:40) were co-deposited on the above obtained film to form a 30 nm-thick film which served as an electron transporting layer (ETL). Finally, Liq was deposited to form a 1 nm-thick film which served as an electron injection layer (EIL) and 120 nm-thick of Al was deposited to form a cathode. The device was then transferred back to the glove box and encapsulated with a glass lid and a moisture absorbent to complete the device, Device Example 6.2

Device Example 6.2 was fabricated in the same manner as in Device Example 6.1, except that in the HIL, Compound 68 was used instead of Compound 56 to serve as a dopant.
Device Example 6.3
Device Example 6,3 was fabricated in the same manner as in Device Example 6.1, except that in the HIL, Compound 70 was used instead of Compound 56 to serve as a dopant Device Example 6.4

Device Example 6.4 was fabricated in the same manner as in Device Example 6.1, except that Compound HT2 was used instead of Compound HT1 to co-deposite with Compound 56 (in a weight ratio of 97:3) to serve as an HIL, and Compound HT2 was used instead of Compound. HT1 to serve as an HTL.

Device Example 6.5

Device Example 6.5 was fabricated in the same manner as in Device Example 6.4, except that in the HIL, Compound 68 was used instead of Compound 56 to serve as a dopant.

The specific structure of the compounds used in the devices is as shown in Device Example 5.

Detailed layer structure and thickness of the devices are shown in the table below. Layers in which more than one material is used are obtained by doping different compounds in the weight ratios described therein.

TABLE 5

Device Structures of Device Examples

| | Device ID | | | | | |
|---|---|---|---|---|---|---|
| | HIL | HTL | EBL | EML | HBL | ETL |
| Device Example 6.1 | Compound 56:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 6.2 | Compound 68:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 6.3 | Compound 70:Compound HT1 (3:97, 10 nm) | Compound HT1 (120 nm) | Compound EB1 (5 nm) | Compound BH:Compound BD (96:4, 25 nm) | Compound HB1 (5 nm) | Compound ET1:Liq (40:60, 30 nm) |
| Device Example 6.4 | Compound 56:Compound HT2 (3:97, 10 nm) | Compound HT2 (120 nm) | Compound EB1 (5 nm) | Compound BH:Compound BD (96:4, 25 nm) | Compound HB1 (5 nm) | Compound ET1:Liq (40:60, 30 nm) |
| Device Example 6.5 | Compound 68:Compound HT2 (3:97, 10 nm) | Compound HT2 (120 nm) | Compound EB1 (5 nm) | Compound BH:Compound BD (96:4, 25 nm) | Compound HB1 (5 nm) | Compound ET1:Liq (40:60, 30 nm) |

The above devices were measured for IVL characteristics at 10 mA/cm², and their voltage (V), power efficiency (PE), and lifetime (LT95) were recorded and shown in Table 6.

TABLE 6

Device Data

| Device ID | Voltage (V) | PE (lm/W) | LT95 (h) |
|---|---|---|---|
| Device Example 6.1 | 4.18 | 5.55 | 94 |
| Device Example 6.2 | 4.17 | 5.65 | 980 |
| Device Example 6.3 | 4.03 | 5.64 | 250 |
| Device Example 6.4 | 4.09 | 5.49 | 328 |
| Device Example 6.5 | 4.11 | 5.60 | 1820 |

Discussion 2:

As can be seen from the above table, when compounds of the 5 preferred Examples of the present invention were used as a dopant in HT1 or HT2 to be a hole injection layer, the voltage of the preferred Examples was only about 4.18 V. The power efficiency of the Examples was also advantageously high as were the lifetimes of the preferred Examples. Therefore, when used as a dopant, the compounds disclosed in the present invention were a class of hole injection materials that provided superior device performance, particularly in reducing voltage and increasing life, and had overwhelming advantages.

Device Example 7

Device Example 7.1

A glass substrate with a 80 nm-thick indium tin oxide (ITO) transparent electrode was subjected to oxygen plasma and UV ozone treatment. The cleaned glass substrate was dried on a hotplate in a glovebox before deposition. The following materials were deposited in sequence onto the surface of the glass at the rate of 0.02-0.2 angstrom/s under the vacuum of around $10^{-8}$ torr. First, Compound 56 was deposited onto the surface of the glass substrate to form a 10 nm-thick film as a hole injection layer (HIL). Next, Compound HT1 was deposited on the above obtained film to form a 35 nm-thick film which served as the hole-transporting layer (HTL). Next, Compound EB2 was deposited on the above obtained film to form a 5 nm-thick film which served as the electronic-blocking layer (EBL). Next, Compound EB2 Compound HB2 and Compound GD1 (in a weight ratio of 46:46:8) were co-deposited on the above obtained film to form a 40 nm-thick film which served as the emitting layer (EML). Next, Compound HB2 was deposited on the above obtained film to form a 5 nm-thick film which served as the hole-blocking layer (HBL). 8-Hydroxyquinolinolato-lithium (Liq) and Compound ET2 (weight ratio 60:40) was codeposited on the above obtained film to form a 35 nm-thick film which served as the electron-transporting layer (ETL). Finally, Liq was deposited to form a 1 nm-thick film which served as the electron-injecting layer (EIL) and 120 nm-thick of Al was deposited to form the cathode. The device was then transferred back to the glove box and sealed with a glass lid and a moisture absorbent to complete the device.

Device Example 7.2

Example 7.2 was fabricated in the same manner as in Example 7.1, except that Compound 56 (as a dopant) and Compound HT1 (in a weight ratio of 3:97) were co-evaporated to serve as a hole injection layer (HIL) instead of Compound 56.

The specific structure of novel compounds used in the devices is shown as follows:

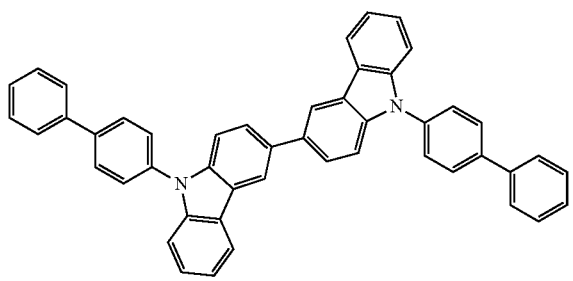
EB2

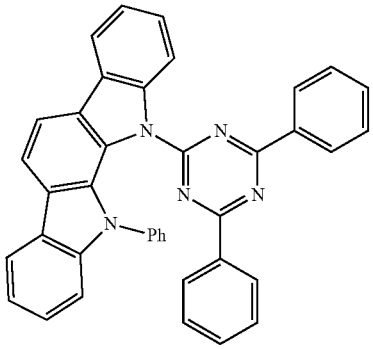
HB2

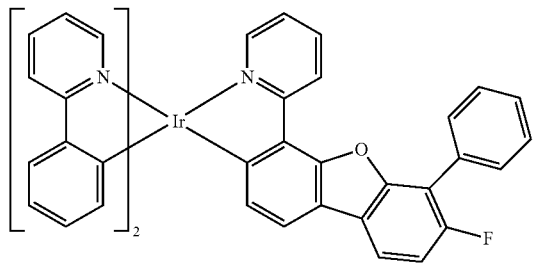
GD1

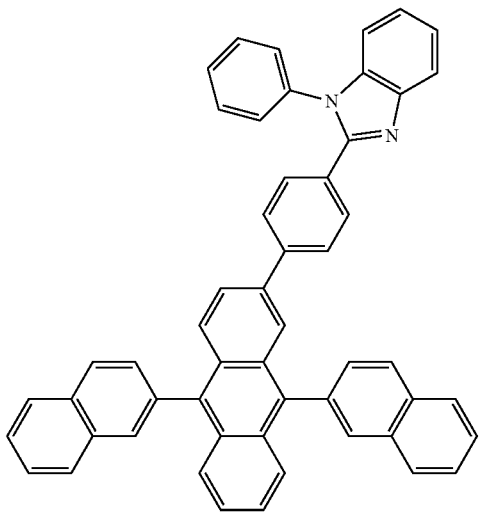
ET2

The detailed layer structure and thickness of the devices are shown in the table below. Layers in which more than one material is used are obtained by doping different compounds in the weight ratios described therein.

TABLE 7

| | Device Structure of Device Examples | | | | | |
|---|---|---|---|---|---|---|
| | Device ID | | | | | |
| | HIL | HTL | EBL | EML | HBL | ETL |
| Device Example 7.1 | Compound 56 (10 nm) | Compound HT1 (35 nm) | Compound EB2 (5 nm) | Compound EB2:Compound HB2:Compound GD1 (46:46:8, 40 nm) | Compound HB2 (5 nm) | Compound Liq:ET2 (60:40, 35 nm) |
| Device Example 7.2 | Compound 56:Compound HT1 (3:97, 10 nm) | Compound HT1 (35 nm) | Compound EB2 (5 nm) | Compound EB2:Compound HB2:Compound GD1 (46:46:8, 40 nm) | Compound HB2 (5 nm) | Compound Liq:ET2 (60:40, 35 nm) |

The above devices were measured for IVL characteristics at 10 mA/cm$^2$, and their voltage (V), power efficiency (PE), and lifetime (LT95) were recorded and shown in Table 8.

TABLE 8

| | Device Data | | |
|---|---|---|---|
| Device ID | Voltage (V) | PE (lm/W) | LT95 (h) |
| Device Example 7.1 | 3.56 | 71.15 | 1245 |
| Device Example 7.2 | 3.51 | 76.77 | 859 |

Discussion 3:

As can be seen from the green light-emitting device, when Compound 56 was used alone to serve as a hole injection layer, excellent voltage, efficiency, and lifetime performance were achieved. When Compound 56 was used as a dopant in a hole injection layer, the voltage in Example 7.2 was similar to, and the efficiency was slightly higher than that in Example 7.1, while a longer lifetime was achieved when Compound 56 was used alone to serve as a hole injecting layer.

Device Example 8

Device Example 8.1

A glass substrate with a 80 nm-thick indium tin oxide (ITO) transparent electrode was subjected to oxygen plasma and UV ozone treatment. The cleaned glass substrate was dried on a hotplate in a glovebox before deposition. The following materials were deposited in sequence onto the surface of the glass at the rate of 0.02-0.2 angstrom/s under the vacuum of around 10$^{-8}$ torr. First, Compound 56 was deposited onto the surface of the glass substrate to form a 10 nm-thick film as a hole injection layer (HIL). Next, Compound. HT1 was deposited on the above obtained film to form a 40 nm-thick film which served as the hole-transporting layer (HTL). Next, Compound EB2 was deposited on the above obtained film to form a 5 nm-thick film which served as the electronic-blocking layer (EBL). Next, Compound RH and Compound RD (in a weight ratio of 98:2) were co-deposited on the above obtained film to form a 40 nm-thick film which served as the emitting layer (EML). Next, Compound HB2 was deposited on the above obtained film to form a 5 nm-thick film which served as the hole-blocking layer (HBL). 8-Hydroxyquinolinolato-lithium (Liq) and Compound ET2 (weight ratio 60:40) was code-posited on the above obtained film to form a 35 nm-thick film which served as the electron-transporting layer (ETL). Finally, Liq was deposited to form a 1 nm-thick film which served as the electron-injecting layer (EIL) and 120 nm-thick of Al was deposited to form the cathode. The device was then transferred back to the glove box and sealed with a glass lid and a moisture absorbent to complete the device.

Example 8.2 was fabricated in the same manner as in Example 8.1, except that Compound 56 (as a dopant) and Compound HT1 (in a weight ratio of 3:97) were co-evaporated onto the surface of a glass substrate to form a 10 nm-thick film to serve as a hole injection layer (HIL).

The specific structure of novel compounds used in the devices is shown as follows:

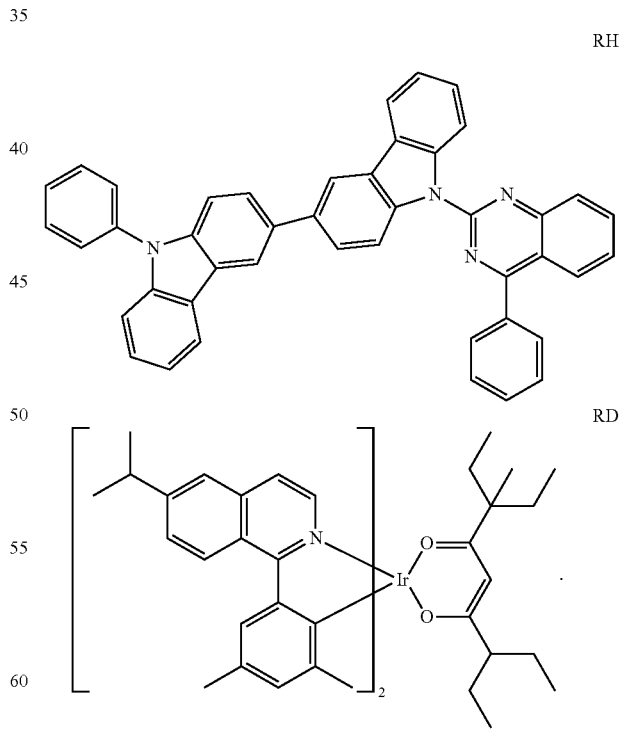

The detailed layer structure and thickness of the devices are shown in the table below. Layers in which more than one material is used are obtained by doping different compounds in the weight ratios described therein.

TABLE 9

Device Structure of Device Examples

| Device ID | HIL | HTL | EBL | EML | HBL | ETL |
|---|---|---|---|---|---|---|
| Device Example 8.1 | Compound 56 (10 nm) | Compound HT1 (40 nm) | Compound EB2 (5 nm) | Compound RH:Compound RD (98:2, 40 nm) | Compound HB2 (5 nm) | Compound Liq:ET2 (60:40, 35 nm) |
| Device Example 8.2 | Compound 56:Compound HT1 (3:97, 10 nm) | Compound HT1 (40 nm) | Compound EB2 (5 nm) | Compound RH:Compound RD (98:2, 40 nm) | Compound HB2 (5 nm) | Compound Liq:ET2 (60:40, 35 nm) |

The above devices were measured for IVL characteristics at 10 mA/cm$^2$, and their voltage (V), power efficiency (PE), and lifetime (LT95) were recorded and shown in Table 10.

TABLE 10

Device Data

| Device ID | Voltage (V) | PE (lm/W) | LT95 (h) |
|---|---|---|---|
| Device Example 8.1 | 4.37 | 13.33 | 7469 |
| Device Example 8.2 | 4.32 | 15.31 | 4325 |

Discussion 4:

As can also be seen from the red light-emitting device, when Compound 56 was used alone to serve as a hole injection layer, excellent voltage, efficiency, and lifetime performance were achieved. When Compound 56 was used as a dopant in a hole injection layer, the voltage in Example 8.2 was similar to, and the efficiency was slightly higher than that in Example 8.1, while a longer lifetime was achieved when Compound 56 was used alone to serve as a hole injecting layer.

Based on the above results, it can be concluded that the dehydrobenzodioxazole derivatives, whether used alone as a hole injection layer or as a dopant, have excellent effect in red, green and blue light-emitting devices, and are rare hole injection materials.

The compounds disclosed in the present invention are dehydrobenzodioxazole, dehydrobenzodithiazole or dehydrobenzodiselenazole derivatives. Because the heteroatoms contained in the molecular parent core are different, the lowest unoccupied molecular orbitals (LUMOs) are different. The LUMOs of dehydrobenzodioxazole (NO compounds), dehydrobenzodithiazole (NS compounds) and dehydrobenzodiselenazole derivatives (NSe compounds) were calculated by DFT (GAUSS-09, under the condition of B3LYP/6-311G(d)). Results are shown in the table below.

TABLE 11

DFT calculation results

| NO Compound | LUMO (eV) |
|---|---|
| Compound 1 | −5.82 |
| Compound 6 | −6.18 |
| Compound 13 | −5.57 |
| Compound 15 | −5.32 |
| Compound 25 | −5.69 |
| Compound 26 | −5.43 |
| Compound 38 | −5.68 |
| Compound 43 | −5.72 |
| Compound 56 | −5.45 |
| Compound 66 | −5.3 |
| Compound 67 | −5.93 |
| Compound 68 | −5.78 |
| Compound 69 | −5.53 |
| Compound 70 | −5.57 |
| Compound 71 | −5.57 |
| Compound 89 | −5.66 |
| Compound 94 | −6.03 |
| Compound 101 | −5.46 |
| Compound 103 | −5.24 |
| Compound 113 | −5.61 |
| Compound 114 | −5.36 |
| Compound 126 | −5.55 |
| Compound 131 | −5.63 |
| Compound 144 | −5.33 |
| Compound 154 | −5.24 |
| Compound 155 | −5.73 |
| Compound 156 | −5.64 |
| Compound 157 | −5.44 |
| Compound 158 | −5.48 |
| Compound 159 | −5.49 |
| Compound 177 | −5.58 |
| Compound 182 | −5.95 |
| Compound 189 | −5.40 |
| Compound 191 | −5.18 |
| Compound 201 | −5.56 |
| Compound 202 | −5.30 |
| Compound 214 | −5.48 |
| Compound 219 | −5.40 |
| Compound 232 | −5.28 |
| Compound 242 | −5.19 |
| Compound 243 | −5.64 |
| Compound 244 | −5.58 |
| Compound 245 | −5.38 |
| Compound 246 | −5.43 |
| Compound 247 | −5.43 |

As can be seen from the results for the aforementioned devices, devices incorporating dehydrobenzodioxazole derivatives had excellent performance in each aspects and the dehydrobenzodioxazole derivatives were high-efficient hole injection materials. As can be seen from the DFT calculation results, when comparing the same series of molecules, the LUMOs of dehydrobenzodioxazole derivatives, dehydrobenzodithiazole derivatives and dehydrobenzodiselenazole derivatives were almost the same, about 0.2 eV, indicating that all three types of compounds may have a deeper LUMO level and are extremely electron-deficient. Therefore, dehydrobenzodithiazole derivatives and dehydrobenzodiselenazole derivatives have the potential to be excellent hole injecting materials which may greatly improve OLED performance, for example, allow a device to have a longer lifetime, higher efficiency and lower voltage, and have a very broad industrial application prospect.

As can be seen from the above device results and DFT calculations, novel compounds of the present invention which have a structure of dehydrobenzodioxazole, dehydrobenzodithiazole or dehydrobenzodiselenazole are very important charge transporting materials. In particular, they have unparalleled advantages in hole transporting and are suitable for use in different types of organic semiconductor devices, including but not limited to fluorescent OLEDs, phosphorescent OLEDs, white OLEDs, stacked OLEDs, OPVs, and the like.

It is understood that the various embodiments described herein are by way of example only, and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:
1. A compound having Formula 1':

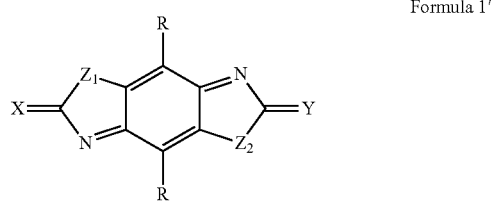

Formula 1' wherein each of X and Y is independently selected from the group consisting of CR"R"', NR', O, S and Se;
wherein each of $Z_1$ and $Z_2$ is independently selected from the group consisting of O, S and Se;
wherein each of R, R', R" and R"' is independently selected from the group consisting of hydrogen, deuterium, halogen, nitroso, nitro, acyl, carbonyl, a carboxylic acid group, an ester group, cyano, isocyano, SCN, OCN, SF$_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 2.0 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;
wherein each R may be same or different, and at least one of R, R', R" and R"' is a group having at least on electron-withdrawing group; and
wherein adjacent substituents can be optionally joined to form a ring or a fused structure.

2. The compound according to claim 1, wherein each of X and Y is independently selected from CR"R"' and NR', R', R" and R"' are groups having at least one electron-withdrawing group; preferably R, R', R" and R"' are groups having at least one electron-withdrawing group.

3. The compound according to claim 1, wherein each of X and Y is independently selected from the group consisting of O, S and Se, and at least one of R groups is a group having at least one electron-withdrawing group; preferably, both R groups are groups having at least one electron-withdrawing group.

4. The compound according to claim 1, wherein the Hammett's constant of the electron-withdrawing group is ≥0.05, preferably ≥0.03 more preferably ≥0.5.

5. The compound according to claim 4, wherein the electron-withdrawing group is selected from the group consisting of halogen, nitroso, nitro, acyl, carbonyl, a carboxylic acid group, an ester group, cyano, isocyano, SCN, OCN, SF$_5$, boranyl, sulfinyl, sulfonyl, phosphoroso, an aza-aromatic ring group, and any one of an alkyl group having 1 to 20 carbon atoms, a cycloalkyl group having 3 to 20 ring carbon atoms, a heteroalkyl group having 1 to 20 carbon atoms, an arylalkyl group having 7 to 30 carbon atoms, an alkoxyl group having 1 to 20 carbon atoms, an aryloxy group having 6 to 30 carbon atoms, an alkenyl group having 2 to 20 carbon atoms, an alkynyl group having 2 to 20 carbon atoms, an aryl group having 6 to 30 carbon atoms, a heteroaryl group having 3 to 30 carbon atoms, an alkylsilyl group having 3 to 20 carbon atoms and an arylsilyl group having 6 to 20 carbon atoms which are substituted with one or more of halogen, nitroso, nitro, acyl, carbonyl, a carboxylic acid group, an ester group, cyano, isocyano, SCN, OCN, SF$_5$, boranyl, sulfinyl, sulfonyl, phosphoroso, an aza-aromatic ring group, and combinations thereof;
preferably, the electron-withdrawing group is selected from the group consisting of F, CF$_3$, OCF$_3$, SF$_5$, SO$_2$CF$_3$, cyano, isocyano, SCN, OCN, pyrimidinyl, triazinyl, and combinations thereof.

6. The compound according to claim 1, wherein each of X and Y is independently selected from the group consisting of:

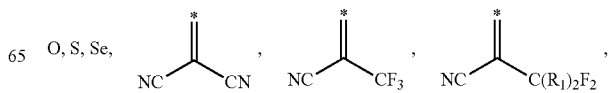

253
-continued

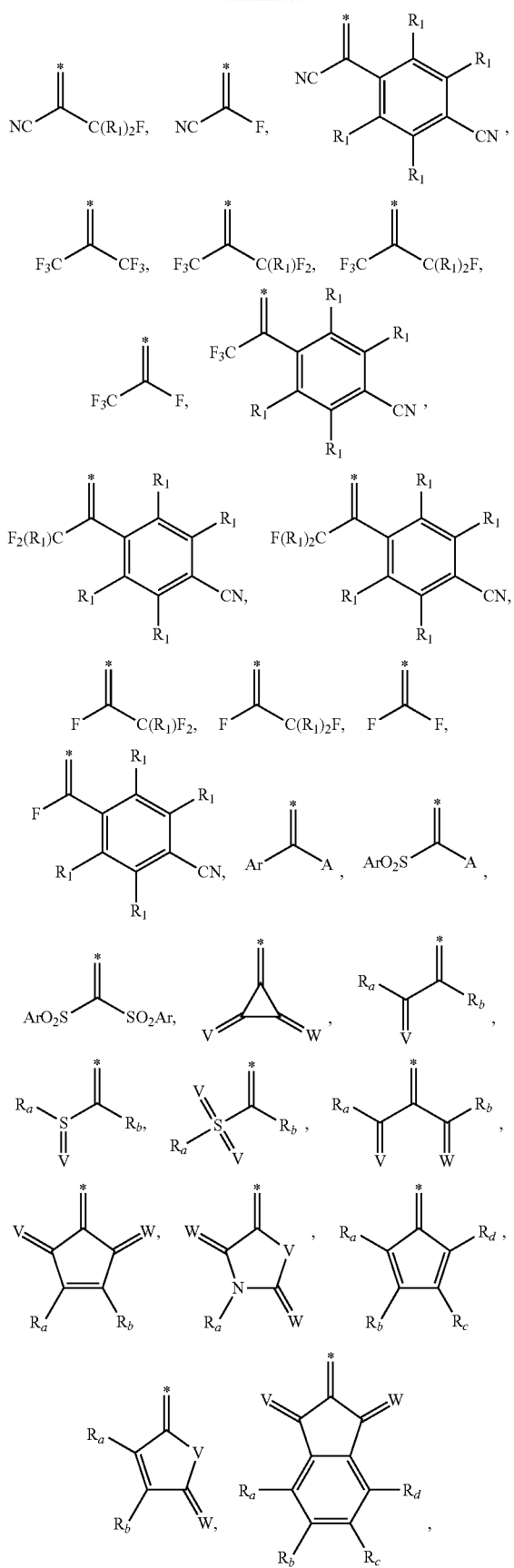

254
-continued

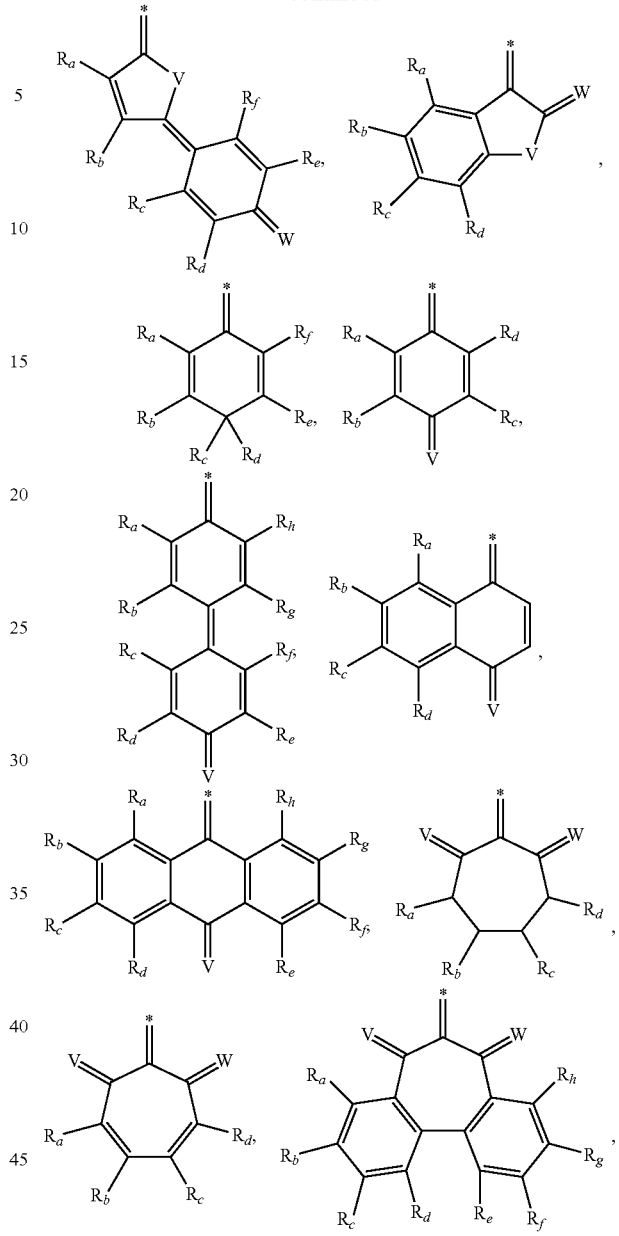

wherein $R_1$ is selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

preferably, $R_1$ is selected, at each occurrence, identically or differently, from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrrolidinyl, and combinations thereof;

wherein V and W are selected, at each occurrence, identically or differently, from the group consisting of $CR_vR_w$, $NR_v$, S and Se;

wherein Ar is selected, at each occurrence, identically or differently, from a substituted or unsubstituted aryl group having 6 to 30 carbon atoms, and a substituted or unsubstituted heteroaryl group having 3 to 30 carbon atoms;

wherein A, $R_a$, $R_b$, $R_c$, $R_d$, $R_e$, $R_f$, $R_g$, $R_h$, $R_v$, and $R_w$ are selected, at each occurrence, identically or differently, from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein A is a group having at least one electron-withdrawing group, and for any one of the structures, when one or more of $R_a$, $R_v$, $R_c$, $R_d$, $R_e$, $R_f$, $R_g$, $R_h$, $R_v$ and $R_w$ is(are) present, at least one of $R_a$, $R_b$, $R_c$, $R_d$, $R_e$, $R_f$, $R_g$, $R_h$, $R_v$ and $R_w$ is a group having at least one electron-withdrawing group; preferably, the group having at least one electron-withdrawing group is selected from the group consisting of F, $CF_3$, $OCF_3$, $SF_5$, $SO_2CF_3$, cyano, isocyano, SCN, OCN, pentafluorophenyl, 4-cyanotetrafluorophenyl, tetrafluoropyridyl, pyrimidinyl, triazinyl, and combinations thereof.

7. The compound according to claim 1, wherein each of X and Y is independently selected, at each occurrence, identically or differently, from the group consisting of:

O, S, Se,

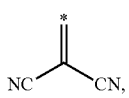
A1

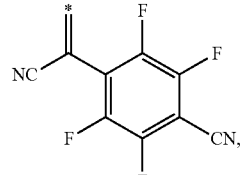
A2

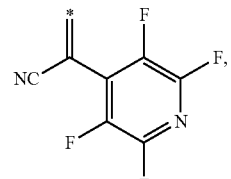
A3

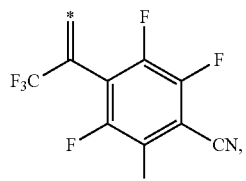
A4

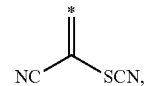
A5

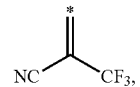
A6

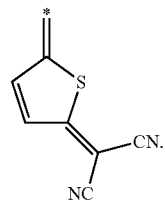
A7

8. The compound according to claim 1, wherein each of R groups is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, an unsubstituted alkyl group having 1 to 20 carbon atoms, an unsubstituted cycloalkyl group having 3 to 20 ring carbon atoms, an unsubstituted alkoxyl group having 1 to 20 carbon atoms, an unsubstituted alkenyl group having 2 to 20 carbon atoms, an unsubstituted aryl group having 6 to 30 carbon atoms, and an unsubstituted heteroaryl group having 3 to 30 carbon atoms, and any one of an alkyl group having 1 to 20 carbon atoms, a cycloalkyl group having 3 to 20 ring carbon atoms, an alkoxyl group having 1 to 20 carbon atoms, an alkenyl group having 2 to 20 carbon atoms, an aryl group having 6 to 30 carbon atoms and a heteroaryl group having 3 to 30 carbon atoms which are substituted with one or more groups selected from the group consisting of halogen, nitroso, nitro, acyl, carbonyl, a carboxylic acid group, an ester group, cyano, isocyano, SCN, OCN, $SF_5$, boranyl, sulfinyl, sulfonyl, phosphoroso, and combinations thereof;

preferably, each of R groups is independently selected from the group consisting of hydrogen, deuterium, methyl, isopropyl, NO₂, SO₂CH₃, SCF₃, C₂F₅, OC₂F₅, OCH₃, p-methylphenyl diphenylmethylsilyl, phenyl, methoxyheptyl, 2,6-diisopropylphenyl, biphenyl, polyfluorophenyl, difluoropyridyl, nitrophenyl, dimethylthiazolyl, vinyl substituted with one or more of CN and CF₃, ethynyl substituted with one of CN and CF₃, dimethylphosphoroso, diphenylphosphoroso, F, CF₃, OCF₃, SF₅, SO₂CF₃, cyano, isocyano, SCN, OCN, trifluoromethylphenyl, trifluoromethoxyphenyl, bis(trifluoromethyl)phenyl, bis(trifluoromethoxy)phenyl, 4-cyanotetrafluorophenyl, phenyl or biphenyl substituted with one or more of F, CN and CF₃, tetrafluoropyridyl, pyrimidinyl, triazinyl, diphenylboranyl, oxaboraanthryl, and combinations thereof.

9. The compound according to claim 8, wherein X and Y are

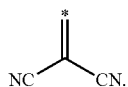

10. The compound according to claim 1, wherein each of R groups is independently selected from the group consisting of:

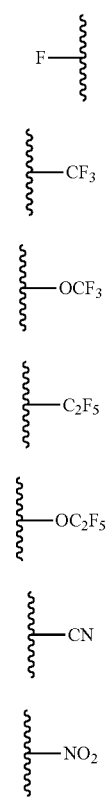

  B10

  B11

  B12

  B13

  B14

  B15

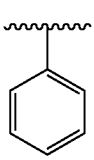  B16

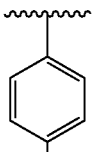  B17

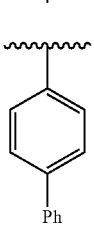  B18

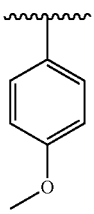  B19

-continued
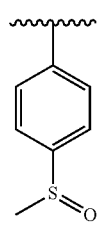
B20
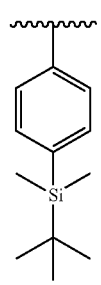
B21
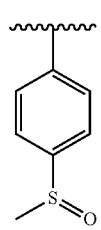
B22
B23
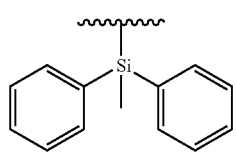
B24
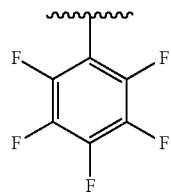
B25
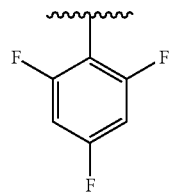
B26
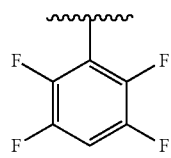
B27
-continued
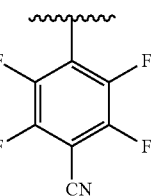
B28
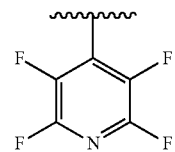
B29
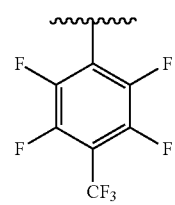
B30
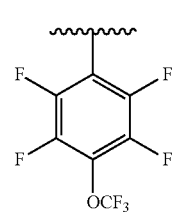
B31
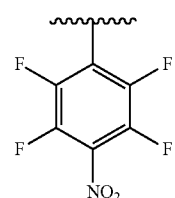
B32
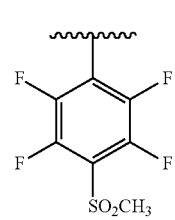
B33
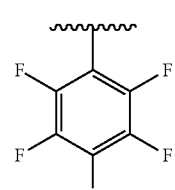
B34
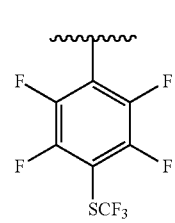
B35

-continued
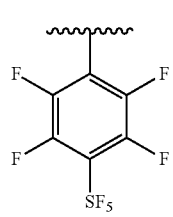 B36
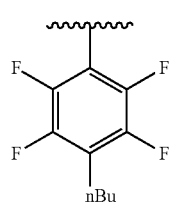 B37
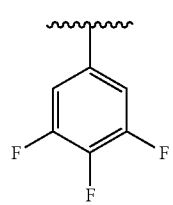 B38
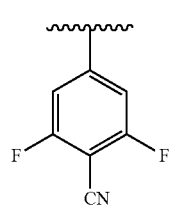 B39
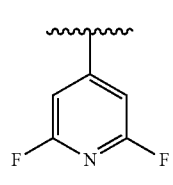 B40
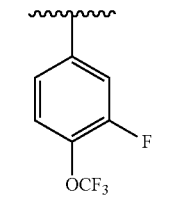 B41
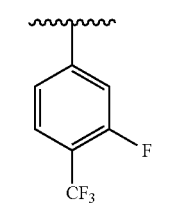 B42
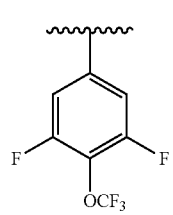 B43
-continued
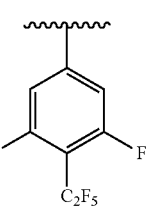 B44
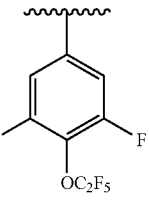 B45
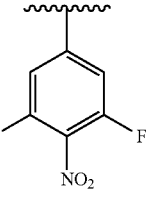 B46
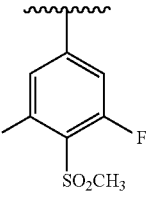 B47
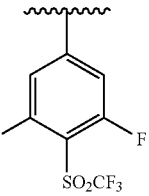 B48
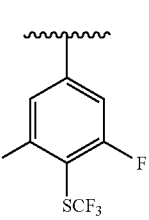 B49
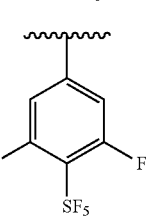 B50
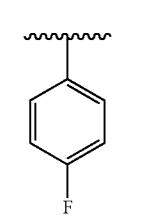 B51

B52 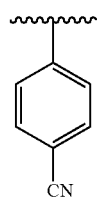
B53 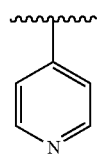
B54 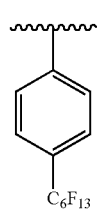
B55 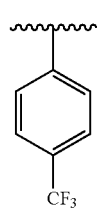
B56 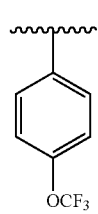
B57 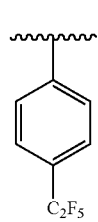
B58 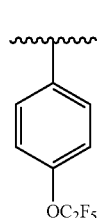
B59 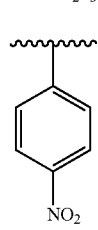
B60 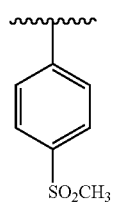
B61 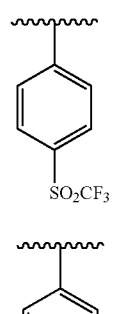
B62 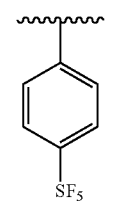
B63 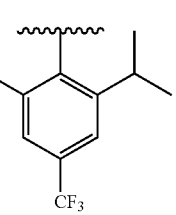
B64 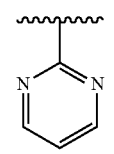
B65 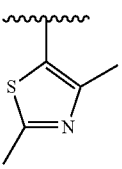
B66 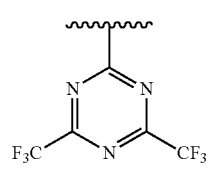
B67

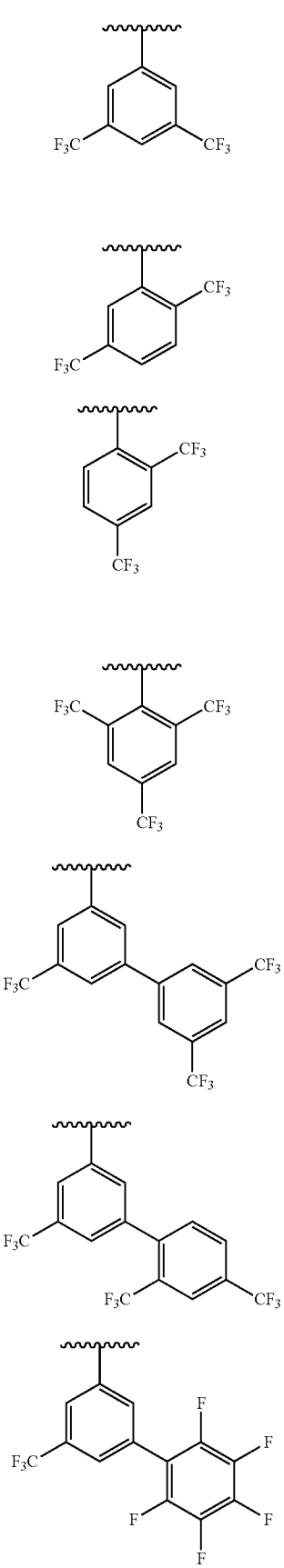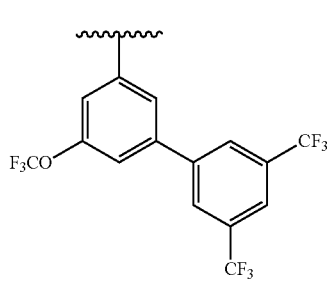

-continued

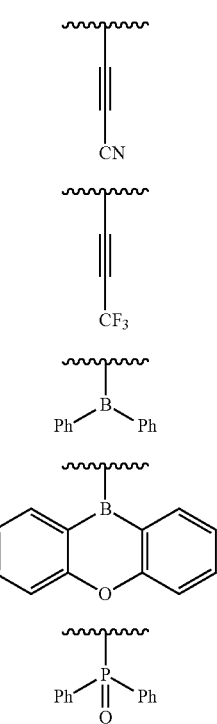

B83 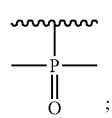

B84 preferably, the two R groups in Formula 1' are the same.

11. The compound according to claim 1, which has the structure represented by Formula 2:

B85

B86 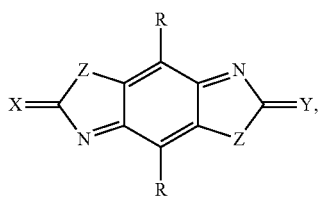

Formula 2

B87 wherein in Formula 2 the structures of the two Z groups are the same, the structures of the two R groups are the same or different, and Z, X, Y and R are correspondingly selected from the atoms or groups as shown in the following table:

| NO. | Z | X | Y | R | R | NO. | Z | X | Y | R | R |
|---|---|---|---|---|---|---|---|---|---|---|---|
| Compound 1 | O | A1 | A1 | B1 | B1 | Compound 2 | O | A1 | A1 | B2 | B2 |
| Compound 3 | O | A1 | A1 | B3 | B3 | Compound 4 | O | A1 | A1 | B4 | B4 |
| Compound 5 | O | A1 | A1 | B5 | B5 | Compound 6 | O | A1 | A1 | B6 | B6 |
| Compound 7 | O | A1 | A1 | B7 | B7 | Compound 8 | O | A1 | A1 | B8 | B8 |
| Compound 9 | O | A1 | A1 | B9 | B9 | Compound 10 | O | A1 | A1 | B10 | B10 |
| Compound 11 | O | A1 | A1 | B11 | B11 | Compound 12 | O | A1 | A1 | B12 | B12 |
| Compound 13 | O | A1 | A1 | B13 | B13 | Compound 14 | O | A1 | A1 | B14 | B14 |
| Compound 15 | O | A1 | A1 | B15 | B15 | Compound 16 | O | A1 | A1 | B16 | B16 |
| Compound 17 | O | A1 | A1 | B17 | B17 | Compound 18 | O | A1 | A1 | B18 | B18 |
| Compound 19 | O | A1 | A1 | B19 | B19 | Compound 20 | O | A1 | A1 | B20 | B20 |
| Compound 21 | O | A1 | A1 | B21 | B21 | Compound 22 | O | A1 | A1 | B22 | B22 |
| Compound 23 | O | A1 | A1 | B23 | B23 | Compound 24 | O | A1 | A1 | B24 | B24 |
| Compound 25 | O | A1 | A1 | B25 | B25 | Compound 26 | O | A1 | A1 | B26 | B26 |
| Compound 27 | O | A1 | A1 | B27 | B27 | Compound 28 | O | A1 | A1 | B28 | B28 |
| Compound 29 | O | A1 | A1 | B29 | B29 | Compound 30 | O | A1 | A1 | B30 | B30 |
| Compound 31 | O | A1 | A1 | B31 | B31 | Compound 32 | O | A1 | A1 | B32 | B32 |
| Compound 33 | O | A1 | A1 | B33 | B33 | Compound 34 | O | A1 | A1 | B34 | B34 |
| Compound 35 | O | A1 | A1 | B35 | B35 | Compound 36 | O | A1 | A1 | B36 | B36 |
| Compound 37 | O | A1 | A1 | B37 | B37 | Compound 38 | O | A1 | A1 | B38 | B38 |
| Compound 39 | O | A1 | A1 | B39 | B39 | Compound 40 | O | A1 | A1 | B40 | B40 |
| Compound 41 | O | A1 | A1 | B41 | B41 | Compound 42 | O | A1 | A1 | B42 | B42 |
| Compound 43 | O | A1 | A1 | B43 | B43 | Compound 44 | O | A1 | A1 | B44 | B44 |

| NO. | Z | X | Y | R | R | NO. | Z | X | Y | R | R |
|---|---|---|---|---|---|---|---|---|---|---|---|
| Compound 45 | O | A1 | A1 | B45 | B45 | Compound 46 | O | A1 | A1 | B46 | B46 |
| Compound 47 | O | A1 | A1 | B47 | B47 | Compound 48 | O | A1 | A1 | B48 | B48 |
| Compound 49 | O | A1 | A1 | B49 | B49 | Compound 50 | O | A1 | A1 | B50 | B50 |
| Compound 51 | O | A1 | A1 | B51 | B51 | Compound 52 | O | A1 | A1 | B52 | B52 |
| Compound 53 | O | A1 | A1 | B53 | B53 | Compound 54 | O | A1 | A1 | B54 | B54 |
| Compound 55 | O | A1 | A1 | B55 | B55 | Compound 56 | O | A1 | A1 | B56 | B56 |
| Compound 57 | O | A1 | A1 | B57 | B57 | Compound 58 | O | A1 | A1 | B58 | B58 |
| Compound 59 | O | A1 | A1 | B59 | B59 | Compound 60 | O | A1 | A1 | B60 | B60 |
| Compound 61 | O | A1 | A1 | B61 | B61 | Compound 62 | O | A1 | A1 | B62 | B62 |
| Compound 63 | O | A1 | A1 | B63 | B63 | Compound 64 | O | A1 | A1 | B64 | B64 |
| Compound 65 | O | A1 | A1 | B65 | B65 | Compound 66 | O | A1 | A1 | B66 | B66 |
| Compound 67 | O | A1 | A1 | B67 | B67 | Compound 68 | O | A1 | A1 | B68 | B68 |
| Compound 69 | O | A1 | A1 | B69 | B69 | Compound 70 | O | A1 | A1 | B70 | B70 |
| Compound 71 | O | A1 | A1 | B71 | B71 | Compound 72 | O | A1 | A1 | B72 | B72 |
| Compound 73 | O | A1 | A1 | B73 | B73 | Compound 74 | O | A1 | A1 | B74 | B74 |
| Compound 75 | O | A1 | A1 | B75 | B75 | Compound 76 | O | A1 | A1 | B76 | B76 |
| Compound 77 | O | A1 | A1 | B77 | B77 | Compound 78 | O | A1 | A1 | B78 | B78 |
| Compound 79 | O | A1 | A1 | B79 | B79 | Compound 80 | O | A1 | A1 | B80 | B80 |
| Compound 81 | O | A1 | A1 | B81 | B81 | Compound 82 | O | A1 | A1 | B82 | B82 |
| Compound 83 | O | A1 | A1 | B83 | B83 | Compound 84 | O | A1 | A1 | B84 | B84 |
| Compound 85 | O | A1 | A1 | B85 | B85 | Compound 86 | O | A1 | A1 | B86 | B86 |
| Compound 87 | O | A1 | A1 | B87 | B87 | Compound 88 | O | A1 | A1 | B88 | B88 |
| Compound 89 | S | A1 | A1 | B1 | B1 | Compound 90 | S | A1 | A1 | B2 | B2 |
| Compound 91 | S | A1 | A1 | B3 | B3 | Compound 92 | S | A1 | A1 | B4 | B4 |
| Compound 93 | S | A1 | A1 | B5 | B5 | Compound 94 | S | A1 | A1 | B6 | B6 |
| Compound 95 | S | A1 | A1 | B7 | B7 | Compound 96 | S | A1 | A1 | B8 | B8 |
| Compound 97 | S | A1 | A1 | B9 | B9 | Compound 98 | S | A1 | A1 | B10 | B10 |
| Compound 99 | S | A1 | A1 | B11 | B11 | Compound 100 | S | A1 | A1 | B12 | B12 |
| Compound 101 | S | A1 | A1 | B13 | B13 | Compound 102 | S | A1 | A1 | B14 | B14 |
| Compound 103 | S | A1 | A1 | B15 | B15 | Compound 104 | S | A1 | A1 | B16 | B16 |
| Compound 105 | S | A1 | A1 | B17 | B17 | Compound 106 | S | A1 | A1 | B18 | B18 |
| Compound 107 | S | A1 | A1 | B19 | B19 | Compound 108 | S | A1 | A1 | B20 | B20 |
| Compound 109 | S | A1 | A1 | B21 | B21 | Compound 110 | S | A1 | A1 | B22 | B22 |
| Compound 111 | S | A1 | A1 | B23 | B23 | Compound 112 | S | A1 | A1 | B24 | B24 |
| Compound 113 | S | A1 | A1 | B25 | B25 | Compound 114 | S | A1 | A1 | B26 | B26 |
| Compound 115 | S | A1 | A1 | B27 | B27 | Compound 116 | S | A1 | A1 | B28 | B28 |
| Compound 117 | S | A1 | A1 | B29 | B29 | Compound 118 | S | A1 | A1 | B30 | B30 |
| Compound 119 | S | A1 | A1 | B31 | B31 | Compound 120 | S | A1 | A1 | B32 | B32 |

| NO. | Z | X | Y | R | R | NO. | Z | X | Y | R | R |
|---|---|---|---|---|---|---|---|---|---|---|---|
| Compound 121 | S | A1 | A1 | B33 | B33 | Compound 122 | S | A1 | A1 | B34 | B34 |
| Compound 123 | S | A1 | A1 | B35 | B35 | Compound 124 | S | A1 | A1 | B36 | B36 |
| Compound 125 | S | A1 | A1 | B37 | B37 | Compound 126 | S | A1 | A1 | B38 | B38 |
| Compound 127 | S | A1 | A1 | B39 | B39 | Compound 128 | S | A1 | A1 | B40 | B40 |
| Compound 129 | S | A1 | A1 | B41 | B41 | Compound 130 | S | A1 | A1 | B42 | B42 |
| Compound 131 | S | A1 | A1 | B43 | B43 | Compound 132 | S | A1 | A1 | B44 | B44 |
| Compound 133 | S | A1 | A1 | B45 | B45 | Compound 134 | S | A1 | A1 | B46 | B46 |
| Compound 135 | S | A1 | A1 | B47 | B47 | Compound 136 | S | A1 | A1 | B48 | B48 |
| Compound 137 | S | A1 | A1 | B49 | B49 | Compound 138 | S | A1 | A1 | B50 | B50 |
| Compound 139 | S | A1 | A1 | B51 | B51 | Compound 140 | S | A1 | A1 | B52 | B52 |
| Compound 141 | S | A1 | A1 | B53 | B53 | Compound 142 | S | A1 | A1 | B54 | B54 |
| Compound 143 | S | A1 | A1 | B55 | B55 | Compound 144 | S | A1 | A1 | B56 | B56 |
| Compound 145 | S | A1 | A1 | B57 | B57 | Compound 146 | S | A1 | A1 | B58 | B58 |
| Compound 147 | S | A1 | A1 | B59 | B59 | Compound 148 | S | A1 | A1 | B60 | B60 |
| Compound 149 | S | A1 | A1 | B61 | B61 | Compound 150 | S | A1 | A1 | B62 | B62 |
| Compound 151 | S | A1 | A1 | B63 | B63 | Compound 152 | S | A1 | A1 | B64 | B64 |
| Compound 153 | S | A1 | A1 | B65 | B65 | Compound 154 | S | A1 | A1 | B66 | B66 |
| Compound 155 | S | A1 | A1 | B67 | B67 | Compound 156 | S | A1 | A1 | B68 | B68 |
| Compound 157 | S | A1 | A1 | B69 | B69 | Compound 158 | S | A1 | A1 | B70 | B70 |
| Compound 159 | S | A1 | A1 | B71 | B71 | Compound 160 | S | A1 | A1 | B72 | B72 |
| Compound 161 | S | A1 | A1 | B73 | B73 | Compound 162 | S | A1 | A1 | B74 | B74 |
| Compound 163 | S | A1 | A1 | B75 | B75 | Compound 164 | S | A1 | A1 | B76 | B76 |
| Compound 165 | S | A1 | A1 | B77 | B77 | Compound 166 | S | A1 | A1 | B78 | B78 |
| Compound 167 | S | A1 | A1 | B79 | B79 | Compound 168 | S | A1 | A1 | B80 | B80 |
| Compound 169 | S | A1 | A1 | B81 | B81 | Compound 170 | S | A1 | A1 | B82 | B82 |
| Compound 171 | S | A1 | A1 | B83 | B83 | Compound 172 | S | A1 | A1 | B84 | B84 |
| Compound 173 | S | A1 | A1 | B85 | B85 | Compound 174 | S | A1 | A1 | B86 | B86 |
| Compound 175 | S | A1 | A1 | B87 | B87 | Compound 176 | S | A1 | A1 | B88 | B88 |
| Compound 177 | Se | A1 | A1 | B1 | B1 | Compound 178 | Se | A1 | A1 | B2 | B2 |
| Compound 179 | Se | A1 | A1 | B3 | B3 | Compound 180 | Se | A1 | A1 | B4 | B4 |
| Compound 181 | Se | A1 | A1 | B5 | B5 | Compound 182 | Se | A1 | A1 | B6 | B6 |
| Compound 183 | Se | A1 | A1 | B7 | B7 | Compound 184 | Se | A1 | A1 | B8 | B8 |
| Compound 185 | Se | A1 | A1 | B9 | B9 | Compound 186 | Se | A1 | A1 | B10 | B10 |
| Compound 187 | Se | A1 | A1 | B11 | B11 | Compound 188 | Se | A1 | A1 | B12 | B12 |
| Compound 189 | Se | A1 | A1 | B13 | B13 | Compound 190 | Se | A1 | A1 | B14 | B14 |
| Compound 191 | Se | A1 | A1 | B15 | B15 | Compound 192 | Se | A1 | A1 | B16 | B16 |
| Compound 193 | Se | A1 | A1 | B17 | B17 | Compound 194 | Se | A1 | A1 | B18 | B18 |
| Compound 195 | Se | A1 | A1 | B19 | B19 | Compound 196 | Se | A1 | A1 | B20 | B20 |

-continued

| NO. | Z | X | Y | R | R | NO. | Z | X | Y | R | R |
|---|---|---|---|---|---|---|---|---|---|---|---|
| Compound 197 | Se | A1 | A1 | B21 | B21 | Compound 198 | Se | A1 | A1 | B22 | B22 |
| Compound 199 | Se | A1 | A1 | B23 | B23 | Compound 200 | Se | A1 | A1 | B24 | B24 |
| Compound 201 | Se | A1 | A1 | B25 | B25 | Compound 202 | Se | A1 | A1 | B26 | B26 |
| Compound 203 | Se | A1 | A1 | B27 | B27 | Compound 204 | Se | A1 | A1 | B28 | B28 |
| Compound 205 | Se | A1 | A1 | B29 | B29 | Compound 206 | Se | A1 | A1 | B30 | B30 |
| Compound 207 | Se | A1 | A1 | B31 | B31 | Compound 208 | Se | A1 | A1 | B32 | B32 |
| Compound 209 | Se | A1 | A1 | B33 | B33 | Compound 210 | Se | A1 | A1 | B34 | B34 |
| Compound 211 | Se | A1 | A1 | B35 | B35 | Compound 212 | Se | A1 | A1 | B36 | B36 |
| Compound 213 | Se | A1 | A1 | B37 | B37 | Compound 214 | Se | A1 | A1 | B38 | B38 |
| Compound 215 | Se | A1 | A1 | B39 | B39 | Compound 216 | Se | A1 | A1 | B40 | B40 |
| Compound 217 | Se | A1 | A1 | B41 | B41 | Compound 218 | Se | A1 | A1 | B42 | B42 |
| Compound 219 | Se | A1 | A1 | B43 | B43 | Compound 220 | Se | A1 | A1 | B44 | B44 |
| Compound 221 | Se | A1 | A1 | B45 | B45 | Compound 222 | Se | A1 | A1 | B46 | B46 |
| Compound 223 | Se | A1 | A1 | B47 | B47 | Compound 224 | Se | A1 | A1 | B48 | B48 |
| Compound 225 | Se | A1 | A1 | B49 | B49 | Compound 226 | Se | A1 | A1 | B50 | B50 |
| Compound 227 | Se | A1 | A1 | B51 | B51 | Compound 228 | Se | A1 | A1 | B52 | B52 |
| Compound 229 | Se | A1 | A1 | B53 | B53 | Compound 230 | Se | A1 | A1 | B54 | B54 |
| Compound 231 | Se | A1 | A1 | B55 | B55 | Compound 232 | Se | A1 | A1 | B56 | B56 |
| Compound 233 | Se | A1 | A1 | B57 | B57 | Compound 234 | Se | A1 | A1 | B58 | B58 |
| Compound 235 | Se | A1 | A1 | B59 | B59 | Compound 236 | Se | A1 | A1 | B60 | B60 |
| Compound 237 | Se | A1 | A1 | B61 | B61 | Compound 238 | Se | A1 | A1 | B62 | B62 |
| Compound 239 | Se | A1 | A1 | B63 | B63 | Compound 240 | Se | A1 | A1 | B64 | B64 |
| Compound 241 | Se | A1 | A1 | B65 | B65 | Compound 242 | Se | A1 | A1 | B66 | B66 |
| Compound 243 | Se | A1 | A1 | B67 | B67 | Compound 244 | Se | A1 | A1 | B68 | B68 |
| Compound 245 | Se | A1 | A1 | B69 | B69 | Compound 246 | Se | A1 | A1 | B70 | B70 |
| Compound 247 | Se | A1 | A1 | B71 | B71 | Compound 248 | Se | A1 | A1 | B72 | B72 |
| Compound 249 | Se | A1 | A1 | B73 | B73 | Compound 250 | Se | A1 | A1 | B74 | B74 |
| Compound 251 | Se | A1 | A1 | B75 | B75 | Compound 252 | Se | A1 | A1 | B76 | B76 |
| Compound 253 | Se | A1 | A1 | B77 | B77 | Compound 254 | Se | A1 | A1 | B78 | B78 |
| Compound 255 | Se | A1 | A1 | B79 | B79 | Compound 256 | Se | A1 | A1 | B80 | B80 |
| Compound 257 | Se | A1 | A1 | B81 | B81 | Compound 258 | Se | A1 | A1 | B82 | B82 |
| Compound 259 | Se | A1 | A1 | B83 | B83 | Compound 260 | Se | A1 | A1 | B84 | B84 |
| Compound 261 | Se | A1 | A1 | B85 | B85 | Compound 262 | Se | A1 | A1 | B86 | B86 |
| Compound 263 | Se | A1 | A1 | B87 | B87 | Compound 264 | Se | A1 | A1 | B88 | B88 |
| Compound 265 | O | A2 | A2 | B1 | B1 | Compound 266 | O | A2 | A2 | B6 | B6 |
| Compound 267 | O | A2 | A2 | B10 | B10 | Compound 268 | O | A2 | A2 | B16 | B16 |
| Compound 269 | O | A2 | A2 | B25 | B25 | Compound 270 | O | A2 | A2 | B28 | B28 |
| Compound 271 | O | A2 | A2 | B29 | B29 | Compound 272 | O | A2 | A2 | B30 | B30 |

| NO. | Z | X | Y | R | R | NO. | Z | X | Y | R | R |
|---|---|---|---|---|---|---|---|---|---|---|---|
| Compound 273 | O | A2 | A2 | B38 | B38 | Compound 274 | O | A2 | A2 | B39 | B39 |
| Compound 275 | O | A2 | A2 | B40 | B40 | Compound 276 | O | A2 | A2 | B41 | B41 |
| Compound 277 | O | A2 | A2 | B43 | B43 | Compound 278 | O | A2 | A2 | B52 | B52 |
| Compound 279 | O | A2 | A2 | B56 | B56 | Compound 280 | O | A2 | A2 | B67 | B67 |
| Compound 281 | O | A2 | A2 | B68 | B68 | Compound 282 | O | A2 | A2 | B69 | B69 |
| Compound 283 | O | A2 | A2 | B70 | B70 | Compound 284 | O | A2 | A2 | B71 | B71 |
| Compound 285 | O | A2 | A2 | B72 | B72 | Compound 286 | O | A2 | A2 | B74 | B74 |
| Compound 287 | O | A2 | A2 | B79 | B79 | Compound 288 | O | A2 | A2 | B80 | B80 |
| Compound 289 | O | A2 | A2 | B82 | B82 | Compound 290 | O | A2 | A2 | B83 | B83 |
| Compound 291 | O | A2 | A2 | B86 | B86 | Compound 292 | O | A2 | A2 | B88 | B88 |
| Compound 293 | S | A2 | A2 | B1 | B1 | Compound 294 | S | A2 | A2 | B6 | B6 |
| Compound 295 | S | A2 | A2 | B10 | B10 | Compound 296 | S | A2 | A2 | B16 | B16 |
| Compound 297 | S | A2 | A2 | B25 | B25 | Compound 298 | S | A2 | A2 | B28 | B28 |
| Compound 299 | S | A2 | A2 | B29 | B29 | Compound 300 | S | A2 | A2 | B30 | B30 |
| Compound 301 | S | A2 | A2 | B38 | B38 | Compound 302 | S | A2 | A2 | B39 | B39 |
| Compound 303 | S | A2 | A2 | B40 | B40 | Compound 304 | S | A2 | A2 | B41 | B41 |
| Compound 305 | S | A2 | A2 | B43 | B43 | Compound 306 | S | A2 | A2 | B52 | B52 |
| Compound 307 | S | A2 | A2 | B56 | B56 | Compound 308 | S | A2 | A2 | B67 | B67 |
| Compound 309 | S | A2 | A2 | B68 | B68 | Compound 310 | S | A2 | A2 | B69 | B69 |
| Compound 311 | S | A2 | A2 | B70 | B70 | Compound 312 | S | A2 | A2 | B71 | B71 |
| Compound 313 | S | A2 | A2 | B72 | B72 | Compound 314 | S | A2 | A2 | B74 | B74 |
| Compound 315 | S | A2 | A2 | B79 | B79 | Compound 316 | S | A2 | A2 | B80 | B80 |
| Compound 317 | S | A2 | A2 | B82 | B82 | Compound 318 | S | A2 | A2 | B83 | B83 |
| Compound 319 | S | A2 | A2 | B86 | B86 | Compound 320 | S | A2 | A2 | B88 | B88 |
| Compound 321 | Se | A2 | A2 | B1 | B1 | Compound 322 | Se | A2 | A2 | B6 | B6 |
| Compound 323 | Se | A2 | A2 | B10 | B10 | Compound 324 | Se | A2 | A2 | B16 | B16 |
| Compound 325 | Se | A2 | A2 | B25 | B25 | Compound 326 | Se | A2 | A2 | B28 | B28 |
| Compound 327 | Se | A2 | A2 | B29 | B29 | Compound 328 | Se | A2 | A2 | B30 | B30 |
| Compound 329 | Se | A2 | A2 | B38 | B38 | Compound 330 | Se | A2 | A2 | B39 | B39 |
| Compound 331 | Se | A2 | A2 | B40 | B40 | Compound 332 | Se | A2 | A2 | B41 | B41 |
| Compound 333 | Se | A2 | A2 | B43 | B43 | Compound 334 | Se | A2 | A2 | B52 | B52 |
| Compound 335 | Se | A2 | A2 | B56 | B56 | Compound 336 | Se | A2 | A2 | B67 | B67 |
| Compound 337 | Se | A2 | A2 | B68 | B68 | Compound 338 | Se | A2 | A2 | B69 | B69 |
| Compound 339 | Se | A2 | A2 | B70 | B70 | Compound 340 | Se | A2 | A2 | B71 | B71 |
| Compound 341 | Se | A2 | A2 | B72 | B72 | Compound 342 | Se | A2 | A2 | B74 | B74 |
| Compound 343 | Se | A2 | A2 | B79 | B79 | Compound 344 | Se | A2 | A2 | B80 | B80 |
| Compound 345 | Se | A2 | A2 | B82 | B82 | Compound 346 | Se | A2 | A2 | B83 | B83 |
| Compound 347 | Se | A2 | A2 | B86 | B86 | Compound 348 | Se | A2 | A2 | B88 | B88 |

-continued

| NO. | Z | X | Y | R | R | NO. | Z | X | Y | R | R |
|---|---|---|---|---|---|---|---|---|---|---|---|
| Compound 349 | O | A3 | A3 | B1 | B1 | Compound 350 | O | A3 | A3 | B6 | B6 |
| Compound 351 | O | A3 | A3 | B10 | B10 | Compound 352 | O | A3 | A3 | B16 | B16 |
| Compound 353 | O | A3 | A3 | B25 | B25 | Compound 354 | O | A3 | A3 | B28 | B28 |
| Compound 355 | O | A3 | A3 | B29 | B29 | Compound 356 | O | A3 | A3 | B30 | B30 |
| Compound 357 | O | A3 | A3 | B38 | B38 | Compound 358 | O | A3 | A3 | B39 | B39 |
| Compound 359 | O | A3 | A3 | B40 | B40 | Compound 360 | O | A3 | A3 | B41 | B41 |
| Compound 361 | O | A3 | A3 | B43 | B43 | Compound 362 | O | A3 | A3 | B52 | B52 |
| Compound 363 | O | A3 | A3 | B56 | B56 | Compound 364 | O | A3 | A3 | B67 | B67 |
| Compound 365 | O | A3 | A3 | B68 | B68 | Compound 366 | O | A3 | A3 | B69 | B69 |
| Compound 367 | O | A3 | A3 | B70 | B70 | Compound 368 | O | A3 | A3 | B71 | B71 |
| Compound 369 | O | A3 | A3 | B72 | B72 | Compound 370 | O | A3 | A3 | B74 | B74 |
| Compound 371 | O | A3 | A3 | B79 | B79 | Compound 372 | O | A3 | A3 | B80 | B80 |
| Compound 373 | O | A3 | A3 | B82 | B82 | Compound 374 | O | A3 | A3 | B83 | B83 |
| Compound 375 | O | A3 | A3 | B86 | B86 | Compound 376 | O | A3 | A3 | B88 | B88 |
| Compound 377 | S | A3 | A3 | B1 | B1 | Compound 378 | S | A3 | A3 | B6 | B6 |
| Compound 379 | S | A3 | A3 | B10 | B10 | Compound 380 | S | A3 | A3 | B16 | B16 |
| Compound 381 | S | A3 | A3 | B25 | B25 | Compound 382 | S | A3 | A3 | B28 | B28 |
| Compound 383 | S | A3 | A3 | B29 | B29 | Compound 384 | S | A3 | A3 | B30 | B30 |
| Compound 385 | S | A3 | A3 | B38 | B38 | Compound 386 | S | A3 | A3 | B39 | B39 |
| Compound 387 | S | A3 | A3 | B40 | B40 | Compound 388 | S | A3 | A3 | B41 | B41 |
| Compound 389 | S | A3 | A3 | B43 | B43 | Compound 390 | S | A3 | A3 | B52 | B52 |
| Compound 391 | S | A3 | A3 | B56 | B56 | Compound 392 | S | A3 | A3 | B67 | B67 |
| Compound 393 | S | A3 | A3 | B68 | B68 | Compound 394 | S | A3 | A3 | B69 | B69 |
| Compound 395 | S | A3 | A3 | B70 | B70 | Compound 396 | S | A3 | A3 | B71 | B71 |
| Compound 397 | S | A3 | A3 | B72 | B72 | Compound 398 | S | A3 | A3 | B74 | B74 |
| Compound 399 | S | A3 | A3 | B79 | B79 | Compound 400 | S | A3 | A3 | B80 | B80 |
| Compound 401 | S | A3 | A3 | B82 | B82 | Compound 402 | S | A3 | A3 | B83 | B83 |
| Compound 403 | S | A3 | A3 | B86 | B86 | Compound 404 | S | A3 | A3 | B88 | B88 |
| Compound 405 | Se | A3 | A3 | B1 | B1 | Compound 406 | Se | A3 | A3 | B6 | B6 |
| Compound 407 | Se | A3 | A3 | B10 | B10 | Compound 408 | Se | A3 | A3 | B16 | B16 |
| Compound 409 | Se | A3 | A3 | B25 | B25 | Compound 410 | Se | A3 | A3 | B28 | B28 |
| Compound 411 | Se | A3 | A3 | B29 | B29 | Compound 412 | Se | A3 | A3 | B30 | B30 |
| Compound 413 | Se | A3 | A3 | B38 | B38 | Compound 414 | Se | A3 | A3 | B39 | B39 |
| Compound 415 | Se | A3 | A3 | B40 | B40 | Compound 416 | Se | A3 | A3 | B41 | B41 |
| Compound 417 | Se | A3 | A3 | B43 | B43 | Compound 418 | Se | A3 | A3 | B52 | B52 |
| Compound 419 | Se | A3 | A3 | B56 | B56 | Compound 420 | Se | A3 | A3 | B67 | B67 |
| Compound 421 | Se | A3 | A3 | B68 | B68 | Compound 422 | Se | A3 | A3 | B69 | B69 |
| Compound 423 | Se | A3 | A3 | B70 | B70 | Compound 424 | Se | A3 | A3 | B71 | B71 |

-continued

| NO. | Z | X | Y | R | R | NO. | Z | X | Y | R | R |
|---|---|---|---|---|---|---|---|---|---|---|---|
| Compound 425 | Se | A3 | A3 | B72 | B72 | Compound 426 | Se | A3 | A3 | B74 | B74 |
| Compound 427 | Se | A3 | A3 | B79 | B79 | Compound 428 | Se | A3 | A3 | B80 | B80 |
| Compound 429 | Se | A3 | A3 | B82 | B82 | Compound 430 | Se | A3 | A3 | B83 | B83 |
| Compound 431 | Se | A3 | A3 | B86 | B86 | Compound 432 | Se | A3 | A3 | B88 | B88 |
| Compound 433 | O | A4 | A4 | B1 | B1 | Compound 434 | O | A4 | A4 | B6 | B6 |
| Compound 435 | O | A4 | A4 | B10 | B10 | Compound 436 | O | A4 | A4 | B16 | B16 |
| Compound 437 | O | A4 | A4 | B25 | B25 | Compound 438 | O | A4 | A4 | B28 | B28 |
| Compound 439 | O | A4 | A4 | B29 | B29 | Compound 440 | O | A4 | A4 | B30 | B30 |
| Compound 441 | O | A4 | A4 | B38 | B38 | Compound 442 | O | A4 | A4 | B39 | B39 |
| Compound 443 | O | A4 | A4 | B40 | B40 | Compound 444 | O | A4 | A4 | B41 | B41 |
| Compound 445 | O | A4 | A4 | B43 | B43 | Compound 446 | O | A4 | A4 | B52 | B52 |
| Compound 447 | O | A4 | A4 | B56 | B56 | Compound 448 | O | A4 | A4 | B67 | B67 |
| Compound 449 | O | A4 | A4 | B68 | B68 | Compound 450 | O | A4 | A4 | B69 | B69 |
| Compound 451 | O | A4 | A4 | B70 | B70 | Compound 452 | O | A4 | A4 | B71 | B71 |
| Compound 453 | O | A4 | A4 | B72 | B72 | Compound 454 | O | A4 | A4 | B74 | B74 |
| Compound 455 | O | A4 | A4 | B79 | B79 | Compound 456 | O | A4 | A4 | B80 | B80 |
| Compound 457 | O | A4 | A4 | B82 | B82 | Compound 458 | O | A4 | A4 | B83 | B83 |
| Compound 459 | O | A4 | A4 | B86 | B86 | Compound 460 | O | A4 | A4 | B88 | B88 |
| Compound 461 | S | A4 | A4 | B1 | B1 | Compound 462 | S | A4 | A4 | B6 | B6 |
| Compound 463 | S | A4 | A4 | B10 | B10 | Compound 464 | S | A4 | A4 | B16 | B16 |
| Compound 465 | S | A4 | A4 | B25 | B25 | Compound 466 | S | A4 | A4 | B28 | B28 |
| Compound 467 | S | A4 | A4 | B29 | B29 | Compound 468 | S | A4 | A4 | B30 | B30 |
| Compound 469 | S | A4 | A4 | B38 | B38 | Compound 470 | S | A4 | A4 | B39 | B39 |
| Compound 471 | S | A4 | A4 | B40 | B40 | Compound 472 | S | A4 | A4 | B41 | B41 |
| Compound 473 | S | A4 | A4 | B43 | B43 | Compound 474 | S | A4 | A4 | B52 | B52 |
| Compound 475 | S | A4 | A4 | B56 | B56 | Compound 476 | S | A4 | A4 | B67 | B67 |
| Compound 477 | S | A4 | A4 | B68 | B68 | Compound 478 | S | A4 | A4 | B69 | B69 |
| Compound 479 | S | A4 | A4 | B70 | B70 | Compound 480 | S | A4 | A4 | B71 | B71 |
| Compound 481 | S | A4 | A4 | B72 | B72 | Compound 482 | S | A4 | A4 | B74 | B74 |
| Compound 483 | S | A4 | A4 | B79 | B79 | Compound 484 | S | A4 | A4 | B80 | B80 |
| Compound 485 | S | A4 | A4 | B82 | B82 | Compound 486 | S | A4 | A4 | B83 | B83 |
| Compound 487 | S | A4 | A4 | B86 | B86 | Compound 488 | S | A4 | A4 | B88 | B88 |
| Compound 489 | Se | A4 | A4 | B1 | B1 | Compound 490 | Se | A4 | A4 | B6 | B6 |
| Compound 491 | Se | A4 | A4 | B10 | B10 | Compound 492 | Se | A4 | A4 | B16 | B16 |
| Compound 493 | Se | A4 | A4 | B25 | B25 | Compound 494 | Se | A4 | A4 | B28 | B28 |
| Compound 495 | Se | A4 | A4 | B29 | B29 | Compound 496 | Se | A4 | A4 | B30 | B30 |
| Compound 497 | Se | A4 | A4 | B38 | B38 | Compound 498 | Se | A4 | A4 | B39 | B39 |
| Compound 499 | Se | A4 | A4 | B40 | B40 | Compound 500 | Se | A4 | A4 | B41 | B41 |

-continued

| NO. | Z | X | Y | R | R | NO. | Z | X | Y | R | R |
|---|---|---|---|---|---|---|---|---|---|---|---|
| Compound 501 | Se | A4 | A4 | B43 | B43 | Compound 502 | Se | A4 | A4 | B52 | B52 |
| Compound 503 | Se | A4 | A4 | B56 | B56 | Compound 504 | Se | A4 | A4 | B67 | B67 |
| Compound 505 | Se | A4 | A4 | B68 | B68 | Compound 506 | Se | A4 | A4 | B69 | B69 |
| Compound 507 | Se | A4 | A4 | B70 | B70 | Compound 508 | Se | A4 | A4 | B71 | B71 |
| Compound 509 | Se | A4 | A4 | B72 | B72 | Compound 510 | Se | A4 | A4 | B74 | B74 |
| Compound 511 | Se | A4 | A4 | B79 | B79 | Compound 512 | Se | A4 | A4 | B80 | B80 |
| Compound 513 | Se | A4 | A4 | B82 | B82 | Compound 514 | Se | A4 | A4 | B83 | B83 |
| Compound 515 | Se | A4 | A4 | B86 | B86 | Compound 516 | Se | A4 | A4 | B88 | B88 |
| Compound 517 | O | A5 | A5 | B1 | B1 | Compound 518 | O | A5 | A5 | B6 | B6 |
| Compound 519 | O | A5 | A5 | B10 | B10 | Compound 520 | O | A5 | A5 | B16 | B16 |
| Compound 521 | O | A5 | A5 | B25 | B25 | Compound 522 | O | A5 | A5 | B28 | B28 |
| Compound 523 | O | A5 | A5 | B29 | B29 | Compound 524 | O | A5 | A5 | B30 | B30 |
| Compound 525 | O | A5 | A5 | B38 | B38 | Compound 526 | O | A5 | A5 | B39 | B39 |
| Compound 527 | O | A5 | A5 | B40 | B40 | Compound 528 | O | A5 | A5 | B41 | B41 |
| Compound 529 | O | A5 | A5 | B43 | B43 | Compound 530 | O | A5 | A5 | B52 | B52 |
| Compound 531 | O | A5 | A5 | B56 | B56 | Compound 532 | O | A5 | A5 | B67 | B67 |
| Compound 533 | O | A5 | A5 | B68 | B68 | Compound 534 | O | A5 | A5 | B69 | B69 |
| Compound 535 | O | A5 | A5 | B70 | B70 | Compound 536 | O | A5 | A5 | B71 | B71 |
| Compound 537 | O | A5 | A5 | B72 | B72 | Compound 538 | O | A5 | A5 | B74 | B74 |
| Compound 539 | O | A5 | A5 | B79 | B79 | Compound 540 | O | A5 | A5 | B80 | B80 |
| Compound 541 | O | A5 | A5 | B82 | B82 | Compound 542 | O | A5 | A5 | B83 | B83 |
| Compound 543 | O | A5 | A5 | B86 | B86 | Compound 544 | O | A5 | A5 | B88 | B88 |
| Compound 545 | S | A5 | A5 | B1 | B1 | Compound 546 | S | A5 | A5 | B6 | B6 |
| Compound 547 | S | A5 | A5 | B10 | B10 | Compound 548 | S | A5 | A5 | B16 | B16 |
| Compound 549 | S | A5 | A5 | B25 | B25 | Compound 550 | S | A5 | A5 | B28 | B28 |
| Compound 551 | S | A5 | A5 | B29 | B29 | Compound 552 | S | A5 | A5 | B30 | B30 |
| Compound 553 | S | A5 | A5 | B38 | B38 | Compound 554 | S | A5 | A5 | B39 | B39 |
| Compound 555 | S | A5 | A5 | B40 | B40 | Compound 556 | S | A5 | A5 | B41 | B41 |
| Compound 557 | S | A5 | A5 | B43 | B43 | Compound 558 | S | A5 | A5 | B52 | B52 |
| Compound 559 | S | A5 | A5 | B56 | B56 | Compound 560 | S | A5 | A5 | B67 | B67 |
| Compound 561 | S | A5 | A5 | B68 | B68 | Compound 562 | S | A5 | A5 | B69 | B69 |
| Compound 563 | S | A5 | A5 | B70 | B70 | Compound 564 | S | A5 | A5 | B71 | B71 |
| Compound 565 | S | A5 | A5 | B72 | B72 | Compound 566 | S | A5 | A5 | B74 | B74 |
| Compound 567 | S | A5 | A5 | B79 | B79 | Compound 568 | S | A5 | A5 | B80 | B80 |
| Compound 569 | S | A5 | A5 | B82 | B82 | Compound 570 | S | A5 | A5 | B83 | B83 |
| Compound 571 | S | A5 | A5 | B86 | B86 | Compound 572 | S | A5 | A5 | B88 | B88 |
| Compound 573 | Se | A5 | A5 | B1 | B1 | Compound 574 | Se | A5 | A5 | B6 | B6 |
| Compound 575 | Se | A5 | A5 | B10 | B10 | Compound 576 | Se | A5 | A5 | B16 | B16 |

-continued

| NO. | Z | X | Y | R | R | NO. | Z | X | Y | R | R |
|---|---|---|---|---|---|---|---|---|---|---|---|
| Compound 577 | Se | A5 | A5 | B25 | B25 | Compound 578 | Se | A5 | A5 | B28 | B28 |
| Compound 579 | Se | A5 | A5 | B29 | B29 | Compound 580 | Se | A5 | A5 | B30 | B30 |
| Compound 581 | Se | A5 | A5 | B38 | B38 | Compound 582 | Se | A5 | A5 | B39 | B39 |
| Compound 583 | Se | A5 | A5 | B40 | B40 | Compound 584 | Se | A5 | A5 | B41 | B41 |
| Compound 585 | Se | A5 | A5 | B43 | B43 | Compound 586 | Se | A5 | A5 | B52 | B52 |
| Compound 587 | Se | A5 | A5 | B56 | B56 | Compound 588 | Se | A5 | A5 | B67 | B67 |
| Compound 589 | Se | A5 | A5 | B68 | B68 | Compound 590 | Se | A5 | A5 | B69 | B69 |
| Compound 591 | Se | A5 | A5 | B70 | B70 | Compound 592 | Se | A5 | A5 | B71 | B71 |
| Compound 593 | Se | A5 | A5 | B72 | B72 | Compound 594 | Se | A5 | A5 | B74 | B74 |
| Compound 595 | Se | A5 | A5 | B79 | B79 | Compound 596 | Se | A5 | A5 | B80 | B80 |
| Compound 597 | Se | A5 | A5 | B82 | B82 | Compound 598 | Se | A5 | A5 | B83 | B83 |
| Compound 599 | Se | A5 | A5 | B86 | B86 | Compound 600 | Se | A5 | A5 | B88 | B88 |
| Compound 601 | O | A6 | A6 | B1 | B1 | Compound 602 | O | A6 | A6 | B6 | B6 |
| Compound 603 | O | A6 | A6 | B10 | B10 | Compound 604 | O | A6 | A6 | B16 | B16 |
| Compound 605 | O | A6 | A6 | B25 | B25 | Compound 606 | O | A6 | A6 | B28 | B28 |
| Compound 607 | O | A6 | A6 | B29 | B29 | Compound 608 | O | A6 | A6 | B30 | B30 |
| Compound 609 | O | A6 | A6 | B38 | B38 | Compound 610 | O | A6 | A6 | B39 | B39 |
| Compound 611 | O | A6 | A6 | B40 | B40 | Compound 612 | O | A6 | A6 | B41 | B41 |
| Compound 613 | O | A6 | A6 | B43 | B43 | Compound 614 | O | A6 | A6 | B52 | B52 |
| Compound 615 | O | A6 | A6 | B56 | B56 | Compound 616 | O | A6 | A6 | B67 | B67 |
| Compound 617 | O | A6 | A6 | B68 | B68 | Compound 618 | O | A6 | A6 | B69 | B69 |
| Compound 619 | O | A6 | A6 | B70 | B70 | Compound 620 | O | A6 | A6 | B71 | B71 |
| Compound 621 | O | A6 | A6 | B72 | B72 | Compound 622 | O | A6 | A6 | B74 | B74 |
| Compound 623 | O | A6 | A6 | B79 | B79 | Compound 624 | O | A6 | A6 | B80 | B80 |
| Compound 625 | O | A6 | A6 | B82 | B82 | Compound 626 | O | A6 | A6 | B83 | B83 |
| Compound 627 | O | A6 | A6 | B86 | B86 | Compound 628 | O | A6 | A6 | B88 | B88 |
| Compound 629 | S | A6 | A6 | B1 | B1 | Compound 630 | S | A6 | A6 | B6 | B6 |
| Compound 631 | S | A6 | A6 | B10 | B10 | Compound 632 | S | A6 | A6 | B16 | B16 |
| Compound 633 | S | A6 | A6 | B25 | B25 | Compound 634 | S | A6 | A6 | B28 | B28 |
| Compound 635 | S | A6 | A6 | B29 | B29 | Compound 636 | S | A6 | A6 | B30 | B30 |
| Compound 637 | S | A6 | A6 | B38 | B38 | Compound 638 | S | A6 | A6 | B39 | B39 |
| Compound 639 | S | A6 | A6 | B40 | B40 | Compound 640 | S | A6 | A6 | B41 | B41 |
| Compound 641 | S | A6 | A6 | B43 | B43 | Compound 642 | S | A6 | A6 | B52 | B52 |
| Compound 643 | S | A6 | A6 | B56 | B56 | Compound 644 | S | A6 | A6 | B67 | B67 |
| Compound 645 | S | A6 | A6 | B68 | B68 | Compound 646 | S | A6 | A6 | B69 | B69 |
| Compound 647 | S | A6 | A6 | B70 | B70 | Compound 648 | S | A6 | A6 | B71 | B71 |
| Compound 649 | S | A6 | A6 | B72 | B72 | Compound 650 | S | A6 | A6 | B74 | B74 |
| Compound 651 | S | A6 | A6 | B79 | B79 | Compound 652 | S | A6 | A6 | B80 | B80 |

| NO. | Z | X | Y | R | R | NO. | Z | X | Y | R | R |
|---|---|---|---|---|---|---|---|---|---|---|---|
| Compound 653 | S | A6 | A6 | B82 | B82 | Compound 654 | S | A6 | A6 | B83 | B83 |
| Compound 655 | S | A6 | A6 | B86 | B86 | Compound 656 | S | A6 | A6 | B88 | B88 |
| Compound 657 | Se | A6 | A6 | B1 | B1 | Compound 658 | Se | A6 | A6 | B6 | B6 |
| Compound 659 | Se | A6 | A6 | B10 | B10 | Compound 660 | Se | A6 | A6 | B16 | B16 |
| Compound 661 | Se | A6 | A6 | B25 | B25 | Compound 662 | Se | A6 | A6 | B28 | B28 |
| Compound 663 | Se | A6 | A6 | B29 | B29 | Compound 664 | Se | A6 | A6 | B30 | B30 |
| Compound 665 | Se | A6 | A6 | B38 | B38 | Compound 666 | Se | A6 | A6 | B39 | B39 |
| Compound 667 | Se | A6 | A6 | B40 | B40 | Compound 668 | Se | A6 | A6 | B41 | B41 |
| Compound 669 | Se | A6 | A6 | B43 | B43 | Compound 670 | Se | A6 | A6 | B52 | B52 |
| Compound 671 | Se | A6 | A6 | B56 | B56 | Compound 672 | Se | A6 | A6 | B67 | B67 |
| Compound 673 | Se | A6 | A6 | B68 | B68 | Compound 674 | Se | A6 | A6 | B69 | B69 |
| Compound 675 | Se | A6 | A6 | B70 | B70 | Compound 676 | Se | A6 | A6 | B71 | B71 |
| Compound 677 | Se | A6 | A6 | B72 | B72 | Compound 678 | Se | A6 | A6 | B74 | B74 |
| Compound 679 | Se | A6 | A6 | B79 | B79 | Compound 680 | Se | A6 | A6 | B80 | B80 |
| Compound 681 | Se | A6 | A6 | B82 | B82 | Compound 682 | Se | A6 | A6 | B83 | B83 |
| Compound 683 | Se | A6 | A6 | B86 | B86 | Compound 684 | Se | A6 | A6 | B88 | B88 |
| Compound 685 | O | A7 | A7 | B1 | B1 | Compound 686 | O | A7 | A7 | B6 | B6 |
| Compound 687 | O | A7 | A7 | B10 | B10 | Compound 688 | O | A7 | A7 | B16 | B16 |
| Compound 689 | O | A7 | A7 | B25 | B25 | Compound 690 | O | A7 | A7 | B28 | B28 |
| Compound 691 | O | A7 | A7 | B29 | B29 | Compound 692 | O | A7 | A7 | B30 | B30 |
| Compound 693 | O | A7 | A7 | B38 | B38 | Compound 694 | O | A7 | A7 | B39 | B39 |
| Compound 695 | O | A7 | A7 | B40 | B40 | Compound 696 | O | A7 | A7 | B41 | B41 |
| Compound 697 | O | A7 | A7 | B43 | B43 | Compound 698 | O | A7 | A7 | B52 | B52 |
| Compound 699 | O | A7 | A7 | B56 | B56 | Compound 700 | O | A7 | A7 | B67 | B67 |
| Compound 701 | O | A7 | A7 | B68 | B68 | Compound 702 | O | A7 | A7 | B69 | B69 |
| Compound 703 | O | A7 | A7 | B70 | B70 | Compound 704 | O | A7 | A7 | B71 | B71 |
| Compound 705 | O | A7 | A7 | B72 | B72 | Compound 706 | O | A7 | A7 | B74 | B74 |
| Compound 707 | O | A7 | A7 | B79 | B79 | Compound 708 | O | A7 | A7 | B80 | B80 |
| Compound 709 | O | A7 | A7 | B82 | B82 | Compound 710 | O | A7 | A7 | B83 | B83 |
| Compound 711 | O | A7 | A7 | B86 | B86 | Compound 712 | O | A7 | A7 | B88 | B88 |
| Compound 713 | S | A7 | A7 | B1 | B1 | Compound 714 | S | A7 | A7 | B6 | B6 |
| Compound 715 | S | A7 | A7 | B10 | B10 | Compound 716 | S | A7 | A7 | B16 | B16 |
| Compound 717 | S | A7 | A7 | B25 | B25 | Compound 718 | S | A7 | A7 | B28 | B28 |
| Compound 719 | S | A7 | A7 | B29 | B29 | Compound 720 | S | A7 | A7 | B30 | B30 |
| Compound 721 | S | A7 | A7 | B38 | B38 | Compound 722 | S | A7 | A7 | B39 | B39 |
| Compound 723 | S | A7 | A7 | B40 | B40 | Compound 724 | S | A7 | A7 | B41 | B41 |
| Compound 725 | S | A7 | A7 | B43 | B43 | Compound 726 | S | A7 | A7 | B52 | B52 |
| Compound 727 | S | A7 | A7 | B56 | B56 | Compound 728 | S | A7 | A7 | B67 | B67 |

-continued

| NO. | Z | X | Y | R | R | NO. | Z | X | Y | R | R |
|---|---|---|---|---|---|---|---|---|---|---|---|
| Compound 729 | S | A7 | A7 | B68 | B68 | Compound 730 | S | A7 | A7 | B69 | B69 |
| Compound 731 | S | A7 | A7 | B70 | B70 | Compound 732 | S | A7 | A7 | B71 | B71 |
| Compound 733 | S | A7 | A7 | B72 | B72 | Compound 734 | S | A7 | A7 | B74 | B74 |
| Compound 735 | S | A7 | A7 | B79 | B79 | Compound 736 | S | A7 | A7 | B80 | B80 |
| Compound 737 | S | A7 | A7 | B82 | B82 | Compound 738 | S | A7 | A7 | B83 | B83 |
| Compound 739 | S | A7 | A7 | B86 | B86 | Compound 740 | S | A7 | A7 | B88 | B88 |
| Compound 741 | Se | A7 | A7 | B1 | B1 | Compound 742 | Se | A7 | A7 | B6 | B6 |
| Compound 743 | Se | A7 | A7 | B10 | B10 | Compound 744 | Se | A7 | A7 | B16 | B16 |
| Compound 745 | Se | A7 | A7 | B25 | B25 | Compound 746 | Se | A7 | A7 | B28 | B28 |
| Compound 747 | Se | A7 | A7 | B29 | B29 | Compound 748 | Se | A7 | A7 | B30 | B30 |
| Compound 749 | Se | A7 | A7 | B38 | B38 | Compound 750 | Se | A7 | A7 | B39 | B39 |
| Compound 751 | Se | A7 | A7 | B40 | B40 | Compound 752 | Se | A7 | A7 | B41 | B41 |
| Compound 753 | Se | A7 | A7 | B43 | B43 | Compound 754 | Se | A7 | A7 | B52 | B52 |
| Compound 755 | Se | A7 | A7 | B56 | B56 | Compound 756 | Se | A7 | A7 | B67 | B67 |
| Compound 757 | Se | A7 | A7 | B68 | B68 | Compound 758 | Se | A7 | A7 | B69 | B69 |
| Compound 759 | Se | A7 | A7 | B70 | B70 | Compound 760 | Se | A7 | A7 | B71 | B71 |
| Compound 761 | Se | A7 | A7 | B72 | B72 | Compound 762 | Se | A7 | A7 | B74 | B74 |
| Compound 763 | Se | A7 | A7 | B79 | B79 | Compound 764 | Se | A7 | A7 | B80 | B80 |
| Compound 765 | Se | A7 | A7 | B82 | B82 | Compound 766 | Se | A7 | A7 | B83 | B83 |
| Compound 767 | Se | A7 | A7 | B86 | B86 | Compound 768 | Se | A7 | A7 | B88 | B88 |
| Compound 769 | O | O | O | B1 | B1 | Compound 770 | O | O | O | B6 | B6 |
| Compound 771 | O | O | O | B10 | B10 | Compound 772 | O | O | O | B22 | B22 |
| Compound 773 | O | O | O | B25 | B25 | Compound 774 | O | O | O | B28 | B28 |
| Compound 775 | O | O | O | B29 | B29 | Compound 776 | O | O | O | B30 | B30 |
| Compound 777 | O | O | O | B38 | B38 | Compound 778 | O | O | O | B39 | B39 |
| Compound 779 | O | O | O | B40 | B40 | Compound 780 | O | O | O | B41 | B41 |
| Compound 781 | O | O | O | B43 | B43 | Compound 782 | O | O | O | B52 | B52 |
| Compound 783 | O | O | O | B56 | B56 | Compound 784 | O | O | O | B67 | B67 |
| Compound 785 | O | O | O | B68 | B68 | Compound 786 | O | O | O | B69 | B69 |
| Compound 787 | O | O | O | B70 | B70 | Compound 788 | O | O | O | B71 | B71 |
| Compound 789 | O | O | O | B72 | B72 | Compound 790 | O | O | O | B74 | B74 |
| Compound 791 | O | O | O | B79 | B79 | Compound 792 | O | O | O | B80 | B80 |
| Compound 793 | O | O | O | B82 | B82 | Compound 794 | O | O | O | B83 | B83 |
| Compound 795 | O | O | O | B86 | B86 | Compound 796 | O | O | O | B88 | B88 |
| Compound 797 | S | O | O | B1 | B1 | Compound 798 | S | O | O | B6 | B6 |
| Compound 799 | S | O | O | B10 | B10 | Compound 800 | S | O | O | B22 | B22 |
| Compound 801 | S | O | O | B25 | B25 | Compound 802 | S | O | O | B28 | B28 |
| Compound 803 | S | O | O | B29 | B29 | Compound 804 | S | O | O | B30 | B30 |

| NO. | Z | X | Y | R | R | NO. | Z | X | Y | R | R |
|---|---|---|---|---|---|---|---|---|---|---|---|
| Compound 805 | S | O | O | B38 | B38 | Compound 806 | S | O | O | B39 | B39 |
| Compound 807 | S | O | O | B40 | B40 | Compound 808 | S | O | O | B41 | B41 |
| Compound 809 | S | O | O | B43 | B43 | Compound 810 | S | O | O | B52 | B52 |
| Compound 811 | S | O | O | B56 | B56 | Compound 812 | S | O | O | B67 | B67 |
| Compound 813 | S | O | O | B68 | B68 | Compound 814 | S | O | O | B69 | B69 |
| Compound 815 | S | O | O | B70 | B70 | Compound 816 | S | O | O | B71 | B71 |
| Compound 817 | S | O | O | B72 | B72 | Compound 818 | S | O | O | B74 | B74 |
| Compound 819 | S | O | O | B79 | B79 | Compound 820 | S | O | O | B80 | B80 |
| Compound 821 | S | O | O | B82 | B82 | Compound 822 | S | O | O | B83 | B83 |
| Compound 823 | S | O | O | B86 | B86 | Compound 824 | S | O | O | B88 | B88 |
| Compound 825 | Se | O | O | B1 | B1 | Compound 826 | Se | O | O | B6 | B6 |
| Compound 827 | Se | O | O | B10 | B10 | Compound 828 | Se | O | O | B22 | B22 |
| Compound 829 | Se | O | O | B25 | B25 | Compound 830 | Se | O | O | B28 | B28 |
| Compound 831 | Se | O | O | B29 | B29 | Compound 832 | Se | O | O | B30 | B30 |
| Compound 833 | Se | O | O | B38 | B38 | Compound 834 | Se | O | O | B39 | B39 |
| Compound 835 | Se | O | O | B40 | B40 | Compound 836 | Se | O | O | B41 | B41 |
| Compound 837 | Se | O | O | B43 | B43 | Compound 838 | Se | O | O | B52 | B52 |
| Compound 839 | Se | O | O | B56 | B56 | Compound 840 | Se | O | O | B67 | B67 |
| Compound 841 | Se | O | O | B68 | B68 | Compound 842 | Se | O | O | B69 | B69 |
| Compound 843 | Se | O | O | B70 | B70 | Compound 844 | Se | O | O | B71 | B71 |
| Compound 845 | Se | O | O | B72 | B72 | Compound 846 | Se | O | O | B74 | B74 |
| Compound 847 | Se | O | O | B79 | B79 | Compound 848 | Se | O | O | B80 | B80 |
| Compound 849 | Se | O | O | B82 | B82 | Compound 850 | Se | O | O | B83 | B83 |
| Compound 851 | Se | O | O | B86 | B86 | Compound 852 | Se | O | O | B88 | B88 |
| Compound 853 | O | S | S | B1 | B1 | Compound 854 | O | O | O | B6 | B6 |
| Compound 855 | O | S | S | B10 | B10 | Compound 856 | O | S | S | B22 | B22 |
| Compound 857 | O | S | S | B25 | B25 | Compound 858 | O | S | S | B28 | B28 |
| Compound 859 | O | S | S | B29 | B29 | Compound 860 | O | S | S | B30 | B30 |
| Compound 861 | O | S | S | B38 | B38 | Compound 862 | O | S | S | B39 | B39 |
| Compound 863 | O | S | S | B40 | B40 | Compound 864 | O | S | S | B41 | B41 |
| Compound 865 | O | S | S | B43 | B43 | Compound 866 | O | S | S | B52 | B52 |
| Compound 867 | O | S | S | B56 | B56 | Compound 868 | O | S | S | B67 | B67 |
| Compound 869 | O | S | S | B68 | B68 | Compound 870 | O | S | S | B69 | B69 |
| Compound 871 | O | S | S | B70 | B70 | Compound 872 | O | S | S | B71 | B71 |
| Compound 873 | O | S | S | B72 | B72 | Compound 874 | O | S | S | B74 | B74 |
| Compound 875 | O | S | S | B79 | B79 | Compound 876 | O | S | S | B80 | B80 |
| Compound 877 | O | S | S | B82 | B82 | Compound 878 | O | S | S | B83 | B83 |
| Compound 879 | O | S | S | B86 | B86 | Compound 880 | O | S | S | B88 | B88 |

-continued

| NO. | Z | X | Y | R | R | NO. | Z | X | Y | R | R |
|---|---|---|---|---|---|---|---|---|---|---|---|
| Compound 881 | S | S | S | B1 | B1 | Compound 882 | S | S | S | B6 | B6 |
| Compound 883 | S | S | S | B10 | B10 | Compound 884 | S | S | S | B22 | B22 |
| Compound 885 | S | S | S | B25 | B25 | Compound 886 | S | S | S | B28 | B28 |
| Compound 887 | S | S | S | B29 | B29 | Compound 888 | S | S | S | B30 | B30 |
| Compound 889 | S | S | S | B38 | B38 | Compound 890 | S | S | S | B39 | B39 |
| Compound 891 | S | S | S | B40 | B40 | Compound 892 | S | S | S | B41 | B41 |
| Compound 893 | S | S | S | B43 | B43 | Compound 894 | S | S | S | B52 | B52 |
| Compound 895 | S | S | S | B56 | B56 | Compound 896 | S | S | S | B67 | B67 |
| Compound 897 | S | S | S | B68 | B68 | Compound 898 | S | S | S | B69 | B69 |
| Compound 899 | S | S | S | B70 | B70 | Compound 900 | S | S | S | B71 | B71 |
| Compound 901 | S | S | S | B72 | B72 | Compound 902 | S | S | S | B74 | B74 |
| Compound 903 | S | S | S | B79 | B79 | Compound 904 | S | S | S | B80 | B80 |
| Compound 905 | S | S | S | B82 | B82 | Compound 906 | S | S | S | B83 | B83 |
| Compound 907 | S | S | S | B86 | B86 | Compound 908 | S | S | S | B88 | B88 |
| Compound 909 | Se | S | S | B1 | B1 | Compound 910 | Se | S | S | B6 | B6 |
| Compound 911 | Se | S | S | B10 | B10 | Compound 912 | Se | S | S | B22 | B22 |
| Compound 913 | Se | S | S | B25 | B25 | Compound 914 | Se | S | S | B28 | B28 |
| Compound 915 | Se | S | S | B29 | B29 | Compound 916 | Se | S | S | B30 | B30 |
| Compound 917 | Se | S | S | B38 | B38 | Compound 918 | Se | S | S | B39 | B39 |
| Compound 919 | Se | S | S | B40 | B40 | Compound 920 | Se | S | S | B41 | B41 |
| Compound 921 | Se | S | S | B43 | B43 | Compound 922 | Se | S | S | B52 | B52 |
| Compound 923 | Se | S | S | B56 | B56 | Compound 924 | Se | S | S | B67 | B67 |
| Compound 925 | Se | S | S | B68 | B68 | Compound 926 | Se | S | S | B69 | B69 |
| Compound 927 | Se | S | S | B70 | B70 | Compound 928 | Se | S | S | B71 | B71 |
| Compound 929 | Se | S | S | B72 | B72 | Compound 930 | Se | S | S | B74 | B74 |
| Compound 931 | Se | S | S | B79 | B79 | Compound 932 | Se | S | S | B80 | B80 |
| Compound 933 | Se | S | S | B82 | B82 | Compound 934 | Se | S | S | B83 | B83 |
| Compound 935 | Se | S | S | B86 | B86 | Compound 936 | Se | S | S | B88 | B88 |
| Compound 937 | O | Se | Se | B1 | B1 | Compound 938 | O | Se | Se | B6 | B6 |
| Compound 939 | O | Se | Se | B10 | B10 | Compound 940 | O | Se | Se | B22 | B22 |
| Compound 941 | O | Se | Se | B25 | B25 | Compound 942 | O | Se | Se | B28 | B28 |
| Compound 943 | O | Se | Se | B29 | B29 | Compound 944 | O | Se | Se | B30 | B30 |
| Compound 945 | O | Se | Se | B38 | B38 | Compound 946 | O | Se | Se | B39 | B39 |
| Compound 947 | O | Se | Se | B40 | B40 | Compound 948 | O | Se | Se | B41 | B41 |
| Compound 949 | O | Se | Se | B43 | B43 | Compound 950 | O | Se | Se | B52 | B52 |
| Compound 951 | O | Se | Se | B56 | B56 | Compound 952 | O | Se | Se | B67 | B67 |
| Compound 953 | O | Se | Se | B68 | B68 | Compound 954 | O | Se | Se | B69 | B69 |
| Compound 955 | O | Se | Se | B70 | B70 | Compound 956 | O | Se | Se | B71 | B71 |

-continued

| NO. | Z | X | Y | R | R | NO. | Z | X | Y | R | R |
|---|---|---|---|---|---|---|---|---|---|---|---|
| Compound 957 | O | Se | Se | B72 | B72 | Compound 958 | O | Se | Se | B74 | B74 |
| Compound 959 | O | Se | Se | B79 | B79 | Compound 960 | O | Se | Se | B80 | B80 |
| Compound 961 | O | Se | Se | B82 | B82 | Compound 962 | O | Se | Se | B83 | B83 |
| Compound 963 | O | Se | Se | B86 | B86 | Compound 964 | O | Se | Se | B88 | B88 |
| Compound 965 | S | Se | Se | B1 | B1 | Compound 966 | S | Se | Se | B6 | B6 |
| Compound 967 | S | Se | Se | B10 | B10 | Compound 968 | S | Se | Se | B22 | B22 |
| Compound 969 | S | Se | Se | B25 | B25 | Compound 970 | S | Se | Se | B28 | B28 |
| Compound 971 | S | Se | Se | B29 | B29 | Compound 972 | S | Se | Se | B30 | B30 |
| Compound 973 | S | Se | Se | B38 | B38 | Compound 974 | S | Se | Se | B39 | B39 |
| Compound 975 | S | Se | Se | B40 | B40 | Compound 976 | S | Se | Se | B41 | B41 |
| Compound 977 | S | Se | Se | B43 | B43 | Compound 978 | S | Se | Se | B52 | B52 |
| Compound 979 | S | Se | Se | B56 | B56 | Compound 980 | S | Se | Se | B67 | B67 |
| Compound 981 | S | Se | Se | B68 | B68 | Compound 982 | S | Se | Se | B69 | B69 |
| Compound 983 | S | Se | Se | B70 | B70 | Compound 984 | S | Se | Se | B71 | B71 |
| Compound 985 | S | Se | Se | B72 | B72 | Compound 986 | S | Se | Se | B74 | B74 |
| Compound 987 | S | Se | Se | B79 | B79 | Compound 988 | S | Se | Se | B80 | B80 |
| Compound 989 | S | Se | Se | B82 | B82 | Compound 990 | S | Se | Se | B83 | B83 |
| Compound 991 | S | Se | Se | B86 | B86 | Compound 992 | S | Se | Se | B88 | B88 |
| Compound 993 | Se | Se | Se | B1 | B1 | Compound 994 | Se | Se | Se | B6 | B6 |
| Compound 995 | Se | Se | Se | B10 | B10 | Compound 996 | Se | Se | Se | B22 | B22 |
| Compound 997 | Se | Se | Se | B25 | B25 | Compound 998 | Se | Se | Se | B28 | B28 |
| Compound 999 | Se | Se | Se | B29 | B29 | Compound 1000 | Se | Se | Se | B30 | B30 |
| Compound 1001 | Se | Se | Se | B38 | B38 | Compound 1002 | Se | Se | Se | B39 | B39 |
| Compound 1003 | Se | Se | Se | B40 | B40 | Compound 1004 | Se | Se | Se | B41 | B41 |
| Compound 1005 | Se | Se | Se | B43 | B43 | Compound 1006 | Se | Se | Se | B52 | B52 |
| Compound 1007 | Se | Se | Se | B56 | B56 | Compound 1008 | Se | Se | Se | B67 | B67 |
| Compound 1009 | Se | Se | Se | B68 | B68 | Compound 1010 | Se | Se | Se | B69 | B69 |
| Compound 1011 | Se | Se | Se | B70 | B70 | Compound 1012 | Se | Se | Se | B71 | B71 |
| Compound 1013 | Se | Se | Se | B72 | B72 | Compound 1014 | Se | Se | Se | B74 | B74 |
| Compound 1015 | Se | Se | Se | B79 | B79 | Compound 1016 | Se | Se | Se | B80 | B80 |
| Compound 1017 | Se | Se | Se | B82 | B82 | Compound 1018 | Se | Se | Se | B83 | B83 |
| Compound 1019 | Se | Se | Se | B86 | B86 | Compound 1020 | Se | Se | Se | B88 | B88 |
| Compound 1021 | O | A1 | A1 | B1 | B6 | Compound 1022 | O | A1 | A1 | B2 | B6 |
| Compound 1023 | O | A1 | A1 | B25 | B26 | Compound 1024 | O | A1 | A1 | B27 | B28 |
| Compound 1025 | O | A1 | A1 | B29 | B30 | Compound 1026 | O | A1 | A1 | B39 | B40 |
| Compound 1027 | O | A1 | A1 | B54 | B41 | Compound 1028 | O | A1 | A1 | B54 | B52 |
| Compound 1029 | O | A1 | A1 | B52 | B56 | Compound 1030 | O | A1 | A1 | B55 | B56 |
| Compound 1031 | O | A1 | A1 | B64 | B56 | Compound 1032 | O | A1 | A1 | B68 | B69 |

-continued

| NO. | Z | X | Y | R | R | NO. | Z | X | Y | R | R |
|---|---|---|---|---|---|---|---|---|---|---|---|
| Compound 1033 | O | A1 | A1 | B69 | B70 | Compound 1034 | O | A1 | A1 | B71 | B72 |
| Compound 1035 | O | A1 | A1 | B68 | B80 | Compound 1036 | O | A1 | A1 | B68 | B83 |
| Compound 1037 | S | A1 | A1 | B1 | B6 | Compound 1038 | S | A1 | A1 | B2 | B6 |
| Compound 1039 | S | A1 | A1 | B25 | B26 | Compound 1040 | S | A1 | A1 | B27 | B28 |
| Compound 1041 | S | A1 | A1 | B29 | B30 | Compound 1042 | S | A1 | A1 | B39 | B40 |
| Compound 1043 | S | A1 | A1 | B54 | B41 | Compound 1044 | S | A1 | A1 | B54 | B52 |
| Compound 1045 | S | A1 | A1 | B52 | B56 | Compound 1046 | S | A1 | A1 | B55 | B56 |
| Compound 1047 | S | A1 | A1 | B64 | B56 | Compound 1048 | S | A1 | A1 | B68 | B69 |
| Compound 1049 | S | A1 | A1 | B69 | B70 | Compound 1050 | S | A1 | A1 | B71 | B72 |
| Compound 1051 | S | A1 | A1 | B68 | B80 | Compound 1052 | S | A1 | A1 | B68 | B83 |
| Compound 1053 | Se | A1 | A1 | B1 | B6 | Compound 1054 | Se | A1 | A1 | B2 | B6 |
| Compound 1055 | Se | A1 | A1 | B25 | B26 | Compound 1056 | Se | A1 | A1 | B27 | B28 |
| Compound 1057 | Se | A1 | A1 | B29 | B30 | Compound 1058 | Se | A1 | A1 | B39 | B40 |
| Compound 1059 | Se | A1 | A1 | B54 | B41 | Compound 1060 | Se | A1 | A1 | B54 | B52 |
| Compound 1061 | Se | A1 | A1 | B52 | B56 | Compound 1062 | Se | A1 | A1 | B55 | B56 |
| Compound 1063 | Se | A1 | A1 | B64 | B56 | Compound 1064 | Se | A1 | A1 | B68 | B69 |
| Compound 1065 | Se | A1 | A1 | B69 | B70 | Compound 1066 | Se | A1 | A1 | B71 | B72 |
| Compound 1067 | Se | A1 | A1 | B68 | B80 | Compound 1068 | Se | A1 | A1 | B68 | B83 |
| Compound 1069 | O | A2 | A2 | B1 | B6 | Compound 1070 | O | A2 | A2 | B2 | B6 |
| Compound 1071 | O | A2 | A2 | B25 | B26 | Compound 1072 | O | A2 | A2 | B27 | B28 |
| Compound 1073 | O | A2 | A2 | B29 | B30 | Compound 1074 | O | A2 | A2 | B39 | B40 |
| Compound 1075 | O | A2 | A2 | B54 | B41 | Compound 1076 | O | A2 | A2 | B54 | B52 |
| Compound 1077 | O | A2 | A2 | B52 | B56 | Compound 1078 | O | A2 | A2 | B55 | B56 |
| Compound 1079 | O | A2 | A2 | B64 | B56 | Compound 1080 | O | A2 | A2 | B68 | B69 |
| Compound 1081 | O | A2 | A2 | B69 | B70 | Compound 1082 | O | A2 | A2 | B71 | B72 |
| Compound 1083 | O | A2 | A2 | B68 | B80 | Compound 1084 | O | A2 | A2 | B68 | B83 |
| Compound 1085 | S | A2 | A2 | B1 | B6 | Compound 1086 | S | A2 | A2 | B2 | B6 |
| Compound 1087 | S | A2 | A2 | B25 | B26 | Compound 1088 | S | A2 | A2 | B27 | B28 |
| Compound 1089 | S | A2 | A2 | B29 | B30 | Compound 1090 | S | A2 | A2 | B39 | B40 |
| Compound 1091 | S | A2 | A2 | B54 | B41 | Compound 1092 | S | A2 | A2 | B54 | B52 |
| Compound 1093 | S | A2 | A2 | B52 | B56 | Compound 1094 | S | A2 | A2 | B55 | B56 |
| Compound 1095 | S | A2 | A2 | B64 | B56 | Compound 1096 | S | A2 | A2 | B68 | B69 |
| Compound 1097 | S | A2 | A2 | B69 | B70 | Compound 1098 | S | A2 | A2 | B71 | B72 |
| Compound 1099 | S | A2 | A2 | B68 | B80 | Compound 1100 | S | A2 | A2 | B68 | B83 |
| Compound 1101 | Se | A2 | A2 | B1 | B6 | Compound 1102 | Se | A2 | A2 | B2 | B6 |
| Compound 1103 | Se | A2 | A2 | B25 | B26 | Compound 1104 | Se | A2 | A2 | B27 | B28 |
| Compound 1105 | Se | A2 | A2 | B29 | B30 | Compound 1106 | Se | A2 | A2 | B39 | B40 |
| Compound 1107 | Se | A2 | A2 | B54 | B41 | Compound 1108 | Se | A2 | A2 | B54 | B52 |

| NO. | Z | X | Y | R | R | NO. | Z | X | Y | R | R |
|---|---|---|---|---|---|---|---|---|---|---|---|
| Compound 1109 | Se | A2 | A2 | B52 | B56 | Compound 1110 | Se | A2 | A2 | B55 | B56 |
| Compound 1111 | Se | A2 | A2 | B64 | B56 | Compound 1112 | Se | A2 | A2 | B68 | B69 |
| Compound 1113 | Se | A2 | A2 | B69 | B70 | Compound 1114 | Se | A2 | A2 | B71 | B72 |
| Compound 1115 | Se | A2 | A2 | B68 | B80 | Compound 1116 | Se | A2 | A2 | B68 | B83 |
| Compound 1117 | O | A3 | A3 | B1 | B1 | Compound 1118 | O | A3 | A3 | B6 | B6 |
| Compound 1119 | O | A3 | A3 | B25 | B25 | Compound 1120 | O | A3 | A3 | B28 | B28 |
| Compound 1121 | O | A3 | A3 | B29 | B29 | Compound 1122 | O | A3 | A3 | B30 | B30 |
| Compound 1123 | O | A3 | A3 | B56 | B56 | Compound 1124 | O | A3 | A3 | B67 | B67 |
| Compound 1125 | O | A3 | A3 | B68 | B68 | Compound 1126 | O | A3 | A3 | B69 | B69 |
| Compound 1127 | O | A3 | A3 | B70 | B70 | Compound 1128 | O | A3 | A3 | B71 | B71 |
| Compound 1129 | O | A3 | A3 | B72 | B72 | Compound 1130 | O | A3 | A3 | B74 | B74 |
| Compound 1131 | O | A3 | A3 | B80 | B80 | Compound 1132 | O | A3 | A3 | B83 | B83 |
| Compound 1133 | S | A3 | A3 | B1 | B1 | Compound 1134 | S | A3 | A3 | B6 | B6 |
| Compound 1135 | S | A3 | A3 | B25 | B25 | Compound 1136 | S | A3 | A3 | B28 | B28 |
| Compound 1137 | S | A3 | A3 | B29 | B29 | Compound 1138 | S | A3 | A3 | B30 | B30 |
| Compound 1139 | S | A3 | A3 | B56 | B56 | Compound 1140 | S | A3 | A3 | B67 | B67 |
| Compound 1141 | S | A3 | A3 | B68 | B68 | Compound 1142 | S | A3 | A3 | B69 | B69 |
| Compound 1143 | S | A3 | A3 | B70 | B70 | Compound 1144 | S | A3 | A3 | B71 | B71 |
| Compound 1145 | S | A3 | A3 | B72 | B72 | Compound 1146 | S | A3 | A3 | B74 | B74 |
| Compound 1147 | S | A3 | A3 | B80 | B80 | Compound 1148 | S | A3 | A3 | B83 | B83 |
| Compound 1149 | Se | A3 | A3 | B1 | B1 | Compound 1150 | Se | A3 | A3 | B6 | B6 |
| Compound 1151 | Se | A3 | A3 | B25 | B25 | Compound 1152 | Se | A3 | A3 | B28 | B28 |
| Compound 1153 | Se | A3 | A3 | B29 | B29 | Compound 1154 | Se | A3 | A3 | B30 | B30 |
| Compound 1155 | Se | A3 | A3 | B56 | B56 | Compound 1156 | Se | A3 | A3 | B67 | B67 |
| Compound 1157 | Se | A3 | A3 | B68 | B68 | Compound 1158 | Se | A3 | A3 | B69 | B69 |
| Compound 1159 | Se | A3 | A3 | B70 | B70 | Compound 1160 | Se | A3 | A3 | B71 | B71 |
| Compound 1161 | Se | A3 | A3 | B72 | B72 | Compound 1162 | Se | A3 | A3 | B74 | B74 |
| Compound 1163 | Se | A3 | A3 | B80 | B80 | Compound 1164 | Se | A3 | A3 | B83 | B83 |
| Compound 1165 | O | O | A1 | B1 | B1 | Compound 1166 | O | O | A1 | B6 | B6 |
| Compound 1167 | O | O | A1 | B25 | B25 | Compound 1168 | O | O | A1 | B28 | B28 |
| Compound 1169 | O | O | A1 | B29 | B29 | Compound 1170 | O | O | A1 | B30 | B30 |
| Compound 1171 | O | O | A1 | B56 | B56 | Compound 1172 | O | O | A1 | B67 | B67 |
| Compound 1173 | O | O | A1 | B68 | B68 | Compound 1174 | O | O | A1 | B69 | B69 |
| Compound 1175 | O | O | A1 | B70 | B70 | Compound 1176 | O | O | A1 | B71 | B71 |
| Compound 1177 | O | O | A1 | B72 | B72 | Compound 1178 | O | O | A1 | B74 | B74 |
| Compound 1179 | O | O | A1 | B80 | B80 | Compound 1180 | O | O | A1 | B83 | B83 |
| Compound 1181 | S | O | A1 | B1 | B1 | Compound 1182 | S | O | A1 | B6 | B6 |
| Compound 1183 | S | O | A1 | B25 | B25 | Compound 1184 | S | O | A1 | B28 | B28 |

-continued

| NO. | Z | X | Y | R | R | NO. | Z | X | Y | R | R |
|---|---|---|---|---|---|---|---|---|---|---|---|
| Compound 1185 | S | O | A1 | B29 | B29 | Compound 1186 | S | O | A1 | B30 | B30 |
| Compound 1187 | S | O | A1 | B56 | B56 | Compound 1188 | S | O | A1 | B67 | B67 |
| Compound 1189 | S | O | A1 | B68 | B68 | Compound 1190 | S | O | A1 | B69 | B69 |
| Compound 1191 | S | O | A1 | B70 | B70 | Compound 1192 | S | O | A1 | B71 | B71 |
| Compound 1193 | S | O | A1 | B72 | B72 | Compound 1194 | S | O | A1 | B74 | B74 |
| Compound 1195 | S | O | A1 | B80 | B80 | Compound 1196 | S | O | A1 | B83 | B83 |
| Compound 1197 | Se | O | A1 | B1 | B1 | Compound 1198 | Se | O | A1 | B6 | B6 |
| Compound 1199 | Se | O | A1 | B25 | B25 | Compound 1200 | Se | O | A1 | B28 | B28 |
| Compound 1201 | Se | O | A1 | B29 | B29 | Compound 1202 | Se | O | A1 | B30 | B30 |
| Compound 1203 | Se | O | A1 | B56 | B56 | Compound 1204 | Se | O | A1 | B67 | B67 |
| Compound 1205 | Se | O | A1 | B68 | B68 | Compound 1206 | Se | O | A1 | B69 | B69 |
| Compound 1207 | Se | O | A1 | B70 | B70 | Compound 1208 | Se | O | A1 | B71 | B71 |
| Compound 1209 | Se | O | A1 | B72 | B72 | Compound 1210 | Se | O | A1 | B74 | B74 |
| Compound 1211 | Se | O | A1 | B80 | B80 | Compound 1212 | Se | O | A1 | B83 | B83 |
| Compound 1213 | O | A1 | A2 | B1 | B1 | Compound 1214 | O | A1 | A2 | B6 | B6 |
| Compound 1215 | O | A1 | A2 | B25 | B25 | Compound 1216 | O | A1 | A2 | B28 | B28 |
| Compound 1217 | O | A1 | A2 | B29 | B29 | Compound 1218 | O | A1 | A2 | B30 | B30 |
| Compound 1219 | O | A1 | A2 | B56 | B56 | Compound 1220 | O | A1 | A2 | B67 | B67 |
| Compound 1221 | O | A1 | A2 | B68 | B68 | Compound 1222 | O | A1 | A2 | B69 | B69 |
| Compound 1223 | O | A1 | A2 | B70 | B70 | Compound 1224 | O | A1 | A2 | B71 | B71 |
| Compound 1225 | O | A1 | A2 | B72 | B72 | Compound 1226 | O | A1 | A2 | B74 | B74 |
| Compound 1227 | O | A1 | A2 | B80 | B80 | Compound 1228 | O | A1 | A2 | B83 | B83 |
| Compound 1229 | S | A1 | A2 | B1 | B1 | Compound 1230 | S | A1 | A2 | B6 | B6 |
| Compound 1231 | S | A1 | A2 | B25 | B25 | Compound 1232 | S | A1 | A2 | B28 | B28 |
| Compound 1233 | S | A1 | A2 | B29 | B29 | Compound 1234 | S | A1 | A2 | B30 | B30 |
| Compound 1235 | S | A1 | A2 | B56 | B56 | Compound 1236 | S | A1 | A2 | B67 | B67 |
| Compound 1237 | S | A1 | A2 | B68 | B68 | Compound 1238 | S | A1 | A2 | B69 | B69 |
| Compound 1239 | S | A1 | A2 | B70 | B70 | Compound 1240 | S | A1 | A2 | B71 | B71 |
| Compound 1241 | S | A1 | A2 | B72 | B72 | Compound 1242 | S | A1 | A2 | B74 | B74 |
| Compound 1243 | S | A1 | A2 | B80 | B80 | Compound 1244 | S | A1 | A2 | B83 | B83 |
| Compound 1245 | Se | A1 | A2 | B1 | B1 | Compound 1246 | Se | A1 | A2 | B6 | B6 |
| Compound 1247 | Se | A1 | A2 | B25 | B25 | Compound 1248 | Se | A1 | A2 | B28 | B28 |
| Compound 1249 | Se | A1 | A2 | B29 | B29 | Compound 1250 | Se | A1 | A2 | B30 | B30 |
| Compound 1251 | Se | A1 | A2 | B56 | B56 | Compound 1252 | Se | A1 | A2 | B67 | B67 |
| Compound 1253 | Se | A1 | A2 | B68 | B68 | Compound 1254 | Se | A1 | A2 | B69 | B69 |
| Compound 1255 | Se | A1 | A2 | B70 | B70 | Compound 1256 | Se | A1 | A2 | B71 | B71 |
| Compound 1257 | Se | A1 | A2 | B72 | B72 | Compound 1258 | Se | A1 | A2 | B74 | B74 |
| Compound 1259 | Se | A1 | A2 | B80 | B80 | Compound 1260 | Se | A1 | A2 | B83 | B83 |

-continued

| NO. | Z | X | Y | R | R | NO. | Z | X | Y | R | R |
|---|---|---|---|---|---|---|---|---|---|---|---|
| Compound 1261 | O | A1 | A3 | B1 | B1 | Compound 1262 | O | A1 | A3 | B6 | B6 |
| Compound 1263 | O | A1 | A3 | B25 | B25 | Compound 1264 | O | A1 | A3 | B28 | B28 |
| Compound 1265 | O | A1 | A3 | B29 | B29 | Compound 1266 | O | A1 | A3 | B30 | B30 |
| Compound 1267 | O | A1 | A3 | B56 | B56 | Compound 1268 | O | A1 | A3 | B67 | B67 |
| Compound 1269 | O | A1 | A3 | B68 | B68 | Compound 1270 | O | A1 | A3 | B69 | B69 |
| Compound 1271 | O | A1 | A3 | B70 | B70 | Compound 1272 | O | A1 | A3 | B71 | B71 |
| Compound 1273 | O | A1 | A3 | B72 | B72 | Compound 1274 | O | A1 | A3 | B74 | B74 |
| Compound 1275 | O | A1 | A3 | B80 | B80 | Compound 1276 | O | A1 | A3 | B83 | B83 |
| Compound 1277 | S | A1 | A3 | B1 | B1 | Compound 1278 | S | A1 | A3 | B6 | B6 |
| Compound 1279 | S | A1 | A3 | B25 | B25 | Compound 1280 | S | A1 | A3 | B28 | B28 |
| Compound 1281 | S | A1 | A3 | B29 | B29 | Compound 1282 | S | A1 | A3 | B30 | B30 |
| Compound 1283 | S | A1 | A3 | B56 | B56 | Compound 1284 | S | A1 | A3 | B67 | B67 |
| Compound 1285 | S | A1 | A3 | B68 | B68 | Compound 1286 | S | A1 | A3 | B69 | B69 |
| Compound 1287 | S | A1 | A3 | B70 | B70 | Compound 1288 | S | A1 | A3 | B71 | B71 |
| Compound 1289 | S | A1 | A3 | B72 | B72 | Compound 1290 | S | A1 | A3 | B74 | B74 |
| Compound 1291 | S | A1 | A3 | B80 | B80 | Compound 1292 | S | A1 | A3 | B83 | B83 |
| Compound 1293 | Se | A1 | A3 | B1 | B1 | Compound 1294 | Se | A1 | A3 | B6 | B6 |
| Compound 1295 | Se | A1 | A3 | B25 | B25 | Compound 1296 | Se | A1 | A3 | B28 | B28 |
| Compound 1297 | Se | A1 | A3 | B29 | B29 | Compound 1298 | Se | A1 | A3 | B30 | B30 |
| Compound 1299 | Se | A1 | A3 | B56 | B56 | Compound 1300 | Se | A1 | A3 | B67 | B67 |
| Compound 1301 | Se | A1 | A3 | B68 | B68 | Compound 1302 | Se | A1 | A3 | B69 | B69 |
| Compound 1303 | Se | A1 | A3 | B70 | B70 | Compound 1304 | Se | A1 | A3 | B71 | B71 |
| Compound 1305 | Se | A1 | A3 | B72 | B72 | Compound 1306 | Se | A1 | A3 | B74 | B74 |
| Compound 1307 | Se | A1 | A3 | B80 | B80 | Compound 1308 | Se | A1 | A3 | B83 | B83 |
| Compound 1309 | O | A2 | A6 | B1 | B1 | Compound 1310 | O | A2 | A6 | B6 | B6 |
| Compound 1311 | O | A2 | A6 | B25 | B25 | Compound 1312 | O | A2 | A6 | B28 | B28 |
| Compound 1313 | O | A2 | A6 | B29 | B29 | Compound 1314 | O | A2 | A6 | B30 | B30 |
| Compound 1315 | O | A2 | A6 | B56 | B56 | Compound 1316 | O | A2 | A6 | B67 | B67 |
| Compound 1317 | O | A2 | A6 | B68 | B68 | Compound 1318 | O | A2 | A6 | B69 | B69 |
| Compound 1319 | O | A2 | A6 | B70 | B70 | Compound 1320 | O | A2 | A6 | B71 | B71 |
| Compound 1321 | O | A2 | A6 | B72 | B72 | Compound 1322 | O | A2 | A6 | B74 | B74 |
| Compound 1323 | O | A2 | A6 | B80 | B80 | Compound 1324 | O | A2 | A6 | B83 | B83 |
| Compound 1325 | S | A2 | A6 | B1 | B1 | Compound 1326 | S | A2 | A6 | B6 | B6 |
| Compound 1327 | S | A2 | A6 | B25 | B25 | Compound 1328 | S | A2 | A6 | B28 | B28 |
| Compound 1329 | S | A2 | A6 | B29 | B29 | Compound 1330 | S | A2 | A6 | B30 | B30 |
| Compound 1331 | S | A2 | A6 | B56 | B56 | Compound 1332 | S | A2 | A6 | B67 | B67 |
| Compound 1333 | S | A2 | A6 | B68 | B68 | Compound 1334 | S | A2 | A6 | B69 | B69 |
| Compound 1335 | S | A2 | A6 | B70 | B70 | Compound 1336 | S | A2 | A6 | B71 | B71 |

-continued

| NO. | Z | X | Y | R | R | NO. | Z | X | Y | R | R |
|---|---|---|---|---|---|---|---|---|---|---|---|
| Compound 1337 | S | A2 | A6 | B72 | B72 | Compound 1338 | S | A2 | A6 | B74 | B74 |
| Compound 1339 | S | A2 | A6 | B80 | B80 | Compound 1340 | S | A2 | A6 | B83 | B83 |
| Compound 1341 | Se | A2 | A6 | B1 | B1 | Compound 1342 | Se | A2 | A6 | B6 | B6 |
| Compound 1343 | Se | A2 | A6 | B25 | B25 | Compound 1344 | Se | A2 | A6 | B28 | B28 |
| Compound 1345 | Se | A2 | A6 | B29 | B29 | Compound 1346 | Se | A2 | A6 | B30 | B30 |
| Compound 1347 | Se | A2 | A6 | B56 | B56 | Compound 1348 | Se | A2 | A6 | B67 | B67 |
| Compound 1349 | Se | A2 | A6 | B68 | B68 | Compound 1350 | Se | A2 | A6 | B69 | B69 |
| Compound 1351 | Se | A2 | A6 | B70 | B70 | Compound 1352 | Se | A2 | A6 | B71 | B71 |
| Compound 1353 | Se | A2 | A6 | B72 | B72 | Compound 1354 | Se | A2 | A6 | B74 | B74 |
| Compound 1355 | Se | A2 | A6 | B80 | B80 | Compound 1356. | Se | A2 | A6 | B83 | B83 |

12. An electroluminescent device comprising:
an anode,
a cathode, and
an organic layer disposed between the anode and the cathode, wherein the organic layer comprises a compound having Formula 1':

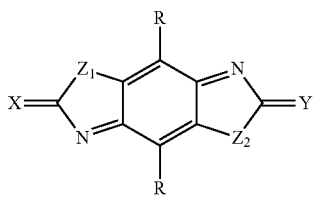

Formula 1' wherein each of X and Y is independently selected from the group consisting of CR"R'", NR', O, S and Se;
wherein each of $Z_1$ and $Z_2$ is independently selected from the group consisting of O, S and Se;
wherein each of R, R', R" and R'" is independently selected from the group consisting of hydrogen, deuterium, halogen, nitroso, nitro, acyl, carbonyl, a carboxylic acid group, an ester group, cyano, isocyano, SCN, OCN, $SF_5$, boranyl, sulfinyl, sulfonyl, phosphoroso, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 2.0 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted alkynyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, and combinations thereof;

wherein each R may be same or different, and at least one of R, R', R" and R'" is a group having at least one electron-withdrawing group; and wherein adjacent substituents can be optionally joined to form a ring or a fused structure.

13. The electroluminescent device according to claim 12, wherein the organic layer is a hole injection layer, and the hole injection layer is formed from the compound alone.

14. The electroluminescent device according to claim 12, wherein the organic layer is a hole injection layer, and the hole injection layer is formed from the compound comprising a dopant which comprises at least one hole transporting material; wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex, wherein the molar doping ratio of the compound to the hole transporting material is from 10000:1 to 1:10000; preferably, the molar doping ratio of the compound to the hole transporting material is from 10:1 to 1:100.

15. The electroluminescent device according to claim 12, wherein the electroluminescent device comprises a plurality of stacks disposed between the anode and the cathode, wherein the stacks comprise a first light-emitting layer and a second light-emitting layer, wherein the first stack comprises a first light-emitting layer, and the second stack comprises a second light-emitting layer, and a charge generation layer is disposed between the first stack and the second stack, wherein the charge generation layer comprises a p-type charge generation layer and an n-type charge generation layer;

wherein the p-type charge generation layer comprises a compound having Formula 1'; preferably, the p-type charge generation layer may further comprises at least one hole transporting material and is formed by doping the compound with at least one hole transporting material, wherein the hole transporting material comprises a compound having a triarylamine unit, a spirobifluorene compound, a pentacene compound, an oligothiophene compound, an oligophenyl compound, an oligophenylene vinyl compound, an oligofluorene compound, a porphyrin complex or a metal phthalocyanine complex, wherein the molar doping ratio of the compound to the hole transporting material is from 10000:1 to 1:10000; preferably, the molar doping ratio of the compound to the hole transporting material is from 10:1 to 1:100.

16. The electroluminescent device according to claim 15, wherein the charge generation layer further includes a buffer layer disposed between the p-type charge generation layer and the n-type charge generation layer, wherein the buffer layer comprises the compound.

17. A compound formulation comprising the compound of claim 1.

18. A compound having Formula 1:

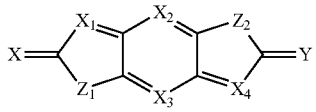

wherein $X_1$, $X_2$, $X_3$, and $X_4$ are each independently selected from the group consisting of CR, and N; when $X_1$, $X_2$, $X_3$, and $X_4$ are each independently selected from CR, each R may be same or different, and at least one of R comprises at least one electron withdrawing group;

$Z_1$ and $Z_2$ are each independently selected from the group consisting of O, S, and X and Y are each independently selected from the group consisting of S, Se, NR', and CR"R'";

R, R', R", and R'" are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphine group, and combinations thereof;

Any adjacent substitution can be optionally joined to form a ring or fused structure.

19. The compound of claim 18, wherein $X_2$ and $X_3$ are each independently selected from CR, each R may be same or different, and at least one of R comprises at least one electron withdrawing group; preferably, each R comprises at least one electron withdrawing group.

20. The compound of claim 18, wherein X and Y are each independently CR"R'".

21. The compound of claim 18, wherein the compound has the formula:

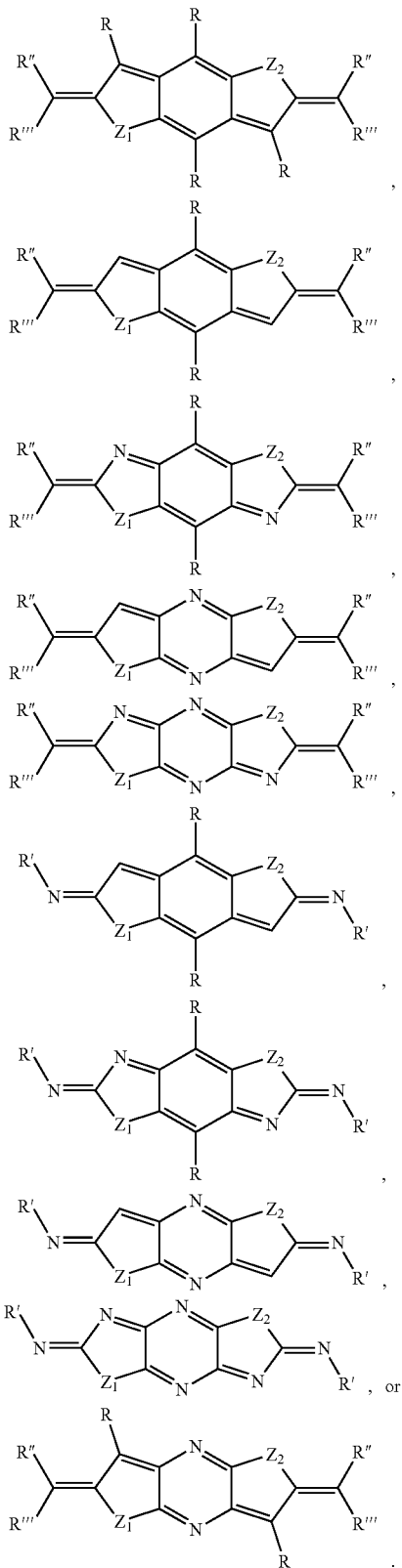

22. The compound of claim 18, wherein the compound has the formula:
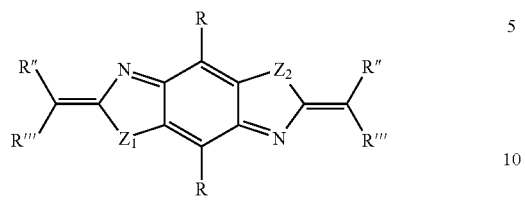

UNITED STATES PATENT AND TRADEMARK OFFICE
CERTIFICATE OF CORRECTION

PATENT NO. : 11,466,009 B2
APPLICATION NO. : 16/689007
DATED : October 11, 2022
INVENTOR(S) : Zhihao Cui et al.

Page 1 of 1

It is certified that error appears in the above-identified patent and that said Letters Patent is hereby corrected as shown below:

In the Specification
Description:
In Line 59, Column 243, "Device Example 6,3" should be "Device Example 6.3"; and
In Line 18, Column 238 and in Line 18, Column 248, recitations of "(Lig)" should be "(Liq)".

In the Claims
In Line 1, Column 252 (Claim 1), "1 to 2.0" should be "1 to 20";
In Line 10, Column 255 (Claim 6), "pyrrolidinyl, and combinations thereof" should be "pyrimidinyl, triazinyl and combinations thereof";
In Line 13, Column 255 (Claim 6), "$NR_v$, S and Se" should be "$NR_v$, O, S and Se";
In Line 47, Column 255 (Claim 6), "$R_a$, $R_v$, $R_c$" should be "$R_a$, $R_b$, $R_c$";
In Line 54, Column 303 (Claim 12), "to 2.0" should be "to 20"; and
In Line 30, Column 305 (Claim 18), "O, S, and X and Y" should be "O, S, and Se; X and Y".

Signed and Sealed this
Twenty-seventh Day of December, 2022

Katherine Kelly Vidal
*Director of the United States Patent and Trademark Office*